US012748112B2

(12) United States Patent
Dard et al.

(10) Patent No.: US 12,748,112 B2
(45) Date of Patent: Sep. 29, 2026

(54) SEROLOGICAL MARKER FOR THE LATENT FORM OF TOXOPLASMOSIS

(71) Applicants: INSERM (INSTITUT NATIONAL DE LA SANTÉ ET DE LA RECHERCHE MÉDICALE), Paris (FR); CENTRE NATIONAL DE LA RECHERCHE SCIENTIFIQUE (CNRS), Paris (FR); UNIVERSITÉ GRENOBLE ALPES, Saint Martin d'Heres (FR); CENTRE HOSPITALIER UNIVERSITAIRE DE GRENOBLE, La Tronche (FR)

(72) Inventors: Céline Dard, La Tronche (FR); Mohamed-Ali Hakimi, La Tronche (FR); Hervé Pelloux, La Tronche (FR); Mariee-Pierre Brenier-Pinchart, La Tronche (FR); Christopher Swale, La Tronche (FR)

(73) Assignees: INSERM (INSTITUT NATIONAL DE LA SANTE ET DE LA RECHERCHE MEDICALE), Paris (FR); CENTRE NATIONAL DE LA RECHERCHE SCIENTIFIQUE (CNRS), Paris (FR); UNIVERSITÉ GRENOBLE ALPES, Saint Martin d'Heres (FR); CENTRE HOSPITALIER UNIVERSITAIRE DE GRENOBLE, La Tronche (FR)

( * ) Notice: Subject to any disclaimer, the term of this patent is extended or adjusted under 35 U.S.C. 154(b) by 949 days.

(21) Appl. No.: 17/776,045

(22) PCT Filed: Nov. 10, 2020

(86) PCT No.: PCT/EP2020/081638
§ 371 (c)(1),
(2) Date: May 11, 2022

(87) PCT Pub. No.: WO2021/094308
PCT Pub. Date: May 20, 2021

(65) Prior Publication Data

US 2022/0390449 A1 Dec. 8, 2022

(30) Foreign Application Priority Data

Nov. 12, 2019 (EP) .................................... 19208644

(51) Int. Cl.
*G01N 33/569* (2006.01)

(52) U.S. Cl.
CPC ... *G01N 33/56905* (2013.01); *G01N 2333/45* (2013.01)

(58) Field of Classification Search
CPC ........... G01N 2469/20; G01N 2333/45; G01N 33/56905
See application file for complete search history.

(56) References Cited

U.S. PATENT DOCUMENTS

2001/0014447 A1* 8/2001 Milhausen .............. A61P 43/00 435/6.15
2022/0390449 A1* 12/2022 Dard ...................... C07K 14/45

FOREIGN PATENT DOCUMENTS

WO 2014/016317 A1 1/2014

OTHER PUBLICATIONS

Sibley et al. "hypothetical protein TGME49_209755 [Toxoplasma gondii ME49]", Oct. 29, 2016, NCBI Reference Sequence: XP_002369725.2. Accessed at https://www.ncbi.nlm.nih.gov/protein/XP_002369725.2 on Feb. 10, 2025. (Year: 2016).*

(Continued)

*Primary Examiner* — Bao-Thuy L Nguyen
*Assistant Examiner* — Amelia Nicole Dickens
(74) *Attorney, Agent, or Firm* — WCF IP

(57) ABSTRACT

In the present invention, inventors report the characterization of BCLA (Brain Cyst Load-associated Antigen), a protein exclusively expressed during the bradyzoite stage of (Continued)

Figure 1C:
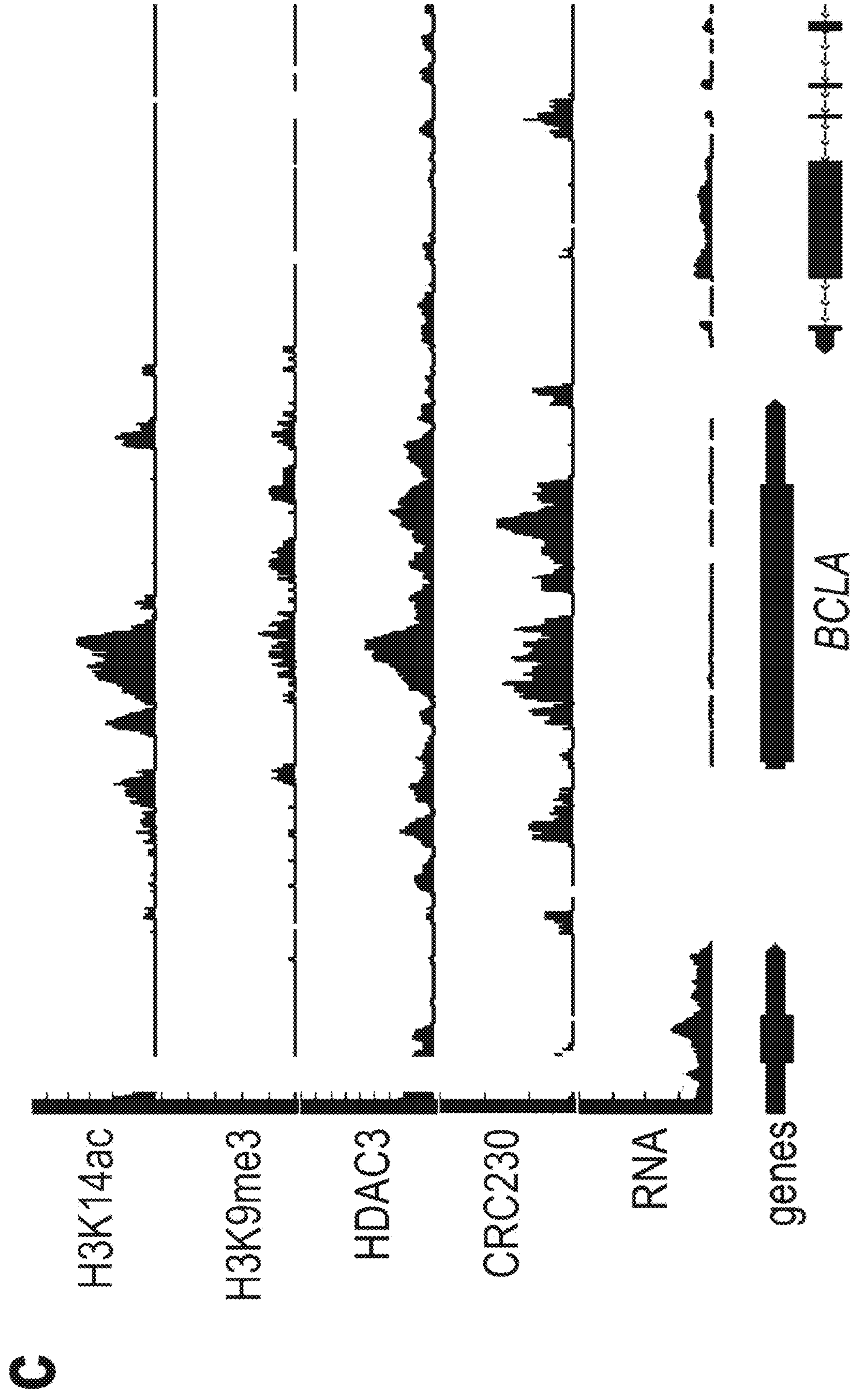

the parasite. In cysts directly purified from the brain of mice, the protein is distributed within and at the surface of the cyst. ELISA antibody capture using a combination of serologically reactive BCLA peptides and a recombinantly expressed c-terminal domain (rBCLA) constitutes an efficient serological marker of latent infection with a high sensitivity that is clearly and exclusively correlated with the presence of cysts in the brain of mice. Antibodies directed against BCLA antigen have been detected in human patients with enriched titers in patients qualified as seropositive to Sag1 or tachyzoite related antigens. Further correlation in humans between anti-BCLA IgG synthesis and cysts is brought by significantly stronger recorded titers in pathological panels strongly related to the presence of cyst. Furthermore, newborn infants with a confirmed congenital toxoplasmosis display significantly higher anti-BCLA IgGs at birth when compared to their mother, suggesting a specific in-utero neosynthesis of such IgGs. Thus the invention relates to a new *Toxoplasma gondii* protein, hereafter referred as BCLA, a new serological marker whose expression is restricted to the latent form of Toxoplasmosis (bradyzoite/cyst). This specific protein and its antigenic fragments can be used to detect autoantibodies in the sera of patient for the diagnosis of the latent form of Toxoplasmosis. The invention also relates to derived antibodies, generated by BCLA immunisation that specifically binds this new protein.

7 Claims, 37 Drawing Sheets

Specification includes a Sequence Listing.

(56) References Cited

OTHER PUBLICATIONS

Reid et al. "tryptophan-rich antigen (Pv-fam-a), related [Neospora caninum Liverpool]", GenBank: CBZ49918.1, Feb. 27, 2015. (Year: 2015).*
Herrmann et al. "Genotyping of samples from German patients with ocular, cerebral and systemic toxoplasmosis reveals a predominance of Toxoplasma gondii type II", Oct. 2014, International Journal of Medical Microbiology, vol. 304, Issue 7, p. 911-916. (Year: 2014).*
Pleyer et al. "Toxoplasmosis in Germany: Epidemiology, Diagnosis, Risk factors, and Treatment", Jun. 21, 2019, Deutsches Arzteblatt, vol. 116, p. 435-444. (Year: 2019).*
Dalimi et al: "Latent toxoplasmosis and human", Iranian Journal of Parisitology, p. 1-17, Jan. 1, 2012.
Database: "hypothetical protein TGME49_209755 [Toxoplasma gondii ME49]", Oct. 20, 2016.
Parmley et al: "Molecular characterization of a 65-kilodalton Toxoplasma gondii antigen expressed abundantly in the matrix of tissue cysts", Molecular and Biochemical Parasitology, vol. 66, No. 2, p. 283-296, Aug. 1, 1994.

* cited by examiner

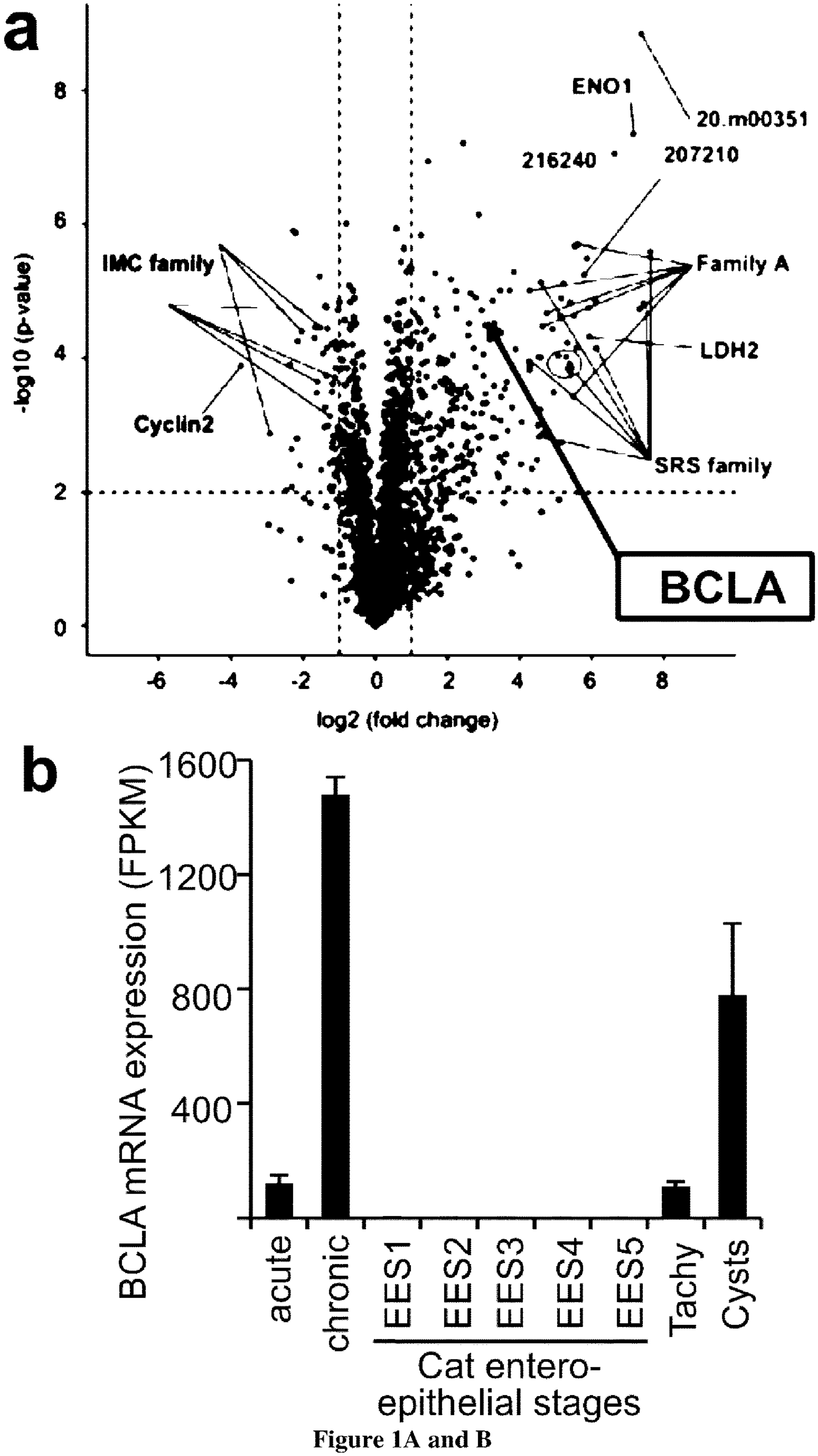
Figure 1A and B

8His tag TEV site

HHHHHHHHENLYFQGMIPGVGDKTEASVLDSIENAVQKVLENLLKAAAGELQPAEAEEARLLVADLKAVVDTAEQVRVEG
EAFFRASVDLYEAVKNLRDSEEKLRPLTKGELVDVVRQFLATQIFVQDRASAFLRVFERLAELLAAEQMKAVFAMVEEGV
SSSERVARVAGELVPMMKKDRERRYGDLVAVTSWFMRRMEHI b

Peptide 1 Peptide 2

| | | |
|---|---|---|
| M.RGTAGSMEEKKpVLPGEGKRHVLPKDETKPALT | EEKRTKPVEPRKE | TgR1 |
| MESPA.RPMEEEKpVLPGEGERHVLPKDERKPALT | DEKRTKPGGPRTE | TgR2 |
| MERPAAGSMEKDKlVLPGEGEGHVLPKHETKPALT | DEKRTKPGGPRTE | TgR3 |
| MERPAAGSMEKEKpVLPGEGEGHVLPKHETKPALT | DEKRTKPGGPRTE | TgR4 |
| MERPAAGSMEKDKlVLPGEGEGHVLPKHETKPALT | DEKRTKPGGPRTE | TgR5 |
| MERPAAGSMEKDKlVLPGEGEGHVLPKHETKPALT | DEKRTKPGGPRTE | TgR6 |
| MERPAAGSMEKDKlVLPGEGEGHVLPKHETKPALT | EEGRTEPIEPRKA | TgR7 |
| MERPA.GAMEKTKpVLPGEGERHVLPKAETKTALT | EEERTEPGGPRMA | TgR8 |
| MERPAAGSMEKKKpVsPGEGEGHVLPKHETKPALT | DEKRTKPGGPRTE | TgR9 |
| MERPAAGSMEKDKlVLPGEGERHVLPKHERKPALT | DEKRTKPGGPPTE | TgR10 |
| MERPAAGSMEKDKlVLPGEGERHVLPKDETKPALT | EEKRTKPGGPRTE | TgR11 |
| MERPAAGSMEKEKpVLPGEGERHASPKDEMKPALT | DEKRTKPGGPRKE | TgR12 |
| MERPAAGSMEKEKpVLPGEGERHVLPKDEQKAALT | QKEVTNPVEPRKE | TgR13 |

c

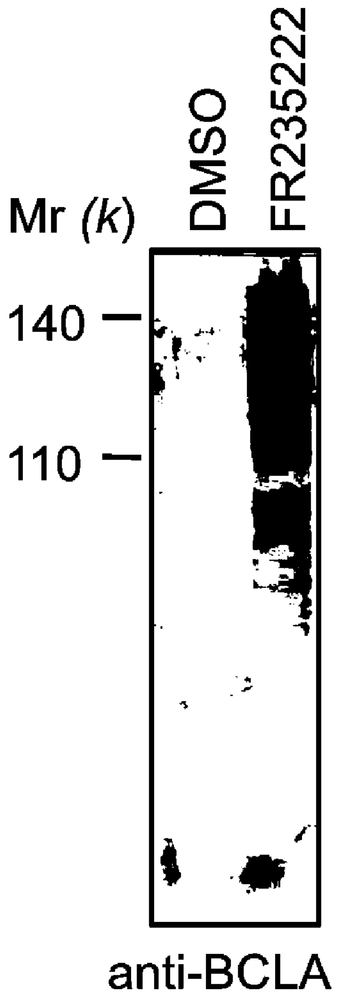

Figure 2B and C a

Assessment of cell invasion (% of infected cells)

Assessment of intracellular tachyzoites proliferation

B

A

C rBLCA peptides

| rBCLA | rBCLA +Peptides | Architecht Toxo IgG / IgM |
|---|---|---|
| >1000 | >1000 | 359 / 2.68 |
| 342 | 702 | 936/0.28 |
| 805 | 1622 | >2000/0.15 |
| 124 | 334 | 432/2.65 |
| 102 | 782 | 32/0.04 |
| 0 | 0 | 0.3 / 0.09 |

SEQUENCE LISTING

<160> NUMBER OF SEQ ID NOS: 64

<210> SEQ ID NO 1
<211> LENGTH: 1275
<212> TYPE: PRT
<213> ORGANISM: Toxoplasma gondii

<400> SEQUENCE: 1

Met Lys Leu Phe Phe Lys Leu Val Leu Ala Gly Val Ser Ser Ile Phe
1 5 10 15

Ala Ala Gln Cys Leu Ala Gly Ala Val Ala Ala Arg Ala Gly Met Pro
20 25 30

Glu Ile Thr Ile Arg Glu Glu Glu Glu Glu Leu Phe Pro Ser Leu Asp
35 40 45

Asp Val Leu Asp Thr Ser Pro Phe Pro Ala Arg Leu Trp Met Gly Pro
50 55 60

Gly Glu Lys Gln Ala Thr Glu Ser His Thr Pro Ala Thr Ile Pro Thr
65 70 75 80

Ala Tyr Lys Ser Thr Pro Gly Leu Ser Ala Thr Val Thr Gly Gly Glu
85 90 95

Asp Gly Ser Ala Lys Met Val Gly Met Asp Val Ala Lys Lys Pro Val
100 105 110

Lys Val Ser Val Lys Lys Glu Glu Glu Asn Lys Asp Val Glu Ala Asn
115 120 125

Glu Asp Gly Trp Asp Tyr Ile Val Ser Lys Gly Val Pro Gly Lys Ile
130 135 140

Pro Ala Thr Val Met Asp Glu Ala Arg Lys Ala Asp Val Val Ala Asp
145 150 155 160

Gly Glu Ala Lys Pro Ala Met Arg Glu Ala Gln Glu Arg Arg Lys Pro
165 170 175

Trp Glu Thr Gln Glu Glu Lys Ile Leu Val Leu Pro Lys Val Gln Arg
180 185 190

Ile Leu Ala Leu Pro Lys Glu Glu Lys Lys His Val Ser Thr Ala Lys
195 200 205

Gly Glu Glu Pro Phe Ser Ser Lys Glu Glu Glu Arg His Val Leu Leu
210 215 220

Asn Gly Glu Glu Arg Lys Pro Val Val Pro Arg Ala Gly Arg Glu Gln
225 230 235 240

Pro Ala Val Pro Arg Gln Glu Glu Gln Lys Leu Val Leu Gln Lys Thr

-continued

```
                245                 250                 255

Glu Arg Lys Pro Val Leu Pro Glu Glu Asp Gln Lys Pro Val Leu Pro
            260                 265                 270

Glu Thr Gly Ala Lys His Val Leu Pro Glu Ile Ala Thr Lys Ser Thr
        275                 280                 285

Leu Thr Gln Lys Glu Val Thr Lys Pro Val Glu Thr Arg Gln Asp Met
    290                 295                 300

Arg Gly Thr Ala Gly Ser Met Glu Glu Lys Lys Pro Val Leu Pro Gly
305                 310                 315                 320

Glu Gly Lys Arg His Val Leu Pro Lys Asp Glu Thr Lys Pro Ala Leu
                325                 330                 335

Thr Glu Glu Lys Arg Thr Lys Pro Val Glu Pro Arg Lys Glu Met Glu
            340                 345                 350

Ser Pro Ala Arg Pro Met Glu Glu Glu Lys Pro Val Leu Pro Gly Glu
        355                 360                 365

Gly Glu Arg His Val Leu Pro Lys Asp Glu Arg Lys Pro Ala Leu Thr
    370                 375                 380

Asp Glu Lys Arg Thr Lys Pro Gly Gly Pro Arg Thr Glu Met Glu Arg
385                 390                 395                 400

Pro Ala Ala Gly Ser Met Glu Lys Asp Lys Leu Val Leu Pro Gly Glu
                405                 410                 415

Gly Glu Gly His Val Leu Pro Lys His Glu Thr Lys Pro Ala Leu Thr
            420                 425                 430

Asp Glu Lys Arg Thr Lys Pro Gly Gly Pro Arg Thr Glu Met Glu Arg
        435                 440                 445

Pro Ala Ala Gly Ser Met Glu Lys Glu Lys Pro Val Leu Pro Gly Glu
    450                 455                 460

Gly Glu Gly His Val Leu Pro Lys His Glu Thr Lys Pro Ala Leu Thr
465                 470                 475                 480

Asp Glu Lys Arg Thr Lys Pro Gly Gly Pro Arg Thr Glu Met Glu Arg
                485                 490                 495

Pro Ala Ala Gly Ser Met Glu Lys Asp Lys Leu Val Leu Pro Gly Glu
            500                 505                 510

Gly Glu Gly His Val Leu Pro Lys His Glu Thr Lys Pro Ala Leu Thr
        515                 520                 525

Asp Glu Lys Arg Thr Lys Pro Gly Gly Pro Arg Thr Glu Met Glu Arg
    530                 535                 540

Pro Ala Ala Gly Ser Met Glu Lys Asp Lys Leu Val Leu Pro Gly Glu
545                 550                 555                 560

Gly Glu Gly His Val Leu Pro Lys His Glu Thr Lys Pro Ala Leu Thr
                565                 570                 575

Asp Glu Lys Arg Thr Lys Pro Gly Gly Pro Arg Thr Glu Met Glu Arg
            580                 585                 590

Pro Ala Ala Gly Ser Met Glu Lys Asp Lys Leu Val Leu Pro Gly Glu
        595                 600                 605

Gly Glu Gly His Val Leu Pro Lys His Glu Thr Lys Pro Ala Leu Thr
    610                 615                 620

Glu Glu Gly Arg Thr Glu Pro Ile Glu Pro Arg Lys Ala Met Glu Arg
625                 630                 635                 640

Pro Ala Gly Ala Met Glu Lys Thr Lys Pro Val Leu Pro Gly Glu Gly
                645                 650                 655

Glu Arg His Val Leu Pro Lys Ala Glu Thr Lys Thr Ala Leu Thr Glu
            660                 665                 670
```

```
Glu Glu Arg Thr Glu Pro Gly Gly Pro Arg Met Ala Met Glu Arg Pro
        675                 680                 685

Ala Ala Gly Ser Met Glu Lys Lys Lys Pro Val Ser Pro Gly Glu Gly
    690                 695                 700

Glu Gly His Val Leu Pro Lys His Glu Thr Lys Pro Ala Leu Thr Asp
705                 710                 715                 720

Glu Lys Arg Thr Lys Pro Gly Gly Pro Arg Thr Glu Met Glu Arg Pro
                725                 730                 735

Ala Ala Gly Ser Met Glu Lys Asp Lys Leu Val Leu Pro Gly Glu Gly
            740                 745                 750

Glu Arg His Val Leu Pro Lys His Glu Arg Lys Pro Ala Leu Thr Asp
        755                 760                 765

Glu Lys Arg Thr Lys Pro Gly Gly Pro Pro Thr Glu Met Glu Arg Pro
    770                 775                 780

Ala Ala Gly Ser Met Glu Lys Asp Lys Leu Val Leu Pro Gly Glu Gly
785                 790                 795                 800

Glu Arg His Val Leu Pro Lys Asp Glu Thr Lys Pro Ala Leu Thr Glu
                805                 810                 815

Glu Lys Arg Thr Lys Pro Gly Gly Pro Arg Thr Glu Met Glu Arg Pro
            820                 825                 830

Ala Ala Gly Ser Met Glu Lys Glu Lys Pro Val Leu Pro Gly Glu Gly
        835                 840                 845

Glu Arg His Ala Ser Pro Lys Asp Glu Met Lys Pro Ala Leu Thr Asp
    850                 855                 860

Glu Lys Arg Thr Lys Pro Gly Gly Pro Arg Lys Glu Met Glu Arg Pro
865                 870                 875                 880

Ala Ala Gly Ser Met Glu Lys Glu Lys Pro Val Leu Pro Gly Glu Gly
                885                 890                 895

Glu Arg His Val Leu Pro Lys Asp Glu Gln Lys Ala Ala Leu Thr Gln
            900                 905                 910

Lys Glu Val Thr Asn Pro Val Glu Pro Arg Lys Glu Met Glu Arg Pro
        915                 920                 925

Ala Ala Pro Ile Glu Gly Glu Lys Gly Val Val Ser Ser Glu Glu Glu
    930                 935                 940

Lys Pro Val Ser Pro Lys Glu Ala Thr Arg Arg Ile Leu Pro Lys Glu
945                 950                 955                 960

Gly Lys Glu Ser Leu Gly Thr Arg Lys Glu Glu Val Lys Pro Ile Val
                965                 970                 975

Arg Arg Ala Lys Arg Gly Arg Arg Ile Ala Gln Lys Gly Lys Glu Lys
            980                 985                 990

Gln Ile Ala Pro Lys Glu Gly Lys  Lys Pro Ala Val Pro  Lys Glu Gly
        995                 1000                1005

Glu Glu  Arg Pro Ala Glu Pro  Thr Glu Gly Glu Glu  Arg Pro Val
    1010                1015                1020

Gly Pro  Lys Glu Gly Glu Glu  Arg Pro Val Gly Pro  Lys Glu Gly
    1025                1030                1035

Glu Glu  Arg Pro Val Val Pro  Asp Val Asp Lys Glu  Lys Pro Val
    1040                1045                1050

Val Pro  Glu Gly Asp Lys Glu  Lys Pro Val Val Pro  Glu Gly Asp
    1055                1060                1065

Lys Asp  His Pro Ala Leu Pro  Glu Gln Asp Glu Glu  Lys His Ala
    1070                1075                1080
```

```
Thr Trp  Glu Lys Glu Met Ile  Pro Gly Val Gly Asp  Lys Thr Glu
    1085                 1090                 1095

Ala Ser  Val Leu Asp Ser Ile  Glu Asn Ala Val Gln  Lys Val Leu
    1100                 1105                 1110

Glu Asn  Leu Leu Lys Ala Ala  Ala Gly Glu Leu Gln  Pro Ala Glu
    1115                 1120                 1125

Ala Glu  Glu Ala Arg Leu Leu  Val Ala Asp Leu Lys  Ala Val Val
    1130                 1135                 1140

Asp Thr  Ala Glu Gln Val Arg  Val Glu Gly Glu Ala  Phe Phe Arg
    1145                 1150                 1155

Ala Ser  Val Asp Leu Tyr Glu  Ala Val Lys Asn Leu  Arg Asp Ser
    1160                 1165                 1170

Glu Glu  Lys Leu Arg Pro Leu  Thr Lys Gly Glu Leu  Val Asp Val
    1175                 1180                 1185

Val Arg  Gln Phe Leu Ala Thr  Gln Ile Phe Val Gln  Asp Arg Ala
    1190                 1195                 1200

Ser Ala  Phe Leu Arg Val Phe  Glu Arg Leu Ala Glu  Leu Leu Ala
    1205                 1210                 1215

Ala Glu  Gln Met Lys Ala Val  Phe Ala Met Val Glu  Glu Gly Val
    1220                 1225                 1230

Ser Ser  Ser Glu Arg Val Ala  Arg Val Ala Gly Glu  Leu Val Pro
    1235                 1240                 1245

Met Met  Lys Lys Asp Arg Glu  Arg Arg Tyr Gly Asp  Leu Val Ala
    1250                 1255                 1260

Val Thr  Ser Trp Phe Met Arg  Arg Met Glu His Ile
    1265                 1270                 1275


<210> SEQ ID NO 2
<211> LENGTH: 187
<212> TYPE: PRT
<213> ORGANISM: Artificial
<220> FEATURE:
<223> OTHER INFORMATION: Synthetic C-terminal antigenic domain (res
      1089-1275)

<400> SEQUENCE: 2

Met Ile Pro Gly Val Gly Asp Lys Thr Glu Ala Ser Val Leu Asp Ser
1               5                   10                  15

Ile Glu Asn Ala Val Gln Lys Val Leu Glu Asn Leu Leu Lys Ala Ala
            20                  25                  30

Ala Gly Glu Leu Gln Pro Ala Glu Ala Glu Glu Ala Arg Leu Leu Val
        35                  40                  45

Ala Asp Leu Lys Ala Val Val Asp Thr Ala Glu Gln Val Arg Val Glu
    50                  55                  60

Gly Glu Ala Phe Phe Arg Ala Ser Val Asp Leu Tyr Glu Ala Val Lys
65                  70                  75                  80

Asn Leu Arg Asp Ser Glu Glu Lys Leu Arg Pro Leu Thr Lys Gly Glu
                85                  90                  95

Leu Val Asp Val Val Arg Gln Phe Leu Ala Thr Gln Ile Phe Val Gln
            100                 105                 110

Asp Arg Ala Ser Ala Phe Leu Arg Val Phe Glu Arg Leu Ala Glu Leu
        115                 120                 125

Leu Ala Ala Glu Gln Met Lys Ala Val Phe Ala Met Val Glu Glu Gly
    130                 135                 140

Val Ser Ser Ser Glu Arg Val Ala Arg Val Ala Gly Glu Leu Val Pro
145                 150                 155                 160
```

```
Met Met Lys Lys Asp Arg Glu Arg Arg Tyr Gly Asp Leu Val Ala Val
                165                 170                 175

Thr Ser Trp Phe Met Arg Arg Met Glu His Ile
            180                 185


<210> SEQ ID NO 3
<211> LENGTH: 204
<212> TYPE: PRT
<213> ORGANISM: Artificial
<220> FEATURE:
<223> OTHER INFORMATION: Synthetic HisTag-rBCLA

<400> SEQUENCE: 3

Met Gly His His His His His His His His Glu Asn Leu Tyr Phe Gln
1               5                   10                  15

Gly Met Ile Pro Gly Val Gly Asp Lys Thr Glu Ala Ser Val Leu Asp
            20                  25                  30

Ser Ile Glu Asn Ala Val Gln Lys Val Leu Glu Asn Leu Leu Lys Ala
        35                  40                  45

Ala Ala Gly Glu Leu Gln Pro Ala Glu Ala Glu Glu Ala Arg Leu Leu
    50                  55                  60

Val Ala Asp Leu Lys Ala Val Val Asp Thr Ala Glu Gln Val Arg Val
65                  70                  75                  80

Glu Gly Glu Ala Phe Phe Arg Ala Ser Val Asp Leu Tyr Glu Ala Val
                85                  90                  95

Lys Asn Leu Arg Asp Ser Glu Glu Lys Leu Arg Pro Leu Thr Lys Gly
            100                 105                 110

Glu Leu Val Asp Val Val Arg Gln Phe Leu Ala Thr Gln Ile Phe Val
        115                 120                 125

Gln Asp Arg Ala Ser Ala Phe Leu Arg Val Phe Glu Arg Leu Ala Glu
    130                 135                 140

Leu Leu Ala Ala Glu Gln Met Lys Ala Val Phe Ala Met Val Glu Glu
145                 150                 155                 160

Gly Val Ser Ser Ser Glu Arg Val Ala Arg Val Ala Gly Glu Leu Val
                165                 170                 175

Pro Met Met Lys Lys Asp Arg Glu Arg Arg Tyr Gly Asp Leu Val Ala
            180                 185                 190

Val Thr Ser Trp Phe Met Arg Arg Met Glu His Ile
        195                 200


<210> SEQ ID NO 4
<211> LENGTH: 47
<212> TYPE: PRT
<213> ORGANISM: Artificial
<220> FEATURE:
<223> OTHER INFORMATION: Synthetic TgR1 domain of BCLA

<400> SEQUENCE: 4

Met Arg Gly Thr Ala Gly Ser Met Glu Glu Lys Lys Pro Val Leu Pro
1               5                   10                  15

Gly Glu Gly Lys Arg His Val Leu Pro Lys Asp Glu Thr Lys Pro Ala
            20                  25                  30

Leu Thr Glu Glu Lys Arg Thr Lys Pro Val Glu Pro Arg Lys Glu
        35                  40                  45


<210> SEQ ID NO 5
<211> LENGTH: 47
<212> TYPE: PRT
```

<213> ORGANISM: Artificial
<220> FEATURE:
<223> OTHER INFORMATION: Synthetic TgR2 domain of BCLA

<400> SEQUENCE: 5

Met Glu Ser Pro Ala Arg Pro Met Glu Glu Glu Lys Pro Val Leu Pro
1               5                   10                  15

Gly Glu Gly Glu Arg His Val Leu Pro Lys Asp Glu Arg Lys Pro Ala
            20                  25                  30

Leu Thr Asp Glu Lys Arg Thr Lys Pro Gly Gly Pro Arg Thr Glu
        35                  40                  45

<210> SEQ ID NO 6
<211> LENGTH: 48
<212> TYPE: PRT
<213> ORGANISM: Artificial
<220> FEATURE:
<223> OTHER INFORMATION: Synthetic TgR3 domain of BCLA

<400> SEQUENCE: 6

Met Glu Arg Pro Ala Ala Gly Ser Met Glu Lys Asp Lys Leu Val Leu
1               5                   10                  15

Pro Gly Glu Gly Glu Gly His Val Leu Pro Lys His Glu Thr Lys Pro
            20                  25                  30

Ala Leu Thr Asp Glu Lys Arg Thr Lys Pro Gly Gly Pro Arg Thr Glu
        35                  40                  45

<210> SEQ ID NO 7
<211> LENGTH: 48
<212> TYPE: PRT
<213> ORGANISM: Artificial
<220> FEATURE:
<223> OTHER INFORMATION: Synthetic TgR4 domain of BCLA

<400> SEQUENCE: 7

Met Glu Arg Pro Ala Ala Gly Ser Met Glu Lys Glu Lys Pro Val Leu
1               5                   10                  15

Pro Gly Glu Gly Glu Gly His Val Leu Pro Lys His Glu Thr Lys Pro
            20                  25                  30

Ala Leu Thr Asp Glu Lys Arg Thr Lys Pro Gly Gly Pro Arg Thr Glu
        35                  40                  45

<210> SEQ ID NO 8
<211> LENGTH: 48
<212> TYPE: PRT
<213> ORGANISM: Artificial
<220> FEATURE:
<223> OTHER INFORMATION: Synthetic TgR5 domain of BCLA

<400> SEQUENCE: 8

Met Glu Arg Pro Ala Ala Gly Ser Met Glu Lys Asp Lys Leu Val Leu
1               5                   10                  15

Pro Gly Glu Gly Glu Gly His Val Leu Pro Lys His Glu Thr Lys Pro
            20                  25                  30

Ala Leu Thr Asp Glu Lys Arg Thr Lys Pro Gly Gly Pro Arg Thr Glu
        35                  40                  45

<210> SEQ ID NO 9
<211> LENGTH: 48
<212> TYPE: PRT
<213> ORGANISM: Artificial
<220> FEATURE:
<223> OTHER INFORMATION: Synthetic TgR6 domain of BCLA

<400> SEQUENCE: 9

Met Glu Arg Pro Ala Ala Gly Ser Met Glu Lys Asp Lys Leu Val Leu
1 5 10 15

Pro Gly Glu Gly Glu Gly His Val Leu Pro Lys His Glu Thr Lys Pro
20 25 30

Ala Leu Thr Asp Glu Lys Arg Thr Lys Pro Gly Gly Pro Arg Thr Glu
35 40 45

<210> SEQ ID NO 10
<211> LENGTH: 48
<212> TYPE: PRT
<213> ORGANISM: Artificial
<220> FEATURE:
<223> OTHER INFORMATION: Synthetic TgR7 domain of BCLA

<400> SEQUENCE: 10

Met Glu Arg Pro Ala Ala Gly Ser Met Glu Lys Asp Lys Leu Val Leu
1 5 10 15

Pro Gly Glu Gly Glu Gly His Val Leu Pro Lys His Glu Thr Lys Pro
20 25 30

Ala Leu Thr Glu Glu Gly Arg Thr Glu Pro Ile Glu Pro Arg Lys Ala
35 40 45

<210> SEQ ID NO 11
<211> LENGTH: 47
<212> TYPE: PRT
<213> ORGANISM: Artificial
<220> FEATURE:
<223> OTHER INFORMATION: Synthetic TgR8 domain of BCLA

<400> SEQUENCE: 11

Met Glu Arg Pro Ala Gly Ala Met Glu Lys Thr Lys Pro Val Leu Pro
1 5 10 15

Gly Glu Gly Glu Arg His Val Leu Pro Lys Ala Glu Thr Lys Thr Ala
20 25 30

Leu Thr Glu Glu Glu Arg Thr Glu Pro Gly Gly Pro Arg Met Ala
35 40 45

<210> SEQ ID NO 12
<211> LENGTH: 48
<212> TYPE: PRT
<213> ORGANISM: Artificial
<220> FEATURE:
<223> OTHER INFORMATION: Synthetic TgR9 domain of BCLA

<400> SEQUENCE: 12

Met Glu Arg Pro Ala Ala Gly Ser Met Glu Lys Lys Lys Pro Val Ser
1 5 10 15

Pro Gly Glu Gly Glu Gly His Val Leu Pro Lys His Glu Thr Lys Pro
20 25 30

Ala Leu Thr Asp Glu Lys Arg Thr Lys Pro Gly Gly Pro Arg Thr Glu
35 40 45

<210> SEQ ID NO 13
<211> LENGTH: 48
<212> TYPE: PRT
<213> ORGANISM: Artificial
<220> FEATURE:
<223> OTHER INFORMATION: Synthetic TgR10 domain of BCLA

<400> SEQUENCE: 13

Met Glu Arg Pro Ala Ala Gly Ser Met Glu Lys Asp Lys Leu Val Leu
1 5 10 15

Pro Gly Glu Gly Glu Arg His Val Leu Pro Lys His Glu Arg Lys Pro
20 25 30

Ala Leu Thr Asp Glu Lys Arg Thr Lys Pro Gly Gly Pro Pro Thr Glu
35 40 45

<210> SEQ ID NO 14
<211> LENGTH: 48
<212> TYPE: PRT
<213> ORGANISM: Artificial
<220> FEATURE:
<223> OTHER INFORMATION: Synthetic TgR11 domain of BCLA

<400> SEQUENCE: 14

Met Glu Arg Pro Ala Ala Gly Ser Met Glu Lys Asp Lys Leu Val Leu
1 5 10 15

Pro Gly Glu Gly Glu Arg His Val Leu Pro Lys Asp Glu Thr Lys Pro
20 25 30

Ala Leu Thr Glu Glu Lys Arg Thr Lys Pro Gly Gly Pro Arg Thr Glu
35 40 45

<210> SEQ ID NO 15
<211> LENGTH: 48
<212> TYPE: PRT
<213> ORGANISM: Artificial
<220> FEATURE:
<223> OTHER INFORMATION: Synthetic TgR12 domain of BCLA

<400> SEQUENCE: 15

Met Glu Arg Pro Ala Ala Gly Ser Met Glu Lys Glu Lys Pro Val Leu
1 5 10 15

Pro Gly Glu Gly Glu Arg His Ala Ser Pro Lys Asp Glu Met Lys Pro
20 25 30

Ala Leu Thr Asp Glu Lys Arg Thr Lys Pro Gly Gly Pro Arg Lys Glu
35 40 45

<210> SEQ ID NO 16
<211> LENGTH: 48
<212> TYPE: PRT
<213> ORGANISM: Artificial
<220> FEATURE:
<223> OTHER INFORMATION: Synthetic TgR13 domain of BCLA

<400> SEQUENCE: 16

Met Glu Arg Pro Ala Ala Gly Ser Met Glu Lys Glu Lys Pro Val Leu
1 5 10 15

Pro Gly Glu Gly Glu Arg His Val Leu Pro Lys Asp Glu Gln Lys Ala
20 25 30

Ala Leu Thr Gln Lys Glu Val Thr Asn Pro Val Glu Pro Arg Lys Glu
35 40 45

<210> SEQ ID NO 17
<211> LENGTH: 11
<212> TYPE: PRT
<213> ORGANISM: Artificial
<220> FEATURE:
<223> OTHER INFORMATION: Synthetic Peptide 1 of TgR1 and TgR11

<400> SEQUENCE: 17

Glu Met Arg Gly Thr Ala Gly Ser Met Glu Glu
1 5 10

```
<210> SEQ ID NO 18
<211> LENGTH: 12
<212> TYPE: PRT
<213> ORGANISM: Artificial
<220> FEATURE:
<223> OTHER INFORMATION: Synthetic Peptide 2 of TgR1

<400> SEQUENCE: 18

Val Leu Pro Lys Asp Glu Thr Lys Pro Ala Leu Thr
1               5                   10


<210> SEQ ID NO 19
<211> LENGTH: 11
<212> TYPE: PRT
<213> ORGANISM: Artificial
<220> FEATURE:
<223> OTHER INFORMATION: Synthetic Peptide 1 of TgR2

<400> SEQUENCE: 19

Glu Met Glu Ser Pro Ala Arg Pro Met Glu Glu
1               5                   10


<210> SEQ ID NO 20
<211> LENGTH: 12
<212> TYPE: PRT
<213> ORGANISM: Artificial
<220> FEATURE:
<223> OTHER INFORMATION: Synthetic Peptide 2 of TgR2

<400> SEQUENCE: 20

Val Leu Pro Lys Asp Glu Arg Lys Pro Ala Leu Thr
1               5                   10


<210> SEQ ID NO 21
<211> LENGTH: 12
<212> TYPE: PRT
<213> ORGANISM: Artificial
<220> FEATURE:
<223> OTHER INFORMATION: Synthetic Peptide 1 of TgR3 to TgR7 and of TgR9
      to TgR13

<400> SEQUENCE: 21

Glu Met Glu Arg Pro Ala Ala Gly Ser Met Glu Lys
1               5                   10


<210> SEQ ID NO 22
<211> LENGTH: 12
<212> TYPE: PRT
<213> ORGANISM: Artificial
<220> FEATURE:
<223> OTHER INFORMATION: Synthetic Peptide 2 of TgR3 to TgR7 and of TgR9

<400> SEQUENCE: 22

Val Leu Pro Lys His Glu Thr Lys Pro Ala Leu Thr
1               5                   10


<210> SEQ ID NO 23
<211> LENGTH: 11
<212> TYPE: PRT
<213> ORGANISM: Artificial
<220> FEATURE:
<223> OTHER INFORMATION: Synthetic Peptide 1 of TgR8

<400> SEQUENCE: 23

Glu Met Glu Arg Pro Ala Gly Ala Met Glu Lys
1               5                   10
```

<210> SEQ ID NO 24
<211> LENGTH: 12
<212> TYPE: PRT
<213> ORGANISM: Artificial
<220> FEATURE:
<223> OTHER INFORMATION: Synthetic Peptide 2 of TgR8

<400> SEQUENCE: 24

Val Leu Pro Lys Ala Glu Thr Lys Thr Ala Leu Thr
1 5 10

<210> SEQ ID NO 25
<211> LENGTH: 12
<212> TYPE: PRT
<213> ORGANISM: Artificial
<220> FEATURE:
<223> OTHER INFORMATION: Synthetic Peptide 2 of TgR10

<400> SEQUENCE: 25

Val Leu Pro Lys His Glu Arg Lys Pro Ala Leu Thr
1 5 10

<210> SEQ ID NO 26
<211> LENGTH: 12
<212> TYPE: PRT
<213> ORGANISM: Artificial
<220> FEATURE:
<223> OTHER INFORMATION: Synthetic Peptide 2 of TgR12

<400> SEQUENCE: 26

Ala Ser Pro Lys Asp Glu Met Lys Pro Ala Leu Thr
1 5 10

<210> SEQ ID NO 27
<211> LENGTH: 12
<212> TYPE: PRT
<213> ORGANISM: Artificial
<220> FEATURE:
<223> OTHER INFORMATION: Synthetic Peptide 2 of TgR13

<400> SEQUENCE: 27

Val Leu Pro Lys Asp Glu Gln Lys Ala Ala Leu Thr
1 5 10

<210> SEQ ID NO 28
<211> LENGTH: 26
<212> TYPE: DNA
<213> ORGANISM: Artificial
<220> FEATURE:
<223> OTHER INFORMATION: Synthetic primer TgBCLA-KO-CRISP-FWD

<400> SEQUENCE: 28
aagttgatca ctattcgtga agaagg 26

<210> SEQ ID NO 29
<211> LENGTH: 26
<212> TYPE: DNA
<213> ORGANISM: Artificial
<220> FEATURE:
<223> OTHER INFORMATION: Synthetic primer TgBCLA-KO-CRISP-REV

<400> SEQUENCE: 29
aaaaccttct tcacgaatag tgatca 26

<210> SEQ ID NO 30
<211> LENGTH: 26

<212> TYPE: DNA
<213> ORGANISM: Artificial
<220> FEATURE:
<223> OTHER INFORMATION: Synthetic primer TgBCLA-HF-CRISP-FWD

<400> SEQUENCE: 30
aagttggaac ggcggtacgg cgaccg 26

<210> SEQ ID NO 31
<211> LENGTH: 26
<212> TYPE: DNA
<213> ORGANISM: Artificial
<220> FEATURE:
<223> OTHER INFORMATION: Synthetic primer TgBCLA-HF-CRISP-REV

<400> SEQUENCE: 31
aaaacggtcg ccgtaccgcc gttcca 26

<210> SEQ ID NO 32
<211> LENGTH: 21
<212> TYPE: PRT
<213> ORGANISM: Artificial
<220> FEATURE:
<223> OTHER INFORMATION: Synthetic domain A of rBCLA

<400> SEQUENCE: 32

```
Gly Glu Leu Gln Pro Ala Glu Ala Glu Glu Ala Arg Leu Leu Val Ala
1               5                   10                  15

Asp Leu Lys Ala Val
            20
```

<210> SEQ ID NO 33
<211> LENGTH: 18
<212> TYPE: PRT
<213> ORGANISM: Artificial
<220> FEATURE:
<223> OTHER INFORMATION: Synthetic domain B of rBCLA

<400> SEQUENCE: 33

```
Val Arg Val Glu Gly Glu Ala Phe Phe Arg Ala Ser Val Asp Leu Tyr
1               5                   10                  15

Glu Ala
```

<210> SEQ ID NO 34
<211> LENGTH: 16
<212> TYPE: PRT
<213> ORGANISM: Artificial
<220> FEATURE:
<223> OTHER INFORMATION: Synthetic domain C of rBCLA

<400> SEQUENCE: 34

```
Lys Leu Arg Pro Leu Thr Lys Gly Glu Leu Val Asp Val Val Arg Gln
1               5                   10                  15
```

<210> SEQ ID NO 35
<211> LENGTH: 15
<212> TYPE: PRT
<213> ORGANISM: Artificial
<220> FEATURE:
<223> OTHER INFORMATION: Synthetic peptide 36 of rBCLA

<400> SEQUENCE: 35

```
Thr Gln Ile Phe Val Gln Asp Arg Ala Ser Ala Phe Leu Arg Val
1               5                   10                  15
```

<210> SEQ ID NO 36
<211> LENGTH: 15
<212> TYPE: PRT
<213> ORGANISM: Artificial
<220> FEATURE:
<223> OTHER INFORMATION: Synthetic peptide 44 of rBCLA

<400> SEQUENCE: 36

Ala Ala Glu Gln Met Lys Ala Val Phe Ala Met Val Glu Glu Gly
1 5 10 15

<210> SEQ ID NO 37
<211> LENGTH: 15
<212> TYPE: PRT
<213> ORGANISM: Artificial
<220> FEATURE:
<223> OTHER INFORMATION: Synthetic peptide 12 of rBCLA

<400> SEQUENCE: 37

Gly Glu Leu Gln Pro Ala Glu Ala Glu Glu Ala Arg Leu Leu Val
1 5 10 15

<210> SEQ ID NO 38
<211> LENGTH: 15
<212> TYPE: PRT
<213> ORGANISM: Artificial
<220> FEATURE:
<223> OTHER INFORMATION: Synthetic peptide 13 of rBCLA

<400> SEQUENCE: 38

Gln Pro Ala Glu Ala Glu Glu Ala Arg Leu Leu Val Ala Asp Leu
1 5 10 15

<210> SEQ ID NO 39
<211> LENGTH: 15
<212> TYPE: PRT
<213> ORGANISM: Artificial
<220> FEATURE:
<223> OTHER INFORMATION: Synthetic peptide 14 of rBCLA

<400> SEQUENCE: 39

Glu Ala Glu Glu Ala Arg Leu Leu Val Ala Asp Leu Lys Ala Val
1 5 10 15

<210> SEQ ID NO 40
<211> LENGTH: 15
<212> TYPE: PRT
<213> ORGANISM: Artificial
<220> FEATURE:
<223> OTHER INFORMATION: Synthetic peptide 21 of rBCLA

<400> SEQUENCE: 40

Val Arg Val Glu Gly Glu Ala Phe Phe Arg Ala Ser Val Asp Leu
1 5 10 15

<210> SEQ ID NO 41
<211> LENGTH: 15
<212> TYPE: PRT
<213> ORGANISM: Artificial
<220> FEATURE:
<223> OTHER INFORMATION: Synthetic peptide 22 of rBCLA

<400> SEQUENCE: 41

Glu Gly Glu Ala Phe Phe Arg Ala Ser Val Asp Leu Tyr Glu Ala
1 5 10 15

<210> SEQ ID NO 42

<211> LENGTH: 15
<212> TYPE: PRT
<213> ORGANISM: Artificial
<220> FEATURE:
<223> OTHER INFORMATION: Synthetic peptide 23 of rBCLA

<400> SEQUENCE: 42

Ala Phe Phe Arg Ala Ser Val Asp Leu Tyr Glu Ala Val Lys Asn
1 5 10 15

<210> SEQ ID NO 43
<211> LENGTH: 15
<212> TYPE: PRT
<213> ORGANISM: Artificial
<220> FEATURE:
<223> OTHER INFORMATION: Synthetic peptide 30 of rBCLA

<400> SEQUENCE: 43

Lys Leu Arg Pro Leu Thr Lys Gly Glu Leu Val Asp Val Val Arg
1 5 10 15

<210> SEQ ID NO 44
<211> LENGTH: 19
<212> TYPE: PRT
<213> ORGANISM: Artificial
<220> FEATURE:
<223> OTHER INFORMATION: Synthetic domain A of TgR4

<400> SEQUENCE: 44

Ala Ala Gly Ser Met Glu Lys Glu Lys Pro Val Leu Pro Gly Glu Gly
1 5 10 15

Glu Gly His

<210> SEQ ID NO 45
<211> LENGTH: 22
<212> TYPE: PRT
<213> ORGANISM: Artificial
<220> FEATURE:
<223> OTHER INFORMATION: Synthetic domain B of TgR4

<400> SEQUENCE: 45

Val Leu Pro Lys His Glu Thr Lys Pro Ala Leu Thr Asp Glu Lys Arg
1 5 10 15

Thr Lys Pro Gly Gly Pro
20

<210> SEQ ID NO 46
<211> LENGTH: 15
<212> TYPE: PRT
<213> ORGANISM: Artificial
<220> FEATURE:
<223> OTHER INFORMATION: Synthetic peptide 3 of TgR4

<400> SEQUENCE: 46

Ala Ala Gly Ser Met Glu Lys Glu Lys Pro Val Leu Pro Gly Glu
1 5 10 15

<210> SEQ ID NO 47
<211> LENGTH: 15
<212> TYPE: PRT
<213> ORGANISM: Artificial
<220> FEATURE:
<223> OTHER INFORMATION: Synthetic peptide 4 of TgR4

<400> SEQUENCE: 47

Gly Ser Met Glu Lys Glu Lys Pro Val Leu Pro Gly Glu Gly Glu 1 5 10 15

<210> SEQ ID NO 48
<211> LENGTH: 15
<212> TYPE: PRT
<213> ORGANISM: Artificial
<220> FEATURE:
<223> OTHER INFORMATION: Synthetic peptide 5 of TgR4

<400> SEQUENCE: 48

Met Glu Lys Glu Lys Pro Val Leu Pro Gly Glu Gly Glu Gly His
1 5 10 15

<210> SEQ ID NO 49
<211> LENGTH: 15
<212> TYPE: PRT
<213> ORGANISM: Artificial
<220> FEATURE:
<223> OTHER INFORMATION: Synthetic peptide 6 of TgR4

<400> SEQUENCE: 49

Lys Glu Lys Pro Val Leu Pro Gly Glu Gly Glu Gly His Val Leu
1 5 10 15

<210> SEQ ID NO 50
<211> LENGTH: 15
<212> TYPE: PRT
<213> ORGANISM: Artificial
<220> FEATURE:
<223> OTHER INFORMATION: Synthetic peptide 7 of TgR4

<400> SEQUENCE: 50

Lys Pro Val Leu Pro Gly Glu Gly Glu Gly His Val Leu Pro Gly
1 5 10 15

<210> SEQ ID NO 51
<211> LENGTH: 16
<212> TYPE: PRT
<213> ORGANISM: Artificial
<220> FEATURE:
<223> OTHER INFORMATION: Synthetic peptide 13 of TgR4

<400> SEQUENCE: 51

His Val Leu Pro Lys His Glu Thr Lys Pro Ala Leu Thr Asp Glu Lys
1 5 10 15

<210> SEQ ID NO 52
<211> LENGTH: 15
<212> TYPE: PRT
<213> ORGANISM: Artificial
<220> FEATURE:
<223> OTHER INFORMATION: Synthetic peptide 14 of TgR4

<400> SEQUENCE: 52

Pro Lys His Glu Thr Lys Pro Ala Leu Thr Asp Glu Lys Arg Thr
1 5 10 15

<210> SEQ ID NO 53
<211> LENGTH: 15
<212> TYPE: PRT
<213> ORGANISM: Artificial
<220> FEATURE:
<223> OTHER INFORMATION: Synthetic peptide 15 of TgR4

<400> SEQUENCE: 53

His Glu Thr Lys Pro Ala Leu Thr Asp Glu Lys Arg Thr Lys Pro
1 5 10 15

<210> SEQ ID NO 54
<211> LENGTH: 15
<212> TYPE: PRT
<213> ORGANISM: Artificial
<220> FEATURE:
<223> OTHER INFORMATION: Synthetic peptide 16 of TgR4

<400> SEQUENCE: 54

Thr Lys Pro Ala Leu Thr Asp Glu Lys Arg Thr Lys Pro Gly Gly
1               5                   10                  15

<210> SEQ ID NO 55
<211> LENGTH: 43
<212> TYPE: PRT
<213> ORGANISM: Artificial
<220> FEATURE:
<223> OTHER INFORMATION: Synthetic Peptide AB_F

<400> SEQUENCE: 55

Met Glu Arg Pro Ala Ala Gly Ser Met Glu Lys Glu Lys Pro Val Leu
1               5                   10                  15

Pro Gly Glu Gly Glu Gly Leu Pro Lys His Glu Thr Lys Pro Ala Leu
            20                  25                  30

Thr Asp Glu Lys Arg Thr Lys Pro Gly Gly Pro
        35                  40

<210> SEQ ID NO 56
<211> LENGTH: 15
<212> TYPE: PRT
<213> ORGANISM: Artificial
<220> FEATURE:
<223> OTHER INFORMATION: Synthetic Peptide A3_B

<400> SEQUENCE: 56

Ala Ala Gly Ser Met Glu Lys Asp Lys Leu Val Leu Pro Gly Glu
1               5                   10                  15

<210> SEQ ID NO 57
<211> LENGTH: 129
<212> TYPE: PRT
<213> ORGANISM: Artificial
<220> FEATURE:
<223> OTHER INFORMATION: Synthetic VHH ERB-1G6

<400> SEQUENCE: 57

Glu Val Gln Leu Val Glu Ser Gly Gly Gly Leu Val Gln Ala Gly Gly
1               5                   10                  15

Ser Leu Gly Leu Ser Cys Ala Ala Ser Gly Arg Pro Gly Arg Ile Phe
            20                  25                  30

Thr Arg Asn Ser Met Ala Trp Phe Arg Gln Ala Pro Gly Lys Glu Arg
        35                  40                  45

Glu Phe Val Ala Ser Ile Asn Trp Ser Gly Thr Ser Thr Ser Tyr Ala
    50                  55                  60

Asp Ser Val Lys Gly Arg Phe Ala Ile Ser Arg Asp Asn Asp Lys Asn
65                  70                  75                  80

Thr Val Tyr Leu Gln Met Asn Ser Leu Lys Pro Glu Asp Thr Ala Val
                85                  90                  95

Tyr Tyr Cys Ala Ala Asp Ser Ala Leu Tyr Gly Ser Met His Lys Thr
            100                 105                 110

Pro Ala Asp Tyr Glu Tyr Trp Gly Gln Gly Thr Gln Val Thr Val Ser
        115                 120                 125

Ser

<210> SEQ ID NO 58
<211> LENGTH: 127
<212> TYPE: PRT
<213> ORGANISM: Artificial
<220> FEATURE:
<223> OTHER INFORMATION: Synthetic VHH ERB-1B11

<400> SEQUENCE: 58

Glu Val Gln Leu Val Glu Ser Gly Gly Gly Leu Val Gln Ala Gly Gly
1 5 10 15

Ser Leu Arg Leu Thr Cys Ala Ala Ser Gly Arg Thr Phe Arg Arg Ser
20 25 30

Asn Met Ala Trp Phe Arg Gln Pro Pro Gly Lys Glu Arg Asp Phe Val
35 40 45

Ala Ala Ile Lys Trp Ser Gly Ser Ser Thr Asn Tyr Ala Asp Ser Val
50 55 60

Lys Gly Arg Phe Thr Ile Ser Arg Asp Asn Asp Lys Asn Thr Val Tyr
65 70 75 80

Leu Gln Met Asn Val Leu Lys Pro Glu Asp Thr Gly Val Tyr Tyr Cys
85 90 95

Ala Gln Glu Ser Ser Leu Tyr Ser Asn Tyr Leu Pro Val Val Ser Ser
100 105 110

Ala Tyr Asp Tyr Trp Gly Gln Gly Thr Gln Val Thr Val Ser Ser
115 120 125

<210> SEQ ID NO 59
<211> LENGTH: 128
<212> TYPE: PRT
<213> ORGANISM: Artificial
<220> FEATURE:
<223> OTHER INFORMATION: Synthetic VHH ERB-1A12

<400> SEQUENCE: 59

Glu Val Gln Leu Val Glu Ser Gly Gly Gly Leu Val Gln Ala Gly Gly
1 5 10 15

Ser Leu Arg Leu Ser Cys Ala Ala Ser Gly Arg Thr Phe Ser Arg Tyr
20 25 30

Phe Met Gly Trp Phe Arg Gln Ala Pro Gly Lys Glu Arg Glu Phe Val
35 40 45

Ala Gly Ile Ile Trp Ser Gly Thr Arg Thr Tyr Tyr Val Asp Ser Val
50 55 60

Lys Gly Arg Phe Thr Ile Ser Arg Asp Asn Asp Lys Arg Met Val Tyr
65 70 75 80

Leu Gln Met Asn Ser Leu Lys Pro Glu Asp Thr Ala Val Tyr Tyr Cys
85 90 95

Ala Ala Tyr Lys Glu Tyr Tyr Gly Thr Pro Ala Gln Leu Tyr Ala Ala
100 105 110

Ala Ser Tyr Asp Tyr Trp Gly Gln Gly Thr Gln Val Thr Val Ser Ser
115 120 125

<210> SEQ ID NO 60
<211> LENGTH: 127
<212> TYPE: PRT
<213> ORGANISM: Artificial
<220> FEATURE:
<223> OTHER INFORMATION: Synthetic VHH ERB-1F1

<400> SEQUENCE: 60

Glu Val Gln Leu Val Glu Ser Gly Gly Gly Leu Val Gln Ala Gly Asp
1               5                   10                  15

Ser Leu Arg Leu Ser Cys Ala Ala Ser Gly Arg Thr Phe Ser Arg Val
            20                  25                  30

Thr Met Gly Trp Phe Arg Gln Ala Pro Gly Lys Glu Arg Glu Phe Val
        35                  40                  45

Ala Gly Ile Ser Trp Ser Gly Thr Arg Thr Asp Tyr Pro Asp Ser Val
    50                  55                  60

Lys Gly Arg Phe Thr Val Ser Arg Asp Asn Ala Lys Lys Thr Met Trp
65                  70                  75                  80

Leu Gln Met Ser Ser Leu Arg Pro Glu Asp Thr Ala Val Tyr His Cys
                85                  90                  95

Ala Ala Asp Ser Thr Leu Tyr Gly Ser Ala Ile Ser Asn Asn Arg Glu
            100                 105                 110

Ala Tyr Ala Tyr Trp Gly Gln Gly Thr Gln Val Thr Val Ser Ser
        115                 120                 125

<210> SEQ ID NO 61
<211> LENGTH: 127
<212> TYPE: PRT
<213> ORGANISM: Artificial
<220> FEATURE:
<223> OTHER INFORMATION: Synthetic VHH ERB-1F2

<400> SEQUENCE: 61

Glu Val Gln Leu Val Glu Ser Gly Gly Gly Leu Val Gln Val Gly Gly
1               5                   10                  15

Ser Leu Arg Leu Ser Cys Ala Ala Ser Gly Arg Thr Phe Arg Arg Asn
            20                  25                  30

Thr Ile Gly Trp Phe Arg Gln Ala Pro Gly Lys Glu Arg Glu Phe Val
        35                  40                  45

Ala Ala Ile Ser Trp Ser Gly Thr Arg Thr Lys Tyr Ala Asp Pro Val
    50                  55                  60

Lys Gly Arg Phe Thr Ile Ser Arg Asp Asn Asp Lys Asn Thr Ala Tyr
65                  70                  75                  80

Leu Gln Met Asn Thr Leu Lys Pro Asp Asp Thr Ala Val Tyr Tyr Cys
                85                  90                  95

Ala Ala Asp Gly Ala Leu Tyr Gly Ser Asp Val Ser Gly Leu Ala Arg
            100                 105                 110

Val Tyr Asp Tyr Trp Gly Gln Gly Thr Gln Val Thr Val Ser Ser
        115                 120                 125

<210> SEQ ID NO 62
<211> LENGTH: 127
<212> TYPE: PRT
<213> ORGANISM: Artificial
<220> FEATURE:
<223> OTHER INFORMATION: Synthetic VHH ERB-1H4

<400> SEQUENCE: 62

Glu Val Gln Leu Val Glu Ser Gly Gly Gly Leu Val Gln Ala Gly Gly
1               5                   10                  15

Ser Leu Arg Leu Ser Cys Val Ala Ser Gly Arg Thr Phe Ser Arg Tyr
            20                  25                  30

Thr Val Gly Trp Phe Arg Gln Ala Pro Gly Lys Glu Arg Glu Phe Val
        35                  40                  45

```
Ala Gly Ile Ser Trp Ser Gly Ser Arg Thr Ser Tyr Ala Asp Ser Val
    50                  55                  60

Lys Gly Arg Phe Thr Ile Ser Arg Asp Asn Asp Lys Thr Thr Gly Tyr
65                  70                  75                  80

Leu Gln Met Asn Ser Leu Lys Pro Glu Asp Thr Ala Val Tyr Tyr Cys
                85                  90                  95

Ala Ala Ile Thr Lys Leu Tyr Glu Asn Asn Ile Pro Arg Ser Val Ser
            100                 105                 110

Asp Tyr Ala Leu Trp Gly Gln Gly Thr Gln Val Thr Val Ser Ser
        115                 120                 125
```

<210> SEQ ID NO 63
<211> LENGTH: 126
<212> TYPE: PRT
<213> ORGANISM: Artificial
<220> FEATURE:
<223> OTHER INFORMATION: Synthetic VHH ERB-1D7

<400> SEQUENCE: 63

```
Lys Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Arg Arg
            20                  25                  30

Gly Met Gly Trp Phe Arg Gln Ala Pro Gly Lys Glu Arg Glu Phe Val
        35                  40                  45

Ala Thr Ile Lys Trp Ser Gly Thr Ser Thr Asp Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Asn Leu Gln Pro Glu Asp Thr Ala Val Tyr Tyr Cys
                85                  90                  95

Ala Ala Asp Arg Gln Leu Tyr Arg Asp Gly Tyr Val Pro Leu Asn Glu
            100                 105                 110

Tyr Glu Asp Trp Gly Gln Gly Thr Gln Val Thr Val Ser Ser
        115                 120                 125
```

<210> SEQ ID NO 64
<211> LENGTH: 48
<212> TYPE: PRT
<213> ORGANISM: Artificial
<220> FEATURE:
<223> OTHER INFORMATION: Synthetic TgRX domain of BCLA
<220> FEATURE:
<221> NAME/KEY: MISC_FEATURE
<222> LOCATION: (2)..(2)
<223> OTHER INFORMATION: E or none
<220> FEATURE:
<221> NAME/KEY: MISC_FEATURE
<222> LOCATION: (3)..(3)
<223> OTHER INFORMATION: R or S
<220> FEATURE:
<221> NAME/KEY: MISC_FEATURE
<222> LOCATION: (4)..(4)
<223> OTHER INFORMATION: P or G
<220> FEATURE:
<221> NAME/KEY: MISC_FEATURE
<222> LOCATION: (5)..(5)
<223> OTHER INFORMATION: A or G
<220> FEATURE:
<221> NAME/KEY: MISC_FEATURE
<222> LOCATION: (6)..(6)
<223> OTHER INFORMATION: A or none
<220> FEATURE:
<221> NAME/KEY: MISC_FEATURE
<222> LOCATION: (7)..(7)

```
<223> OTHER INFORMATION: G or R
<220> FEATURE:
<221> NAME/KEY: MISC_FEATURE
<222> LOCATION: (8)..(8)
<223> OTHER INFORMATION: S or P or A
<220> FEATURE:
<221> NAME/KEY: MISC_FEATURE
<222> LOCATION: (11)..(11)
<223> OTHER INFORMATION: K or E
<220> FEATURE:
<221> NAME/KEY: MISC_FEATURE
<222> LOCATION: (12)..(12)
<223> OTHER INFORMATION: K or E or D
<220> FEATURE:
<221> NAME/KEY: MISC_FEATURE
<222> LOCATION: (14)..(14)
<223> OTHER INFORMATION: P or L
<220> FEATURE:
<221> NAME/KEY: MISC_FEATURE
<222> LOCATION: (16)..(16)
<223> OTHER INFORMATION: L or S
<220> FEATURE:
<221> NAME/KEY: MISC_FEATURE
<222> LOCATION: (21)..(21)
<223> OTHER INFORMATION: E or K
<220> FEATURE:
<221> NAME/KEY: MISC_FEATURE
<222> LOCATION: (22)..(22)
<223> OTHER INFORMATION: G or R
<220> FEATURE:
<221> NAME/KEY: MISC_FEATURE
<222> LOCATION: (24)..(24)
<223> OTHER INFORMATION: V or A
<220> FEATURE:
<221> NAME/KEY: MISC_FEATURE
<222> LOCATION: (25)..(25)
<223> OTHER INFORMATION: L or S
<220> FEATURE:
<221> NAME/KEY: MISC_FEATURE
<222> LOCATION: (28)..(28)
<223> OTHER INFORMATION: H or D or A
<220> FEATURE:
<221> NAME/KEY: MISC_FEATURE
<222> LOCATION: (30)..(30)
<223> OTHER INFORMATION: T or R or M or Q
<220> FEATURE:
<221> NAME/KEY: MISC_FEATURE
<222> LOCATION: (32)..(32)
<223> OTHER INFORMATION: P or T or A
<220> FEATURE:
<221> NAME/KEY: MISC_FEATURE
<222> LOCATION: (36)..(36)
<223> OTHER INFORMATION: D or E or Q
<220> FEATURE:
<221> NAME/KEY: MISC_FEATURE
<222> LOCATION: (37)..(37)
<223> OTHER INFORMATION: E or K
<220> FEATURE:
<221> NAME/KEY: MISC_FEATURE
<222> LOCATION: (38)..(38)
<223> OTHER INFORMATION: K or E or G
<220> FEATURE:
<221> NAME/KEY: MISC_FEATURE
<222> LOCATION: (39)..(39)
<223> OTHER INFORMATION: R or V
<220> FEATURE:
<221> NAME/KEY: MISC_FEATURE
<222> LOCATION: (41)..(41)
<223> OTHER INFORMATION: K or E or N
<220> FEATURE:
<221> NAME/KEY: MISC_FEATURE
<222> LOCATION: (43)..(43)
<223> OTHER INFORMATION: G or V or I
<220> FEATURE:
<221> NAME/KEY: MISC_FEATURE
<222> LOCATION: (44)..(44)
<223> OTHER INFORMATION: G or E
<220> FEATURE:
<221> NAME/KEY: MISC_FEATURE
```

```
<222> LOCATION: (46)..(46)
<223> OTHER INFORMATION: R or P
<220> FEATURE:
<221> NAME/KEY: MISC_FEATURE
<222> LOCATION: (47)..(47)
<223> OTHER INFORMATION: T or K or M
<220> FEATURE:
<221> NAME/KEY: MISC_FEATURE
<222> LOCATION: (48)..(48)
<223> OTHER INFORMATION: E or A

<400> SEQUENCE: 64

Met Xaa Xaa Xaa Xaa Xaa Xaa Xaa Met Glu Xaa Xaa Lys Xaa Val Xaa
1               5                   10                  15

Pro Gly Glu Gly Xaa Xaa His Xaa Xaa Pro Lys Xaa Glu Xaa Lys Xaa
            20                  25                  30

Ala Leu Thr Xaa Xaa Xaa Xaa Thr Xaa Pro Xaa Xaa Pro Xaa Xaa Xaa
        35                  40                  45
```

SEROLOGICAL MARKER FOR THE LATENT FORM OF TOXOPLASMOSIS

SEQUENCE LISTING

This document incorporates by reference an electronic sequence listing text file, which was electronically submitted along with this document. The text file is named 2022-05-11_11450758US_SequenceListing.txt, is 41988 bytes, and was created on Apr. 12, 2022.

FIELD OF THE INVENTION

The invention relates to a new *Toxoplasma gondii* protein, hereafter referred as BCLA (Brain Cyst Load-associated Antigen), a new serological marker whose expression was restricted to the latent form of Toxoplasmosis (bradyzoite/cyst). The invention also relates to antibody that specifically binds this new protein. This specific protein and its antigenic fragments can be used to detect autoantibodies in the sera of patient for the diagnosis of the latent form of Toxoplasmosis.

BACKGROUND OF THE INVENTION

The ancient phylum Apicomplexa includes many of the world's pre-eminent protozoan pathogens. Most deadly to humans is *Plasmodium*, the agent of malaria, which kills nearly half a million people annually. *T. gondii* is the etiologic agent of toxoplasmosis, one of the most widespread protozoan parasites of domestic, wild, and companion animals. Toxoplasmosis is a widespread foodborne infection in humans that poses significant public health problems, being recognized as a leading cause of foodborne deaths in the United States (Scallan et al., 2015). Toxoplasmosis is a usually mild disease in immunocompetent humans that can turn into a major threat in immunocompromised patients who experience life-threatening cerebral, pulmonary, cardiac, or disseminated pathologies. Transplacental infection can cause congenital infection with varied degree of clinical manifestations, ranging from congenital abnormalities (e.g. hydrocephaly, microcephaly, intracranial calcification) to fetal loss.

The cyst-forming enteric coccidian parasite *T. gondii* is transmitted by an alternating two-host life cycle relying on a feline definitive host for sexual transmission while undergoing asexual transmission in a variety of alternative hosts, including rodents and humans. Over its prolonged residence in non-felid warm blooded metazoans, *T. gondii* initiates complex developmental programs in response environmental cues including host innate defenses and adaptation to different hosts. During initial infection in the intermediate host, the parasite replicates as tachyzoites, which expand dramatically in numbers before disseminating to many tissues in the body. While the initial infection is generally controlled by a potent Th1-mediated proinflammatory host response that lead to the massive destruction of the bulk tachyzoite population, a minor subpopulation of tachyzoite differentiates to a slow-growing bradyzoite stage which persists for the lifetime of the host within tissue cysts that reside in long-lived cells, including neurons and skeletal muscle cells (Dubey, 1997). Ingestion of tissue cysts by the feline definitive host completes the cycle, giving rise to oocyst shedding, the latter being highly infectious (Dubey, 2001).

The tissue cyst is a major source of human infection via carnivorism and as such a key contributing factor in human disease as complications of toxoplasmosis are tightened to the capacity of bradyzoite to inflict irreversible damages while differentiating back to the replicative tachyzoite stage. Indeed, while the asymptomatic parasitism offers life-long equilibrium and protection in immune competent hosts, sustained immune dysfunction is known to break parasite dormancy, promoting bradyzoite to tachyzoite transition and further tachyzoite population expansion. These combined processes eventually result in encephalitis, pneumonitis, retinochoroiditis or even disseminated toxoplasmosis as major outcomes in immunocompromised individuals (Dard et al., 2018). Therefore, the strategy of *T. gondii* as an obligate intracellular parasite is based on a quest for avirulence, a capacity to attenuate, but not to fully counteract the host innate immune response to infection, thus securing the permanent residence required to await transmission.

Despite the importance of the tissue cyst in the life cycle of *T. gondii* and its critical role as a reservoir for the reactivation of toxoplasmosis in immunocompromised host, the biology of the bradyzoites and the cyst they form are poorly understood. Cysts are thought to grow over time and disseminate to sustain chronic infection without passing through an intermediate tachyzoite stage, via both the migration of free bradyzoites and the fission of bradyzoite cysts (Dzierszinski et al., 2004; Frenkel and Escajadillo, 1987). The notion that bradyzoites within tissue cysts are dormant entities was recently challenged by compelling evidence showing that bradyzoites display cyclical, episodic growth within tissue cysts in vivo (Watts et al., 2015) by replicating asynchronously, using both endodyogeny and endopolygeny (Dzierszinski et al., 2004).

The developmental transitions from tachyzoite to bradyzoite are bidirectional and typified by a drastic alteration of the parasite's gene expression, resulting in major changes in metabolism, remodeling of the parasite surface with the restricted expression of stage-specific surface antigens, and the formation of the cyst wall. The latter is thought to protect bradyzoites from harsh gastrointestinal environmental conditions and likely to provide a physical barrier to host immune defenses. *T. gondii* differentiation has been difficult to study in that the stage transitions are steered by complex and still unknown developmental genetic programs yet also influenced by the host cell physiology (Lueder and Rahman, 2017). In the laboratory, tachyzoite-to-bradyzoite conversion can be triggered by exogenous stress (e.g. alkaline stress, nutrient deprivation and drugs) in the absence of host immunity in vitro.

Transcriptional regulation clearly plays a key role in bradyzoite development as evidenced by many studies showing stage-specific gene expression. How these changes are regulated at the molecular level remains to a large extent unknown, yet we and others brought strong evidence that epigenetic variations are the driving forces of parasite differentiation. Early evidence came from the observation that tachyzoites promptly recovered from mice during in vivo infection are especially prone to differentiate and gradually lose this "primed" state over time. As such, long-term passage of tachyzoites in tissue culture drastically attenuate the ability of type II strains to develop high cyst burden in vivo. Thus, epigenetic mechanisms by fostering the developmental plasticity, i.e. the manifestation of a variety of phenotypes from the same genome, may allow the parasite to adapt to thousands of potential intermediate hosts and respond to strikingly different immune systems.

*T. gondii* has evolved sophisticated ways to promote epigenetic alterations such as the active changes in histone marks and chromatin remodeling that rival the strategies adopted by the cells they infect and provide zoites with remarkable capacities to undergo stage differentiation in response to environmental cues or as part of developmental programs. We took an early interest in histone post-translational modifications (PTMs) specifically acetylation (Saksouk et al., 2005) that led us to show that the alteration in the rate of histone H4 acetylation in the vicinity of stage-specific genes is one of the epigenetic molecular motors that drive parasite differentiation (Bougdour et al., 2009). Acetylation of core histones is mediated by histone acetyltransferases (HATs) and, in many instances, results in relaxation of chromatin structure and transcriptional activation of associated genes. Histone deacetylases (HDACs) counteract HAT activity by catalyzing the removal of acetyl moieties from lysine residues in histone tails, thereby inducing chromatin condensation and transcriptional repression (Kurdistani and Grunstein, 2003).

The importance of histone acetylation for the control of differentiation is underscored by the finding that chemical inhibition of TgHDAC3 with low doses of the compound FR235222 induces in vitro tachyzoite to bradyzoite stage conversion (Bougdour et al., 2009; Maubon et al., 2010). A recombinant strain transfected with a TgHDAC3 allele resistant to the compound does not exhibit these effects, confirming TgHDAC3 specificity of the compound and suggesting that the activity of TgHDAC3 actively prevents bradyzoite differentiation (Bougdour et al., 2009). The in vitro conversion was accompanied by hyperacetylation of the upstream regions of >350 genes, one-third of which are specific to bradyzoites (Bougdour et al., 2009). TgHDAC3 seems to primarily oppose the action of the HAT TgGCN5b, which by ChIP localizes to promoters of active genes, whereas TgHDAC3 localizes by ChIP to promoters of bradyzoite genes (Saksouk et al., 2005). While those data represent a step towards the comprehension of the causal relationship between histone acetylation and gene expression in *T. gondii* and have pointed out the crucial role of TgHDAC3 in stage conversion, they were exclusively performed in the virulent RH strain that does not readily develop tissue cysts or latent infections in laboratory mice. Finally, there is a continued need to develop novel diagnosis for latent form of Toxoplasmosis.

In this study, inventors revisited the ability of FR235222 to stimulate an in vitro tachyzoite to bradyzoite conversion using strains of type II origin that are prone to cyst formation in vivo. Quantitative analysis of *T. gondii* proteome response to the FR235222 uncovered many proteins that have been previously identified as stage-specific proteins including those recognized as restricted to bradyzoite. Due to their likely importance to the parasite's biology (Hakimi et al., 2017), inventors chose to focus our attention on novel proteins predicted to be secreted. ~ 200 putative FR235222 responsive bradyzoite-secreted effectors were identified by this approach. One candidate, BCLA (Brain Cyst Load-associated Antigen), was chosen for further investigation. BCLA was exclusively expressed upon FR235222 treatment and following its secretion in the vacuole space the protein was shown to accumulate at the parasitophorous vacuole membrane (PVM). Under in vivo conditions, BCLA lies in the matrix space of the cyst as well as at the cyst wall, the latter being thought to originate from the PVM at the latent stage. While assessing its function, inventors uncover that BCLA deficiency is affecting the integrity of brain cysts isolated from chronically infected mice, yet the protein is dispensable for proper cyst function at least in our mice model of chronic toxoplasmosis.

Given the restricted expression of BCLA by bradyzoites and its location at the cyst wall, inventors next sought to investigate its potential application in serodiagnosis. Here inventors found that the C-terminal peptide of BCLA produced by recombinant techniques is strongly antigenic and constitutes an excellent antigen candidate for the detection of anti-*T. gondii* IgG in chronically infected mice. Inventors provide strong data showing a clear correlation between the presence of cysts in the brain of chronically infected mice and the detection in sera of the antigen BCLA. Positive assays with human sera validate the antigenic character of BCLA and pave the way for the use of this antigen for anti-*Toxoplasma* diagnosis with an interesting perspective of serological detection of cyst burden in chronically infected hosts.

SUMMARY OF THE INVENTION

The invention provides an isolated *Toxoplasma gondii* polypeptide, hereafter referred as BCLA (Brain Cyst Load-associated Antigen) which comprises the amino acids SEQ ID NO: 1 and immunogenic peptides fragments.

The invention further relates to antibodies generated against the isolated polypeptide of the invention.

The invention further relates to a method for detecting *Toxoplasma gondii* polypeptide according to the invention, and/or evaluating its amount in a biological sample, especially in the solid sample.

The invention further relates to a diagnostic method of latent form of Toxoplasmosis using the polypeptide according to the invention in order to detect anti BCLA antibodies in a biological sample especially in the fluid sample.

DETAILED DESCRIPTION OF THE INVENTION

By modulating the tachyzoite genome expression using epi-drugs inventors were able to identify genes whose expression were restricted to bradyzoites. In the present invention, inventors report the characterization of the protein BCLA (Brain Cyst Load-associated Antigen) that, when expressed under bradyzoite-induced condition, accumulates at the parasitophorous vacuole membrane in vitro. In mice brain, the protein is scattered within and at the surface of the cyst. The deletion of the gene results in reduced brain cyst burden in mice, the remaining cysts being typified by deformations of their wall surface ranging from loss of circularity to peculiar budding phenotype. Finally, when synthetized as a recombinant protein, BCLA constitutes an efficient serological marker of latent infection with a high sensitivity that was clearly and exclusively correlated with the presence of cysts in mice brain. With a first ELISA BCLA test developed by the inventors, antibodies directed against BCLA antigen have been detected in human patients with a strong suspicion or a proven ocular toxoplasmosis, exclusively in serum or both in serum and aqueous humour. Serological assays have long been the first line test to confirm *T. gondii* infection, yet the current serological diagnosis does not always distinguish between acute, latent and reactivation disease states. Moreover, the current serology does not evaluate the cyst burden in tissues and the subsequent risk of toxoplasmosis reactivation in seropositive immunocompromised patients. Some of these limitations could now be overcome with the discovery of BCLA, a serious antigen candidate for serological detection of cysts in chronically infected hosts.

Figure 12A:
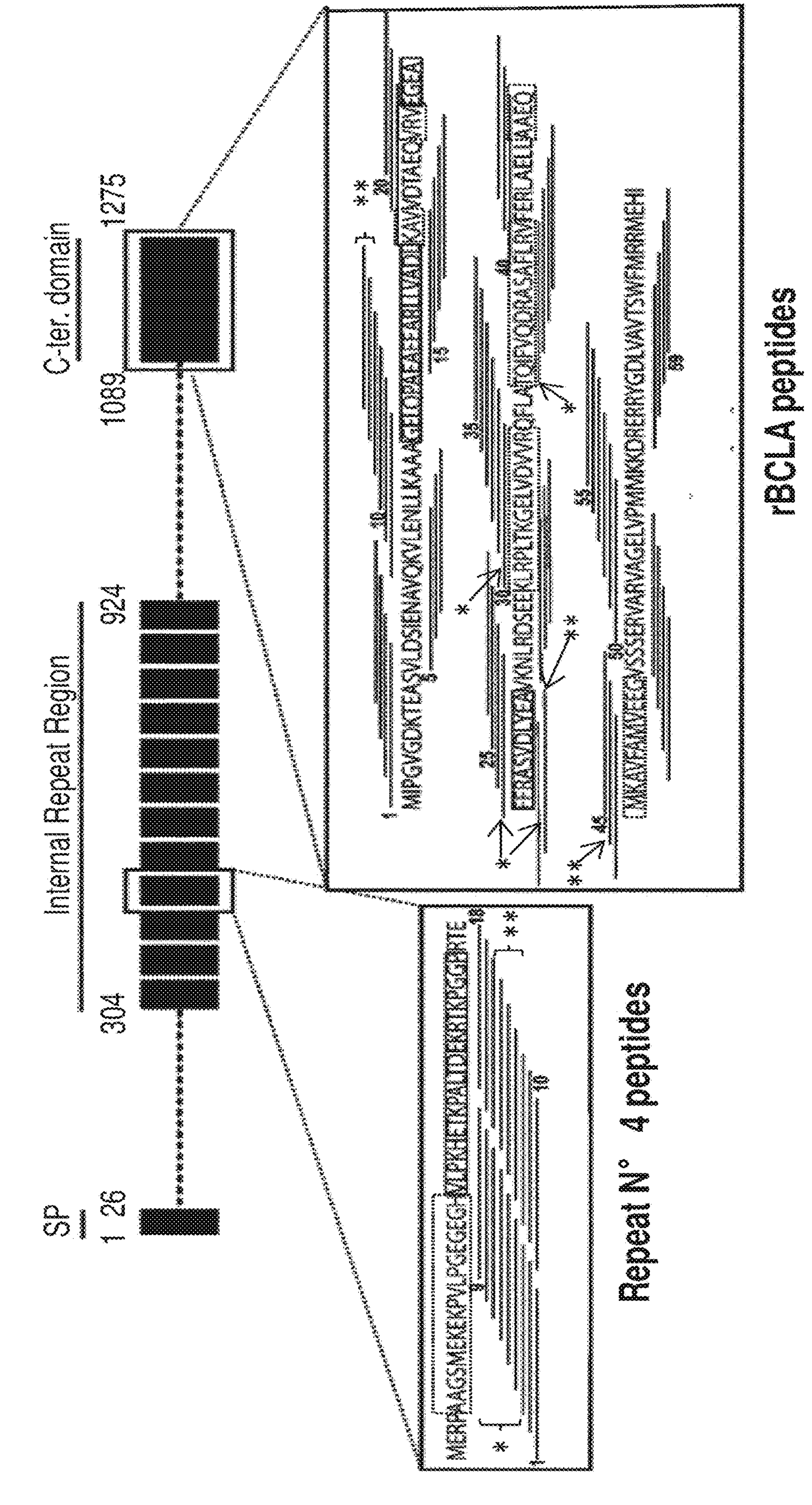
Figure 12B:
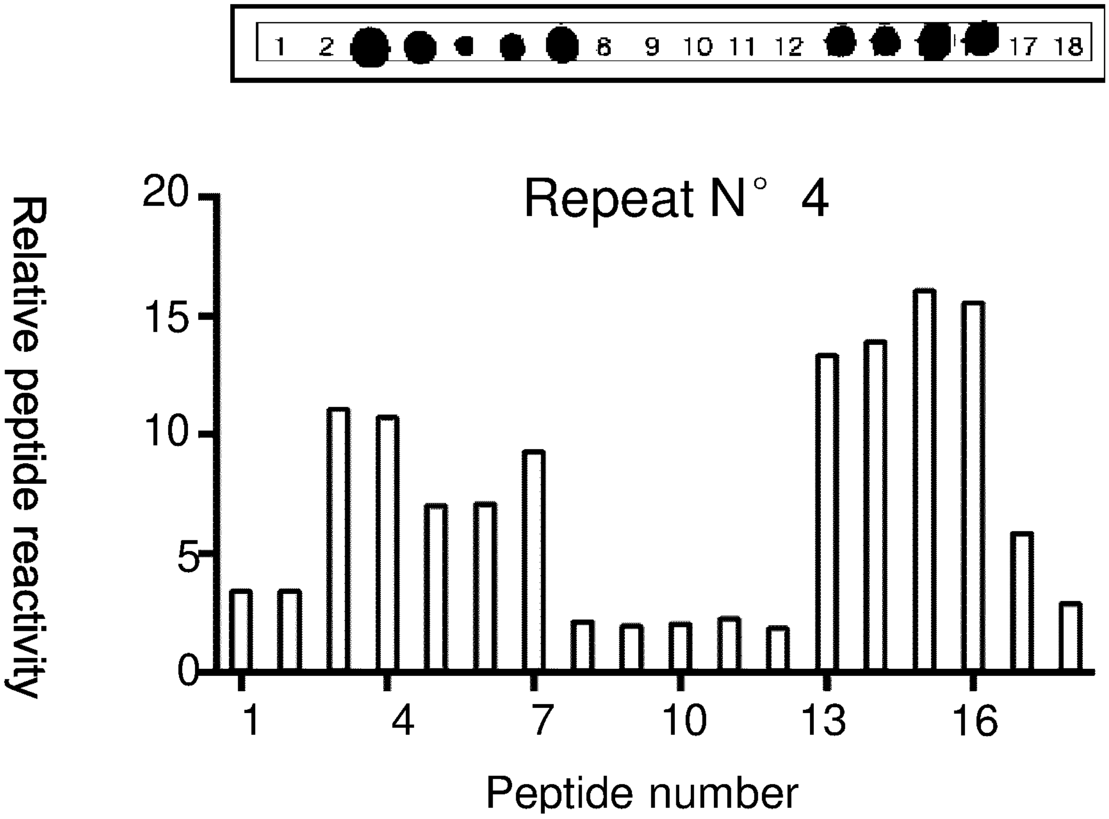
Figure 12B:
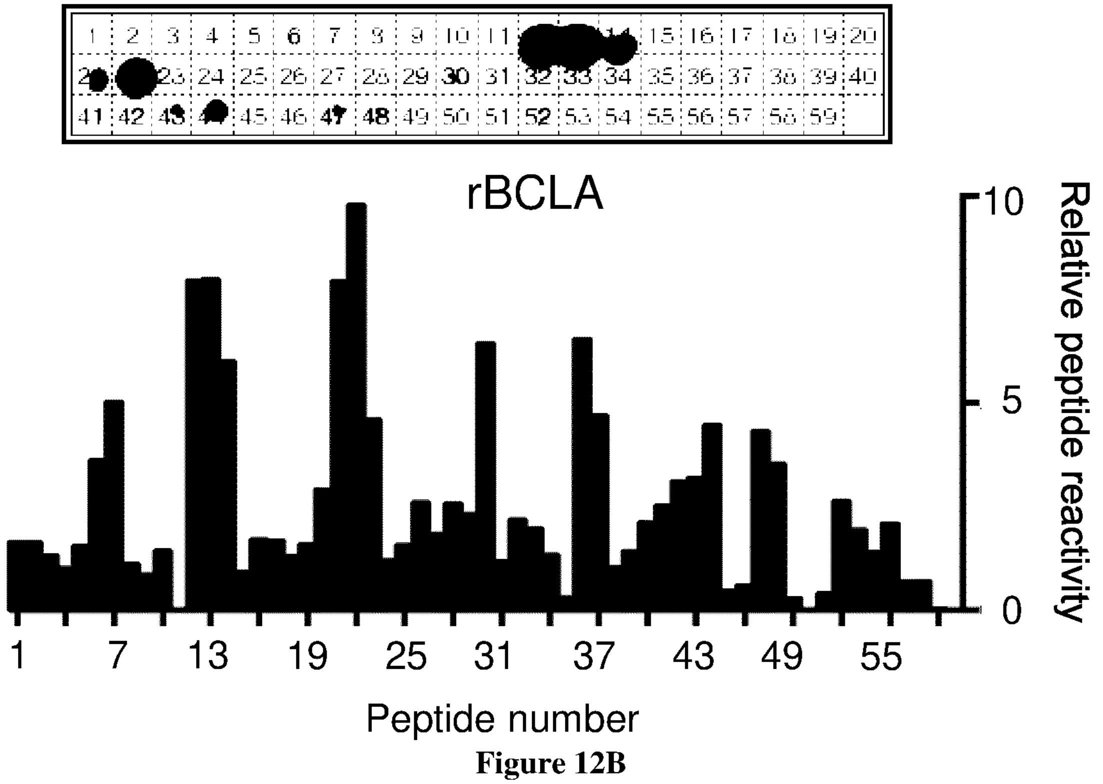
Figure 12C:
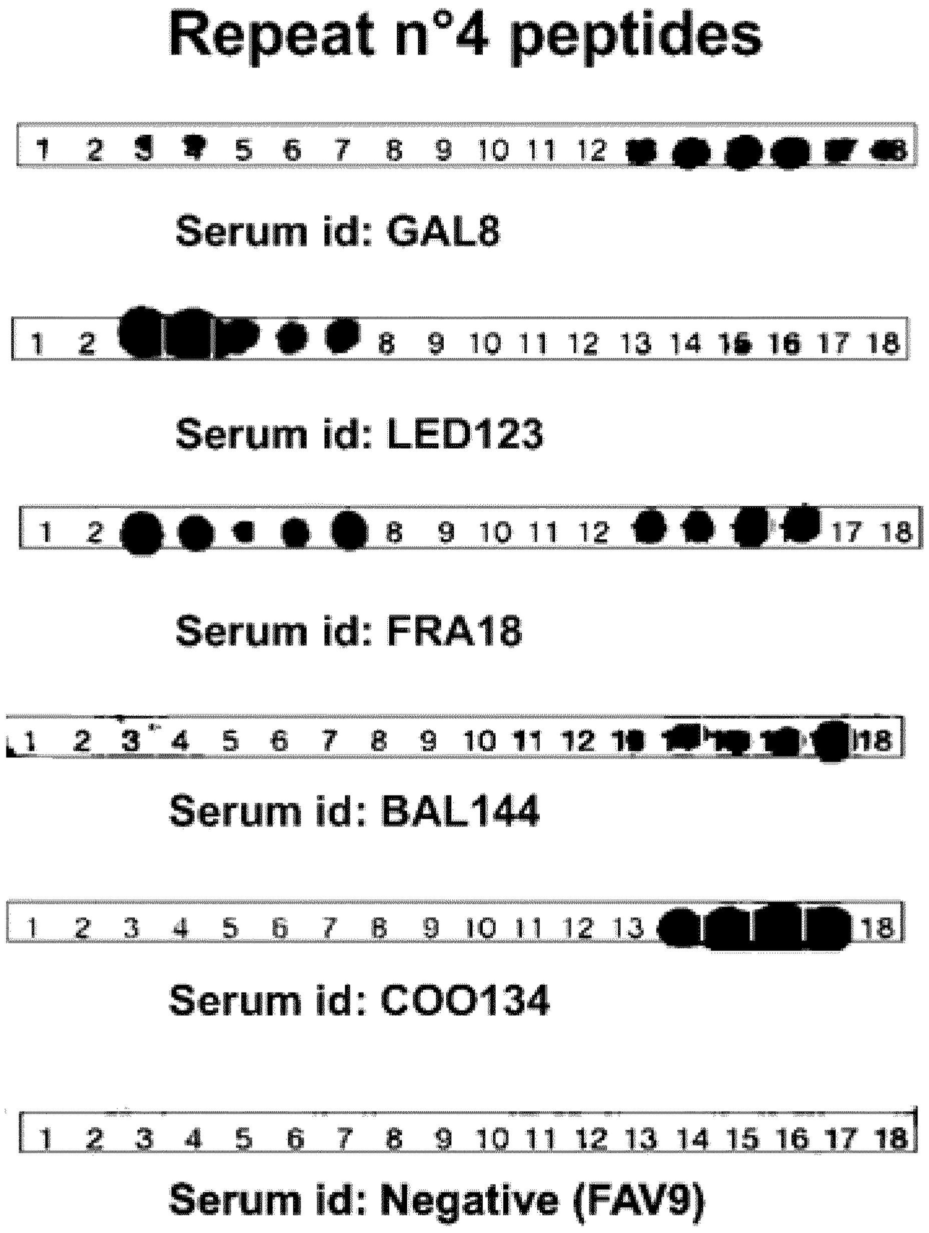
Figure 12C:
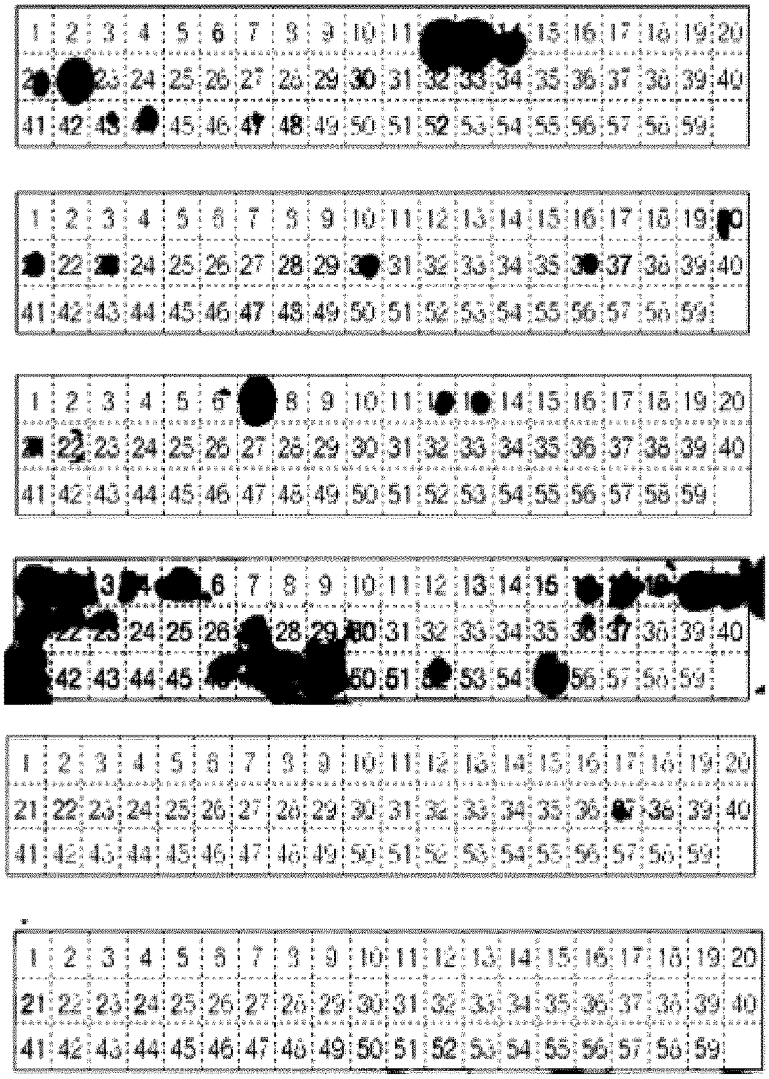
Figure 13:
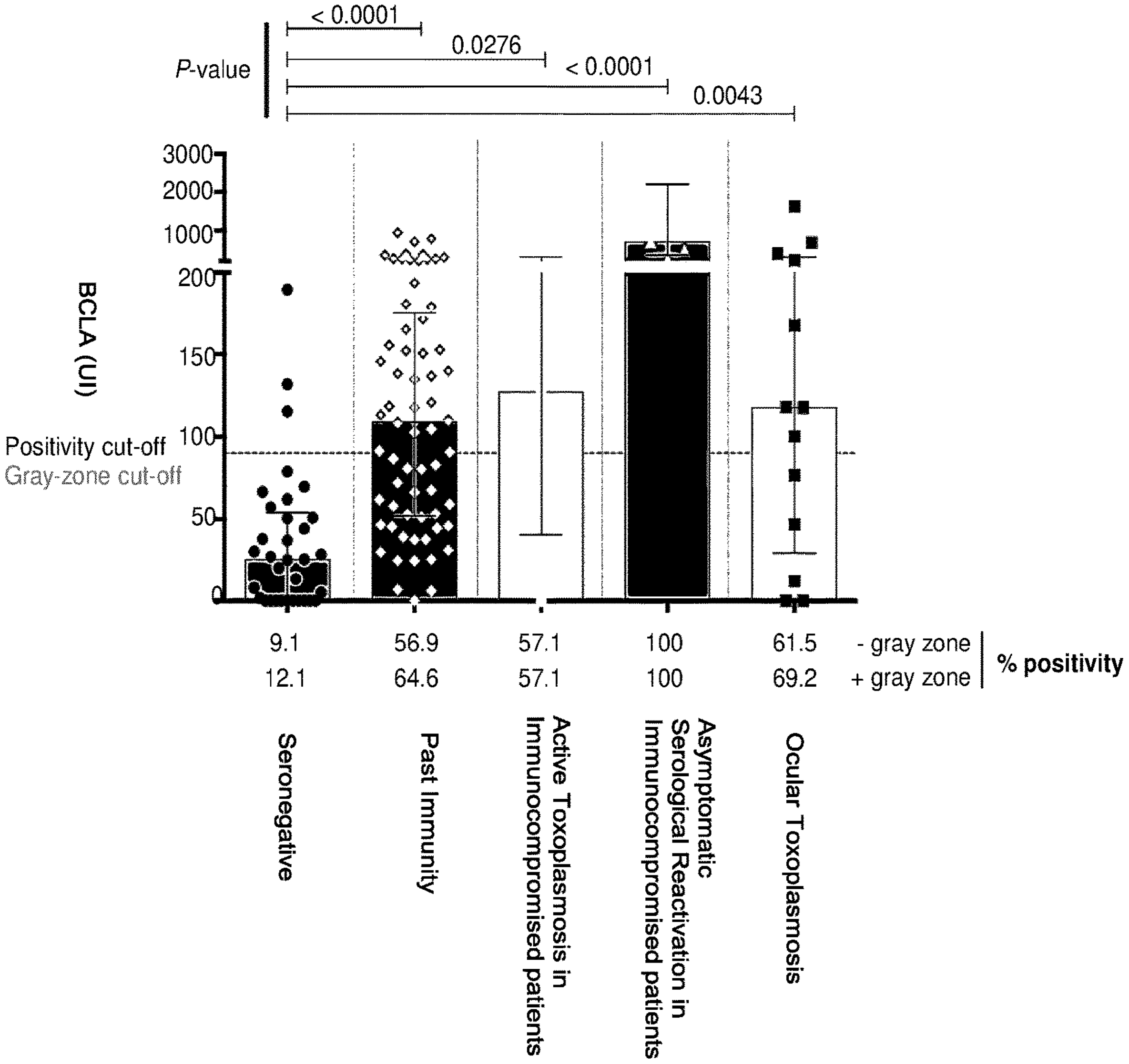

The first ELISA test was optimized for the detection of BCLA immunogenic peptides. First, peptide microarrays designed using both the BCLA C-terminal domain, and the most conserved internal peptide repeat sequences TgR4 (FIG. 12*a*) were screened for high resolution BCLA epitope mapping (FIG. 12*b* and FIG. 12*c*) using peptide dot blot screening. In contrast to mice, all positive human sera showed a robust reactivity to peptides derived from the internal repeat that significantly increased the test sensitivity, once added to rBCLA. Therefore, the BCLA ELISA was customized based on the most sensitive peptide and polypeptide combination, and was proved optimal for a high confidence discrimination between humans diagnosed with either an ocular toxoplasmosis or a confirmed past-immunity (FIG. 13). The ELISA test also detected significant amounts of circulating anti-BCLA antibodies in sera from immunocompromised patients undergoing either «asymptomatic» or symptomatic chronic toxoplasmosis episodes (FIG. 13).

Isolated Peptides

The invention relates to an isolated *Toxoplasma gondii* polypeptide referred as BCLA (Brain Cyst Load-associated Antigen) which comprises the amino acids SEQ ID NO:1.

The invention also provides an isolated *Toxoplasma gondii* polypeptide selected from the group consisting of:

(i) the amino acids sequence consisting of *Toxoplasma gondii* polypeptide BCLA (SEQ ID N 0:1);

(ii) the amino acids sequence consisting of C-terminal antigenic domain (res 1089-1275 of BCLA referred as rBCLA) (SEQ ID NO:2);

(iii) the amino acids sequence consisting of internal repeated domain of BCLA selected from the group consisting of: TgR1 (SEQ ID NO:4), TgR2 (SEQ ID NO: 5), TgR3 (SEQ ID NO:6), TgR4 (SEQ ID NO:7), TgR5 (SEQ ID NO:8), TgR6 (SEQ ID NO:9), TgR7 (SEQ ID NO: 10), TgR8 (SEQ ID NO:11), TgR9 (SEQ ID NO:12), tgR10 (SEQ ID NO:13), TgR11 (SEQ ID NO:14), TgR12 (SEQ ID NO:15) and TgR13 (SEQ ID NO: 16);

(iv) an amino acid sequence substantially homologous to the sequence of (i), to (iii) preferably an amino acid sequence at least 80% identical to the sequence of (i) to (iii);

(v) a fragment of at least 9 consecutive amino acids of the sequence of (i), to (iv).

Using peptide dot blot screening (see FIG. 12) allows to identify the most potent of BCLA immunogenic peptides in the C-terminal antigenic domain of BCLA (res 1089-1275 of BCLA referred as rBCLA) as well as in the internal repeated domain of BCLA (res 304-924) of BCLA referred as TgR1 to TgR13 (SEQ ID NO: 4 to SEQ ID NO: 16)

Accordingly, in a particular embodiment, the isolated *Toxoplasma gondii* polypeptide from rBCLA polypeptide is selected from the group consisting of:

```
(i)
                                   (SEQ ID No 32)
GELQPAEAEEARLLVADLKAV

(ii)
                                   (SEQ ID No 33)
VRVEGEAFFRASVDLYEA

(iii)
                                   (SEQ ID No 34)
KLRPLTKGELVDVVRQ

(iv)
                                   (SEQ ID No 35)
TQIFVQDRASAFLRV (peptide 36 of rBCLA)

(v)
                                   (SEQ ID No 36)
AAEQMKAVFAMVEEG (peptide 44 of rBCLA)
```

(vi) an amino acid sequence substantially homologous to the sequence of (i) to (v), preferably an amino acid sequence at least 95% identical to the sequence of (i) to (v)

(vii) a fragment of at least 9 consecutive amino acids of the sequence of (i), to (vi).

In a more particular embodiment, the isolated *Toxoplasma gondii* polypeptide from rBCLA polypeptide is selected from the group consisting of selected from the group:

```
(i)
                                   (SEQ ID No 37)
GELQPAEAEEARLLV (peptide 12 of rBCLA);

(ii)
                                   (SEQ ID No 38)
QPAEAEEARLLVADL (peptide 13 of rBCLA),

(iii)
                                   (SEQ ID No 39)
EAEEARLLVADLKAV (peptide 14 of rBCLA),

(iv)
                                   (SEQ ID No 40)
VRVEGEAFFRASVDL (peptide 21 of rBCLA),

(v)
                                   (SEQ ID No 41)
EGEAFFRASVDLYEA (peptide 22 of rBCLA);

(vi)
                                   (SEQ ID No 42)
AFFRASVDLYEAVKN (peptide 23 of rBCLA),

(vii)
                                   (SEQ ID No 43)
KLRPLTKGELVDVVR (peptide 30 of rBCLA)
```

(viii) an amino acid sequence substantially homologous to the sequence of (i) to (vii), preferably an amino acid sequence at least 95% identical to the sequence of (i) to (vii)

(vii) a fragment of at least 9 consecutive amino acids of the sequence of (i), to (viii).

Accordingly, in a particular embodiment, the isolated *Toxoplasma gondii* polypeptide from internal repeated domain of BCLA is selected from the group consisting of:

(i) the amino acids sequence consisting of internal repeated domain of TgR4, MERPAAGSMEKEKPVLPGEGEGHVLPKHETKPALTDEKRTKPGGPRTE (SEQ ID NO: 7)

(ii) an amino acid sequence substantially homologous to the sequence of (i), preferably an amino acid sequence at least 80% identical to the sequence of (i)

(iii) a fragment of at least 9 consecutive amino acids of the sequence of (i), to (ii).

In a more particular embodiment, the isolated *Toxoplasma gondii* polypeptide from internal repeated domain of BCLA is selected from the group consisting of:

```
(i)
                                   (SEQ ID No 44)
AAGSMEKEKPVLPGEGEGH (domain A of TgR4);

(ii)
                                   (SEQ ID No 45)
VLPKHETKPALTDEKRTKPGGP (domain B of TgR4),
```

(iii) an amino acid sequence substantially homologous to the sequence of (i) to (ii), preferably an amino acid sequence at least 95% identical to the sequence of (i) to (ii)

(iv) a fragment of at least 9 consecutive amino acids of the sequence of (i), to (iii).

In a more particular embodiment, the isolated *Toxoplasma gondii* polypeptide from internal repeated domain of BCLA is selected from the group consisting of:

```
(i)
                                    (SEQ ID No 46)
AAGSMEKEKPVLPGE (peptide 3 of TgR4);

(ii)
                                    (SEQ ID No 47)
GSMEKEKPVLPGEGE (peptide 4 of TgR4)

(iii)
                                    (SEQ ID No 48)
MEKEKPVLPGEGEGH (peptide 5 of TgR4)

(iv)
                                    (SEQ ID No 49)
KEKPVLPGEGEGHVL (peptide 6 of TgR4)

(v)
                                    (SEQ ID No 50)
KPVLPGEGEGHVLPG (peptide 7 of TgR4)

(vi)
                                    (SEQ ID No 51)
HVLPKHETKPALTDEK (peptide 13 of TgR4),

(vii)
                                    (SEQ ID No 52)
PKHETKPALTDEKRT (peptide 14 of TgR4),

(viii)
                                    (SEQ ID No 53)
HETKPALTDEKRTKP (peptide 15 of TgR4)

(ix)
                                    (SEQ ID No 54)
TKPALTDEKRTKPGG (peptide 16 of TgR4)
```

(x) an amino acid sequence substantially homologous to the sequence of (i) to (ix), preferably an amino acid sequence at least 95% identical to the sequence of (i) to (ix)

(xi) a fragment of at least 9 consecutive amino acids of the sequence of (i), to (x).

As BCLA polypeptide has a multitude of epitopes throughout the different domain (especially in rBCLA as well as in the internal repeated domain of BCLA TgR1 to TgR13) it may advantageous to combine the BCLA immunogenic peptides fragments of the invention.

Accordingly, in another embodiment, the isolated polypeptide of the present invention is a fusion between two peptides fragments according to the invention.

Regarding the improved ELISA assay, the following BCLA peptides (with a least a fusion peptide which combines 2 internal repeat peptide) were used in combination with full length recombinant BCLA polypeptide (SEQ ID N°1) are used. Peptide AB_F: MERPAAGSMEKEKPVLPGEGEGLPKHETKPALTDEKRTKPGGP (fusion of peptide fragments from a repeat motif present in Tgr4/Trg12/Tgr13 and a repeat motif present in Tgr3/Trg4/Tgr5/Tgr6/Tgr9) (SEQ ID N°55)

Peptide A3_B: AAGSMEKDKLVLPGE (peptide fragments from a repeat motif present in Tgr3/Tgr5/Tgr6/Tgr7/Trg10/Tgr11) (SEQ ID N°56)

Accordingly, the isolated *Toxoplasma gondii* polypeptide from internal repeated domain of BCLA is selected from the group consisting of:

(i) MERPAAGSMEKEKPVLPGEGEGLPKHETKPALTDEKRTKPGGP (fusion of peptide fragments from a repeat motif present in Tgr4/Trg12/Tgr13 and a repeat motif present in Tgr3/Trg4/Tgr5/Tgr6/Tgr9) (SEQ ID N°55), (ii) AAGSMEKDKLVLPGE (peptide fragments from a repeat motif present in Tgr3/Tgr5/Tgr6/Tgr7/Trg10/Tgr11) (SEQ ID N°56)

(iii) an amino acid sequence substantially homologous to the sequence of (i) to (ii), preferably an amino acid sequence at least 95% identical to the sequence of (i) to (ii)

(iv) fragment of at least 9 consecutive amino acids of the sequence of (i), to (iii).

As BCLA polypeptide has a multitude of epitopes throughout the different internal repeated domain of BCLA (TgR1 to TgR13) it may advantageous to combine amino acid residues of the internal repeated domain of BCLA.

Accordingly, the invention also related to a BCLA polypeptide, comprising the internal repeated domain of BCLA (TgRx) having the following sequence:

M-Xaa1-Xaa2-Xaa3-Xaa4-Xaa5-Xaa6-Xaa7-M-E-Xaa8-Xaa9-K-Xaa10-V-Xaa11-P-G-E-G-Xaa12-Xaa13-H-Xaa14-Xaa15-P—K-Xaa16-E-Xaa17-Xaa18-L-T-Xaa19-Xaa20-Xaa21-Xaa22-T-Xaa23-P-Xaa24-Xaa25-P-Xaa26-Xaa27-Xaa28 (SEQ ID N°64)

Wherein Xaa1 is) Glutamic acid (E) or no amino acid residues

Wherein Xaa2 is Arginine (R) or Serine(S)

Wherein Xaa3 is Proline (P) or Glycine (G)

Wherein Xaa4 is Alanine (A) or Glycine (G)

Wherein Xaa5 is Alanine (A) or no amino acid residues

Wherein Xaa6 is Glycine (G) or Arginine (R)

Wherein Xaa7 is Serine(S), Proline (P) or Alanine (A)

Wherein Xaa8 is Lysine (K) or Glutamic acid (E)

Wherein Xaa9 is Lysine (K), Glutamic acid (E) or Aspartic acid (D)

Wherein Xaa10 is Proline (P) or Leucine (L)

Wherein Xaa11 is Leucine (L) or Serine(S)

Wherein Xaa12 is Glutamic acid (E) or Lysine (K)

Wherein Xaa13 is Glycine (G) or Arginine (R)

Wherein Xaa14 is Valine (V) or Alanine (A)

Wherein Xaa15 is Leucine (L) or Serine(S)

Wherein Xaa16 is Histidine (H), Aspartic acid (D) or Alanine (A)

Wherein Xaa17 is Threonine (T), Arginine (R), Methionine (M) or Glutamine (Q)

Wherein Xaa18 is Proline (P), Threonine (T) or Alanine (A)

Wherein Xaa19 is Aspartic acid (D), Glutamic acid (E) or Glutamine (Q)

Wherein Xaa20 is Glutamic acid (E) or Lysine (K)

Wherein Xaa21 is Lysine (K), Glycine (G) or Glutamic acid (E)

Wherein Xaa22 is Arginine (R) or Valine (V)

Wherein Xaa23 is Lysine (K), Glutamic acid (E) or Asparagine (N)

Wherein Xaa24 is Glycine (G), Valine or Isoleucine (I)

Wherein Xaa25 is Glycine (G) or Glutamic acid (E)

Wherein Xaa26 is Arginine (R) or Proline (P)

Wherein Xaa27 is Threonine (T) Cystein (C) Lysine (K) or Methionine (M)

Wherein Xaa28 is Glutamic acid (E) or Alanine (A) and a fragment of at least 9 consecutive amino acids of the sequence SEQ ID N°64.

As used herein, the term "amino acid" refers to natural or unnatural amino acids in their D and L stereoisomers for chiral amino acids. It is understood to refer to both amino acids and the corresponding amino acid residues, such as are present, for example, in peptidyl structure. Natural and unnatural amino acids are well known in the art. Common natural amino acids include, without limitation, alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), Lysine (Lys), methionine (Met), phenylalanine (Phe), proline (Pro), serine (Ser), threonine (Thr), tryptophan (Trp), tyrosine (Tyr), and valine (Val). Uncommon and unnatural amino acids include, without limitation, allyl glycine (AllylGly), norleucine, norvaline, biphenylalanine (Bip), citrulline (Cit), 4-guanidinophenylalanine (Phe (Gu)), homoarginine (hArg), homolysine (hLys), 2-naphtylalanine (2-Nal), ornithine (Orn) and pentafluorophenylalanine.

Amino acids are typically classified in one or more categories, including polar, hydrophobic, acidic, basic and aromatic, according to their side chains. Examples of polar amino acids include those having side chain functional groups such as hydroxyl, sulfhydryl, and amide, as well as the acidic and basic amino acids. Polar amino acids include, without limitation, asparagine, cysteine, glutamine, histidine, selenocysteine, serine, threonine, tryptophan and tyrosine. Examples of hydrophobic or non-polar amino acids include those residues having nonpolar aliphatic side chains, such as, without limitation, leucine, isoleucine, valine, glycine, alanine, proline, methionine and phenylalanine. Examples of basic amino acid residues include those having a basic side chain, such as an amino or guanidino group. Basic amino acid residues include, without limitation, arginine, homolysine and lysine. Examples of acidic amino acid residues include those having an acidic side chain functional group, such as a carboxy group. Acidic amino acid residues include, without limitation aspartic acid and glutamic acid. Aromatic amino acids include those having an aromatic side chain group. Examples of aromatic amino acids include, without limitation, biphenylalanine, histidine, 2-napthylalananine, pentafluorophenylalanine, phenylalanine, tryptophan and tyrosine. It is noted that some amino acids are classified in more than one group, for example, histidine, tryptophan and tyrosine are classified as both polar and aromatic amino acids. Amino acids may further be classified as non-charged, or charged (positively or negatively) amino acids. Examples of positively charged amino acids include without limitation lysine, arginine and histidine. Examples of negatively charged amino acids include without limitation glutamic acid and aspartic acid. Additional amino acids that are classified in each of the above groups are known to those of ordinary skill in the art.

A peptide "substantially homologous" to a reference peptide may derive from the reference sequence by one or more conservative substitutions. Two amino acid sequences are "substantially homologous" or "substantially similar" when one or more amino acid residue are replaced by a biologically similar residue or when greater than 80% of the amino acids are identical, or greater than about 90%, preferably greater than about 95%, are similar (functionally identical). Preferably, the similar, identical or homologous sequences are identified by alignment using, for example, the GCG (Genetics Computer Group, Program Manual for the GCG Package, Version 7, Madison, Wisconsin) pileup program, or any of the programs known in the art (BLAST, CLUSTAL, FASTA, etc.). The percentage of identity may be calculated by performing a pairwise global alignment based on the Needleman-Wunsch alignment algorithm to find the optimum alignment (including gaps) of two sequences along their entire length, for instance using Needle, and using the BLOSUM62 matrix with a gap opening penalty of 10 and a gap extension penalty of 0.5.

The term "conservative substitution" as used herein denotes the replacement of an amino acid residue by another, without altering the overall conformation and function of the peptide, including, but not limited to, replacement of an amino acid with one having similar properties (such as, for example, polarity, hydrogen bonding potential, acidic, basic, shape, hydrophobic, aromatic, and the like). Amino acids with similar properties are well known in the art. For example, arginine, histidine and lysine are hydrophilic-basic amino acids and may be interchangeable. Similarly, isoleucine, a hydrophobic amino acid, may be replaced with leucine, methionine or valine. Neutral hydrophilic amino acids, which can be substituted for one another, include asparagine, glutamine, serine and threonine.

By "substituted" or "modified" the present invention includes those amino acids that have been altered or modified from naturally occurring amino acids.

As such, it should be understood that in the context of the present invention, a conservative substitution is recognized in the art as a substitution of one amino acid for another amino acid that has similar properties.

According to the invention a first amino acid sequence having at least 80% of identity with a second amino acid sequence means that the first sequence has 80; 81; 82; 83; 84; 85; 86; 87; 88; 89; 90; 91; 92; 93; 94; 95; 96; 97; 98; or 99% of identity with the second amino acid sequence. Amino acid sequence identity is preferably determined using a suitable sequence alignment algorithm and default parameters, such as BLAST P (Karlin and Altschul, 1990).

In some embodiments, the isolated peptide of the invention comprises at most 1275 amino acids (and at least 9). In some embodiments, the polypeptide of the invention comprises 1275, 1270, 1265, 1260,1255,1250, 1245, 1240, 1235, 1230, 1225, 1220, 1215, 1210; 1205, 1200, 1199, 1198, 1197, 1196, 1195, 1194, 1193, 1192, 1191, 1190, 1189, 1188, 1187, 1186, 1185, 1184, 1183, 1182, 1181, 1180, 1179, 1175, 1174, 1173, 1172, 1171, 1170, 1169, 1168, 1167, 1166, 1165, 1164, 1163, 1162, 1161, 1160, 1159, 1158, 1157, 1156, 1155, 1154, 1153, 1152, 1151, 1150, 1149, 1148, 1147, 1146, 1145, 1144, 1143, 1142, 1141, 1140, 1139, 1138, 1137, 1136, 1135, 1134, 1133, 1132, 1131, 1130, 1129, 1128, 1127, 1126, 1125, 1124, 1123, 1122, 1121, 1120, 1119, 1118, 1117, 1116, 1115, 1114, 1113, 1112, 1111, 1110, 1109, 1108, 1107, 1106, 1105, 1104, 1103, 1102, 1101, 1100, 1099, 1098, 1097, 1096, 1095, 1094, 1093, 1092, 1091, 1090, 1089, 1088, 1087, 1086, 1085, 1084, 1083, 1082, 1081, 1080, 1079, 1078, 1077, 1076, 1075, 1074, 1073, 1072, 1071, 1070, 1069, 1068, 1067, 1066, 1065, 1064, 1063, 10162, 1061, 1060, 1059, 1058, 1057, 1056, 1055, 1054, 1053, 1052, 1051, 1050, 1049, 1048, 1047, 1046, 1045, 1044, 1043, 1042, 1041, 1040, 1039, 1038, 1037, 1036, 1035, 1034, 1033, 1032, 1031, 1030, 1029, 1028, 1027, 1026, 1025, 1024, 1023, 1022, 1021, 1020, 1019, 1018, 1017, 1016, 1115, 1014, 1013, 1012, 1011, 1010, 1009, 1008, 1007, 1006, 1005, 1004, 1003, 1002, 1001, 1000, 999, ( . . . ),800, 799, 798, 797, 796, 795, 794, 793, 792, 791, 790, 789, 788, 787, 786, 785, 784, 783, 782, 781, 780, 779, 778, 777, 766, 765, 764, 763, 762, 761, 760, 759, 758, 757, 756, 755, 754, 753, 752, 751, 750, 749, 748, 747, 746, 745, 744, 743, 742, 741, 740, 739, 738, 737, 736, 735, 734, 733, 732, 731, 730, 729, 728, 727, 726, 725, 724, 723, 722, 721, 720, 719, 718, 717, 716, 715, 714, 713, 712, 711, 710, 709, 708, 707, 706, 705, 704, 703, 702, 701, 700, 699, 698, 697, 696, 695, 694, 693, 692, 691, 690, 689, 688, 687, 686, 685, 684, 683, 682, 681, 680, 679, 678, 677, 676, 675, 674, 673, 672, 671, 670, 669, 668, 667, 666, 665, 664, 663, 662, 661, 660, 659, 658, 657, 656, 655, 654, 653, 652, 651, 650, 649, 648, 647, 646, 645, 644, 643, 642, 641, 640, 639, 638, 637, 636, 635, 634, 633, 632, 631, 630, 629, 628, 627, 626, 625, 624, 623, 622, 621, 620, 619, 618, 617, 616, 615, 614, 613, 612, 611, 610, 609, 608, 607, 606, 605, 604, 603, 602, 601, 600, 599, 598, 597, 596, 595, 594, 593, 592, 591, 590, 589, 588, 587, 586, 585, 584, 583, 582, 581, 580, 579, 578, 577, 576, 575, 574, 573, 572, 571, 570, 569, 568, 567, 566, 565, 564, 563, 562, 561, 560,559 558, 557, 556, 555, 554, 553, 552, 551, 550, 549, 548, 547, 546, 545, 544, 543, 542, 541, 540, 539, 538, 537, 536, 535, 534, 533, 532, 531, 530, 529, 528, 527, 526, 525, 524, 523, 522, 521, 520, 519, 518, 517, 516, 515, 514, 513, 512, 511, 510, 509, 508, 507, 506, 505, 504, 503, 502, 501, 500, 499, 498,497, 496, 495, 494, 493, 492, 491, 490, 489, 488, 487, 486, 485, 484, 483, 482, 481, 480, 479, 478, 477, 476, 475, 474, 473, 472, 471, 470, 469, 468, 467, 466, 465, 464, 463, 462, 461, 460, 459, 458, 457, 456, 455, 454, 453, 452, 451, 450, 449, 448, 447, 446, 445, 444, 443; 442, 441, 440, 439, 438, 437, 436, 435, 434, 433, 432, 431, 430, 429, 428, 427, 426, 425, 424, 423, 422, 421, 420, 419, 418, 417, 416, 415, 414, 413, 412, 411, 410, 409, 408, 407, 406, 405, 404, 403, 402, 401, 400, 399, 398, 397, 396, 395, 394, 393, 392, 391, 390, 389, 388, 387, 386, 385, 384, 383, 382, 381, 380, 379, 378, 377, 376, 375, 374, 373, 372, 371, 370, 369, 368, 367, 366, 365, 364, 363, 362, 361, 360, 359, 358, 357, 356, 355, 354, 353, 352, 351, 350, 349, 348, 347, 346, 345, 344, 343, 342, 341, 340, 339, 338, 337, 336, 335, 334, 333, 332, 331, 330, 329, 328, 327, 326, 325, 324, 323, 322, 321, 320, 319, 318, 317, 316, 315, 314, 313, 312, 311, 310, 309, 308, 307, 306, 305, 304, 303, 302, 301, 300, 299, 298, 297, 296, 295, 294, 293, 292, 291, 290, 289, 288, 287, 286, 285, 284, 283, 282,281, 280, 279, 278, 277, 276, 275, 274,273 272, 271, 270, 269, 268, 267, 266, 265,264 263, 262, 261, 260, 259, 258, 257, 256, 255, 254, 253,252, 251, 250, 249, 248, 247, 246, 245, 244, 243, 242,241, 240, 239, 238, 237, 236, 235, 234, 233, 232, 231, 230, 229, 228, 227, 226, 225, 224, 223, 222, 221, 220, 219, 218, 217, 216, 215, 214, 213, 212, 211, 210, 209, 208, 207, 206, 205, 204, 203, 202, 201, 200, 199, 198, 197, 196, 195, 194, 193, 192, 191, 190, 189, 188, 187, 186, 185, 184, 183, 182, 181, 180, 179, 178, 177, 176, 175, 174, 173, 172, 171, 170, 169, 168, 167, 166, 165, 164, 163, 162, 161, 160, 159, 158, 157, 156, 155, 154, 153, 152, 151, 150, 149, 148, 147, 146, 145, 144, 143, 142, 141, 140, 139, 138, 137, 136, 135, 134, 133, 132, 131, 130, 129, 128, 127, 126, 125, 124, 123, 122, 121, 120, 119, 118, 117, 116, 115, 114, 113, 112, 111, 110, 109, 108, 107, 106, 105, 104, 103, 102, 101, 100; 99; 98; 97; 96; 95; 94; 93; 92; 91; 90; 89; 88; 87; 86; 85; 84; 83; 82; 81; 80; 79; 78; 77; 76; 75; 74; 73; 72; 71; 70; 69; 68; 67; 66; 65; 64; 63; 62; 61; 60; 59; 58; 57; 56; 55; 54; 53; 52; 51; 50; 49; 48; 47; 46; 45; 44; 43; 42; 41; 40; 39; 38; 37; 36; 35; 34; 33; 32; 31; 30; 29; 28; 27; 26; 25; 24; 23; 22; 21; 20; 19; 18; 17; 16; 15; 14; 13; 12; 11; 10 or 9 amino acids. In some embodiments, the polypeptide of the invention comprises less than 50 amino acids. In some embodiments, the polypeptide of the invention comprises less than 30 amino acids. In some embodiments, the polypeptide of the invention comprises less than 25 amino acids. In some embodiments, the polypeptide of the invention comprises less than 20 amino acids. In some embodiments, the polypeptide of the invention comprises less than 15 amino acids.

The isolated polypeptides according to the invention may be produced using any method known in the art. They may for example be produced as recombinant polypeptides in a host cell (e.g. in a bacterial, yeast or eukaryotic host cell), or chemically synthesized (see for review Kent S. B. H. Chem. Soc. Rev., 2009,38, 338-351 and Bradley L. et al Annu Rev Biophys Biomol Struct. 2005; 34:91-118 or R. B. Merrifield (1969). "Solid-phase peptide synthesis." Advances in enzymology and related areas of molecular biology 32:221-96.; R. B. Merrifield (1969). "The synthesis of biologically active peptides and proteins." JAMA 210 (7): 1247-54. and Raibaut, L., O. El Mahdi and O. Melnyk (2015). "Solid Phase Protein Chemical Synthesis." Topics in current chemistry).

Antibodies according to the invention The inventors have generated specific antibodies directed against the polypeptide of the invention First, to assay the in-situ kinetics of BLCA in *T. gondii*, inventors raised polyclonal antibodies against two synthetic peptides located respectively at the extreme end of the conserved repeat of BCLA protein (see Example 1 and FIG. 2*b*). In house antibodies directed against two peptides (peptides 1 and 2) contained in these repetitions were generated. BCLA expression monitoring by western-blot using the home-made antibodies raised against the two BCLA-derived peptides shows up-regulation of BCLA after FR235222 treatment (see FIG. 2*c*)

Secondly, single domain antibodies (or nanobodies or VHH) were produced by immunizing mice with the synthetic peptides, the C-terminal antigenic domain of BCLA (res 1089-1275) (SEQ ID NO:2). More precisely, the inventors have found that antibodies screened for their capacity to recognize specifically the isolated polypeptide of the invention and to stain cell lines samples infected with *Toxoplasma gondii* as well as brain samples from Toxoplasmosis patients (detection of tissue cyst) and from mouse model of Toxoplasmosis. Screening step of the antibodies of the invention has shown that these antibodies are specific of isolated polypeptide of the invention especially with antigenic domain of BCLA.

The invention provides an antibody that specifically binds to an isolated polypeptide of the invention.

According to the present invention, "antibody" or "immunoglobulin" have the same meaning, and will be used equally in the present invention. The term "antibody" as used herein refers to immunoglobulin molecules and immunologically active portions of immunoglobulin molecules, i.e., molecules that contain an antigen binding site that immunospecifically binds an antigen. As such, the term antibody encompasses not only whole antibody molecules, but also antibody fragments as well as variants (including derivatives) of antibodies and antibody fragments. In natural antibodies, two heavy chains are linked to each other by disulfide bonds and each heavy chain is linked to a light chain by a disulfide bond. There are two types of light chain, lambda (l) and kappa (k). There are five main heavy chain classes (or isotypes) which determine the functional activity of an antibody molecule: IgM, IgD, IgG, IgA and IgE. Each chain contains distinct sequence domains. The light chain includes two domains, a variable domain (VL) and a constant domain (CL). The heavy chain includes four domains, a variable domain (VH) and three constant domains (CH1, CH2 and CH3, collectively referred to as CH). The variable regions of both light (VL) and heavy (VH) chains determine binding recognition and specificity to the antigen. The constant region domains of the light (CL) and heavy (CH) chains confer important biological properties such as antibody chain association, secretion, trans-placental mobility, complement binding, and binding to Fc receptors (FcR). The Fv fragment is the N-terminal part of the Fab fragment of an immunoglobulin and consists of the variable portions of one light chain and one heavy chain. The specificity of the antibody resides in the structural complementarity between the antibody combining site and the antigenic determinant. Antibody combining sites are made up of residues that are primarily from the hypervariable or complementarity determining regions (CDRs). Occasionally, residues from non-hypervariable or framework regions (FR) influence the overall domain structure and hence the combining site. Complementarity Determining Regions or CDRs refer to amino acid sequences which together define the binding affinity and specificity of the natural Fv region of a native immunoglobulin binding site. The light and heavy chains of an immunoglobulin each have three CDRs, designated VL-CDR1, VL-CDR2, VL-CDR3 and VH-CDR1, VH-CDR2, VH-CDR3, respectively. An antigen-binding site, therefore, includes six CDRs, comprising the CDR set from each of a heavy and a light chain V region. Framework Regions (FRs) refer to amino acid sequences interposed between CDRs.

Antibody binding to isolated polypeptide of the invention can be assayed by conventional methods known in the art. The mature form of polypeptide of the invention is preferably used for assaying antibody binding to epitope of polypeptide of the invention. Alternatively, any variant form of isolated polypeptide of the invention that retains binding of nanobodies XX can be used. Many different competitive binding assay format(s) can be used for determining epitope binding. The immunoassays which can be used include, but are not limited to, competitive assay systems using techniques such as radioimmunoassays, ELISA, "sandwich" immunoassays, immunoprecipitation assays, fluorescent immunoassays, protein A immunoassays, and complement-fixation assays. Such assays are routine and well known in the art (see, e.g., Ausubel et al., eds, 1994 Current Protocols in Molecular Biology, Vol. 1, John Wiley & sons, Inc., New York). For example, the BIACORE® (GE Healthcare, Piscataway, NJ) is one of a variety of surface plasmon resonance assay formats that are routinely used to epitope bin panels of monoclonal antibodies. Additionally, routine cross-blocking assays such as those described in Antibodies, A Laboratory Manual, Cold Spring Harbor Laboratory, Ed Harlow and David Lane, 1988, can be performed. An example of a suitable ELISA assay is also described in the Example below.

As used herein, the term "Affinity" refers to the strength of interaction between antibody and antigen at single antigenic sites. Within each antigenic site, the variable region of the antibody "arm" interacts through weak non-covalent forces with the antigen at numerous sites; the more interactions, the stronger the affinity. Affinity can be determined by measuring $K_D$. The term "$K_D$", as used herein, is intended to refer to the dissociation constant, which is obtained from the ratio of Ka to Ka (i.e. Ka/Ka) and is expressed as a molar concentration (M). $K_D$ values for antibodies can be determined using methods well established in the art. A method for determining the $K_D$ of an antibody is by using surface plasmon resonance, or using a biosensor system such as a Biacore® system.

The invention provides an antibody that specifically binds to an isolated polypeptide comprising or consisting of:

(i) the amino acids sequence consisting of *Toxoplasma gondii* polypeptide BCLA (SEQ ID N 0:1);

(ii) the amino acids sequence consisting of C-terminal antigenic domain (res 1089-1275 of BCLA) (SEQ ID NO:2);

(iii) the amino acids sequence consisting of internal repeated domain of BCLA selected from the group consisting of: TgR1 (SEQ ID NO:4), TgR2 (SEQ ID NO: 5), TgR3 (SEQ ID NO:6), TgR4 (SEQ ID NO:7), TgR5 (SEQ ID NO:8), TgR6 (SEQ ID NO:9), TgR7 (SEQ ID NO: 10), TgR8 (SEQ ID NO:11), TgR9 (SEQ ID NO:12), tgR10 (SEQ ID NO:13), TgR11 (SEQ ID NO:14), TgR12 (SEQ ID NO:15) and TgR13 (SEQ ID NO: 16);

(iv) an amino acid sequence substantially homologous to the sequence of (i), to (iii) preferably an amino acid sequence at least 80% identical to the sequence of (i) to (iii)

(v) a fragment of at least 9 consecutive amino acids of the sequence of (i), to (iv).

These antibodies can recognize an epitope located within, or comprising at least one amino acid located within, the fragment of at least 9 consecutive amino acids of any one of isolated polypeptide (i) to (v).

Preferably, said epitope is located within the fragment comprising or consisting of any one of isolated polypeptide (i) to (v).

Most preferably said epitope is located within the C-terminal antigenic domain of BCLA (SEQ ID NO:2) and within the internal repeat domain of BCLA (res 304-924) of BCLA referred as TgR1 to TgR13 (SEQ ID NO: 4 to SEQ ID NO: 16). Such antibodies are characterized in that they specifically bind to *Toxoplasma gondii* BCLA polypeptide of the invention.

In a particular embodiment, the antibody that specifically binds rBCLA polypeptide, specifically binds the amino acids sequence selected from the group consisting of:

```
(i)
                                    (SEQ ID No 32)
GELQPAEAEEARLLVADLKAV

(ii)
                                    (SEQ ID No 33)
VRVEGEAFFRASVDLYEA

(iii)
                                    (SEQ ID No 34)
KLRPLTKGELVDVVRQ

(iv)
                                    (SEQ ID No 35)
TQIFVQDRASAFLRV (peptide 36 of rBCLA)

(v)
                                    (SEQ ID No 36)
AAEQMKAVFAMVEEG (peptide 44 of rBCLA)
```

(vi) an amino acid sequence substantially homologous to the sequence of (i) to (v), preferably an amino acid sequence at least 95% identical to the sequence of (i) to (v)

(vii) a fragment of at least 9 consecutive amino acids of the sequence of (i), to (vi). In a more particular embodiment, the antibody that specifically binds rBCLA polypeptide specifically binds the amino acids sequence selected from the group consisting of:

```
(i)
                                        (SEQ ID No 37)
GELQPAEAEEARLLV (peptide 12 of rBCLA);

(ii)
                                        (SEQ ID No 38)
QPAEAEEARLLVADL (peptide 13 of rBCLA),

(iii)
                                        (SEQ ID No 39)
EAEEARLLVADLKAV (peptide 14 of rBCLA),

(iv)
                                        (SEQ ID No 40)
VRVEGEAFFRASVDL (peptide 21 of rBCLA),

(v)
                                        (SEQ ID No 41)
EGEAFFRASVDLYEA (peptide 22 of rBCLA);

(vi)
                                        (SEQ ID No 42)
AFFRASVDLYEAVKN (peptide 23 of rBCLA),

(vii)
                                        (SEQ ID No 43)
KLRPLTKGELVDVVR (peptide 30 of rBCLA)
```

(viii) an amino acid sequence substantially homologous to the sequence of (i) to (vii), preferably an amino acid sequence at least 95% identical to the sequence of (i) to (vii)

(vii) a fragment of at least 9 consecutive amino acids of the sequence of (i), to (viii).

The invention further provides an antibody that specifically binds the amino acids sequence consisting of the internal repeat domain of BCLA (res 304-924) of BCLA referred as TgR1 to TgR13 (SEQ ID NO: 4 to SEQ ID NO: 16)

Accordingly, in a particular embodiment, the antibody that specifically binds the internal repeat domain of BCLA binds the amino acids sequence selected from the group consisting of:

(i) the amino acids sequence consisting of internal repeated domain of TgR4, MERPAAGSMEKEKPVLPGEGEGHVLPKHETKPALTDEKRTKPGGPRTE (SEQ ID NO: 7)

(ii) an amino acid sequence substantially homologous to the sequence of (i), preferably an amino acid sequence at least 80% identical to the sequence of (i)

(iii) a fragment of at least 9 consecutive amino acids of the sequence of (i), to (ii).

In a more particular embodiment, the antibody that specifically binds the internal repeat domain of BCLA TgR4 binds the amino acids sequence selected from the group consisting of:

```
(i)
                                        (SEQ ID No 44)
AAGSMEKEKPVLPGEGEGH (domain A of TgR4);

(ii)
                                        (SEQ ID No 45)
VLPKHETKPALTDEKRTKPGGP (domain B of TgR4),
```

In a more particular embodiment, the antibody that specifically binds the internal repeat domain of BCLA TgR4 binds the amino acids sequence selected from the group consisting of:

```
(i)
                                        (SEQ ID No 46)
AAGSMEKEKPVLPGE (peptide 3 of TgR4);
```

-continued

```
(ii)
                                        (SEQ ID No 47)
GSMEKEKPVLPGEGE (peptide 4 of TgR4)

(iii)
                                        (SEQ ID No 48)
MEKEKPVLPGEGEGH (peptide 5 of TgR4)

(iv)
                                        (SEQ ID No 49)
KEKPVLPGEGEGHVL (peptide 6 of TgR4)

(v)
                                        (SEQ ID No 50)
KPVLPGEGEGHVLPG (peptide 7 of TgR4)

(vi)
                                        (SEQ ID No 51)
HVLPKHETKPALTDEK (peptide 13 of TgR4),

(vii)
                                        (SEQ ID No 52)
PKHETKPALTDEKRT (peptide 14 of TgR4),

(viii)
                                        (SEQ ID No 53)
HETKPALTDEKRTKP (peptide 15 of TgR4)

(ix)
                                        (SEQ ID No 54)
TKPALTDEKRTKPGG (peptide 16 of TgR4)
```

In a particular embodiment, the antibody specifically binds the internal repeat domain of BCLA (TgRx) having the following sequence:

M-Xaa1-Xaa2-Xaa3-Xaa4-Xaa5-Xaa6-Xaa7-M-E-Xaa8-Xaa9-K-Xaa10-V-Xaa11-P-G-E-G-Xaa12-Xaa13-H-Xaa14-Xaa15-P—K-Xaa16-E-Xaa17-Xaa18-L-T-Xaa19-Xaa20-Xaa21-Xaa22-T-Xaa23-P-Xaa24-Xaa25-P-Xaa26-Xaa27-Xaa28 (SEQ ID N°64) Wherein Xaa1 is) Glutamic acid (E) or no amino acid residues Wherein Xaa2 is Arginine (R) or Serine(S)

Wherein Xaa3 is Proline (P) or Glycine (G)

Wherein Xaa4 is Alanine (A) or Glycine (G)

Wherein Xaa5 is Alanine (A) or no amino acid residues

Wherein Xaa6 is Glycine (G) or Arginine (R)

Wherein Xaa7 is Serine(S), Proline (P) or Alanine (A)

Wherein Xaa8 is Lysine (K) or Glutamic acid (E)

Wherein Xaa9 is Lysine (K), Glutamic acid (E) or Aspartic acid (D)

Wherein Xaa10 is Proline (P) or Leucine (L)

Wherein Xaa11 is Leucine (L) or Serine(S)

Wherein Xaa12 is Glutamic acid (E) or Lysine (K)

Wherein Xaa13 is Glycine (G) or Arginine (R)

Wherein Xaa14 is Valine (V) or Alanine (A)

Wherein Xaa15 is Leucine (L) or Serine(S)

Wherein Xaa16 is Histidine (H), Aspartic acid (D) or Alanine (A)

Wherein Xaa17 is Threonine (T), Arginine (R), Methionine (M) or Glutamine (Q)

Wherein Xaa18 is Proline (P), Threonine (T) or Alanine (A)

Wherein Xaa19 is Aspartic acid (D), Glutamic acid (E) or Glutamine (Q)

Wherein Xaa20 is Glutamic acid (E) or Lysine (K)

Wherein Xaa21 is Lysine (K), Glycine (G) or Glutamic acid (E)

Wherein Xaa22 is Arginine (R) or Valine (V)

Wherein Xaa23 is Lysine (K), Glutamic acid (E) or Asparagine (N)

Wherein Xaa24 is Glycine (G), Valine or Isoleucine (I)

Wherein Xaa25 is Glycine (G) or Glutamic acid (E)

Wherein Xaa26 is Arginine (R) or Proline (P)

Wherein Xaa27 is Threonine (T) Cystein (C) Lysine (K) or Methionine (M)

Wherein Xaa28 is Glutamic acid (E) or Alanine (A) and a fragment of at least 9 consecutive amino acids of the sequence SEQ ID N°64.

The invention further provides an antibody that specifically binds the amino acids sequence consisting of any of peptide 1 and peptide 2 (SEQ ID NO 17 to 27) within the internal repeat domain of BCLA referred as TgR1 to TgR13 (SEQ ID NO: 4 to SEQ ID NO: 16).

In a particular embodiment, the peptide 1 and 2 used in the present study are

```
peptide 1:
                                (SEQ ID No 21)
EMERPAAGSMEK

peptide 2:
                                (SEQ ID No 22)
VLPKHETKPALT
```

These antibodies can be polyclonal or monoclonal. When the antibodies are monoclonal, they can for example correspond to chimeric, humanized or fully human antibodies, antibody fragment and single domain antibody.

The term "chimeric antibody" refers to an antibody which comprises a VH domain and a VL domain of an antibody, and a CH domain and a CL domain of a human antibody.

According to the invention, the term "humanized antibody" refers to an antibody having variable region framework and constant regions from a human antibody but retains the CDRs of a previous non-human antibody.

The term "antibody fragment" refers to a fragment of an antibody which contain the variable domains comprising the CDRs of said antibody. The basic antibody fragments include Fab, Fab', F(ab')2 Fv, scFv, dsFv. For example of antibody fragment see also for review, Holliger et al Nature Biotechnology 23, issue 9 1126-1136 (2005), which are includes herein by reference.

The term "Fab" denotes an antibody fragment having a molecular weight of about 50,000 and antigen binding activity, in which about a half of the N-terminal side of H chain and the entire L chain, among fragments obtained by treating IgG with a protease, papaine, are bound together through a disulfide bond.

The term "F(ab')2" refers to an antibody fragment having a molecular weight of about 100,000 and antigen binding activity, which is slightly larger than the Fab bound via a disulfide bond of the hinge region, among fragments obtained by treating IgG with a protease, pepsin.

The term "Fab'" refers to an antibody fragment having a molecular weight of about 50,000 and antigen binding activity, which is obtained by cutting a disulfide bond of the hinge region of the F(ab')2.

A single chain Fv ("scFv") polypeptide is a covalently linked VH::VL heterodimer which is usually expressed from a gene fusion including VH and VL encoding genes linked by a peptide-encoding linker. "dsFv" is a VH::VL heterodimer stabilised by a disulfide bond. Divalent and multivalent antibody fragments can form either spontaneously by association of monovalent scFvs, or can be generated by coupling monovalent scFvs by a peptide linker, such as divalent sc(Fv)2.

The term "diabodies" "tribodies" or "tetrabodies" refers to small antibody fragments with multivalent antigen-binding sites (2, 3 or four), which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites.

As used herein the term "single domain antibody" has its general meaning in the art and refers to the single heavy chain variable domain of antibodies of the type that can be found in Camelid mammals which are naturally devoid of light chains. Such single domain antibody are also called VHH or "nanobody®". For a general description of (single) domain antibodies, reference is also made to the prior art cited above, as well as to EP 0 368 684, Ward et al. (Nature 1989 Oct. 12; 341 (6242): 544-6), Holt et al., Trends Biotechnol., 2003, 21 (11): 484-490; and WO 06/030220, WO 06/003388. The nanobody has a molecular weight approximately one-tenth that of a human IgG molecule, and the protein has a physical diameter of only a few nanometers. One consequence of the small size is the ability of camelid nanobodies to bind to antigenic sites that are functionally invisible to larger antibody proteins, i.e., camelid nanobodies are useful as reagents detect antigens that are otherwise cryptic using classical immunological techniques, and as possible therapeutic agents. Thus yet another consequence of small size is that a nanobody can inhibit as a result of binding to a specific site in a groove or narrow cleft of a target protein, and hence can serve in a capacity that more closely resembles the function of a classical low molecular weight drug than that of a classical antibody. The low molecular weight and compact size further result in nanobodies being extremely thermostable, stable to extreme pH and to proteolytic digestion, and poorly antigenic. Another consequence is that nanobodies readily move from the circulatory system into tissues, and even cross the blood-brain barrier and can treat disorders that affect nervous tissue. Nanobodies can further facilitated drug transport across the blood brain barrier. See U.S. patent application Ser. No. 20/040,161738 published Aug. 19, 2004. These features combined with the low antigenicity to humans indicate great therapeutic potential. The amino acid sequence and structure of a single domain antibody can be considered to be comprised of four framework regions or "FRs" which are referred to in the art and herein as "Framework region 1" or "FR1 "; as "Framework region 2" or "FR2"; as "Framework region 3" or "FR3"; and as "Framework region 4" or "FR4" respectively; which framework regions are interrupted by three complementary determining regions or "CDRs", which are referred to in the art as "Complementarity Determining Region for "CDR1"; as "Complementarity Determining Region 2" or "CDR2" and as "Complementarity Determining Region 3" or "CDR3", respectively. Accordingly, the single domain antibody can be defined as an amino acid sequence with the general structure: FR1-CDR1-FR2-CDR2-FR3-CDR3-FR4 in which FR1 to FR4 refer to framework regions 1 to 4 respectively, and in which CDR1 to CDR3 refer to the complementarity determining regions 1 to 3. In the context of the invention, the amino acid residues of the single domain antibody are numbered according to the general numbering for VH domains given by the International ImMunoGeneTics information system aminoacid numbering (http://imgt.cines.fr/).

5 Several VHH (single domain antibody) were generated after mmunization of the llamas which resulted in a good immune response. The generated libraries were of a good size and insert frequency. Phage display selections on His rBCLA (SEQ ID N°3) has resulted in a number of good clones of which 3 (ERB-1G6, ERB-1B11 and ERB-1A12) show a very good apparent affinity of which ERB-1G6 also shows a high production level in *E. coli.*

Sequences of ERB-1F1, ERB-1F2, ERB 1H4, ERB-1D7, ERB-1G6, ERB-1B11 and ERB-1A12 VHH are described below in Table 1 for the variable heavy chain (VH) of the single domain antibodies

TABLE 1

| Single Domain antibody | Aminoacid Sequence |
|---|---|
| VH ERB-1 G6 | EVQLVESGGGLVQAGGSLGLSCAASGRPGRIFTRNSM<br>AWFRQAPGKEREFVASINWSGTSTSYADSVKGRFAIS<br>RDNDKNTVYLQMNSLKPEDTAVYYCAADSALYGSMHK<br>TPADYEYWGQGTQVTVSS<br>(SEQ ID NO: 57) |
| VH ERB-1 B11 | EVQLVESGGGLVQAGGSLRLTCAASGRTFRRSNMAW<br>FRQPPGKERDFVAAIKWSGSSTNYADSVKGRFTISRDN<br>DKNTVYLQMNVLKPEDTGVYYCAQESSLYSNYLPVVS<br>SAYDYWGQGTQVTVSS<br>(SEQ ID NO: 58) |
| VH ERB-1A12 | EVQLVESGGGLVQAGGSLRLSCAASGRTFSRYFMGW<br>FRQAPGKEREFVAGIIWSGTRTYYVDSVKGRFTISRDN<br>DKRMVYLQMNSLKPEDTAVYYCAAYKEYYGTPAQLYA<br>AASYDYWGQGTQVTVSS<br>(SEQ ID NO: 59) |
| VH ERB-1F1 | EVQLVESGGGLVQAGDSLRLSCAASGRTFSRVTMGW<br>FRQAPGKEREFVAGISWSGTRTDYPDSVKGRFTVSRD<br>NAKKTMWLQMSSLRPEDTAVYHCAADSTLYGSAISNN<br>REAYAYWGQGTQVTVSS<br>(SEQ ID NO: 60) |
| VH ERB-1F2 | EVQLVESGGGLVQVGGSLRLSCAASGRTFRRNTIGWF<br>RQAPGKEREFVAAISWSGTRTKYADPVKGRFTISRDND<br>KNTAYLQMNTLKPDDTAVYYCAADGALYGSDVSGLAR<br>VYDYWGQGTQVTVSS<br>(SEQ ID NO: 61) |
| VH ERB-1H4 | EVQLVESGGGLVQAGGSLRLSCVASGRTFSRYTVGWF<br>RQAPGKEREFVAGISWSGSRTSYADSVKGRFTISRDN<br>DKTTGYLQMNSLKPEDTAVYYCAAITKLYENNIPRSVSD<br>YALWGQGTQVTVSS<br>(SEQ ID NO: 62) |
| VH ERB-1D7 | KVQLVESGGGLVQAGGSLRLSCAASGRTFSRRGMGW<br>FRQAPGKEREFVATIKWSGTSTDYADSVKGRFTISRDN<br>AKNTVYLQMNNLQPEDTAVYYCAADRQLYRDGYVPLN<br>EYEDWGQGTQVTVSS<br>(SEQ ID NO: 63) |

Methods for obtaining such antibodies are well known in the art. For example, monoclonal antibodies according to the invention can be obtained through immunization of a non-human mammal with said fragment comprising or consisting of any one of (i) to (vii). Starting from the polyclonal antibodies, one can then obtain monoclonal antibodies using standard methods.

An antibody of the invention can be conjugated with a detectable label to form an immunoconjugate. Suitable detectable labels include, for example, a radioisotope, a fluorescent label, a chemiluminescent label, an enzyme label, a bioluminescent label or colloidal gold. Methods of making and detecting such detectably-labeled immunoconjugates are well-known to those of ordinary skill in the art, and are described in more detail below.

The detectable label can be a radioisotope that is detected by autoradiography. Isotopes that are particularly useful for the purpose of the present invention are 3H, 1251, 1311, 35S and 14C.

Immunoconjugates can also be labeled with a fluorescent compound. The presence of a fluorescently-labeled antibody is determined by exposing the immunoconjugate to light of the proper wavelength and detecting the resultant fluorescence. Fluorescent labeling compounds include fluorescein isothiocyanate, rhodamine, phycoerytherin, phycocyanin, allophycocyanin, o-phthaldehyde and fluorescamine.

Alternatively, immunoconjugates can be detectably labeled by coupling an antibody to a chemiluminescent compound. The presence of the chemiluminescent-tagged immunoconjugate is determined by detecting the presence of luminescence that arises during the course of a chemical reaction. Examples of chemiluminescent labeling compounds include luminol, isoluminol, an aromatic acridinium ester, an imidazole, an acridinium salt and an oxalate ester.

Similarly, a bioluminescent compound can be used to label immunoconjugates of the present invention. Bioluminescence is a type of chemiluminescence found in biological systems in which a catalytic protein increases the efficiency of the chemiluminescent reaction. The presence of a bioluminescent protein is determined by detecting the presence of luminescence. Bioluminescent compounds that are useful for labeling include luciferin, luciferase and aequorin.

Alternatively, immunoconjugates can be detectably labeled by linking a monoclonal antibody to an enzyme. When the enzyme conjugate is incubated in the presence of the appropriate substrate, the enzyme moiety reacts with the substrate to produce a chemical moiety which can be detected, for example, by spectrophotometric, fluorometric or visual means. Examples of enzymes that can be used to detectably label polyspecific immunoconjugates include β-galactosidase, glucose oxidase, peroxidase and alkaline phosphatase.

An antibody of the invention may be labelled with a metallic chemical element such as lanthanides. Lanthanides offer several advantages over other labels in that they are stable isotopes, there are a large number of them available, up to 100 or more distinct labels, they are relatively stable, and they are highly detectable and easily resolved between detection channels when detected using mass spectrometry. Lanthanide labels also offer a wide dynamic range of detection. Lanthanides exhibit high sensitivity, are insensitive to light and time, and are therefore very flexible and robust and can be utilized in numerous different settings. Lanthanides are a series of fifteen metallic chemical elements with atomic numbers 57-71. They are also referred to as rare earth elements. Lanthanides may be detected using CyTOF technology. CyTOF is inductively coupled plasma time-of-flight mass spectrometry (ICP-MS). CyTOF instruments are capable of analyzing up to 1000 cells per second for as many parameters as there are available stable isotope tags.

Those of skill in the art will know of other suitable labels which can be employed in accordance with the present invention. The binding of marker moieties to monoclonal antibodies can be accomplished using standard techniques known to the art.

Moreover, the convenience and versatility of immunochemical detection can be enhanced by using monoclonal antibodies that have been conjugated with avidin, streptavidin, and biotin.

Another object of the invention is a method for detecting antibodies directed against *T. gondii* polypeptide BCLA using at least one isolated *Toxoplasma gondii* polypeptide according to the invention as described above, and/or evaluating its amount in a biological sample.

As used herein, the term "biological sample" refers to any biological sample of a subject; tissue sample or body fluid sample. In a preferred embodiment regarding a method to detect antibody directed against *T. gondii* polypeptide BCLA, the biological sample is a body fluid of said subject. Non-limiting examples of such samples include, but are not limited to, blood, serum, plasma, urine, saliva, and cerebrospinal fluid (CSF) and aqueous humor.

More particularly the body fluid sample, is serum or aqueous humor sample. In a preferred embodiment regarding the detection of antibodies directed *T. gondii* BCLA polypeptide of the invention, the biological sample is a fluid sample, more particularly a brain sample.

Detecting and Diagnostic Methods of the Invention:

In some embodiments, the method of the present invention are performed in vitro or ex vivo Method for Detecting *T. gondii* BCLA Polypeptide An object of the invention is a method for detecting *T. gondii* polypeptide BCLA of the invention, and/or evaluating its amount in a biological sample.

Biological sample, means without limitation a tissue sample, a culture medium and cell samples, a whole blood sample, a serum sample, a plasma sample, aqueous humor sample, a salivary sample, a cerebrospinal fluid sample, muscle sample or a brain tissue sample.

In a preferred embodiment regarding the detection of *T. gondii* BCLA polypeptide, the biological sample is a tissue sample, more particularly a muscle sample or a brain sample.

Detecting the *T. gondii* polypeptide BCLA may include separation of the proteins/polypeptides: centrifugation based on the protein's molecular weight; electrophoresis based on mass and charge; HPLC based on hydrophobicity; size exclusion chromatography based on size; and solid-phase affinity based on the protein's affinity for the particular solid-phase that is use. Once separated, *T. gondii* polypeptide BCLA may be identified based on the known "separation profile" e.g., retention time, for that protein and measured using standard techniques. Alternatively, the separated proteins may be detected and measured by, for example, a mass spectrometer (see example section).

The detection and amount of the *T. gondii* polypeptide BCLA species of the invention may be determined by using standard electrophoretic and immunodiagnostic techniques, including immunoassays such as competition, direct reaction such as immunohistochemistry, or sandwich type assays. Such assays include, but are not limited to, Western blots; agglutination tests; enzyme-labelled and mediated immunoassays, such as ELISAs; biotin/avidin type assays; radioimmunoassays; immunoelectrophoresis; immunoprecipitation, etc. The reactions generally include revealing labels such as fluorescent, chemiluminescent, radioactive, enzymatic labels or dye molecules, or other methods for detecting the formation of a complex between the antigen and the antibody or antibodies reacted therewith.

For example, determination of the *T. gondii* polypeptide BCLA amount can be performed by a variety of techniques and method any well-known method in the art: RIA kits (DiaSorin; IDS, Diasource) Elisa kits (Fujirebio, Thermo Fisher, EHTGFBI, R&D DY2935, IDS (manual) IDS (adapted on open analyzers) Immunochemiluminescent automated methods (MesoScaleDiscovery, DiaSorin Liaison, Roche Elecsys family, IDS iSYS) (Janssen et al., 2012) Simoa/Quanterix.

In a particular embodiment, the methods of the invention comprise contacting the biological sample with a binding partner.

As used therein, binding partner refers to a molecule capable of selectively interacting with *T. gondii* polypeptide BCLA of the invention.

The binding partner may be generally an antibody that may be polyclonal or monoclonal, preferably monoclonal.

In another embodiment, the binding partner may be an aptamer. Aptamers are a class of molecule that represents an alternative to antibodies in term of molecular recognition. Aptamers are oligonucleotide or oligopeptide sequences with the capacity to recognize virtually any class of target molecules with high affinity and specificity. Such ligands may be isolated through Systematic Evolution of Ligands by EXponential enrichment (SELEX) of a random sequence library, as described in Tuerk et al. (1990) Science, 249, 505-510. The random sequence library is obtainable by combinatorial chemical synthesis of DNA. In this library, each member is a linear oligomer, eventually chemically modified, of a unique sequence. Possible modifications, uses and advantages of this class of molecules have been reviewed in Jayasena 1999. Peptide aptamers consist of conformationally constrained antibody variable regions displayed by a platform protein, such as *E. coli* Thioredoxin A, that are selected from combinatorial libraries by two hybrid methods (Colas et al. (1996) Nature, 380, 548-50).

The binding partners of the invention such as antibodies or aptamers, may be labelled with a detectable molecule or substance, such as a fluorescent molecule, a radioactive molecule or any others labels known in the art. Labels are known in the art that generally provide (either directly or indirectly) a signal.

As used herein, the term "labelled", with regard to the binding partner, is intended to encompass direct labelling of the antibody or aptamer by coupling (i.e., physically linking) a detectable substance, such as a radioactive agent or a fluorophore (e.g. fluorescein isothiocyanate (FITC) or phycoerythrin (PE) or Indocyanine (Cy5) to the antibody or aptamer, as well as indirect labelling of the probe or antibody by reactivity with a detectable substance. An antibody or aptamer of the invention may be labelled with a radioactive molecule by any method known in the art. For example radioactive molecules include but are not limited radioactive atom for scintigraphic studies such as I123, 1124, In111, Re186, Re188.

The aforementioned assays generally involve the bounding of the binding partner (i.e., antibody or aptamer) in a solid support. Solid supports which can be used in the practice of the invention include substrates such as nitrocellulose (e.g., in membrane or microtiter well form); polyvinylchloride (e.g., sheets or microtiter wells); polystyrene latex (e.g., beads or microtiter plates); polyvinylidine fluoride; diazotized paper; nylon membranes; activated beads, magnetically responsive beads, and the like. More particularly, an ELISA method can be used, wherein the wells of a microtiter plate are coated with a set of antibodies against *T. gondii* polypeptide BCLA. A body fluid sample containing or suspected of containing *Toxoplasma gondii* polypeptide BCLA is then added to the coated wells. After a period of incubation sufficient to allow the formation of binding partner-*T. gondii* polypeptide BCLA complexes, the plate(s) can be washed to remove unbound material and a labelled secondary binding molecule added. The secondary binding molecule is allowed to react with any captured sample marker protein, the plate washed and the presence of the secondary binding molecule detected using methods well known in the art.

As the binding partner, the secondary binding molecule may be labelled.

Antibodies of the present invention and immunoconjugates can be used for detecting *T. gondii* polypeptide BCLA of the invention, and/or evaluating its amount in a biological sample, in particular a tissue sample a culture medium and cell samples, a whole blood sample, a serum sample, a plasma sample, a cerebrospinal fluid sample, or a brain tissue sample. Therefore, they can be used for diagnosing all diseases associated with *Toxoplasma gondii* agent.

Method of Diagnosis of Latent Form of Toxoplasmosis (Detection of *T. gondii* Polypeptide BCLA)

Accordingly, the method of detection of the *T. gondii* BCLA polypeptide according to the invention is consequently useful for the in vitro diagnosis of Toxoplasmosis from a biological sample. In particular, the method of detection of the invention is consequently useful for the in vitro diagnosis of latent form of Toxoplasmosis or congenital toxoplasmosis from a biological sample. As used herein, the term "biological sample" refers to any biological sample of a subject. Biological sample, means without limitation any tissue sample, a culture medium and cell samples, a whole blood sample, a serum sample, a plasma sample, an urinary sample, a salivary sample, a cerebrospinal fluid sample, In a preferred embodiment regarding a method using the detection of *T. gondii* BCLA polypeptide, the biological sample is a tissue sample, more particularly a brain tissue sample or muscle tissue sample.

A further object of the invention is a method for detecting *T. gondii* polypeptide BCLA of the invention, and/or evaluating its amount in a biological sample, wherein said method comprises contacting said sample with an antibody or immunoconjugate of the invention under conditions allowing the formation of an immune complex between *Toxoplasma gondii* polypeptide BCLA and said antibody/immunoconjugate, and detecting or measuring the immune complex formed.

A further object of the invention is a method for detecting bradyzoite cyst, and/or evaluating its amount in a biological sample, wherein said method comprises contacting said sample with an antibody or immunoconjugate of the invention under conditions allowing the formation of an immune complex between *Toxoplasma gondii* polypeptide BCLA at the surface of the cyst and said antibody/immunoconjugate, and detecting or measuring the immune complex formed.

The immune complex formed can be detected or measured by a variety of methods using standard techniques, including, by way of non-limitative examples, enzyme-linked immunosorbent assay (ELISA) or other solid phase immunoassays, radioimmunoassay, electrophoresis, immunofluorescence, or Western blot.

A further object of the invention is a method for in vitro diagnosing a Toxoplasmosis, wherein said method comprising detecting the presence of *Toxoplasma gondii* polypeptide BCLA, as indicated above, in a biological sample from a subject to be tested.

The term "Toxoplasmosis" has its general meaning in the art and refers to a worldwide distributed zoonotic infection with medical importance in pregnant women and immunocompromised patients. *Toxoplasma gondii*, the etiologic agent of toxoplasmosis, has co-evolved with its homeothermic hosts, including humans, strategies to persist usually as a quasi-cryptic population and accordingly with subclinical signs, hence optimizing the chance of transmission to new hosts. Over its prolonged residence in warm blooded metazoans, the proliferative stage (tachyzoite) switches into a persistent stage (cyst-enclosed bradyzoites) that affords the parasite a unique opportunity to spread to new hosts without proceeding through its sexual stage, which is restricted to felids. Uncontrolled amplification of tachyzoite population as it occurs when the immune balance is transiently or more sustainably ruptured can lead to life-threatening disease, and in the case of congenital toxoplasmosis, to birth defects.

Persistence, which depends both on the acquisition of slow replicative skills by a subset of parasites and the destruction of the fast-replicative population, critically requires the IL-12/IFN-γ immune axis, yet *T. gondii* has singularly evolved a finely tuned and epigenetically regulated developmental program to operate stage conversion.

In some embodiment, the toxoplasmosis is congenital toxoplasmosis.

Thus, the invention refers to a method for in vitro diagnosing a congenital toxoplasmosis, wherein said method comprising detecting the presence of polypeptide, according to claim 1, in a biological sample from a subject to be tested.

As used herein, the term "latent form of Toxoplasmosis" refers to persistent stage (cyst-enclosed bradyzoites) of the Toxoplasmosis disease. Following the initial period of infection characterized by tachyzoite proliferation throughout the body, pressure from the host's immune system causes *T. gondii* tachyzoites to convert into bradyzoites, the semi-dormant, slowly dividing cellular stage of the parasite. Inside host cells, clusters of these bradyzoites are known as tissue cysts. The cyst wall is formed by the parasitophorous vacuole membrane. Although bradyzoite-containing tissue cysts can form in virtually any organ, tissue cysts predominantly form and persist in the brain, the eyes, and striated muscle (including the heart). However, specific tissue tropisms can vary between intermediate host species; in pigs, the majority of tissue cysts are found in muscle tissue, whereas in mice, the majority of cysts are found in the brain. Cysts usually range in size between five and 50 μm in diameter, (with 50 μm being about two-thirds the width of the average human hair).

Furthermore, the invention also provides kits comprising at least one antibody of the invention or a fragment thereof. Kits of the invention can contain an antibody coupled to a solid support, e.g., a tissue culture plate or beads (e.g., sepharose beads). Kits can be provided which contain antibodies for detection and quantification of *Toxoplasma gondii* polypeptide BCLA in vitro, e.g. in an ELISA or a Western blot. Such antibody useful for detection may be provided with a label such as a fluorescent or radiolabel.

Method of Diagnosis of Latent Form of Toxoplasmosis (Detection of Autoantibodies of *T. gondii* Polypeptide BCLA)

Figure 10A:
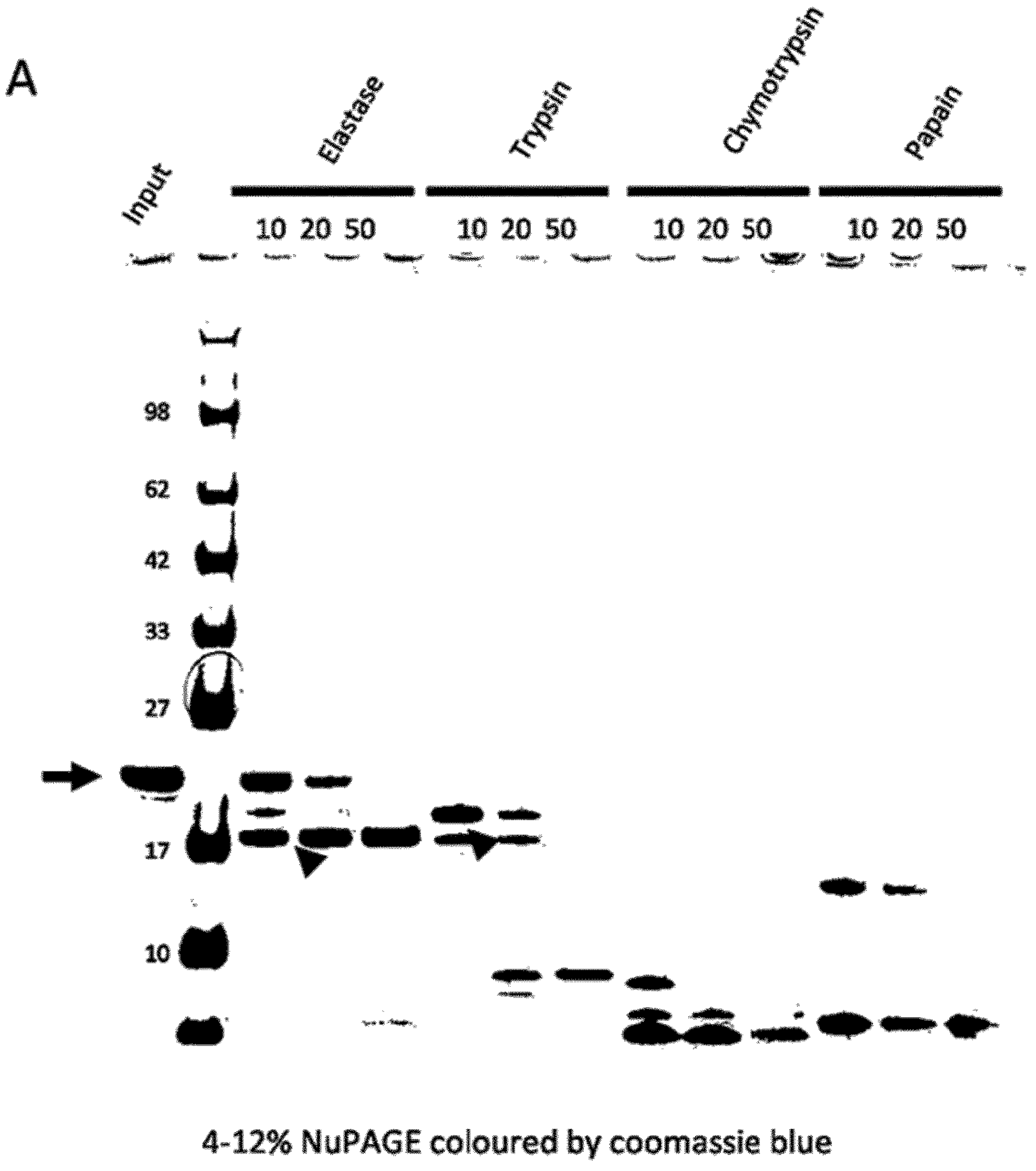
Figure 10B:
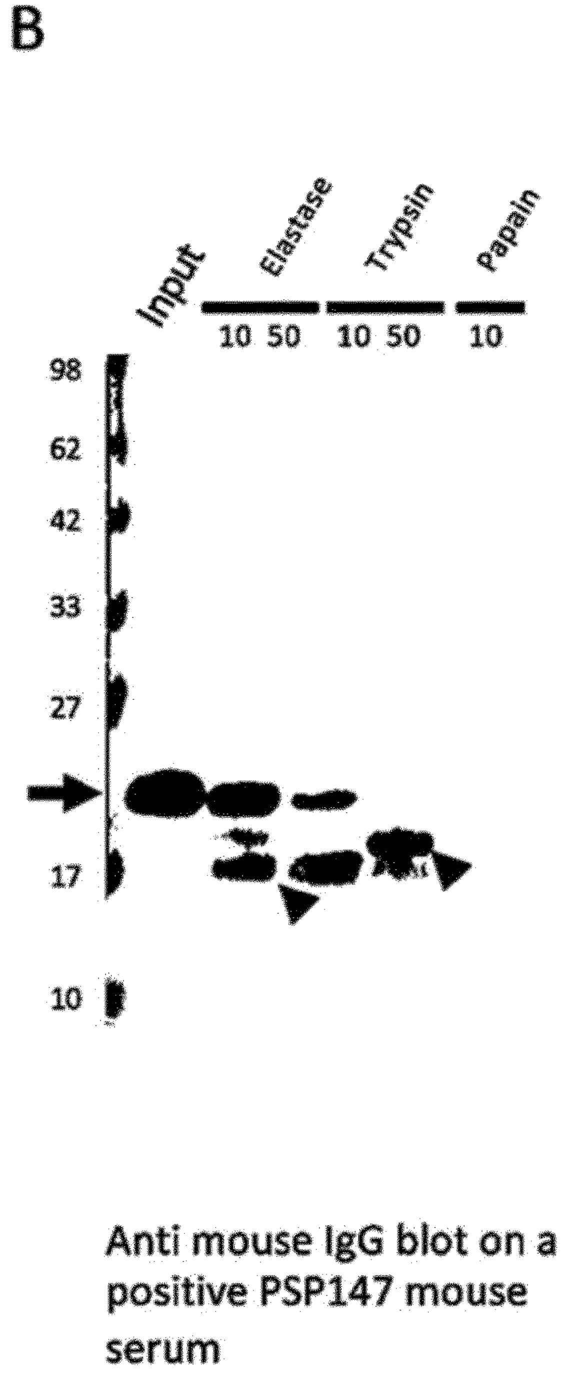
Figure 10C:
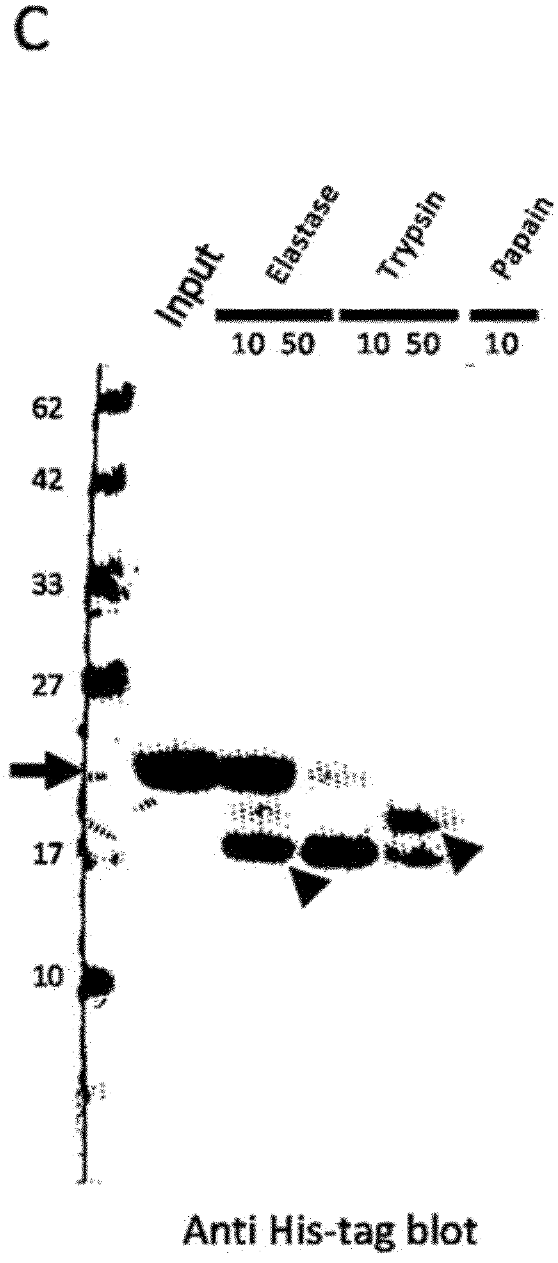

When synthetized as a recombinant protein, inventors clearly demonstrate that BCLA constitutes an efficient serological marker of latent infection with a high sensitivity that was clearly and exclusively correlated with the presence of cysts in mice brain. Antibodies directed against BCLA antigen have been detected in human patients. Enriched titers were detected in patients qualified as seropositive to Sag1 or tachyzoite related antigens. Further correlation in humans between anti-BCLA IgG synthesis and cysts is brought by significantly stronger recorded titers in pathological panels strongly related to the presence of cyst. Notably, in patients undergoing a serological reactivation and those suffering from a proven ocular toxoplasmosis (see experimental data in Example FIGS. 10 and 13). In the latter case, the developed ELISA assay can also detect BCLA antibodies within the aqueous humor and serum of some of these patients. Detection of toxoplasmic antibodies directed against semi-dormant cysts is a significant improvement to the serological diagnosis of toxoplasmosis by opening new diagnostic perspectives. Indeed, few components of the cyst wall or surface bradyzoite have been identified, and none were shown to serve as antigen for serology purpose, at least in commercial kits. The ideal antigen should be expressed exclusively in latent bradyzoite stage and ideally should be exposed to the surface of the cyst, two features found in BCLA polypeptide.

Furthermore, the inventors have demonstrated that child neo-synthetizes specifically anti-BCLA IgGs prior to birth. Thus BCLA reactivity can further better orient the diagnosis of congenital toxoplasmosis at the moment of birth in comparison with the titration of Toxo IgGs by Vidas® and Architect® (see example 3).

Accordingly, the method of detection of autoantibodies of *T. gondii* polypeptide according to the invention is consequently useful for the in vitro diagnosis of Toxoplasmosis from a biological sample. In particular, the method of detection of the invention is consequently useful for the in vitro diagnosis of latent form of Toxoplasmosis or congenital toxoplasmosis from a biological sample.

A further object of the invention is a method for in vitro diagnosing a Toxoplasmosis, wherein said method comprising detecting the presence of T autoantibodies of *T. gondii* polypeptide according to the invention, as indicated above, in a biological sample from a subject to be tested.

Thus present invention relates to a method of determining if a subject is afflicted with a latent form of Toxoplasmosis, said method comprising:

a) detecting in a biological sample of the patient immunoreactivity toward a *T. gondii* polypeptide of the invention; and optionally b) deducing from the result of step a) whether the patient is afflicted with latent form of Toxoplasmosis, immunoreactivity toward a *T. gondii* polypeptide of the invention is indicative of latent form of Toxoplasmosis.

The present invention also relates to the use of antibody directed against latent form of Toxoplasmosis as a biomarker for diagnosing (or confirming) latent form of Toxoplasmosis in a patient.

The present invention also relates to an in vitro method for diagnosing or confirming a diagnosis of a latent form of Toxoplasmosis in a patient who is suffering, or is suspected to be suffering, a latent form of Toxoplasmosis, comprising:

a) obtaining a biological sample from the patient, and b) detecting, in the biological sample, antibodies toward a *T. gondii* polypeptide of the invention;

wherein the presence of antibodies in the biological sample diagnoses or confirms a diagnosis of latent form of Toxoplasmosis in a patient.

Thus, present invention relates to a method of determining if a subject is afflicted with congenital Toxoplasmosis, said method comprising:

a) detecting in a biological sample of the patient immunoreactivity toward a *T. gondii* polypeptide of the invention; and optionally b) deducing from the result of step a) whether the patient is afflicted with congenital Toxoplasmosis, immunoreactivity toward a *T. gondii* polypeptide of the invention is indicative of congenital Toxoplasmosis.

The present invention also relates to the use of antibody directed against congenital Toxoplasmosis as a biomarker for diagnosing (or confirming) congenital Toxoplasmosis in a patient.

The present invention also relates to an in vitro method for diagnosing or confirming a diagnosis of congenital Toxoplasmosis in a patient who is suffering, or is suspected to be suffering, congenital Toxoplasmosis, comprising:

b) obtaining a biological sample from the patient, and b) detecting, in the biological sample, antibodies toward a *T. gondii* polypeptide of the invention;

wherein the presence of antibodies in the biological sample diagnoses or confirms a diagnosis of congenital Toxoplasmosis in a patient.

As used herein, the term "biological sample" refers to any biological sample of a subject. In a preferred embodiment regarding a method using the detection of antibody directed against *T. gondii* BCLA polypeptide, the biological sample is a body fluid of said subject. Non-limiting examples of such samples include, but are not limited to, blood, serum, plasma, urine, saliva, and cerebrospinal fluid (CSF) and aqueous humor.

More particularly the body fluid sample, is serum or aqueous humor sample.

In a preferred embodiment, the patient to be tested is suffering, or is suspected to be suffering, from Toxoplasmosis.

In another preferred embodiment, the patient to be tested is suspected to be suffering from Toxoplasmosis and the method is performed to confirm that the patient is actually afflicted with the latent form of Toxoplasmosis disease.

In another embodiment, the patient to be tested is a pregnant woman and/or an immunocompromised patient (i.e., HIV patient or patient treated by immunomodulatory before receiving a graft) and the method is performed to determine if the patient is actually afflicted with latent form of Toxoplasmosis.

The current treatment for toxoplasmosis, when a subject presents signs and symptoms of acute toxoplasmosis, is the following:

Pyrimethamine (Daraprim). This medication, typically used for malaria, is a folic acid antagonist. It may prevent the body from absorbing the B vitamin folate (folic acid, vitamin B-9), especially when patient take high doses over a long period. For that reason, it may recommend taking additional folic acid. Other potential side effects of pyrimethamine include bone marrow suppression and liver toxicity.

Sulfadiazine. This antibiotic is used with pyrimethamine to treat toxoplasmosis.

For HIV/AIDS patients, the treatment of choice for toxoplasmosis is also pyrimethamine and sulfadiazine, with folic acid (leucovorin). An alternative is pyrimethamine taken with clindamycin (Cleocin).

For pregnant women and babies infected with toxoplasmosis,:

If infection occurred before the 16th week of pregnancy, pregnant women receive the antibiotic spiramycin. Use of this drug may reduce the baby's risk of neurological problems from congenital toxoplasmosis.

If infection occurred after the 16th week of pregnancy, or if tests show that the unborn child has toxoplasmosis, pregnant women may be given pyrimethamine and sulfadiazine and folic acid (leucovorin).

The present invention also provides an in vitro method for selecting a patient afflicted with an latent form of Toxoplasmosis suitable to be treated with at least one folic acid antagonist and/or antibiotic compound, comprising:

a) detecting in a biological sample of the patient immunoreactivity toward a *T. gondii* polypeptide of the invention; and optionally b) selecting the patient as suitable to be treated with at least one folic acid antagonist (i.e. Pyrimethamine) and/or antibiotic compound (i.e. Sulfadiazine or spiramycin) when immunoreactivity toward a *T. gondii* polypeptide of the invention is detected.

The method of determining if a patient is afflicted with latent form of Toxoplasmosis, the use of antibody directed against a *T. gondii* polypeptide of the invention as a biomarker for diagnosing (or confirming) latent form of Toxoplasmosis, and the method of selecting a patient afflicted with latent form of Toxoplasmosis suitable to be treated with at least one folic acid antagonist and/or antibiotic compound of the invention may be, for instance, in vitro or ex vivo methods.

The invention also concerns a method for treating a patient infected with latent form of Toxoplasmosis who shows immunoreactivity toward a *T. gondii* polypeptide of the invention, which method comprises administering to the patient folic acid antagonist (i.e. Pyrimethamine) and/or antibiotic compound (i.e. Sulfadiazine or spiramycin), or a pharmaceutical composition comprising said compounds.

The invention also provides folic acid antagonist (i.e., Pyrimethamine) and/or antibiotic compound (i.e., Sulfadiazine or spiramycin), or a pharmaceutical composition comprising said compounds, for use in the treatment of a patient suffering from latent form of Toxoplasmosis who shows immunoreactivity toward a *T. gondii* polypeptide of the invention.

In some embodiments, the *T. gondii* polypeptide of the invention which immunoreactivity is tested is the BCLA (Brain Cyst Load-associated Antigen) protein (abbreviated as "BCLA") the C-terminal domain end of BCLA (res 1089 to 1275, SEQ ID N°2) (abbreviated as "rBCLA"), or the internal repeat domain of BCLA (res 304-924 of BCLA) referred as TgR1 to TgR13 (SEQ ID NO: 4 to SEQ ID NO: 16).

In particular embodiments, the protein against which immunoreactivity is tested is a rBCLA polypeptide.

In another particular embodiment, the protein against which immunoreactivity is tested is a peptidic fragment of at least 9 consecutive amino acids of the BCLA, rBCLA sequence or the internal repeat domain of BCLA (res 304-924 of BCLA) referred as TgR1 to TgR13 (SEQ ID NO: 4 to SEQ ID NO: 16).

In particular, the terms *T. gondii* polypeptide of the invention against which immunoreactivity is tested refer to:

(i) the amino acids sequence consisting of *Toxoplasma gondii* polypeptide BCLA (SEQ ID N 0:1);

(ii) the amino acids sequence consisting of C-terminal antigenic domain (res 1089-1275 of BCLA referred as rBCLA) (SEQ ID NO:2);

(iii) the amino acids sequence consisting of internal repeated domain of BCLA selected from the group consisting of: TgR1 (SEQ ID NO:4), TgR2 (SEQ ID NO: 5), TgR3 (SEQ ID NO:6), TgR4 (SEQ ID NO:7), TgR5 (SEQ ID NO:8), TgR6 (SEQ ID NO:9), TgR7 (SEQ ID NO: 10), TgR8 (SEQ ID NO:11), TgR9 (SEQ ID NO:12), tgR10 (SEQ ID NO:13), TgR11 (SEQ ID NO:14), TgR12 (SEQ ID NO:15) and TgR13 (SEQ ID NO: 16);

(iv) an amino acid sequence substantially homologous to the sequence of (i), to (iii) preferably an amino acid sequence at least 80% identical to the sequence of (i) to (iii)

(v) a fragment of at least 9 consecutive amino acids of the sequence of (i), to (iv).

Accordingly, in a particular embodiment, the isolated *Toxoplasma gondii* polypeptide from rBCLA polypeptide against which immunoreactivity is tested is selected from the group consisting of:

```
(i)
                                          (SEQ ID No 32)
GELQPAEAEEARLLVADLKAV (domain A of rBCLA)

(ii)
                                          (SEQ ID No 33)
VRVEGEAFFRASVDLYEA (domain B of rBCLA

(iii)
                                          (SEQ ID No 34)
KLRPLTKGELVDVVRQ (domain C of rBCLA)

(iv)
                                          (SEQ ID No 35)
TQIFVQDRASAFLRV (peptide 36 of rBCLA and domain
D of rBCLA)

(v)
                                          (SEQ ID No 36)
AAEQMKAVFAMVEEG (peptide 44 of rBCLA and domain
E of rBCLA)
```

(vi) an amino acid sequence substantially homologous to the sequence of (i) to (v), preferably an amino acid sequence at least 95% identical to the sequence of (i) to (v)

(vii) a fragment of at least 9 consecutive amino acids of the sequence of (i), to (vi).

In a more particular embodiment, the isolated *Toxoplasma gondii* polypeptide from rBCLA polypeptide against which immunoreactivity is tested is selected from the group consisting of selected from the group:

```
(i)
                                    (SEQ ID No 37)
GELQPAEAEEARLLV (peptide 12 of rBCLA);

(ii)
                                    (SEQ ID No 38)
QPAEAEEARLLVADL (peptide 13 of rBCLA),

(iii)
                                    (SEQ ID No 39)
EAEEARLLVADLKAV (peptide 14 of rBCLA),

(iv)
                                    (SEQ ID No 40)
VRVEGEAFFRASVDL (peptide 21 of rBCLA),

(v)
                                    (SEQ ID No 41)
EGEAFFRASVDLYEA (peptide 22 of rBCLA);

(vi)
                                    (SEQ ID No 42)
AFFRASVDLYEAVKN (peptide 23 of rBCLA),

(vii)
                                    (SEQ ID No 43)
KLRPLTKGELVDVVR (peptide 30 of rBCLA)
```

(viii) an amino acid sequence substantially homologous to the sequence of (i) to (vii), preferably an amino acid sequence at least 95% identical to the sequence of (i) to (vii)

(vii) a fragment of at least 9 consecutive amino acids of the sequence of (i), to (viii).

Accordingly, in a particular embodiment, the isolated *Toxoplasma gondii* polypeptide from internal repeated domain of BCLA against which immunoreactivity is tested is selected from the group consisting of:

(i) the amino acids sequence consisting of internal repeated domain of TgR4, MERPAAGSMEKEKPVL-PGEGEGHVLPKHETKPALTDEKRTKPGGPRTE (SEQ ID NO: 7)

(ii) an amino acid sequence substantially homologous to the sequence of (i), preferably an amino acid sequence at least 80% identical to the sequence of (i)

(iii) a fragment of at least 9 consecutive amino acids of the sequence of (i), to (ii).

In a more particular embodiment, the isolated *Toxoplasma gondii* polypeptide from internal repeated domain of BCLA against which immunoreactivity is tested is selected from the group consisting of:

```
(i)
                                    (SEQ ID No 44)
AAGSMEKEKPVLPGEGEGH (domain A of TgR4);

(ii)
                                    (SEQ ID No 45)
VLPKHETKPALTDEKRTKPGGP (domain B of TgR4),
```

(iii) an amino acid sequence substantially homologous to the sequence of (i) to (ii), preferably an amino acid sequence at least 95% identical to the sequence of (i) to (ii)

(iv) a fragment of at least 9 consecutive amino acids of the sequence of (i), to (iii).

In a more particular embodiment, the isolated *Toxoplasma gondii* polypeptide from internal repeated domain of BCLA against which immunoreactivity is tested is selected from the group consisting of:

```
(i)
                                    (SEQ ID No 46)
AAGSMEKEKPVLPGE (peptide 3 of TgR4);

(ii)
                                    (SEQ ID No 47)
GSMEKEKPVLPGEGE (peptide 4 of TgR4)

(iii)
                                    (SEQ ID No 48)
MEKEKPVLPGEGEGH (peptide 5 of TgR4)

(iv)
                                    (SEQ ID No 49)
KEKPVLPGEGEGHVL (peptide 6 of TgR4)

(v)
                                    (SEQ ID No 50)
KPVLPGEGEGHVLPG (peptide 7 of TgR4)

(vi)
                                    (SEQ ID No 51)
HVLPKHETKPALTDEK (peptide 13 of TgR4),

(vii)
                                    (SEQ ID No 52)
PKHETKPALTDEKRT (peptide 14 of TgR4),

(viii)
                                    (SEQ ID No 53)
HETKPALTDEKRTKP (peptide 15 of TgR4)

(ix)
                                    (SEQ ID No 54)
TKPALTDEKRTKPGG (peptide 16 of TgR4)
```

(x) an amino acid sequence substantially homologous to the sequence of (i) to (ix), preferably an amino acid sequence at least 95% identical to the sequence of (i) to (ix)

(xi) a fragment of at least 9 consecutive amino acids of the sequence of (i), to (x).

As BCLA polypeptide has a multitude of epitopes throughout the different domain (especially in rBCLA as well as in the internal repeated domain of BCLA TgR1 to TgR13) it may advantageous to combine the BCLA immunogenic peptides fragments of the invention.

Accordingly, in another embodiment, the polypeptide of the present invention against which immunoreactivity is tested, is a fusion between two immunogenic peptides fragments of the invention, such as Peptide AB_F: MERPAAGSMEKEKPVLPGEGEG-LPKHETKPALTDEKRTKPGGP (fusion of peptide fragments from a repeat motif present in Tgr4/Trg12/Tgr13 and a repeat motif present in Tgr3/Trg4/Tgr5/Tgr6/Tgr9) (SEQ ID N°55)

Peptide A3_B: AAGSMEKDKLVLPGE (peptide fragments from a repeat motif present in Tgr3/Tgr5/Tgr6/Tgr7/Trg10/Tgr11) (SEQ ID N°56)

Accordingly, in another embodiment, the polypeptide of the present invention from internal repeated domain of BCLA (TgRx) against which immunoreactivity is tested has the following sequence:

M-Xaa1-Xaa2-Xaa3-Xaa4-Xaa5-Xaa6-Xaa7-M-E-Xaa8-Xaa9-K-Xaa10-V-Xaa11-P-G-E-G-Xaa12-Xaa13-H-Xaa-14-Xaa15-P—K-Xaa16-E-Xaa17-Xaa18-L-T-Xaa19-Xaa-20-Xaa21-Xaa22-T-Xaa23-P-Xaa24-Xaa25-P-Xaa26-Xaa-27-Xaa28 (SEQ ID N°64)

Wherein Xaa1 is) Glutamic acid (E) or no amino acid residues

Wherein Xaa2 is Arginine (R) or Serine(S)

Wherein Xaa3 is Proline (P) or Glycine (G)

Wherein Xaa4 is Alanine (A) or Glycine (G)

Wherein Xaa5 is Alanine (A) or no amino acid residues

Wherein Xaa6 is Glycine (G) or Arginine (R)

Wherein Xaa7 is Serine(S), Proline (P) or Alanine (A)

Wherein Xaa8 is Lysine (K) or Glutamic acid (E)

Wherein Xaa9 is Lysine (K), Glutamic acid (E) or Aspartic acid (D)

Wherein Xaa10 is Proline (P) or Leucine (L)

Wherein Xaa11 is Leucine (L) or Serine(S)

Wherein Xaa12 is Glutamic acid (E) or Lysine (K)

Wherein Xaa13 is Glycine (G) or Arginine (R)

Wherein Xaa14 is Valine (V) or Alanine (A)

Wherein Xaa15 is Leucine (L) or Serine(S)

Wherein Xaa16 is Histidine (H), Aspartic acid (D) or Alanine (A)

Wherein Xaa17 is Threonine (T), Arginine (R), Methionine (M) or Glutamine (Q)

Wherein Xaa18 is Proline (P), Threonine (T) or Alanine (A)

Wherein Xaa19 is Aspartic acid (D), Glutamic acid (E) or Glutamine (Q)

Wherein Xaa20 is Glutamic acid (E) or Lysine (K)

Wherein Xaa21 is Lysine (K), Glycine (G) or Glutamic acid (E)

Wherein Xaa22 is Arginine (R) or Valine (V)

Wherein Xaa23 is Lysine (K), Glutamic acid (E) or Asparagine (N)

Wherein Xaa24 is Glycine (G), Valine or Isoleucine (I)

Wherein Xaa25 is Glycine (G) or Glutamic acid (E)

Wherein Xaa26 is Arginine (R) or Proline (P)

Wherein Xaa27 is Threonine (T) Cystein (C) Lysine (K) or Methionine (M)

Wherein Xaa28 is Glutamic acid (E) or Alanine (A) or a fragment of at least 9 consecutive amino acids of the sequence SEQ ID N°64.

By "polypeptide with amino acid sequence substantially homologous" is meant a polypeptide that has at least about 80%, 81%, 82%, 83%, 84%, 85%, 86%, 87%, 88%, 89%, 90%, 91%, 92%, 93%, 94%, 95%, 96%, 97%, 98%, or 99% amino acid sequence identity to a full-length polypeptide reference sequence. In the context of the present application, the percentage of identity is calculated using a global alignment (i.e. the two sequences are compared over their entire length). Methods for comparing the identity of two or more sequences are well known in the art. The «needle» program, which uses the Needleman-Wunsch global alignment algorithm (Needleman and Wunsch, 1970 J. Mol. Biol. 48:443-453) to find the optimum alignment (including gaps) of two sequences when considering their entire length, may for example be used. The needle program is for example available on the ebi.ac.uk world wide web site. The percentage of identity in accordance with the invention is preferably calculated using the EMBOSS::needle (global) program with a "Gap Open" parameter equal to 10.0, a "Gap Extend" parameter equal to 0.5, and a Blosum62 matrix.

As used throughout the present application, the expression "Immunoreactivity toward a target protein" (here *T. gondii* polypeptide of the invention) is intended to mean that the sample from the patient to be tested comprises antibodies specifically directed against the target.

Therefore, immunoreactivity toward a target protein can be easily detected by demonstrating in the biological sample to be tested the presence of antibodies specifically directed against the target protein or a fragment of this target protein.

Fragments of the target proteins may be truncated at the N-terminus or C-terminus, or may lack internal residues, for example, when compared with a full-length protein. Preferably, said fragments are at least about 9, 10, 20, 30, 40, 50, 60, 70, 80, 90, 100, 110, 120, 150, 250, 300, 350, 400, 450, 500 or more amino acids in length.

Such a test can be performed by one of ordinary skill in the art by using standard methods, for instance Enzyme-linked immunosorbent assay ("ELISA"), Western Blot/Dot Blot, Immunohistochemistry on transfected cells, Luminex (see for review Immunodiagnostics: A Practical Approach, R. Edwards Editor, Oxford University Press 2000; Manual of Molecular And Clinical Laboratory Immunology, J. D. Folds R. G. Hamilton, B. Detrick Editors ASM Press 2006; Immunology and Serology in Laboratory Medicine, M. L. Turgeon, Mosby Inc, 2008).

For instance, for determining the presence of anti-BCLA antibodies in a sample, the target protein can be the full-length BCLA polypeptide, the C-terminal antigenic domain (res 1089-1275 of BCLA) referred as rBCLA (SEQ ID N°2), the internal repeat domain of BCLA (res 304-924 of BCLA) referred as TgR1 to TgR13 (SEQ ID NO: 4 to SEQ ID NO: 16) or a fragment thereof. Preferably the target protein consists of, or comprises, the C-terminal antigenic domain (res 1089-1275 of BCLA referred as rBCLA (SEQ ID N°2)), the internal repeat domain of BCLA (res 304-924 of BCLA) referred as TgR1 to TgR13 (SEQ ID NO: 4 to SEQ ID NO: 16) or a fragment thereof.

As used herein, the term "patient" denotes a mammal and more particularly a human being.

In the context of the invention, the term "treating" is used herein to characterize a therapeutic method or process that is aimed at (1) slowing down or stopping the progression, aggravation, or deterioration of the symptoms of the disease state or condition to which such term applies; (2) alleviating or bringing about ameliorations of the symptoms of the disease state or condition to which such term applies; and/or (3) reversing or curing the disease state or condition to which such term applies.

The folic acid antagonist and/or antibiotic compound used in the above recited method or use for treating patients afflicted with latent form of Toxoplasmosis are provided in a pharmaceutically acceptable carrier, excipient or diluent which is not prejudicial to the patient to be treated.

Pharmaceutically acceptable carriers and excipient that may be used in the compositions of this invention include, but are not limited to, ion exchangers, alumina, aluminum stearate, lecithin, self-emulsifying drug delivery systems (SEDDS) such as d-a-tocopherol polyethylene glycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

As appreciated by skilled artisans, compositions are suitably formulated to be compatible with the intended route of administration. Examples of suitable routes of administration include parenteral route, including for instance intramuscular, subcutaneous, intravenous, intraperitoneal or local injections. The oral route can also be used, provided that the composition is in a form suitable for oral administration, able to protect the active principle from the gastric and intestinal enzymes.

Further, the amount of folic acid antagonist and/or antibiotic compound used in the above recited method or use for treating patients afflicted with latent form of Toxoplasmosis is a therapeutically effective amount.

The exact amount of folic acid antagonist and/or antibiotic compound to be used and the composition to be administered will vary according to the age and the weight of the patient being treated, the type of disease, the mode of administration, the frequency of administration as well as the other ingredients in the composition which comprises the folic acid antagonist and/or antibiotic compound. Such concentrations can be routinely determined by those of skilled in the art. The amount of the compound actually administered will typically be determined by a physician, in the light of the relevant circumstances, including the condition to be treated, the chosen route of administration, the actual folic acid antagonist and/or antibiotic compound administered, the age, weight, and response of the individual patient, the severity of the patient's symptoms, etc.

Generally, the folic acid antagonist and/or antibiotic compound used in the above recited method or use for treating patients afflicted with latent form of Toxoplasmosis may be administered in the typical range. Effective doses will also vary depending on route of administration, as well as the possibility of co-usage with other agents. For instance, typical dose of The invention further provides kits that are useful in the above methods for diagnosing latent form of Toxoplasmosis or for selecting a patient afflicted with latent form of Toxoplasmosis suitable to be treated with at least one folic acid antagonist and/or antibiotic compound.

Such kits comprise means for detecting antibodies directed toward at least one *T. gondii* polypeptide of the invention.

Preferably, the kit comprises at least means for detecting antibodies directed toward BCLA polypeptide, or the C-terminal antigenic domain (res 1089-1275 of BCLA) or fragment thereof.

Such means can be the target protein(s), i.e. the *T. gondii* polypeptide of the invention against which immunoreactivity is tested, or fragments thereof as described above. For instance, when immunoreactivity toward BCLA is tested, the target protein is the full-length BCLA protein, consists of, or comprises, the C-terminal antigenic domain (res 1089-1275 of BCLA) referred as rBCLA (SEQ ID N°2), the internal repeat domain of BCLA (res 304-924 of BCLA) referred as TgR1 to TgR13 (SEQ ID NO: 4 to SEQ ID NO: 16), preferably the target protein consists of, or comprises, the C-terminal antigenic domain (res 1089-1275 of BCLA) referred as rBCLA (SEQ ID N°2), the internal repeat domain of BCLA (res 304-924 of BCLA) referred as TgR1 to TgR13 (SEQ ID NO: 4 to SEQ ID NO: 16).

Means for detecting antibodies directed toward at least one *T. gondii* polypeptide of the invention may also include an antibody specifically binding to human antibodies (used as a "secondary antibody" which binds to antibodies from the sample to be tested specifically binding to the target protein). Such antibodies can be labeled with detectable compound such as fluorophores or radioactive compounds.

In a preferred embodiment, the kit according to the invention may further comprises a control sample comprising a known amount of antibodies and/or instructions for the use of said kit in diagnosing latent form of Toxoplasmosis or in selecting a patient afflicted with latent form of Toxoplasmosis suitable to be treated with at least one folic acid antagonist and/or antibiotic compound.

The means may be present, e.g., in vials or microtiter plates, or be attached to a solid support. For instance the target protein can be attached to a membrane or to an array.

A further object of the invention is a method for detecting bradyzoite cyst, and/or evaluating its amount in a subject, wherein said method comprises a) detecting in a fluid sample of the subject immunoreactivity toward a *T. gondii* polypeptide according to any of claims 1 to 2; and optionally
b) deducing from the result of step a) the presence and/or amount of bradyzoite cyst, immunoreactivity toward a *T. gondii* polypeptide of the invention is indicative of presence and/or amount of bradyzoite cyst in said subject.

In a preferred embodiment the biological sample is a body fluid of said subject. Non-limiting examples of such samples include, but are not limited to, blood, serum, plasma, urine, saliva, and cerebrospinal fluid (CSF) and aqueous humor.

More particularly the body fluid sample, is serum or aqueous humor sample.

All references cited herein, including journal articles or abstracts, published patent applications, issued patents or any other references, are entirely incorporated by reference herein, including all data, tables, figures and text presented in the cited references.

The invention will be further evaluated in view of the following examples and figures.

FIGURES

FIG. 1. BCLA is a bradyzoite-specific gene regulated by TgHDAC3

(a) Quantitative proteome-wide analysis by LC-MS/MS after TgHDAC3 inhibition with FR235222 reveals the expression of bradyzoite-specific proteins among them BCLA. The volcano plot shows the distribution of *T. gondii* proteins comparing untreated (DMSO, 0.1%) versus FR235222 treated (90 nM) primary human fibroblasts infected with type II (PruAku80) strain. The log 2 ratios (x-axis) for proteins counts were obtained by dividing intensities of FR235222 treated samples by intensities of DMSO-treated samples (control). The down- and up-regulated proteins are shown in red spots on respectively the left and the right side of the graph. The vertical black lines indicate log 2 fold changes values. The horizontal dashed black lines distinguish the proteins (red spots) showing at least a 2-fold abundance change with p-values <0.01. (b) Bar graphs showing the expression (fragments per kilobase of transcript per million mapped reads [FPKM] values) of BCLA gene during: acute (tachyzoite) or chronic (cyst-enclosed bradyzoites) infection in mice, in various cat entero-epithelial stages (EES) samples (EES1: very early EES; EES2: early EES; EES3: mixed EES; EES4; late EES; EES5: very late EES) from day 3 to day 7 after oral infection with *T. gondii* cysts (CZ clone H3), and in cysts from mouse brain and in in vitro cultivated tachyzoites. BCLA is only expressed during the chronic stage in cyst-enclosed bradyzoites and is not found in cat entero-epithelial stages (EES) from EES1 to EES5 (data source: www.ToxoDB.org). (c) A genome browser (IGB) screenshot of BCLA locus (in magenta) on chromosome Ib of *T. gondii*, showing reads for two histone marks (H3K14ac, H3K9me3), TgHDAC3, TgCRC230 as well as RNA-seq (expressed in FPKM, in black). The y-axis depicts read density. This view shows an enrichment of H3K14ac, H3K9me3, TgHDAC3 and TgCRC230 at BCLA gene. (d) Left panel: CRISPR-mediated gene disruption of TgHDAC3 leads to TgHDAC3 signal suppression when monitored by immunofluorescence assay. Right panel: CRISPR-mediated gene disruption of TgHDAC3 triggers BCLA overexpression when monitored by immunofluorescence assay.

FIG. 2. BCLA protein reveal a peculiar architecture typified by unstructured and tandemly repeats.

(a) Chart illustration showing the disorder score as a function of protein amino acid position (generated via the IUPred server). SEQ ID NO: 3 is shown. The C-terminal domain end of BCLA (residues 1089 to 1275, hereafter referred as rBCLA) is predicted as structured, as opposed to the rest of the protein containing core repeated motifs. (b) BCLA protein encoded by a type II (ME49) *T. gondii* strain displays 13 repetitions in its structure (TgR1 to TgR13; From top to bottom: SEQ ID Nos 4-16). In house antibodies directed against two peptides (peptides 1 and 2) contained in these repetitions were made by Eurogentec company. (c) BCLA expression monitoring by western-blot using the home-made antibodies raised against the two BCLA-derived peptides shows up-regulation of BCLA after FR235222 treatment compared to DMSO (control).

FIG. 3. BCLA upon FR235222 induction resides within the vacuole space and at the membrane of the vacuole.

(a) Quantification of the intensity of BCLA in each PV following FR235222 stimulation. Each symbol marks the BCLA density of a single PV. The results are represented as mean±standard deviations from two independent experiments; the number of PVs quantified was at least 70. Asterisks indicate statistical significance when comparing each individual FR235222-treated strain and the corresponding control (DMSO, 0.1%) as determined by an unpaired two-tailed Student's t-test (Mann Whitney test) (**** $p<0.0001$; NS, not significant).

Figure 4A:
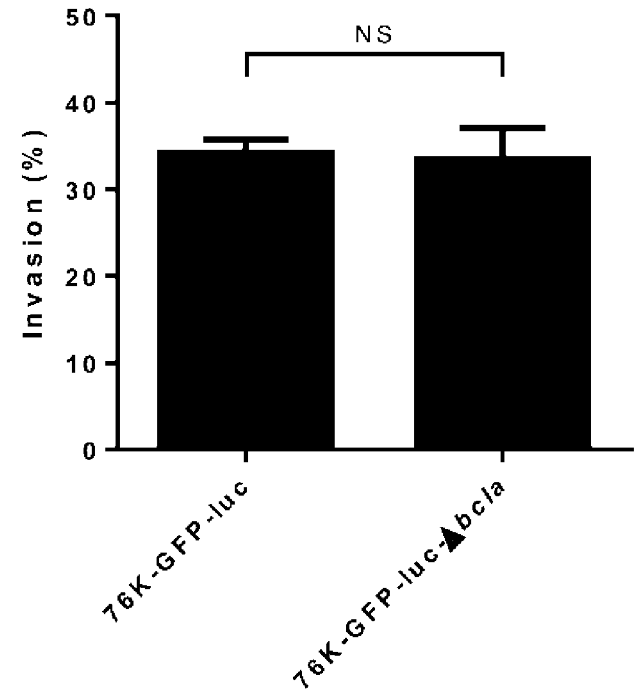
Figure 4A:
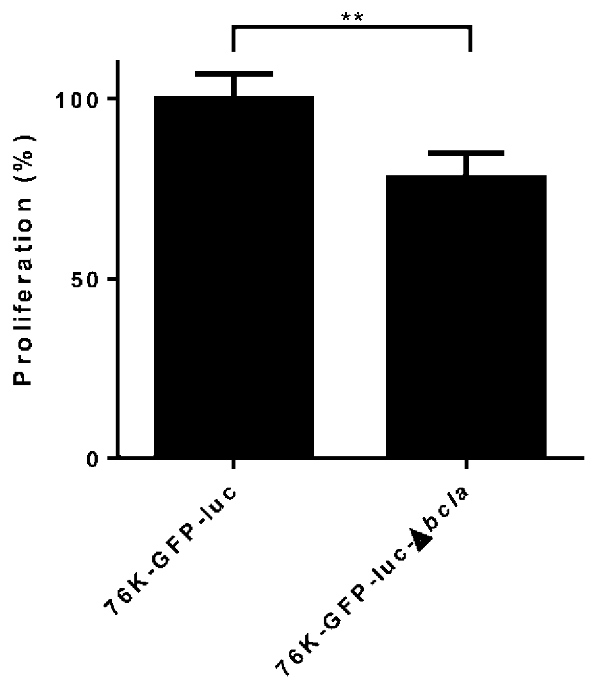

FIG. 4. BCLA deletion is not affecting dramatically parasite growth in vitro nor vacuole formation and maturation.

(a) Evaluation of the percentage of invasion (left panel) in HFFs as well as the intracellular proliferation rate (right panel) of 76k-GFP-luc-Δbcla tachyzoites cultivated in vitro compared to the WT strain. The % of HFFs invasion is quite similar in both strains but the deletion of BCLA induces a 30% decrease of intracellular proliferation. The results are represented as mean±standard deviations from two independent experiments. Asterisks indicate statistical significance when comparing 76k-GFP-luc-Δbcla and 76k-GFP-luc by the Mann Whitney test (an unpaired two-tailed Student's t-test), ** $p<0.01$; NS, not significant.

Figure 5A:
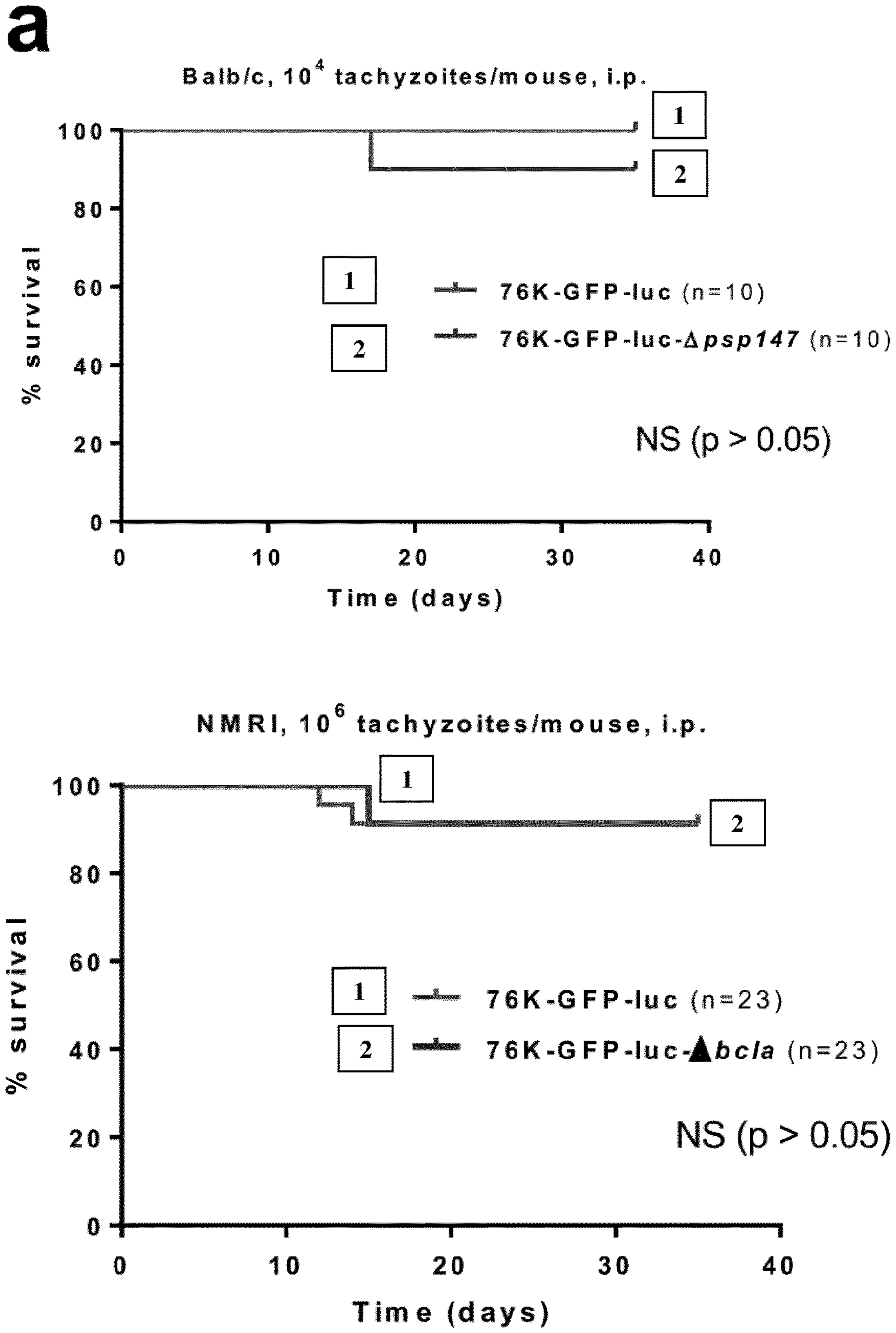
Figure 5B:
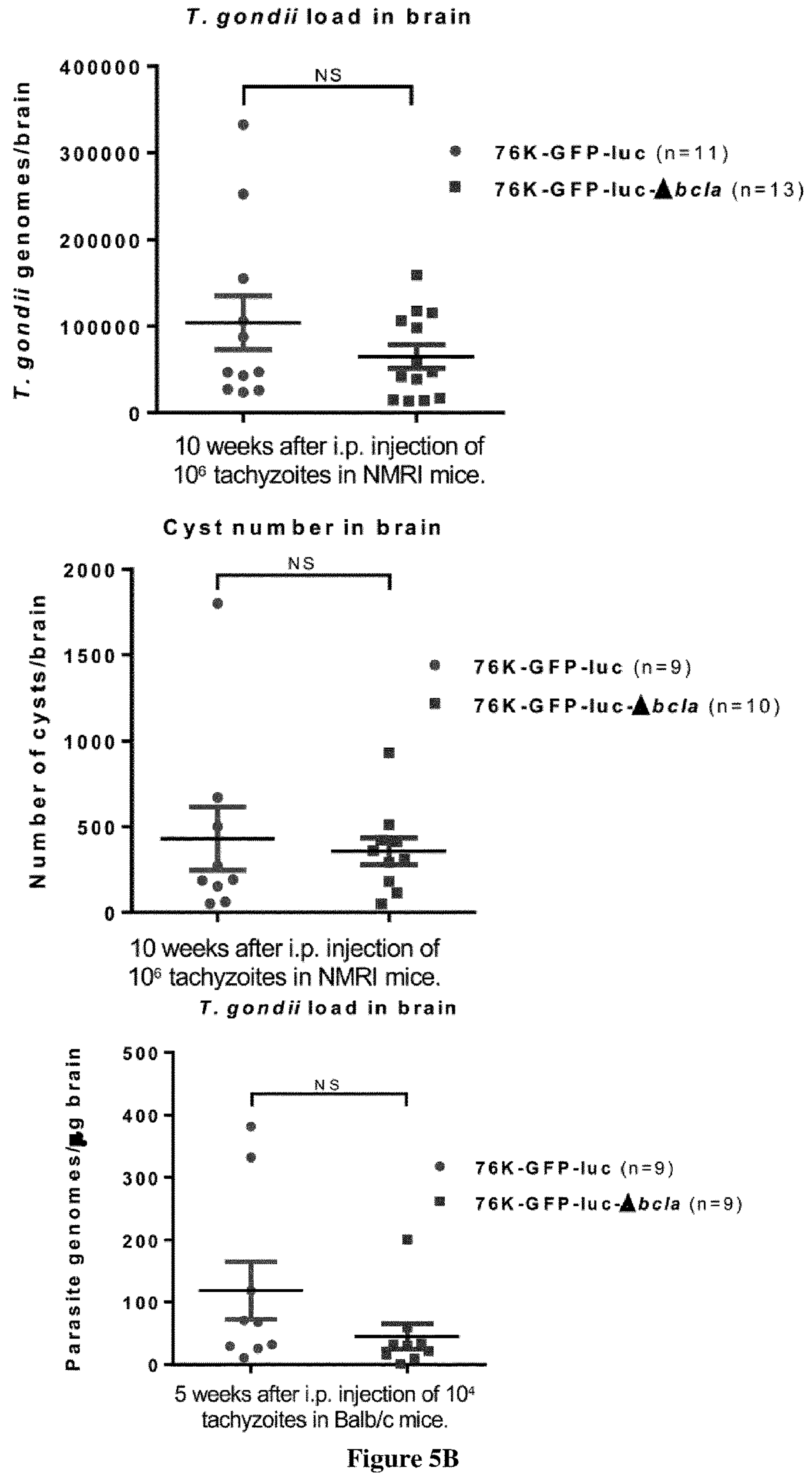

FIG. 5. BCLA deletion does not alter significantly *T. gondii* virulence or cyst burden in mice intraperitoneally infected with tachyzoites.

(a) Comparison of the virulence of 76k-GFP-luc-Δbcla strain with its parental strain 76k-GFP-luc (WT) in Balb/c and NMRI mice. Balb/c mice (n=20) and NMRI mice (n=43) were inoculated by intraperitoneal (i.p.) injection with $10^4$ and $10^6$ tachyzoites respectively, and survival was monitored during 35 days. Significance was tested using Log-rank (Mantel-Cox) test and Gehan-Breslow-Wilcoxon test. Mice infected with Δbcla tachyzoites survived to infection with the same time frame than the WT strain (NS, not significant). (b) Evaluation of the ability of Δbcla strain compared to the WT strain to migrate through the brain blood barrier and to form *T. gondii* cysts in brains of mice chronically infected with *T. gondii*. Brains of NMRI mice and Balb/c mice that survive to challenge presented in (a) were harvested and tested by quantitative PCR±cyst count using microscopy to evaluate the parasitic load and the number of cysts respectively. The results are represented as mean±standard deviations from at least two independent experiments. Statistical significance was tested by an unpaired two-tailed Student's t-test (Mann Whitney test). Mice infected with Δbcla strains show a trends in decrease (but not significant, NS) of the parasitic load and the number of cysts in brain.

Figure 6A:
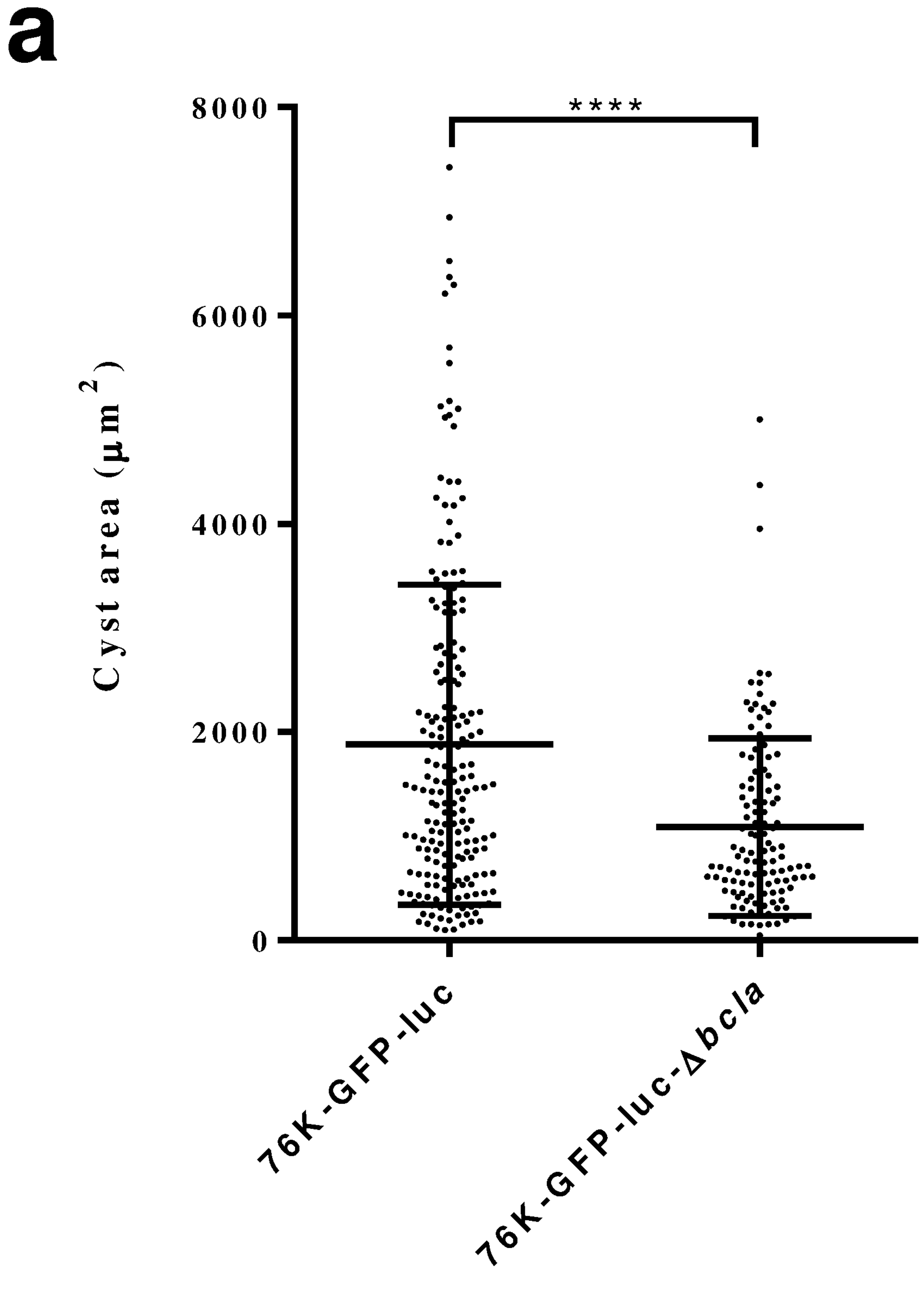

FIG. 6. BCLA-deficient cysts are typified by drastic morphological changes

The cyst morphology of Δbcla bradyzoite-containing cysts was compared with those from the parental 76k-GFP-luc (WT) strain. Brains of NMRI mice that survive to challenge presented in FIG. 6*a* were harvested, the cysts were purified using the Percoll gradient method and were characterized morphologically under microscope. (a) Cyst area and (b) GFP-fluorescence intensity of Δbcla-containing cysts cysts were measured using ZEN software (Zeiss) and compared to those obtained with the WT cysts. Δbcla-containing cysts have a significant lower size and lower GFP-intensity than the WT cysts. The results are represented as mean±standard deviations from at least two independent experiments. Asterisks indicate statistical significance when comparing cyst area of Δbcla-containing cysts and the WT cysts as determined by an unpaired two-tailed Student's t-test (Mann Whitney test) (*** $p<0.001$). Scale bar, 10 μm.

FIG. 7. BCLA deletion is not altering infectivity nor the host immune responses of mice orally fed with cysts.

Evaluation of the virulence and infectivity of the 76k-GFP-luc-Δbcla-containing cysts comparing to the 76k-GFP-luc parental strain (WT). C56BL/6 mice (n=6) and NMRI mice (n=20) were orally infected with 46 cysts and 20 cysts respectively of Δbcla or WT strains. Acute response in ilea was observed in C56BL/6 mice 8 days post-infection. Chronic response in brains was evaluated in NMRI mice 8 to 10 weeks post-infection. (a) Parasitic load in ilea quantified by qPCR of C56BL/6 mice orally infected 8 days earlier. Statistical significance between Δbcla and WT strains was tested by an unpaired two-tailed Student's t-test (Mann Whitney test). No significant difference was observed (NS, not significant). (b) qRT-PCR analysis of cytokines (IFNγ, IL-22, IL-18 and IL-1β) and chemokines (CCL2) in ilea of C56BL/6 mice orally infected 8 days earlier. RNA levels were normalized using TBP levels. Mean values±standard deviations are shown. Statistical significance between Δbcla and WT was tested by the Mann Whitney test. No significant difference was observed (NS, not significant). (c) Brains of NMRI mice orally infected 8-10 weeks earlier were harvested and tested by quantitative PCR and cyst count using microscopy to evaluate the parasitic load and the number of cysts respectively. The results are represented as mean±standard deviations from two independent experiments. Statistical significance between Δbcla and WT was tested by the Mann Whitney test. No significant difference was observed (NS, not significant). Mice infected with Δbcla strains show a trends in decrease (but not significant, NS) of the parasitic load and the number of cysts in brain. (d) qRT-PCR analysis of cytokines (TNF-α, IFNγ, IL-6, IL-22) in brains of NMRI mice orally infected 8-10 weeks earlier. RNA levels were normalized using TBP levels. Mean values±standard deviations are shown. Statistical significance between Δbcla and WT was tested by the Mann Whitney test. No significant difference was observed (NS, not significant).

FIG. 8. rBCLA is not reacting with acutely infected mice sera

Single western-blot strips were loaded with 0.5 μg of recombinant rBCLA. The strips were tested on sera collected from mice in acute phase of toxoplasmosis with various *T. gondii* strains, route of infection and mice genetic background. rBCLA is not reacting with mice antibodies during the acute phase of infection (7-8 days). (a) Immunoblot on sera from NMRI mice infected by intraperitoneal injection (i.p.) of 104 tachyzoites of COUG and COUG-Amyrl (atypical haplotype 11) strains for 7 days. The sera are not reacting with rBCLA. (b) Immunoblot on sera from CBA mice infected by i.p. with 103 tachyzoites of RH (type I) strain for 7 days. The sera are not reacting with rBCLA. (c) Immunoblot on sera from C57BL/6 mice infected by oral route with 47 cysts of 76k-GFP-luc or 76k-GFP-luc-Δbcla (type II) strains for 8 days. The sera are not reacting with rBCLA.

FIG. 9. rBCLA is a serological marker of *T. gondii* chronic infection in mouse model Single western-blot strips were loaded with 0.5 μg of rBCLA and tested on sera collected from mice in sub-chronic (21-41 days) or chronic phase (>42 days) of toxoplasmosis. rBCLA only reacts with anti-*T. gondii* IgG antibodies of mice with sub-chronic or chronic toxoplasmosis following infection by type II cystogenic strains (PruA7, ME49 or 76k-GFP-luc). (a) Immunoblots on sera from Balb/c mice infected by i.p. with 103 to 106 tachyzoites/mouse of PruA7 (type II) strain during 42 days. The sera are reacting quite proportionally with rBCLA according to the tachyzoite load. (b) Immunoblots on sera from CBA mice infected by i.p. with 106 tachyzoites/mouse of ME49 (type II) strain during 80 days. The sera are strongly reacting with rBCLA. (c) Immunoblots on sera from NMRI mice orally infected with 20 cysts of 76k-GFP-luc (type II) strain during 22 months. The sera are strongly reacting with rBCLA. (d) Immunoblots on sera from Balb/c mice infected by i.p. with 106 tachyzoites/mouse of 76k-GFP-luc or 76k-GFP-luc-Δbcla (type II) strains during 21 days. The sera from mice infected with 76k-GFP-luc are strongly reacting with rBCLA, whereas those infected with 76k-GFP-luc-Δbcla are barely reacting with rBCLA. (e) Immunoblots on sera from CBA mice infected by i.p. with $10^3$ tachyzoites/mouse of RH (type I) strain followed by pyrimethamine (PYR) or sulfadiazine (Sulfa) treatment for 22 days. The sera are very slightly reacting with rBCLA. (f, g) Immunoblot on sera from NMRI mice infected by i.p. with (f) CTG (type III) strain or (g) PruAku80 (type II) strain by i.p. with 106 tachyzoites/mouse for 42 days. The sera are not reacting with rBCLA. (h) Immunoblots on sera from Balb/c mice infected by i.p. with 105 tachyzoites/mouse of 76k-GFP-luc (type II) strain and reactivating or not using corticosteroids treatment during 42 days. All the sera are strongly reacting with rBCLA.

FIG. 10. Proteolysis analysis of rBCLA reveals the boundaries of the minimal antigenic region of BCLA.

(a) Analysis of the proteolysis reaction by SDS PAGE. Coomassie coloured SDS PAGE showing the input sample and all these time points (10, 20 and 50 minutes) for every protease (trypsin, chymotrypsin, elastase and papain). (b) Blotted gel incubated with a positive mouse serum and revealed by anti-mouse IgG antibodies. (c) Blotted gel incubated with anti 6his IgGs coupled to peroxidase. The black arrow shows non degraded rBCLA. Red and blue cursor arrows show recurring N-terminal degradations, showing that rBCLA is quickly degraded by chymotrypsin and partially degraded by elastase, trypsin and papain generating stable fragments around the 17-kDa marker.

Figure 11A:
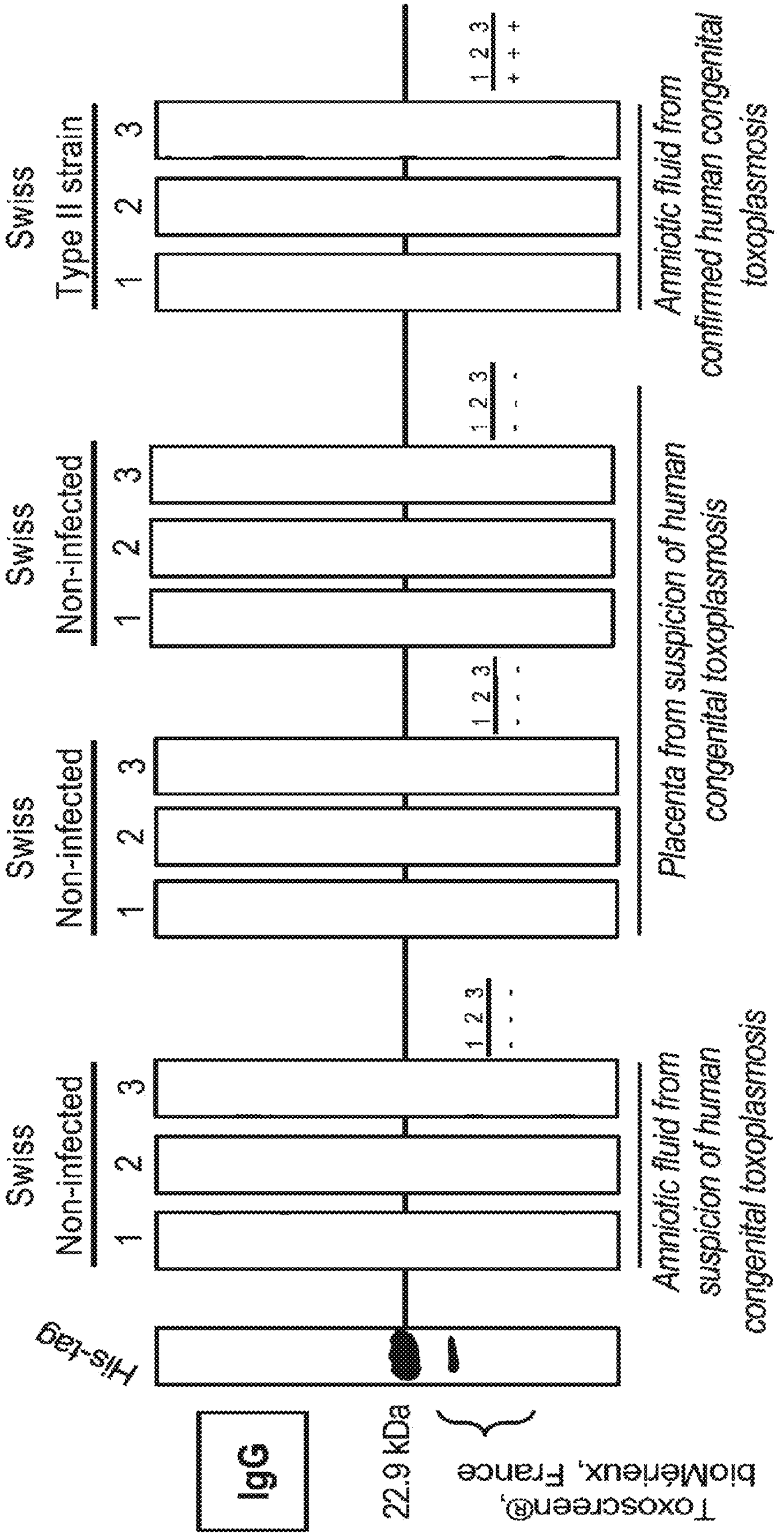

FIG. 11. Evaluation of rBCLA as a serological marker in humans.

Single western-blot strips were loaded with 0.5 μg of rBCLA and tested on mice sera infected with strains isolated from humans or directly on human sera. (a) Immunoblots on sera from Swiss mice i.p. infected with amniotic fluid or placenta from women with suspected (clinically suspected but *T. gondii* PCR negative on amniotic fluid or placenta) or confirmed (*T. gondii* PCR positive on amniotic fluid) congenital toxoplasmosis. The sera from mice infected with positive amniotic fluid are strongly reacting with rBCLA. (b) Immunoblots on sera(S) or aqueous humor (HA) from human patients with or without toxoplasmosis infection. Human sera and aqueous humor were randomly selected from the biobank of the Parasitology-Mycology Clinical Laboratory of Grenoble Alpes University Hospital. For each sample, *Toxoplasma* serological assay was performed using the Vidas® (bioMérieux) and the Architect® (Abbott)) systems, both based on ELISA-derived techniques, and the clinical status was evaluated using the medical records of each patient. Of note, Vidas® is based on rSAG1 antigen, and Architect® on rSAG1 and rGRA8 antigens. The serological results obtained with rBCLA were compared to the serological and clinical status of each patient to evaluate if they were correlated to a specific *T. gondii* serological and/or clinical status. Sera of patients with (α) proven or suspected ocular toxoplasmosis, (β) toxoplasmosis reactivation during hematological disease (immunosuppression) and (γ) recent primary infection (between 1 and 2 months) are reacting with rBCLA. (δ) Sera from 3 seropositive patients qualified as "past immunity" and 1 serum from a quite recent infection (2.5 months) are not reacting with rBCLA. (ζ) All the sera tested from the seronegative patients are not reacting with rBCLA, showing a good specificity of this antigen in humans.

FIG. 12 | Evaluation of BCLA as a serological marker in humans.

(α), Schematic representation of the epitope mapped regions in both the repeat n°4 and rBCLA region (left: SEQ ID NO: 6 and right: SEQ ID NO: 2). Peptide coverage is displayed as a line representing the individual 15aa peptides above or below the peptidic sequence, with partial numbering displayed. Regions displaying significant or strong reactivity are highlighted in full or dashed boxes respectively and each individual peptidic fragment are marked with (* or **).

(b), Epitope mapping of BCLA positive sera. Below, histograms displaying the relative reactivity of peptides on both the core repeat region and rBCLA region, calculated using 5 different positive blots with a negative background subtraction. Above is an example of a dot blot membrane revelation pattern with numbered peptides, performed on a positive human serum. (c), Peptidic dot blots for 5 positive sera and one negative serum with peptide numbering and regions covered. On the right, ELISA titrations for rBCLA and SAG1 (Architect) are shown for these same sera.

FIG. 13. BCLA reactivity in human sera. Scatter plot of individual BCLA ELISA titrations (in UI) grouped within clinical status categories assessed through classical SAG1 serologies (Vidas and Architect IgG/IgM) and other medical pre-conditions. These groups are as follows: SAG1 seronegative patients (blue dot), past immunity patients (diamonds), active *toxoplasma* in immunocompromised patients (cubes), asymptomatic serological reactivation in immunocompromised patients (triangle) and proven ocular toxoplasmosis patients (cube). Histograms display the median BCLA titration value per group and interquartile range. Statistical significance was calculated using the Kruskal-Wallis nonparametric test followed by Dunn's post-test to compare individually all the latter groups with the seronegative patients' groups. Grey zone (70 to 90 UI) and positivity cut-off line (at 90 UI) are indicated.

FIG. 14 rBCLA immunogenicity correlates with cystogenic strains at a chronic stage of infection in mice ($\alpha$) ELISA serological titration of rBCLA reactivity in mice over time and depending *T. gondii* strain. Individual ELISA measurements given in UI are grouped according to *T. gondii* strain type with cystogenic strains (ME49, PruA7, 76K) shown with spots, non cystogenic strains (RH, PruKU80, CTG) shown with stars and ΔBCLA strains (in 76K or PruKU80 backgrounds) shown in triangles. A time segmentation post infection is displayed to distinguish between the acute phase (≤8 days), sub-chronic (21-22 days) and chronic phase (>42 days). (b), rBCLA ELISA reactivity correlation with parasitic load, miR-155 and miR-146a expression. Superposed titrations of rBCLA IgGs (in UI), parasitic load (in parasite qPRC count) and miR-155/miR-142-a are shown for different mice strains (NMRI, Balb-C), non-infected or infected with different *T. gondii* strains all within a chronic infection timeframe (≥11 weeks). Cystogenic strains (ME49, PruA7, 76K) shown with circles, non cystogenic strains (RH, PruKU80, CTG) are shown with stars and ΔBCLA strains (in 76K or PruKU80 backgrounds) are shown in triangles.

FIG. 15: BCLA reactivity in mothers and newborns sera at risk of congenital toxoplasmosis..

(A-B) Violin plots of BCLA ELISA titrations (in UI) in sera of 23 mothers and respective newborns collected at the delivery (mothers) or between birth and 5.5 months of age (babies). (C-D) Violin plots of Sag1 titrations (Vidas® and Architect® IgG/IgM). The sera were grouped within clinical status categories of "mother-newborn" couples without congenital toxoplasmosis (A and C) and couples with confirmed congenital toxoplasmosis (B and D). On the top of each panel the values of the mean±SD are represented while the difference between medians was calculated with Mann Whitney test.

EXAMPLE 1

Materials and Methods

Host cells and parasites culture. HFF primary cells (Bougdour et al., 2009), RAW264.7, L929, HCT116, A549 and HEK293 cells were cultured in Dulbecco's Modified eagle Medium (DMEM) (Thermo fischer Scientific, France) supplemented with 10% heat-inactivated fetal Bovine Serum (FBS) (Invitrogen), 10 mM (4-(2-hydroxyethyl)-1-piperazine ethanesulphonic acid) (HEPES) buffer pH 7.2, 2 mM L-glutamine and 50 μg/ml of penicillin and streptomycin (Thermo Fisher Scientific). Cells were incubated at 37° C. in 5% CO2. The following *Toxoplasma* strains were used in this study: type I (RH, GT1), type II (ME49), type III (CTG), atypical (COUG), *Neospora caninum*; RHΔku80 (Huynh and Carruthers, 2009), PruΔku80 (Fox et al., 2011), PruA7 (Saeij et al., 2007), COUGΔmyrl (Hakimi, unpublished), PruΔku80Δbcla, PruΔku80-HF-BCLA and 76k-GFP-luc-Δbcla obtained in this study. All parasite strains were maintained in vitro by serial passage on monolayers of HFFs. *T. gondii* transfection. *T. gondii* RHΔku80, PruΔku80 and 76k-GFP-luc were electroporated with vectors in cytomix buffer (120 mM KCl, 0.15 mM CaCl2, 10 mM K2HPO4/KH2PO4, pH 7.6, 25 mM HEPES pH 7.6, 2 mM EGTA, 5 mM $MgCl_2$) using a BTX ECM 630 machine (Harvard Apparatus). Electroporation was performed in a 2 mm cuvette at 1.100 V, 25 (2 and 25 μF. Stable transgenic parasites were selected with 1 μM pyrimethamine, single-cloned in 96 well plates by limiting dilution and verified by immunofluorescence assay.

Cas9-mediated C-terminal tagging and gene disruption in *T. gondii*. The plasmid pTOXO_Cas9-CRISPR was described by (Sangaré et al., 2016). The gene of interest (GOI) was BCLA (TGME49_209755) for both C-terminal tagging (HA-Flag (HF)) and gene disruption (KO) using the CRISPR/Cas9 system. Four oligonucleotides corresponding to BCLA were cloned using the Golden strategy. Briefly, primers TgBCLA-CRISP_FWD and TgBCLA-CRISP_REV containing the sgRNA targeting TgBCLA genomic sequence were phosphorylated, annealed and ligated into the linearized pTOXO_Cas9-CRISP plasmid with Bsal, leading to pTOXO_Cas-CRISPR::sgTgBCLA. *T. gondii* tachyzoites were then transfected with the plasmid and grown on HFF cells for 18-36 hours.

Cloning oligonucleotides used in this study were:

```
TgBCLA-KO-CRISP-FWD:
                                        (SEQ ID No 28)
5'-AAGTTGATCACTATTCGTGAAGAAGG-3'

TgBCLA-KO-CRISP-REV:
                                        (SEQ ID No 29)
5'-AAAACCTTCTTCACGAATAGTGATCA-3'

TgBCLA-HF-CRISP-FWD:
                                        (SEQ ID No 30)
5'-AAGTTGGAACGGCGGTACGGCGACCG-3'

TgBCLA-HF-CRISP-REV:
                                        (SEQ ID No 31)
5'-AAAACGGTCGCCGTACCGCCGTTCCA-3'
```

FR235222 treatment and induction. FR235222 was provided by Astellas Pharma Inc. (Osaka, Japan) and dissolved into DMSO as described by Bougdour et al., 2009 and the final concentration in culture medium was either 25 ng/ml or 50 ng/mL. The media containing FR235222 was added to infected HFF cells 16 hours after infection for 24 h to 7 days. Mice and Experimental Infection. 6-weeks-old BALBC/c, CBA, NMRI or Swiss mice were obtained from Janvier Laboratories (Le Genest-Saint-Isle, France). Mouse care and experimental procedures were performed under pathogen free conditions in accordance with established institutional guidance and approved protocols from the Institutional Animal Care and Use Committee of the University Grenoble Alpes (agreement n°B3851610006). Female mice were used for all studies. For intraperitoneal (i.p.) infection, tachyzoites were grown in vitro and extracted from host cells by passage through a 27-gauge needle, washed three times in PBS, and quantified with a haemocytometer. Parasites were diluted in Hank's Balanced Salt Solution (Life), and mice were inoculated by the i.p. route with tachyzoites of each strain (in 200 μl) using a 28-gauge needle. For oral gavage of infective cysts, brains from chronically infected mice (76k-GFP-luc and 76k-GFP-luc-Δbcla) were crushed in PBS, the number of cysts was microscopically quantified and the mice were forced fed with 100 μl of brain homogenate containing 20 to 40 cysts using ball-tipped feeding needle. Blood was collected by caudal puncture or by intracardiac puncture when the mice were euthanised. Animal euthanasia was completed in an approved CO2 chamber. For histological analysis of ileum and immunolabeling on histological sections of brains or, the ilea and brains were removed from mice, entirely embedded in a paraffin wax block and cut in 5 μm-thick layers using microtome. For statistical analysis of mice survival data, the Mantel-Cox and Gehan-Breslow-Wilcoxon tests were used.

Cysts purification. Cysts were isolated from brains of mice chronically infected with the 76k-GFP-luc or the 76k-GFP-luc-Δbcla strains for at least 6 weeks, either using the Percoll gradient method as described previously (Cornelissen et al., 1981), either directly by the cysts using a 10 μl pipet for the dyes experimentation in order not to deteriorate the cyst wall for permeability studies. Neither saponin nor trypsin was added at the end of the experiment.

Cyst quantification. 5 to 12 weeks post-infection, a brain of each of the recipient mice was homogenized in 2 ml of PBS. Numbers of cysts in three or ten aliquots (20 μl each) of the brain suspensions were counted microscopically. The total number of cysts was determined by enumerating the cysts in a 20-μl aliquot and multiplying by 100. For statistical analysis of cysts quantification differences between mice infected with 76k-GFP-luc and 76k-GFP-luc-Δbcla, the non-parametric Wilcoxon-Mann-Whitney test was used.

Cyst characterization. Images of purified cysts were acquired between slide and slip cover with a fluorescence ZEISS ApoTome.2 microscope. Cysts areas and GFP intensities were measured using the ZEN software (Zeiss). For statistical analysis of cysts areas and GFP-intensity differences between 76k-GFP-luc and 76k-GFP-luc-Δbcla cysts, the non-parametric Wilcoxon-Mann-Whitney test was used.

Quantitative PCR. The parasite loads in brain or ileum were quantified following DNA extraction (QiAmp DNA mini kit, Qiagen) using the quantitative PCR targeting of the *Toxoplasma*-specific 529-bp repeat element (Reischl et al., 2003). For statistical analysis of parasitic load differences between mice infected with 76k-GFP-luc and 76k-GFP-luc-Δbcla, the non-parametric Wilcoxon-Mann-Whitney test was used.

qRT-PCR analysis of interleukins in brain and ileum. Total RNA was isolated from brains or ilea using TRIzol (Thermo Fisher Scientific). cDNA was synthesized with random hexamers by using the high Capacity RNA-to-cDNA kit (Applied Biosystems). Samples were analysed by real-time quantitative PCR for appropriate probes (brain: TNF-α, INF-γ, IL-6, IL-22B; ileum: INF-y, CCL2, IL-22β, IL-18 and IL-1β) using TaqMan Gene Expression Master Mix (Applied Biosystems). RNA levels were normalized using TBP levels. qRT-PCR was repeated for three independent biological replicates of each sample and the mean of the results was used. For statistical analysis of RNA levels between mice infected with 76k-GFP-luc and 76k-GFP-luc-Δbcla, the non-parametric Wilcoxon-Mann-Whitney test was used.

Immunofluorescence microscopy. Immunofluorescence assays on in vitro parasites were performed as described previously (Braun et al., 2013). In brief, *T. gondii*-infected HFF cells grown on coverslips or cysts purified from brains of mice were fixed in 3% formaldehyde for 20 min at room temperature, permeabilised with 0.1% (v/v) Triton X-100 for 15 min and blocked in phosphate-buffered saline (PBS) containing 3% (v/v) bovine serum albumin (BSA). For immunolabeling on histological sections of brains, the brain layers spotted on glass slides were first solvent-dewaxed using toluene for 3*10 min and absolute alcohol for 3*10 min. The slides were then treated with citrate buffer pH 6, heated at 100° C. during 1 hour, rinsed with water for 2*10 min and blocked in PBS containing 3% (v/v) bovine serum albumin (BSA). The cells or brain layers were then incubated for 1 hour with the primary antibodies indicated in the figures followed by the addition of secondary antibodies conjugated to Alexa Fluor 488 or 594 (Molecular Probes) at a 1:1,000 dilution for 1 hour. Nuclei of both host cells and parasites were stained for 10 min at room temperature with Hoechst 33258 at 2 μg/ml in PBS. Coverslips were mounted on a glass slide with Mowiol mounting medium, images were acquired with a fluorescence ZEISS ApoTome.2 microscope and images were processed by ZEN software (Zeiss).

Antibodies. Primary antibodies: rabbit anti-BCLA (Eurogentec), mouse anti-HA (Roche, RRID: ab_2314622), rat anti-flag (SIGMA), mouse anti-CC2 (gift from Pr. Louis Weiss), mouse anti-GRA1, mouse anti-GRA5, mouse anti-GRA7. Western blot secondary antibodies were conjugated to alkaline phosphatase (Promega), whereas immunofluorescence secondary antibodies were coupled with Alexa Fluor 488 or Alexa Fluor 494 (Thermo Fisher Scientific).

Western Blot. Proteins were separated by SDS-PAGE and transferred to a polyvinylidene fluoride membrane (Immobilon-P; EMP Millipore) by liquid transfer, and Western blots were probed using appropriate primary antibodies followed by phosphatase-conjugated goat secondary antibodies (Promega). Signals were detected using NBT-BCIP (Amresco).

DBA lectin labelling on in vitro FR235222 parasites and ex vivo cysts. *T. gondii*-infected HFF cells grown on coverslips or cysts purified from brains of mice were fixed in 3% formaldehyde for 20 min at room temperature, permeabilised with 0.1% (v/v) Triton X-100 for 15 min and blocked in phosphate-buffered saline (PBS) containing 3% (v/v) bovine serum albumin (BSA). The infected cells or cysts were stained with 1:100-diluted *Dolichos* lectin for 30 min. The stained vacuoles or cysts were examined with a fluorescence ZEISS ApoTome.2 microscope and images were processed by ZEN software (Zeiss).

Cyst wall permeability. 76k-GFP-luc and 76k-GFP-luc-Δbcla isolated cysts purified from brains of mice were incubated with different dyes of different size (dextran, Texas Red or Cascade Blue, from 3 000 to 40 000 Da, neutral or anionic lysine fixable) (Promega) in 1:100 dilution. After 20 min of incubation at room temperature, the images were acquired with a fluorescence ZEISS ApoTome.2 microscope and images were processed by ZEN software (Zeiss). A minimum of 5 cysts were analysed for each different dye. Cysts incubated in the absence of the dyes were taken as negative controls.

Recombinant Expression of the C-Terminal Domain of BCLA (Cter-BCLA)

Design and cloning. Disorder propensity search (using Dis-EMBL or IUPred) predicts BCLA to be highly disordered throughout most of its sequence including the core repeated motifs. The C-terminal end (approximately from aa 1100 to 1275) is however predicted as structured and may constitute a separate domain. To recombinantly express this domain, the N-terminal boundary was chosen at the methionine 1089 and the original C-terminal end was conserved. DNA synthesis was performed by Genscript to generate a fusion construct composed of Cter-BCLA (1089-1275) with a TEV cleavable N-terminal His-tag (FIG. 1*b*). Codon optimization for *E. coli* was performed and the gene was cloned by Genscript within a pet30-(α) vector (Addgene) using Ndel and Xhol sites.

Recombinant expression. Transformation was performed using BL21 (DE3)-CodonPlus RIL chemically competent *E. coli* (Stratagene) which were incubated on ice with 1 μg of the pet30-(α) Cter-BCLA plasmid for 10 minutes, heat shocked at 42° C. for 45 seconds, pre-incubated 45 min in LB at 37° C. then spread on a LB agar plate containing Kanamycin (Kan) and Chloramphenicol (Chlo) and incubated for 12 h. A single colony was then picked to inoculate a LB/Kan/Chlo 50 ml pre-culture grown for 16 h. 5 ml of grown pre-culture were then used to inoculate 1L flasks of Terrific Broth medium (Formedium) containing Chlo/Kan. Cultures were grown at 37° C. until reaching an OD600 of 0.5-0.8 then induced by adding 0.7 mM IPTG (VWR) and further incubated at 18° C. ON. After incubation, cells were centrifuged 25 min at 3000 G, the supernatant was discarded and the pellet flash frozen in liquid nitrogen and kept at −80° C.

Lysis. Purification was performed on 3 pellets of 1L cultures, each resuspended in 50 ml of lysis buffer containing 600 mM NaCl, 50 mM Tris pH 8, 5 mM Beta-mercaptoethanol (BME), 0.2% w/v N-Lauryl Sarkozine and 1 Complete anti protease cocktail (Roche) tab per 50 ml. Lysis was performed using a 10 mini-pulsed sonication (15 sec ON, 30 sec OFF) at 50° amplitude over ice with the lysate never reaching a temperature over 13° C. After sonication, the lysate was centrifuged at 4° C. for 1 h at 15 000 G and the pellet was discarded. All the following steps were subsequent at 4° C. Prior to incubation with 5 mL of pre-equilibrated Ni-NTA resin, the clarified lysate was supplemented with 30 mM Imidazol. Batch incubation was performed for 30 minutes at 4° C. with a gentle stirring. After incubation, the resin was retained on a vertical column then washed with 3* 20 ml of wash buffer containing 600 mM NaCl, 50 mM Tris pH 8, 5 mM BME, 0.2% w/v N-Lauryl Sarkosine and 30 mM Imidazol. Direct elution with 1.5 ml fractionations was then performed using a buffer containing 300 mM NaCl, 50 mM Tris pH 8, 5 mM BME and 300 mM Imidazole. Fractions of interest (FIG. 8) were then pooled and dialysed in 50 mM NaCl, 50 mM Tris pH 8.5 mM BME using a 10 KDa cut-off dialysis cassette (Thermo Scientific).

Ion exchange and size exclusion chromatography. The entire sample was then directly pumped through the chromatography system (Akta Pure, GE healthcare) onto a HL-Mono-Q (GE healthcare) 5 ml column pre-equilibrated with the same buffer as for dialysis. The column was washed with 2 column volumes (CV) then eluted by a salt gradient (50 mM to 2M NaCl) over 40 ml, 1.5 ml fractions and 280 nm absorbance monitoring was performed for the entirety of the elution. During the elution, SDS PAGE analysis (FIG. 3) reveals that the sample is purified in the later stages of the gradient elution and that the early elution fractions present most of the bacterial contaminants visible at higher molecular weight. Desired fractions were collected, pooled and concentrated to 600 μl using a 10 KDa cut-off concentrator (Amicon-Ultra, Millipore). After concentration, the sample was injected on a S75 (GE healthcare) with a running buffer containing 150 mM NaCl, 50 mM Tris pH 8, 5 mM BME and eluted in a heterogeneous peak consistent with a multimeric state, starting close to the void volume and eluting over 3 ml. All elution fractions were pooled to generate the final sample.

Ammonium sulphate precipitation. To avoid nucleic acid contamination, an ammonium precipitation was performed by adding 15% w/v of ammonium sulphate (Sigma), gentle rolling at 4° C. for 1 h then 30 minutes of centrifugation at 10 000*G. The supernatant was discarded and the pellet resuspended in the same initial volume of buffer. To clear all ammonium sulphate, the sample was dialysed in the same buffer as for the size exclusion.

Limited proteolysis to find antigenic sub-fragments within Cter-BCLA. To recover a highly antigenic sub-fragment of Cter-BCLA, a limited proteolysis on the purified sample was undertaken using trypsin, chymotrypsin, elastase and papain (all Sigma Aldrich). Reactions were carried out in 30 μl reaction volume in 50 mM Tris pH 8.0, 150 mM NaCl, 5 mM BME and 0.5 mM $MgCl_2$. In each reaction, 3 μg of Cter-BCLA were digested by 100 ng of protease (1/30 w/w) over the course of 50 minutes at 37° C. Reactions were stopped at each time point by the addition of 10 μl of SDS PAGE loading buffer followed by 5 minutes heating at 95° C. then kept on ice until loading on the gel.

Western-blot BCLA serological testing. Single western blot strips were prepared using 15 well 4-12% NuPage gels (Life technologies) loaded with 5 μl of sample at 0.1 mg/ml. The gels were run at 185v for 40 minutes in MES buffer then electro-transferred at 105v for 1.5 h on PVDF membranes. The transferred lanes were then cut-out into individualized strips. The strips were then blocked in TTBS with 5% powdered milk (w/v) for 1h. Serum testing was then performed in TTBS with a dilution of 1/400 of the serum for 1 h at 4° C. The strips were then washed 3 times in TTBS and further incubated 1 h with a 1/7500 dilution of secondary antibody targeting either mouse IgGs or human IgGs and coupled with a phosphatase alkaline enzyme (Promega). Following a 3-time TTBS wash, the blots were revealed by the addition of the chromogenic substrate at RT (Invitrogen). Bands in the positive sera appear within 1 to 5 minutes. In parallel to the serum testing, a single strip was always used as an internal antigen control for each blot set. After blocking, this strip was incubated for 1 h with a peroxidase coupled anti poly-histidine monoclonal antibody (Sigma) diluted 1/2000 in TTBS. After three wash steps in TTBS, the blot was revealed using the SigmaFast DAB with metal enhancers (Sigma). For each series of i.p. or orally infected mice, a serum of at least on mouse of each series was checked for *Toxoplasma* antibodies using Western blot analysis of the IgG immune response using the commercial kit LD bio *Toxoplasma* mouse IgG (LD bio), with the same anti-mouse IgG-alkaline phosphatase conjugate and chromogenic substrate previously described for BCLA.

Human sera. Human sera were retrospectively selected from the biobank collection of the Parasitology-Mycology Clinical Laboratory in Grenoble Alpes University Hospital in France. This biobank is registered with the French Ministry of Health number DC-2008-582. The selected sera were stored for toxoplasmosis serological routine analysis between Jan. 1, 2014 and May 1, 2018. The analyses with Vidas® Toxo IgM and IgG (bioMérieux, France) and Architect Toxo IgG and IgM (Abbott, Germany) were performed in the Parasitology-Mycology Clinical Laboratory of Grenoble Alpes University Hospital Protein purification-, immunoblotting- and mass spectrometry-based proteomic analysis. PruΔku80-BCLA-HA-Flag infected host HFFs cells extracts containing Flag-tagged protein were incubated with anti-FLAG M2 affinity gel (Sigma-Aldrich) for 1 hour at 4° C. Beads were washed with 10 column volumes of BC500 buffer (20% glycerol, 20 mM Tris-HCl pH 8.0, 500 mM KCl, 0.05% NP-40, 100 mM PMSF (phenylmethylsulphonyl fluoride), 0.5 mM DTT and 1X protease inhibitor). Bound peptides were eluted stepwise with 250 g/ml FLAG peptide (Sigma-Aldrich) diluted in BC100 buffer. Protein bands were excised from colloidal blue-stained gels (Thermo Fisher Scientific), treated with DTT and iodoacetamide to alkylate the cysteines before in-gel digestion using modified trypsin (Sequencing grade; Promega). Resulting peptides from individual bands were analysed by online nanoLC-MS/MS (UltiMate 3000 coupled to LTQ-Orbitrap Velos Pro; Thermo Fisher Scientific) using a 25-min gradient. Peptides and proteins were identified and quantified using MaxQuant (version 1.5.3.17) through concomitant searches against ToxoDB (20151112 version), and the frequently observed contaminant database embedded in MaxQuant. Minimum peptide length was set to 7 amino acids. Minimum number of peptides, razor+unique peptides, and unique peptides were all set to 1. Maximum false discovery rates were set to 0.01 at peptide and protein levels. Epitope mapping of BCLA repeat and rBCLA. Dot blot peptide assays were custom synthetized by JPT Peptide technologies on cellulose membranes with N-Acetyl moieties on the N-terminus. Two sets of membranes were screened: 1) covering the rBCLA region (res 1089-1275) with a total of 59 peptides, each 15 aa long with an overlap of 12 and an offset of 3; 2) covering repeat 4 (res 446-493) with a total of 18 peptides, each 15 aa long with an overlap of 12 and an offset of 3. Dot blot assays were performed as described by the manufacturer. Briefly, the membranes were first activated 5 min in 100% ethanol then washed 3 times 3 min in DPBS-tween. Blocked O.N at 4° C. in DPBS-Tween 0.5% powdered milk then washed again 3*3 min in DPBS-tween. Tested sera were diluted to 1/400 in DPBS-tween 0.1% BSA and incubated for 3 h at RT with the membrane. Following a 3*3 min DPBS-tween wash, membranes were incubated with anti-IgG peroxidase coupled Ab (Sigma A0170) diluted to 1/100 000 for 2 h at RT. Following a 3*3 min wash in DPBS-tween the membrane was briefly immerged in in the freshly prepared SuperSignal West Pico Chemiluminescent Substrate (ThermoFisher) and revealed using the C-Digit (Licor) scanner. Dot intensity was integrated using ImageJ. Dot intensity was integrated using ImageJ. For data analysis of independent dot blots, integrated intensities from every peptide dot [$I_{(p)}$] were normalised into enrichment factors Fe (p) using the baseline integrated intensity of peptide 59 [$I_{(p=59)}$] which never reacts with any sera. The following can be expressed with the following equation:

$$Fe_{(p)} = I_{(p)} / I_{(p=59)}$$

Where p represents the peptide number.

In order to increase the reactivity score over several independent positive sera blots symbolised as (+), Fe (p) enrichment scores were summed with each other and to subtract the non-specific reactivity, the same sum was performed on the same number of negative sera peptides, symbolised as (−) and subtracted. Peptide reactivity scores can be expressed though the following equation:

$$RS_{(p)}=[\Sigma(Fe_{(p)})^{(+)}-\Sigma(Fe_{(p)})^{(-)}]$$

Where $Rs_{(p)}$ is the total reactivity score at a specific peptide position.

BCLA ELISA. Peptide synthesis: The following BCLA peptides were synthetized by Genscript with N-terminal Acetyl groups:

```
AB_F:
                                        (SEQ ID NNo 55)
Nter-MERPAAGSMEKEKPVLPGEGEGLPKHETKPALTDEKRTKPGGP-
Cter

A3_B:
                                        (SEQ ID No 56)
Nter-AAGSMEKDKLVLPGE-Cter
```

Plate preparation: Midisorp plates (Nunc) were coated O.N at 4° C. with rBCLA, peptides AB_F and A3_B all at 2 μg/ml in 100 mM calcium carbonate buffer pH: 9.6 with 100 μl per well. After coating, plates were washed twice with 350 μl of DPBS 0.05% Tween 20 (DPBS/Tween) then blocked for at least 2 h with 300 μL Superblock blocking buffer (ThermoFisher) after which the buffer was removed and the plates dried upside down. Once dried, the plates can be stored for extended periods of time at 4° C. with no loss in serological reactivity.

Sample preparation: All sera dilutions were prepared in DPBS 0.05% Tween 20, 0.1% BSA no more than 2 h prior to the assay. For both mouse and human tested sera, 1/400 dilutions were prepared. 11 standards were also freshly prepared in both tests, consisting of 10 serial dilutions of a positive frozen stock serum set at 100 UI. Starting at a dilution 1/200 and following a 3/4 dilution increment, the following titration points were prepared: 200 UI (1/200), 150 UI (1/266), 112.5 UI (1/356), 84.4 UI (1/474), 63.3 UI (1/632), 47.5 UI, (1/843) 35.6 UI (1/1124), 26.7 UI (1/1498), 20 UI (1/1998), 15 UI (1/2663). A 0 UI standard was prepared with a seronegative serum diluted at 1/400.

Assay: All the subsequent steps were implemented on the Gemini ELISA automation platform (Stratec) but can also be performed by hand at RT. Dried plates were first washed twice with 350 μl of DPBS/Tween. Dilutions of the tested sera and standards were then distributed in the plates as row duplicates with 100 μl per well. Plates were then incubated 1 h at RT. After the incubation period, plates were washed 4 times with 350 μl of DPBS/Tween, 100 μl of peroxidase coupled secondary antibody dilution (1/50 000 anti-mouse IgG or 1/60 000 anti-human IgG, Sigma Aldrich ref A0168 and A0170 respectively) in DPBS 0.05% Tween 20, 0.1% BSA were then rapidly distributed in all wells. After 1 h at RT, plates were washed 4 times in DPBS tween. Revelation reaction were performed by adding 100 μl of TMB Substrate (Thermofisher ref 34029) for 20 min precisely at RT then stopping the reaction with 50 μl of H2SO4 0.2M followed by 30 sec of mixing. Well absorbance measurement was then performed using the Gemini integrated spectrophotometer at 450 nm.

Data treatment: Blank subtractions were performed on duplicate blank wells, were no primary antibody/sera was disposed in the well but all subsequent steps (washes, secondary Ab, substrate) were performed. Standard sera dilutions were averaged and fitted with a 4-parameter logistic regression with the upper asymptote value (Di) fixed at 2.5 AU and all other variables ($A_i$, $B_i$, $C_i$) allowed to fit. From this regression, tested dilution duplicates could have their apparent UI calculated and averaged, if in a duplicate measurement the coefficient of variation was observed above 10%, then the sample would be re-tested. All the ELISA data presented in this work was obtained several times in independent titrations.

Results

Figure 1D:
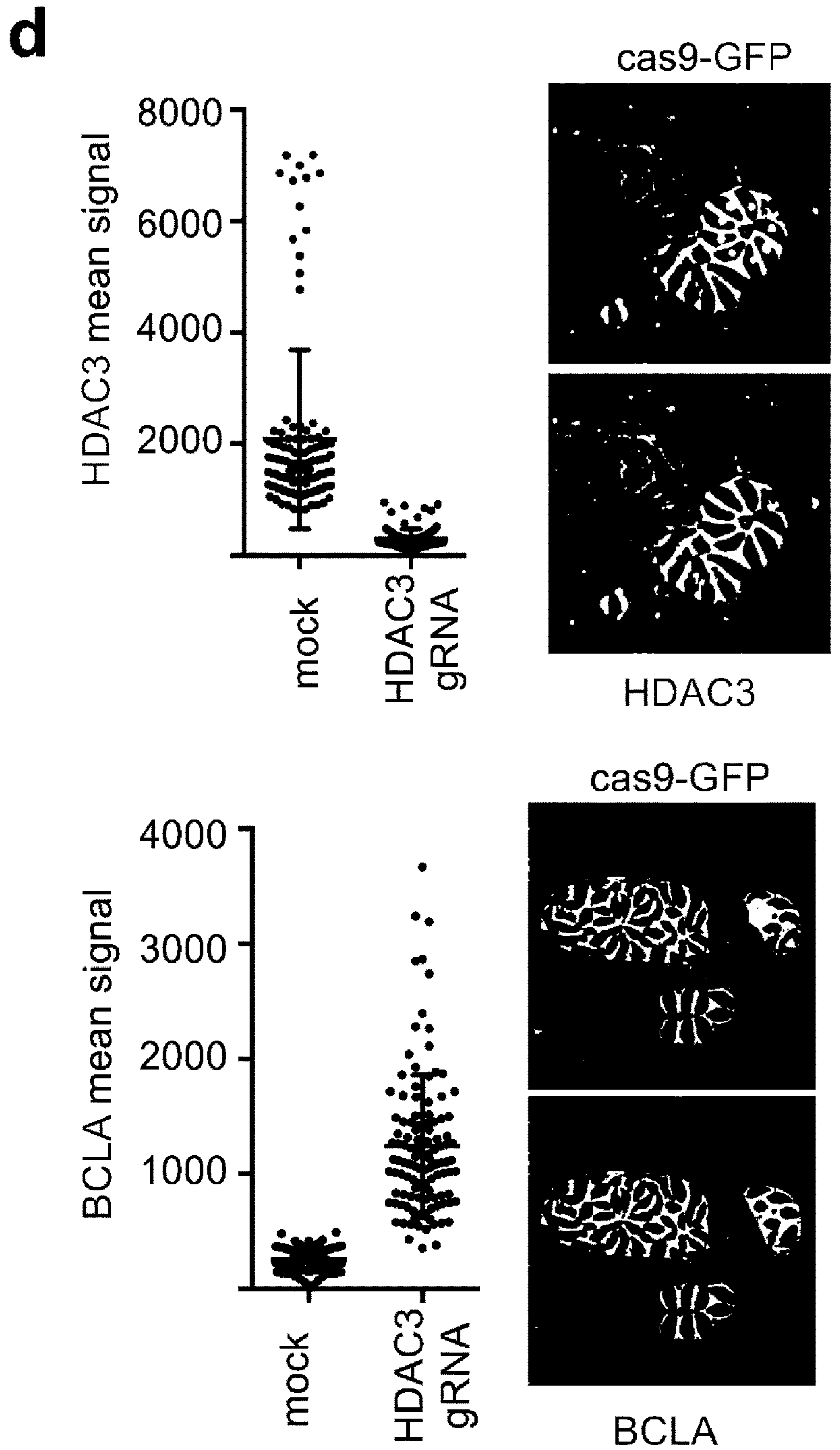

Quantitative Analysis of the Proteome Response to FR235222 in Tachyzoites Identifies BCLA as a Novel Bradyzoite-Specific Protein Specific inhibition of TgHDAC3 by the cyclopeptide FR235222 was shown to disrupt the steady-state level of histone H4 acetylation across the *T. gondii* genome inducing derepression of stage-specific genes (Bougdour et al., 2009; Sindikubwabo et al., 2017). We have exploited the properties of FR235222 to develop an in vitro cystogenesis system capable of producing the quantities of protein needed for large-scale proteome studies (Farhat D et al., manuscript in preparation). Following a treatment at low dose and for a short period of time of a cystogenic type II (PruΔku80) strain, we performed quantitative proteomics studies and uncovered that the FR235222-treated proteome was significantly enriched in stage-specific proteins including those recognized as restricted to bradyzoite stage (FIG. 1*a*). From this analysis, we found that the protein TGME49_209755, hereafter referred as BCLA (Brain Cyst Load-associated Antigen), was significantly induced upon FR235222 treatment (FIG. 1*a*) in the same way that several proteins involved in the chronic phase of infection. This is consistent with its expression profile that was reported as restricted to the bradyzoite data set (FIG. 1*b*, source ToxoDB). Other evidence supports epigenetic regulation of BCLA expression. We recently reported that H3K14ac and H3K9me3 PTMs bookmark genes that are repressed temporally, which await parasite-stage differentiation for stage-specific expression (Sindikubwabo et al., 2017). In tachyzoite, BCLA locus is displaying this dual PTM enrichment that distinctively mark 'poised' stage-specific genes (FIG. 1*c*). Moreover, recent TgHDAC3 ChIP-seq analysis (Farhat D et al., manuscript in preparation) revealed that the presence of the histone deacetylase at the BCLA locus (FIG. 1*c*). Definitive genetic evidence underlying the involvement of TgHDAC3 in its regulation was brought by the CRISPR-mediated gene disruption of TgHDAC3 that caused BCLA induction in transfected tachyzoites (FIG. 1*d*), thereby mimicking the effect of FR235222 on the enzyme. We concluded from these data that BCLA belongs to the family of bradyzoite genes regulated by TgHDAC3 and whose surrounding heterochromatin is typified by the so-called bivalent chromatin domain capable of silencing developmental genes while keeping them poised for rapid activation upon cell differentiation (Sindikubwabo et al., 2017).

Figure 2A:
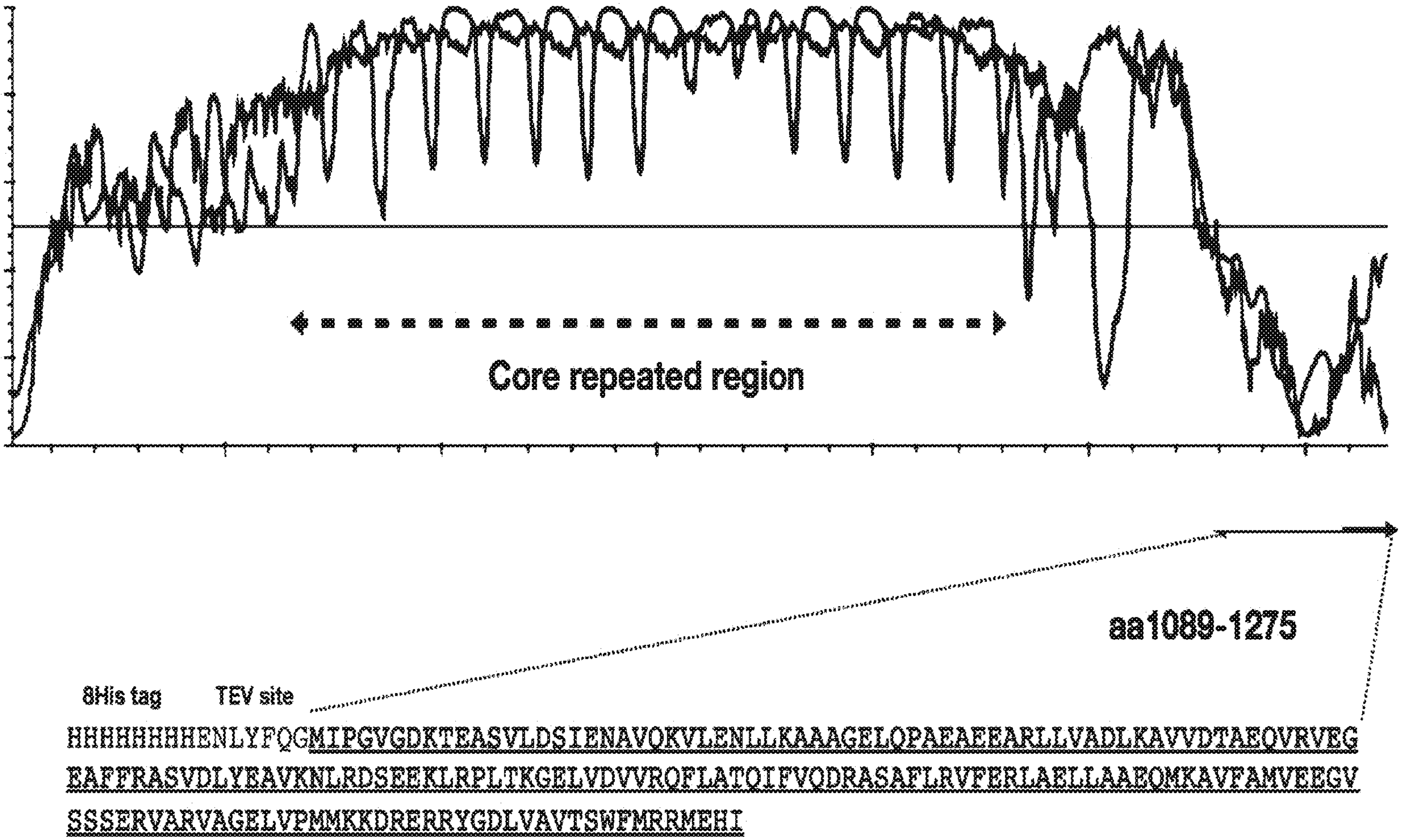

BCLA is Secreted into the PV and Associates with the PVM of In Vitro Converted Bradyzoites-Containing Vacuoles BCLA is a single open reading frame encoding a 140-kDa protein with a predicted N-terminal signal peptide and a conserved C-terminal region of ~150 residues that border a central core domain typified by a motif of 48 amino acids repeated 13 times (FIG. 2*a*), whose the composition and frequency have evolved through coccidian subclasses and among *T. gondii* lineages (FIG. 2*b*). While the BCLA homologous protein is poorly conserved in *Neospora caninum*, it has the overall same architecture with shorter repeats harboring a common signature with BCLA repetitions (data not shown). Disorder propensity search (using dis-embl or IUPred) predicts BCLA to be highly disordered throughout most of its sequence including the core repeated motifs (FIG. 2*a*). The C-terminal end (approximately from aa 1100 to 1275) is however predicted as structured and may constitute a separate domain (FIG. 2*a*).

Although BCLA was unequivocally and exclusively identified by mass spectrometry in FR235222-treated samples (FIG. 1*a*), the dynamics and subcellular distribution of the protein during infection remain understudied. To further probe in situ the kinetics of BLCA in *T. gondii*, we raised polyclonal antibodies against two synthetic peptides located respectively at the extreme end of the conserved repeat (FIG. 2*a*). We first validate the proteome data by showing that exposing cells to FR235222 significantly increased BCLA signal intensity as a protein band at the expected size of ~140-kDa which is otherwise undetectable in untreated tachyzoites (FIG. 2*c*).

In fibroblasts hosting tachyzoites expressing a C-terminal HA-Flag-tagged version of bradyzoite-specific markers, BCLA is distinctly detected upon FR235222 stimulation in the vacuolar space and clearly accumulates at the PVM while its expression coincides with the induction of the bradyzoite markers ENO1 and LDH2 (data not shown). Conversely, BCLA was no longer detected in cells infected with tachyzoites genetically engineered to lack BCLA (Δbcla, Table 2), thereby validating the in-house antibodies specificity (data not shown). Finally, when we monitor BCLA dynamics in type I (RHΔku80) and II (PruΔku80) lines expressing the endogenous protein in fusion with the HA-Flag tags, we show that once stimulated by FR235222 HA-tagged BCLA protein is targeted into the vacuolar space and at the membrane regardless of the strain type (data not shown). Thus, the presence of the C-terminal fusion tag does not affect the subcellular localisation of BCLA as it is similar to those seen while using anti-BCLA sera in the untagged strain.

Figure 3A:
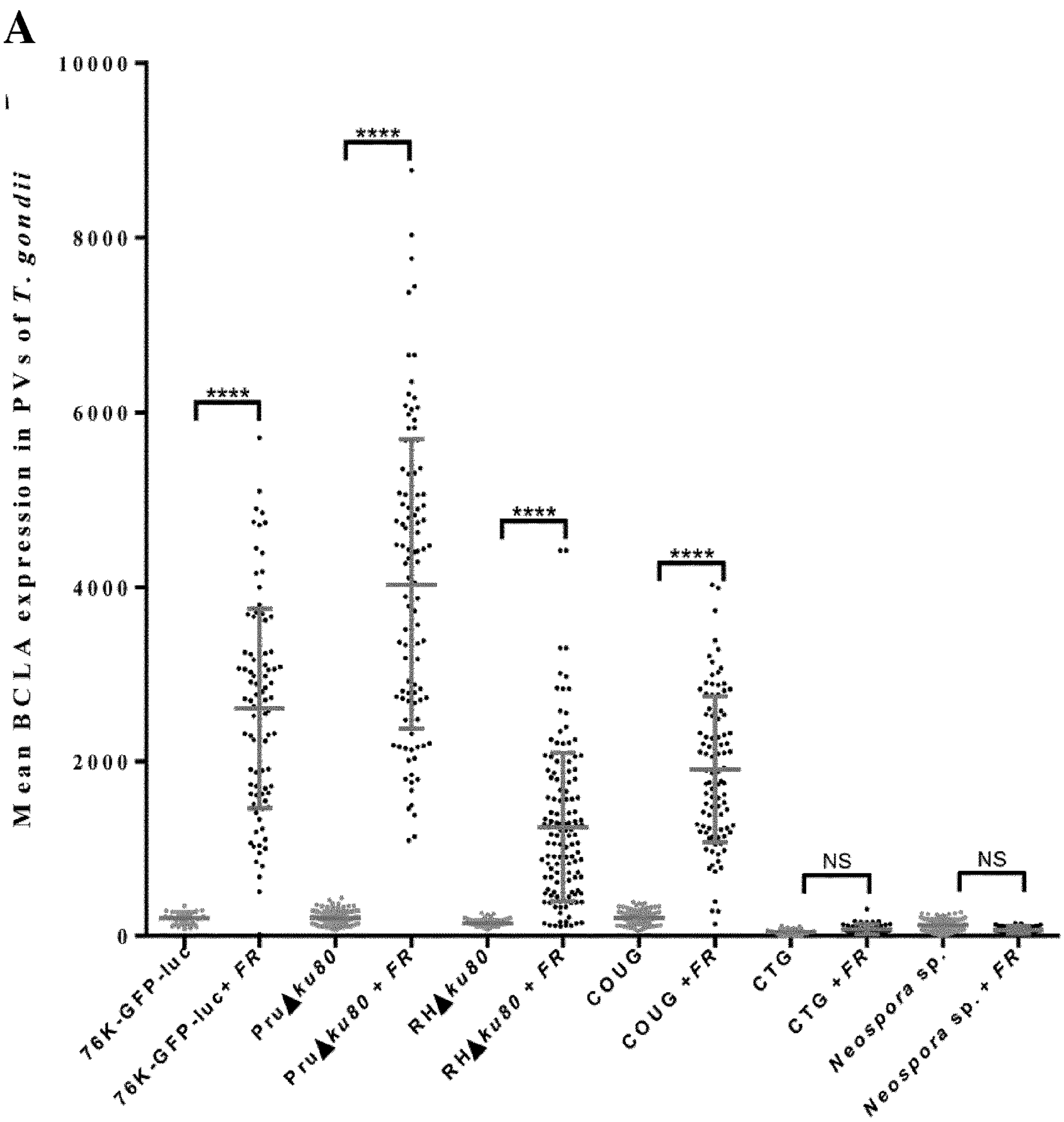

While exposing different parasite strains of *T. gondii* to FR235222, we finally uncovered that BCLA signal intensity greatly varies depending of the infecting strains, ranging from a very strong induction in type II (PruΔku80, ME49, 76K-GFP-Luc) strain, rather moderate with type I (GT1 and RHΔku80) and haplogroup 11 (COUG) strains, and surprisingly a faint (if no) signal was detected in cells infected by a type III (CTG) strain (FIG. 3*a* and data not shown). This discrepancy that could be explained by the ability of the strain to readily develop tissue cysts will be discussed below.

BCLA Localizes In Vivo to the Cyst Matrix and Cyst Wall

The glycosylated cyst wall to which the lectin *Dolichos biflorus* agglutinin (DBA) binds is the key structural feature that facilitates persistence and oral transmission of *T. gondii* (Tomita et al., 2013). Here we brought strong evidence of a co-staining of BCLA with DBA exclusively at the membrane surrounding in vitro converted bradyzoites (data not shown) strongly indicating that BCLA, following its delivery into the vacuolar space, accumulates overtime at the wall of immature cysts (based on thin DBA-positive cyst walls).

Yet, considering that in vitro bradyzoite development in tissue culture does not lead to completely mature cysts, we re-examined the localization of BCLA in bradyzoite-containing cysts isolated from mice chronically infected by *T. gondii* type II strains. In chronically-infected mice, in-house antibodies raised against BCLA stain the cyst wall as well as the matrix space surrounding bradyzoites (data not shown) The immunofluorescence results did not allow to determine unambiguously, whether the BCLA was located in the inner or in the outer layer of the cyst wall, however and interestingly, non-permeabilized ex-vivo cysts are readily stained by the antibodies, suggesting the outside location of the protein (data not shown) and therefore its exposure to the cytoplasm of the host cell. No signals were detected on cysts hosting Δbcla bradyzoites (data not shown), therefore validating in vivo the specificity of the anti-BCLA antibodies.

There is not much evidence of extra-vacuolar function of BCLA yet occasionally the protein appears to be exported beyond the vacuolar membrane into the cytoplasm of the host cell (data not shown). Unfortunately, despite many attempts, we did not find the ad hoc conditions underlying BCLA export beyond the PVM to further study in more detail its function in the host cell, if any, as we did for other effectors (Hakimi et al., 2017). Nevertheless, we were able to show that BCLA export was Myrl-independent (data not shown) and as such does not require the *T. gondii* translocon of exported proteins (Franco et al., 2016). An elegant way to explain the accumulation of the protein in the cytosol of the infected cell is its release after a processing that would take place at the PVM likely under the control of a protease of the host but this remains to be demonstrated. An analysis of the BCLA-associated proteome of an infected and FR235222-stimulated host cell will be performed to determine whether BCLA interactions, if any, with host cell proteins (including protease) occur on the outward-facing side of the PVM or even in the cytoplasm of the infected cell when BCLA is delivered there.

BCLA is Dispensable for Proper Cyst Function In Vivo

To determine the function of BCLA in the bradyzoite tissue cyst, we created two parasite line in which the coding region of BCLA was either deleted (Prusku80Δbcla) or interrupted by a DHFR cassette using Cas9-mediated gene editing (76K-GFP-LucΔbcla) (Table 2). We then investigated pathogenesis and cyst formation. First, BCLA-deficient strains showed no obvious growth phenotype when compared to their parental strains in vitro under tachyzoite conditions (FIG. 4*a* and data not shown). BCLA mutation does not impair the expression nor the localization of PV-resident or PVM-associated proteins recognized in previous studies as involved in the formation and maturation of the PV (i.e., GRA1, GRA5, GRA7; data not shown). No difference was either detected in the ability of the BCLA-deficient parasites to convert in vitro to the bradyzoite stage and to form cysts as shown by the Δbcla-containing vacuoles positively labeled by the lectin DBA following FR235222 stimulation (data not shown).

BCLA is not Essential for Initiating an In Vivo Infection with Tachyzoites.

To investigate the importance of BCLA in vivo during acute infection, we compared the parasitic process in BALB/c or NMRI mice infected intraperitoneally (i.p.) of either WT or BCLA-deficient parasites from type II background, the inoculum content ranging from $1\times10^4$ to $1\times10^6$ tachyzoites. At 5-8 days after infection, all mice infected with type II BCLA-deficient tachyzoites began to show signs of infection (i.e. weight loss and ruffled fur) and survived to infection with the same time frame that the parental strain 76K, regardless of the inoculum and the genetic background of mice (FIG. 5*a*). Thus, BCLA appears to be unnecessary for in vivo growth and pathogenesis during the acute phase of infection in mice. Animals that survived challenge were subsequently tested 10 weeks post-infection for serological responses to parasite antigens by Western blot (data not shown). Distinctly, BCLA deletion does not impair the infectivity as all mice showed IgG against *T. gondii* with the same pattern regardless of the parasite strain (data not shown).

BCLA Deficiency Affects Integrity of Brain Cyst Isolated from Chronically Infected Mice.

Figure 6B:
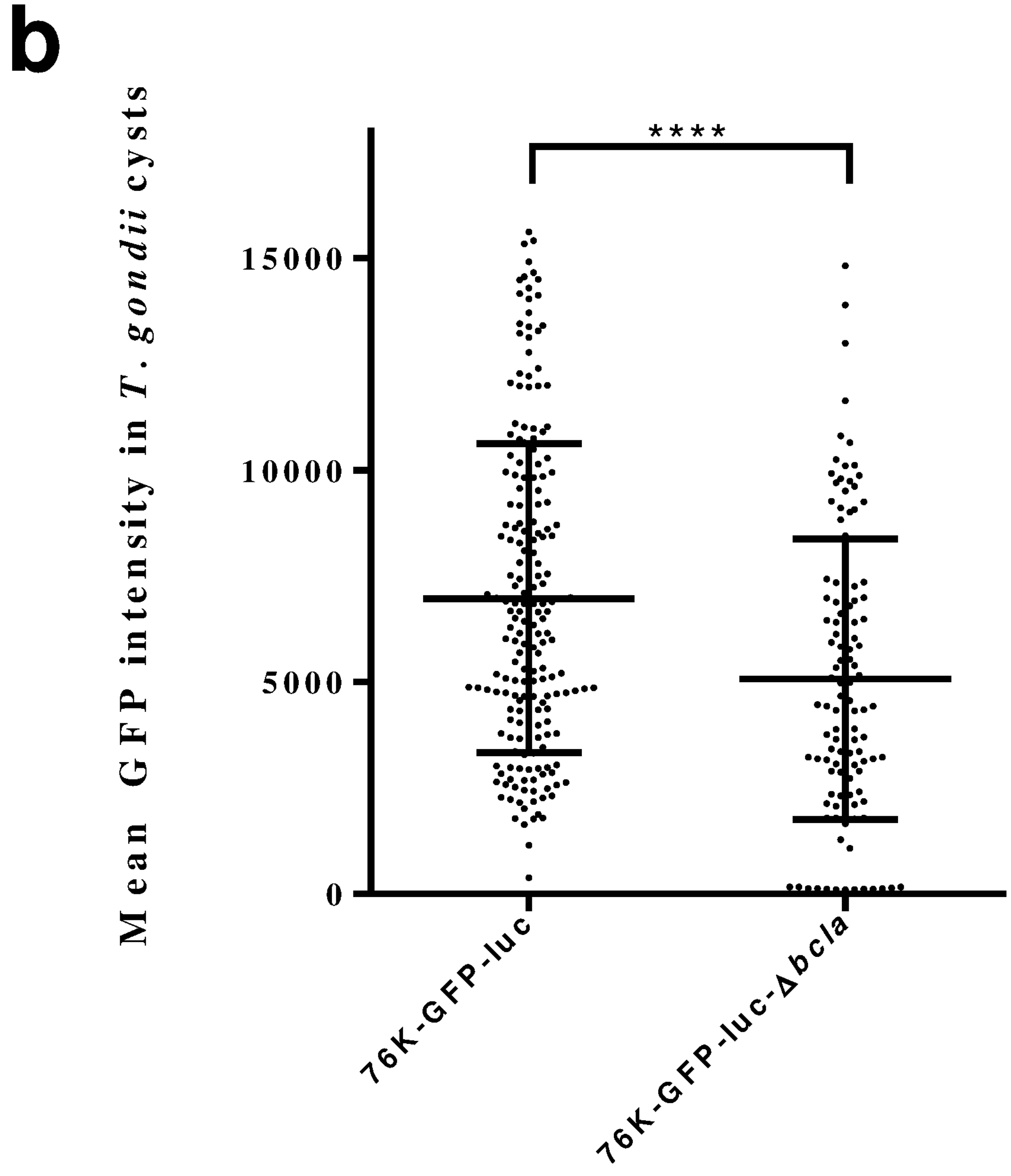

Examination of brains of mice infected with Δbcla mutants demonstrated that cyst formation could still occur in the context of the mutated strains (FIG. 6*b*). Yet BCLA-deficient mutants produce a rather reduced parasite burden in the CNS of chronically infected mice compared to the parental strain but the differences did not reach statistical significance (FIG. 6*b* and data not shown), attesting that BCLA is not dispensable at least for establishing and maintaining cysts during a chronic infection. A thorough examination of the cysts revealed however that those isolated from mice infected with the mutant parasites are relatively smaller (FIG. 6*a*) and contain fewer bradyzoites resulting in "a lower packing density" (Watts et al., 2015) and overall decline in GFP fluorescence (FIG. 6*b*), which is quite consistent with the slight decline in parasite load measured in the total brain (FIG. 6*b*). Beyond these quantitative indicators, Δbcla-containing cysts were peculiarly typified by significant deformations of their cyst wall surface leading to the loss of the circularity and to some extent by peculiar "budding" and "segmented or cracked" phenotypes (FIG. 6*a* and data not shown), revealing a possible role of BCLA in cyst growth, maintenance, and/or stability.

We then assessed whether the surface deformities would make the cyst fragile, a phenotype previously reported for brain Δcstl-containing cysts (Tomita et al., 2013). While during their isolation cysts were subjected to mechanical stress to release them from brain tissue to purify them by isopycnic centrifugation (see method), we did not observe during this harsh procedure that Δbcla-containing cysts were more fragile than the WT cysts (data not shown), yet few of them broke apart regardless of the genetic background.

The deletion of BCLA does not impair either the wall staining by *Dolichos* bifluorus lectin (DBA) of cysts isolated from the brain of chronically infected mice (data not shown). Therefore and as already concluded on tachyzoites treated by FR235222, BCLA is not directly implied in the GalNAc glycosylation of the cyst wall. The viability of bradyzoite within the cysts is conditioned to the permeability of the wall to the nutrients that come from the host cell, yet the latter is very limited, the wall functioning as a sieve, to avoid the components of the immune response. To test if the wall permeability was altered to some way in absence of BCLA we monitored the entry into the cysts of fluorophores, typified by different sizes ranging from 3 to 40 kDa. Only intact cysts (with no leak of parasites) were visualized under the microscope and examined. The permeability was quite similar between WT and BCLA-deficient cysts with either the 3-kDa (diffuse pattern throughout the cyst matrix) or the 10-kDa (diffuse pattern with punctuated location) dyes. Interestingly, the fluorescent tracer with higher molecular mass (40-kDa) was not efficiently able to cross the cyst wall as reported previously (Lemgruber et al., 2011). Moreover, the weak labelling was even different between the strains, likely because Δbcla-containing cysts are more "loosed" and permeable than those containing the parental strain, more filled with bradyzoites surrounded by a less permeable, well defined and continuous cyst wall (data not shown). Overall our results show that BCLA is dispensable for proper cyst function in vivo yet the protein has an architectural role in the cyst wall that may lead to a cyst wall permeability defect phenotype.

BCLA is not Essential for Efficient Oral Infection by *Toxoplasma* Bradyzoite-Containing Cysts.

Figure 7A:
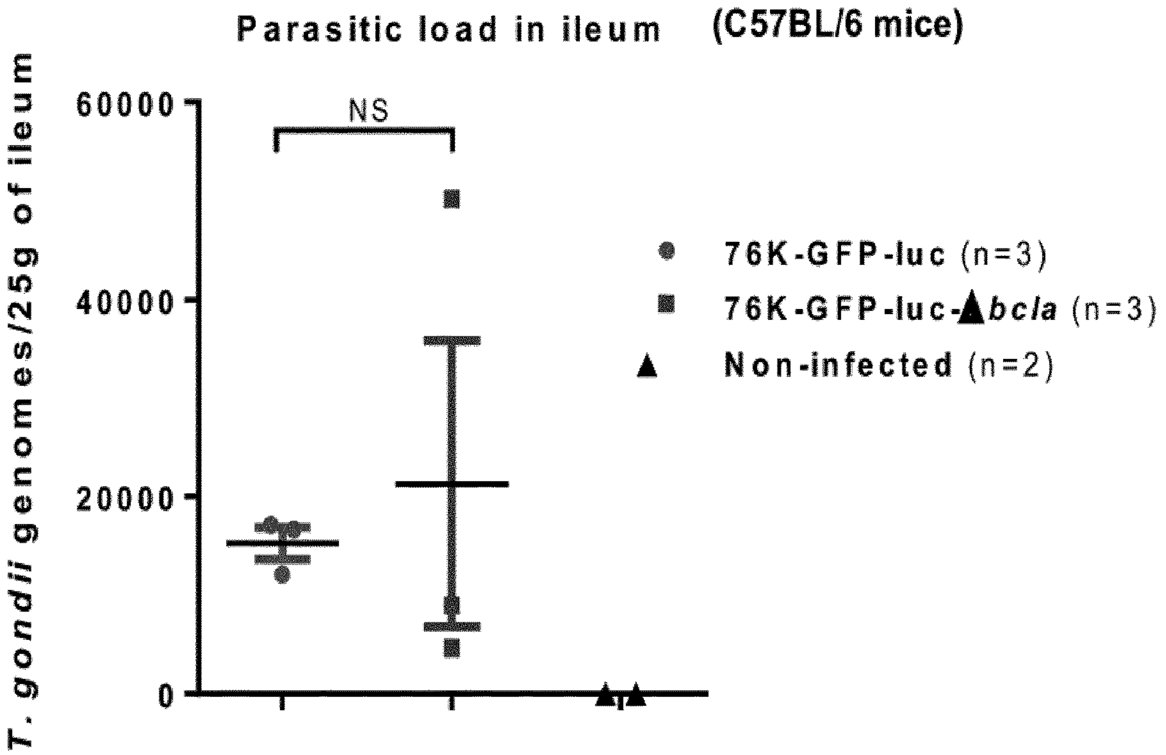
Figure 7B:
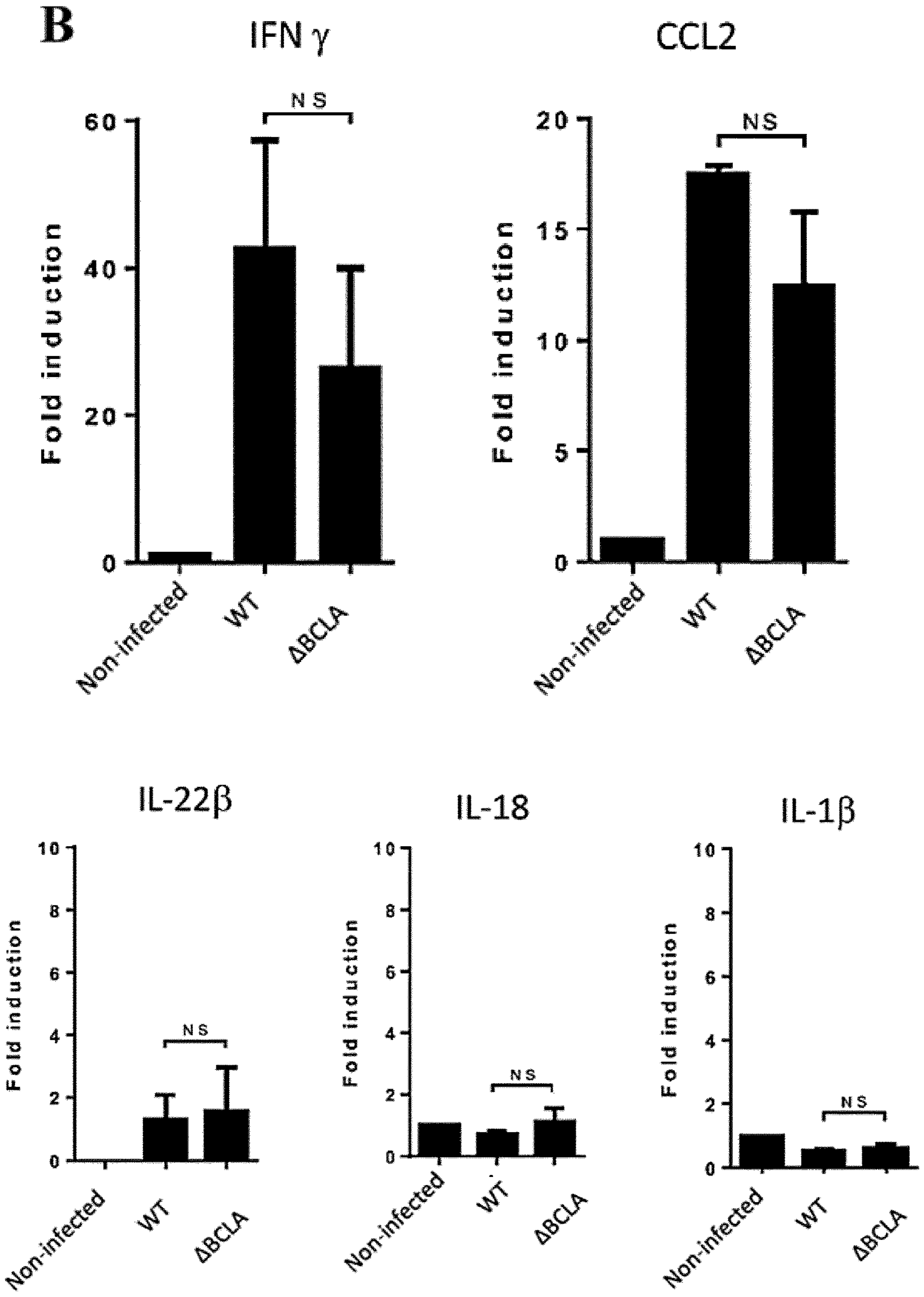
Figure 7C:
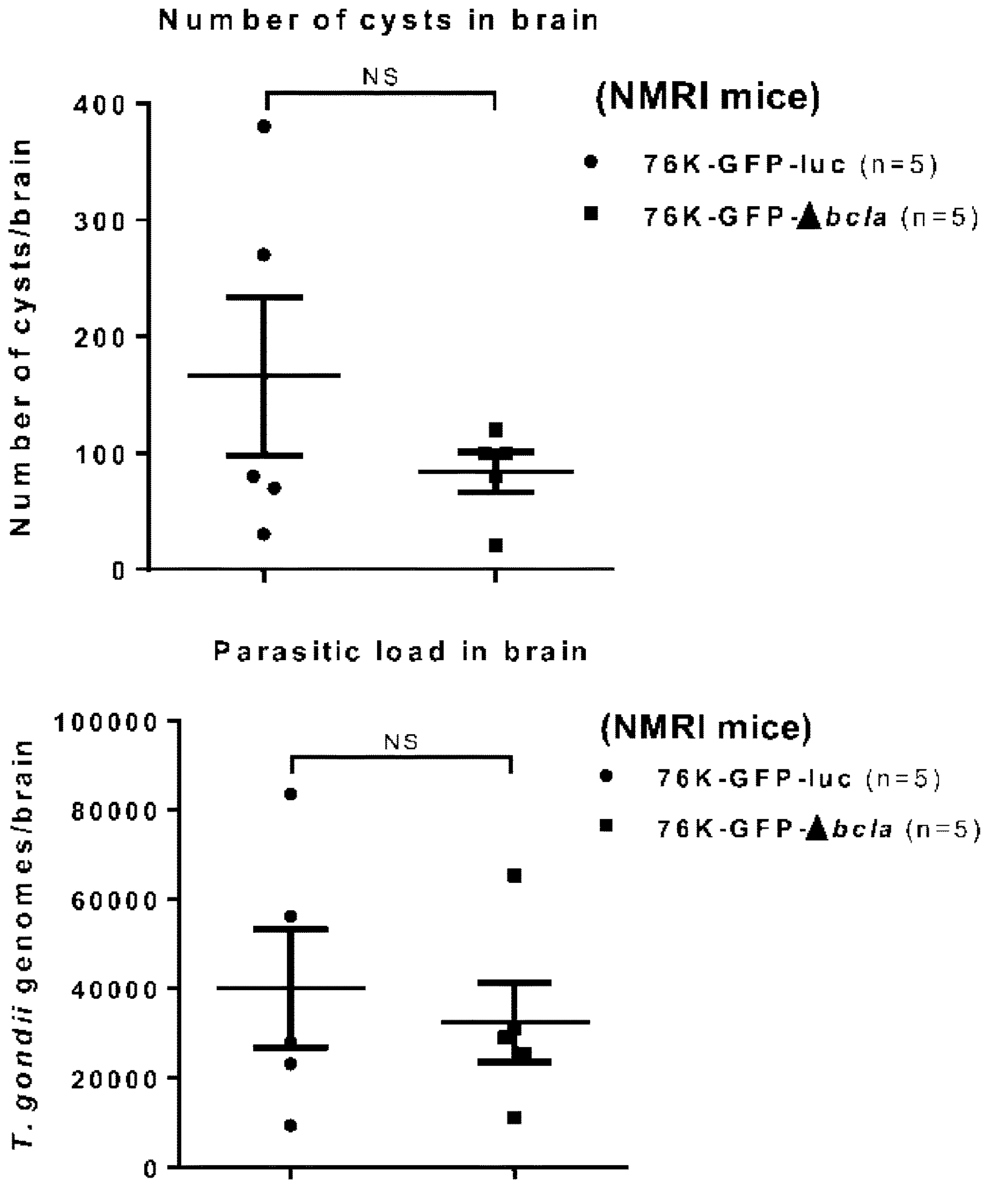
Figure 7D:
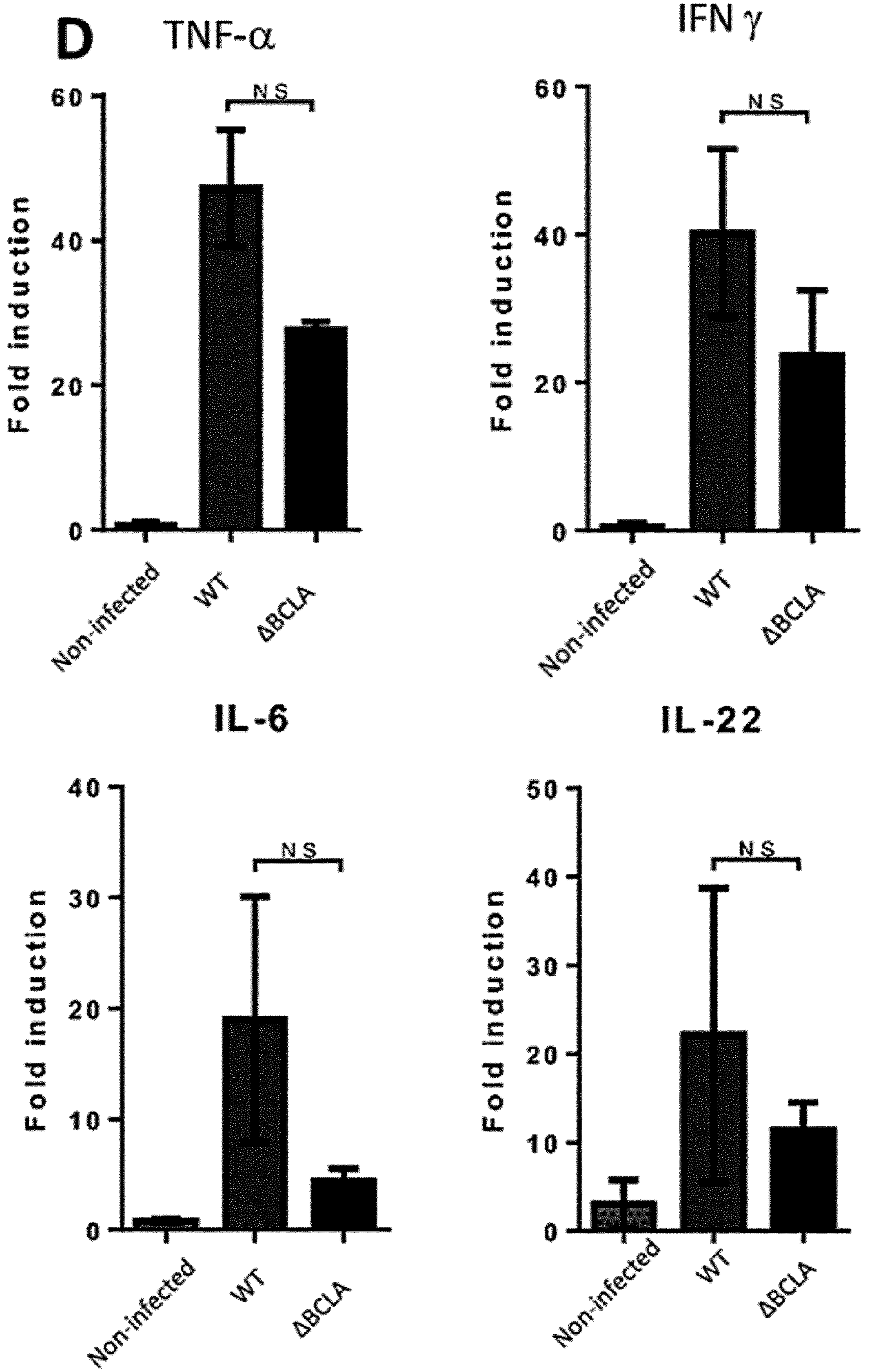

To examine the functional consequences in vivo of BCLA-dependent cysts deformation, we fed mice with Δbcla- or parental strains-containing cysts and assessed the virulence and infectivity in two different mice genetic backgrounds. C57BL/6 mice were orally infected with 46 cysts of the 76k-GFP-luc-Δbcla or 76k-GFP-WT strains and the kinetics of invasion and dissemination of the parasite in the gut as well as the local immune responses elicited by the parasite were studied. At day 8 of infection, the levels of *T. gondii*-specific IgG in mouse sera were quite similar (data not shown) and they were no significant differences in the parasite load in ilea (FIG. 7*a*). Histological analysis of the ilea show the overall loss of intestinal epithelial architecture with altered crypt-villus morphology (data not shown) with inflammatory loci (data not shown), regardless of the strain genetic background. The cytokine profile displays the same pattern with a clear increase in proinflammatory cytokines (IFNγ) and chemokine (CCL2) in the ileum but in BCLA-independent manner (FIG. 7*b*). We next orally infected NMRI mice with 20 cysts to evaluate the ability of Δbcla cysts to disseminate into the blood stream and to form new cysts in deep tissues. All the orally infected mice showed signs of illness (drop in weight) through the acute phase of infection and sero-converted (data not shown). After 10 weeks and for all mice, no significant difference in cyst number, nor in parasitic load were detected between the strains (FIG. 7*c*). These data indicate that BCLA-deficient cysts are able to transmit infection by the oral route and to set up a chronic infection in mice typified by a mild inflammation status. Profiling of pro-inflammatory cytokines in brains of NMRI mice chronically infected suggested that inflammation was less severe in Δbcla than the wild-type yet this did not achieve statistical significance likely due to the low sample size (3 mice for each condition; FIG. 7*d*). This relatively mild inflammation in the brain can be a result of the relatively small number of cysts in Δbcla-infected mice, yet this has to be determined.

High-Level Expression and Purification of BCLA Chimeric Peptides for Serological Diagnosis The humoral and cellular defences of the innate immune system are the body's first lines of defense against *T. gondii*. Antibodies were reported to assist the clearing of parasites during acute infection and mediate resistance to secondary *Toxoplasma* infection (Sayles et al., 2000). As such, once immunity has been established, IgG protects the fetus from a vertical transmission during pregnancy. While serologic differentiation between acute and chronic infections has clinical and epidemiological relevance, yet there is currently no bradyzoite-specific serological assay for toxoplasmosis to estimate accurately the time of infection as well as the presence of cysts. Moreover, since reactivation can both occur in perfectly immunocompetent patient (e.g. retinochoroiditis) and in immunocompromised patients, and cyst presence in brain was recently suspected to be linked to some neuropsychiatric disorders. Thus, detecting toxoplasmic antibodies directed against semi-dormant cysts would be a significant improvement to the serological diagnosis of toxoplasmosis by opening new diagnostic perspectives. However, few components of the cyst wall or surface bradyzoite have been identified, and none were shown to serve as antigen for serology purpose, at least in commercial kits. The ideal antigen should be expressed exclusively in latent bradyzoite stage and ideally should be exposed to the surface of the cyst, two features found in BCLA that motivated us to test its antigenicity.

Figures 8A, 8B:
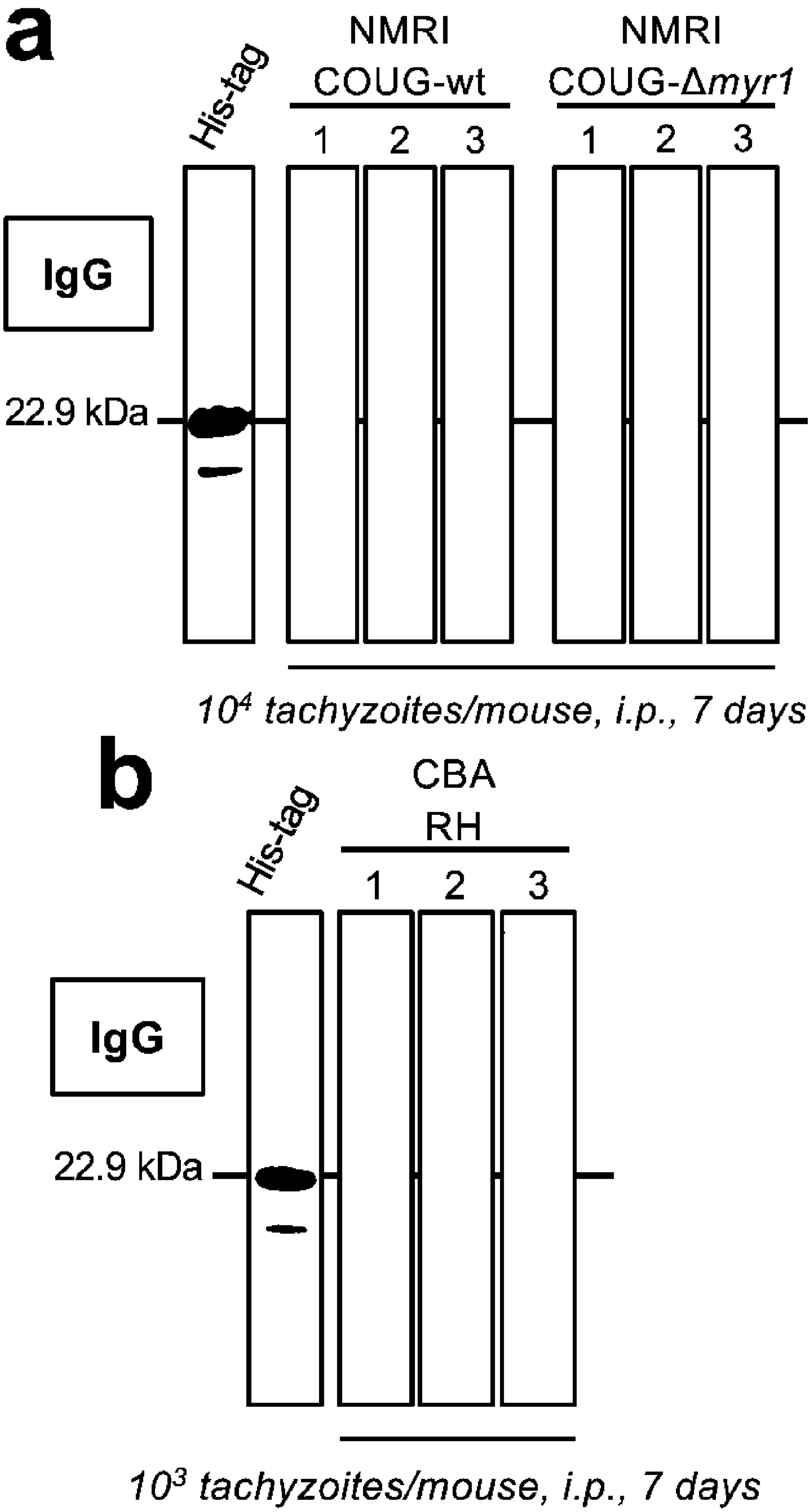
Figure 8C:
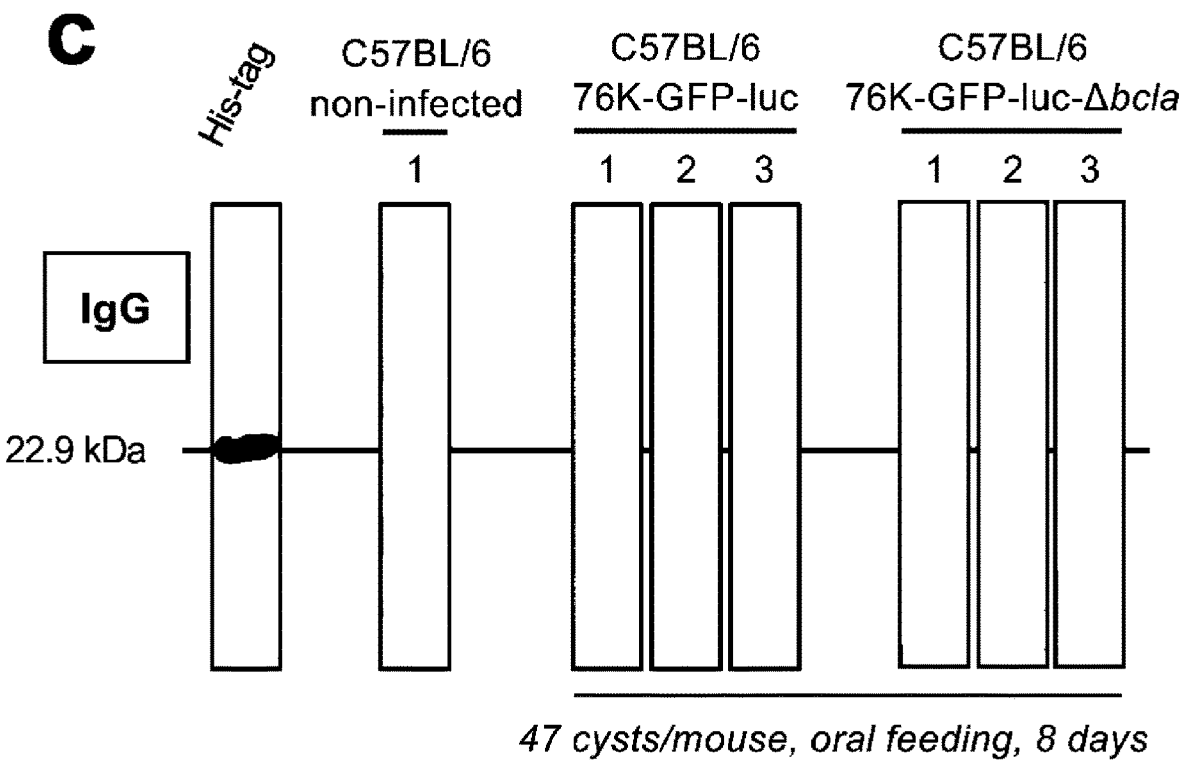
Figures 9A, 9B:
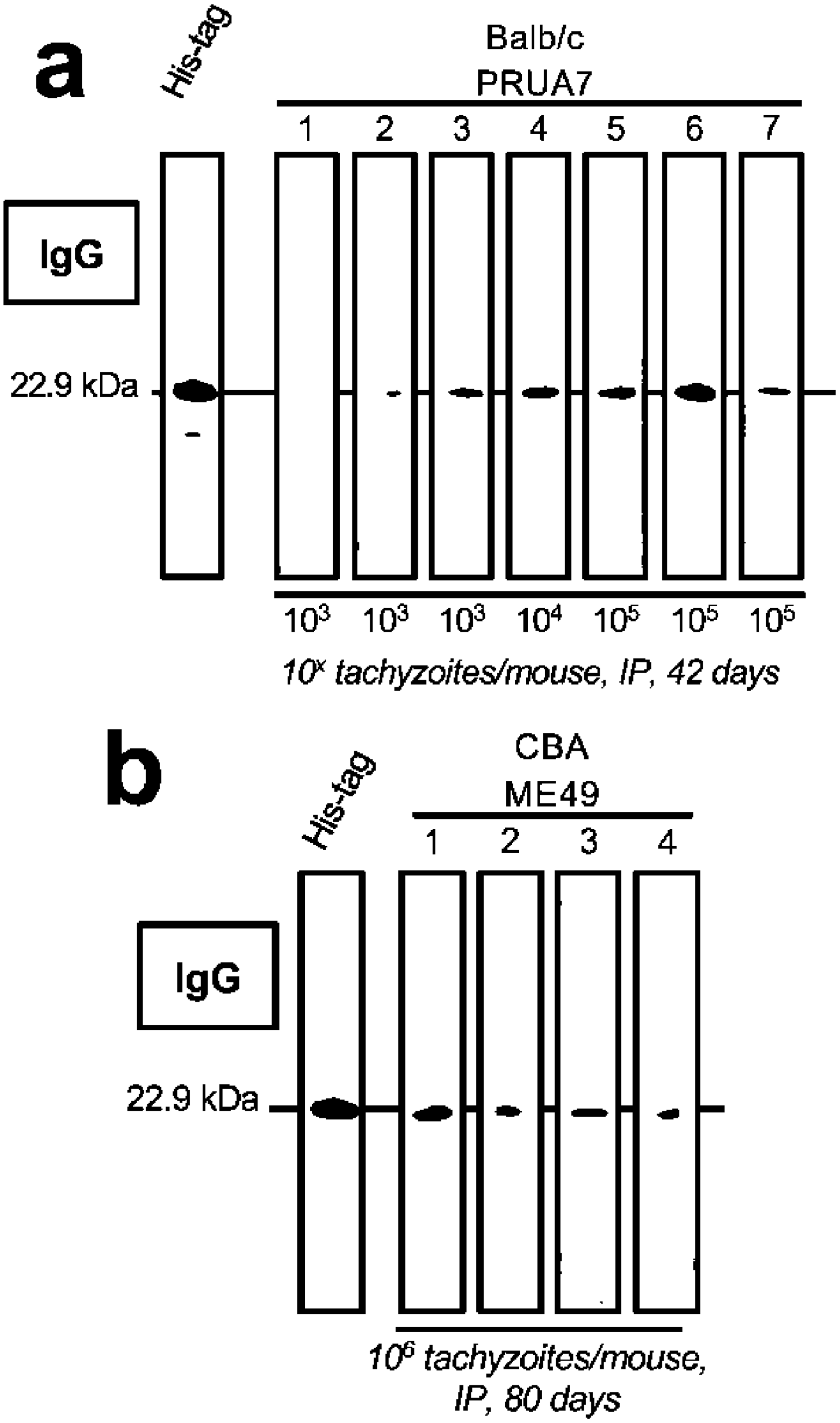
Figures 9C, 9D:
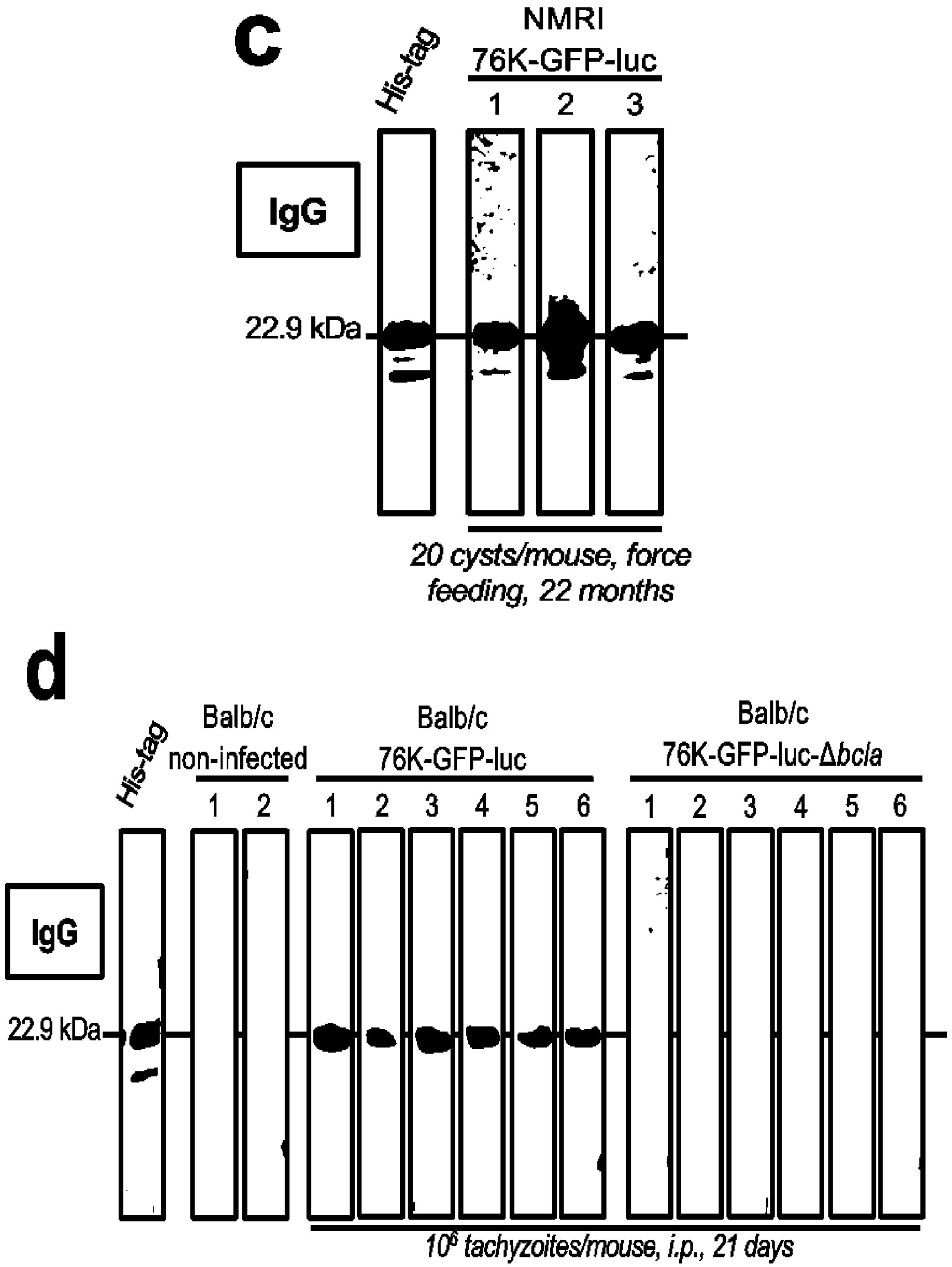
Figure 9E:
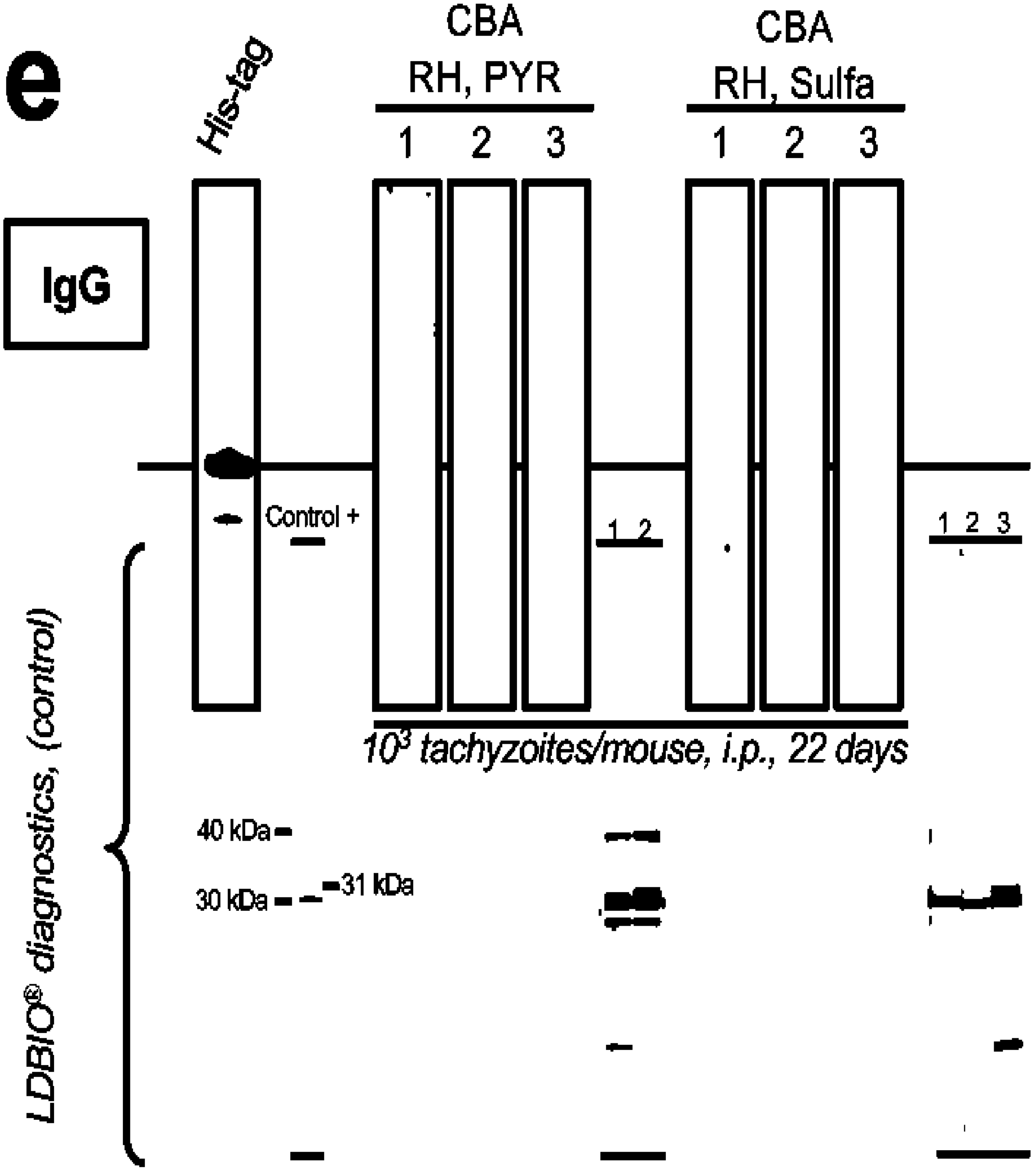
Figure 9F:
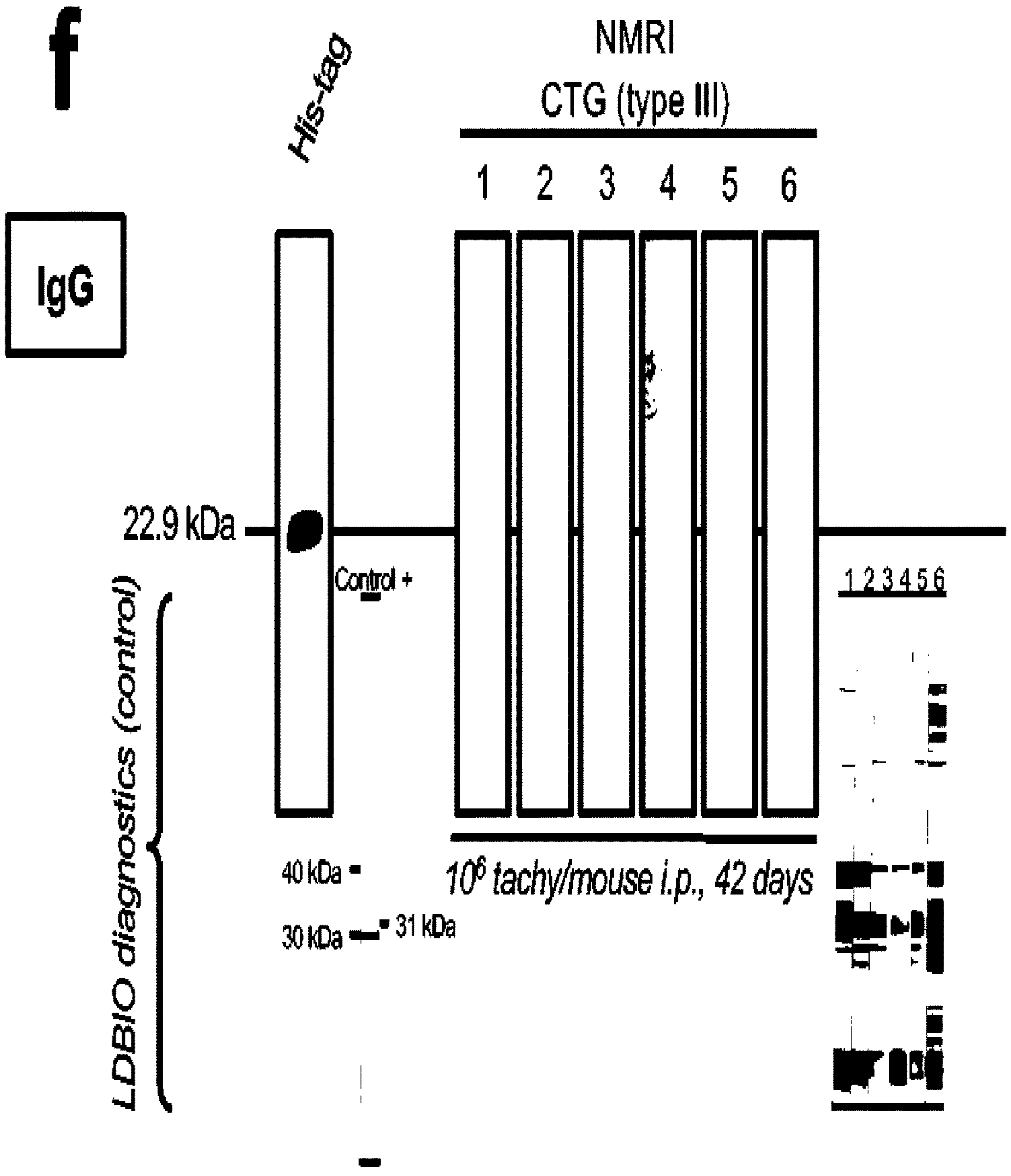
Figure 9G:
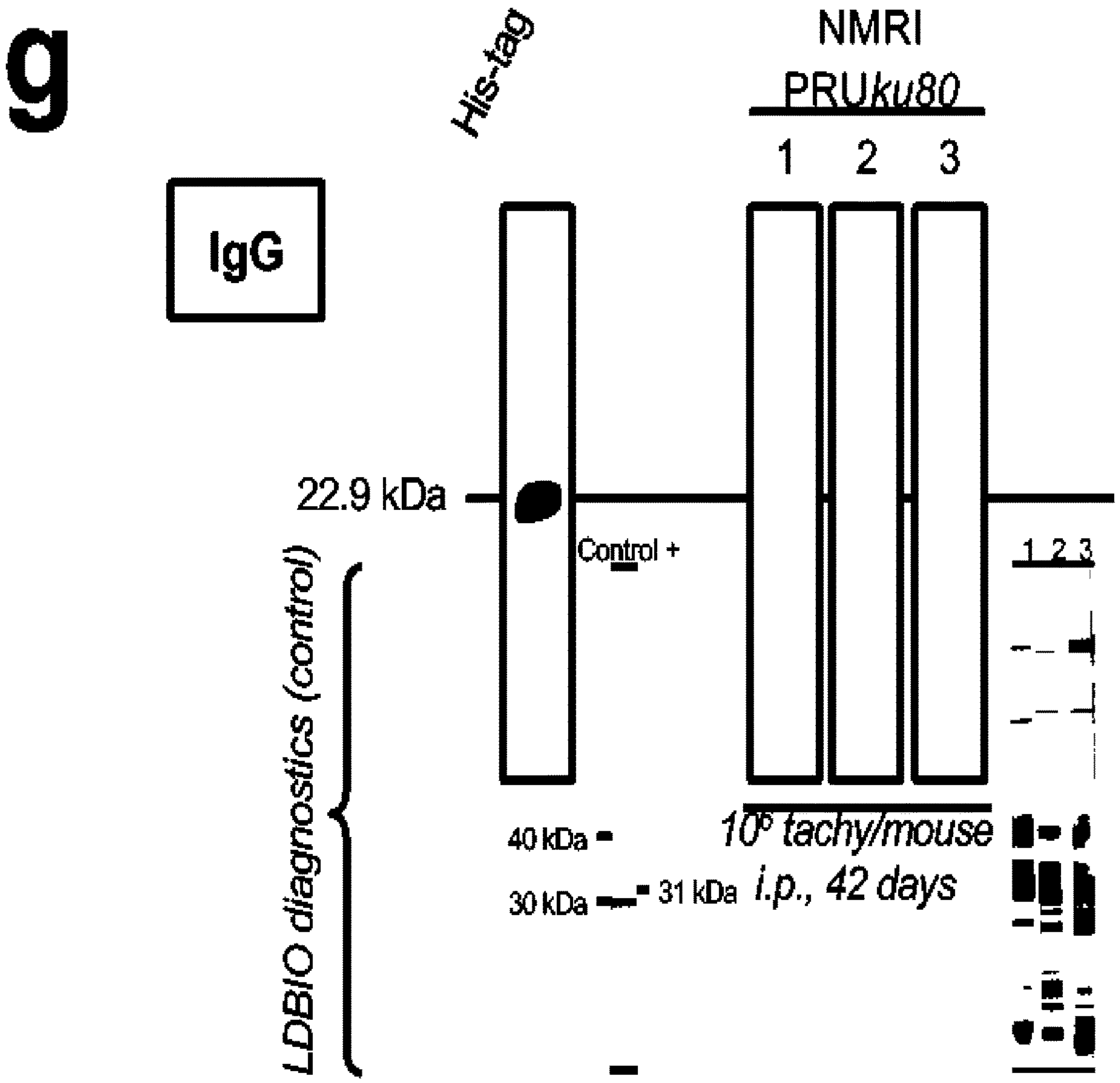
Figure 9H:
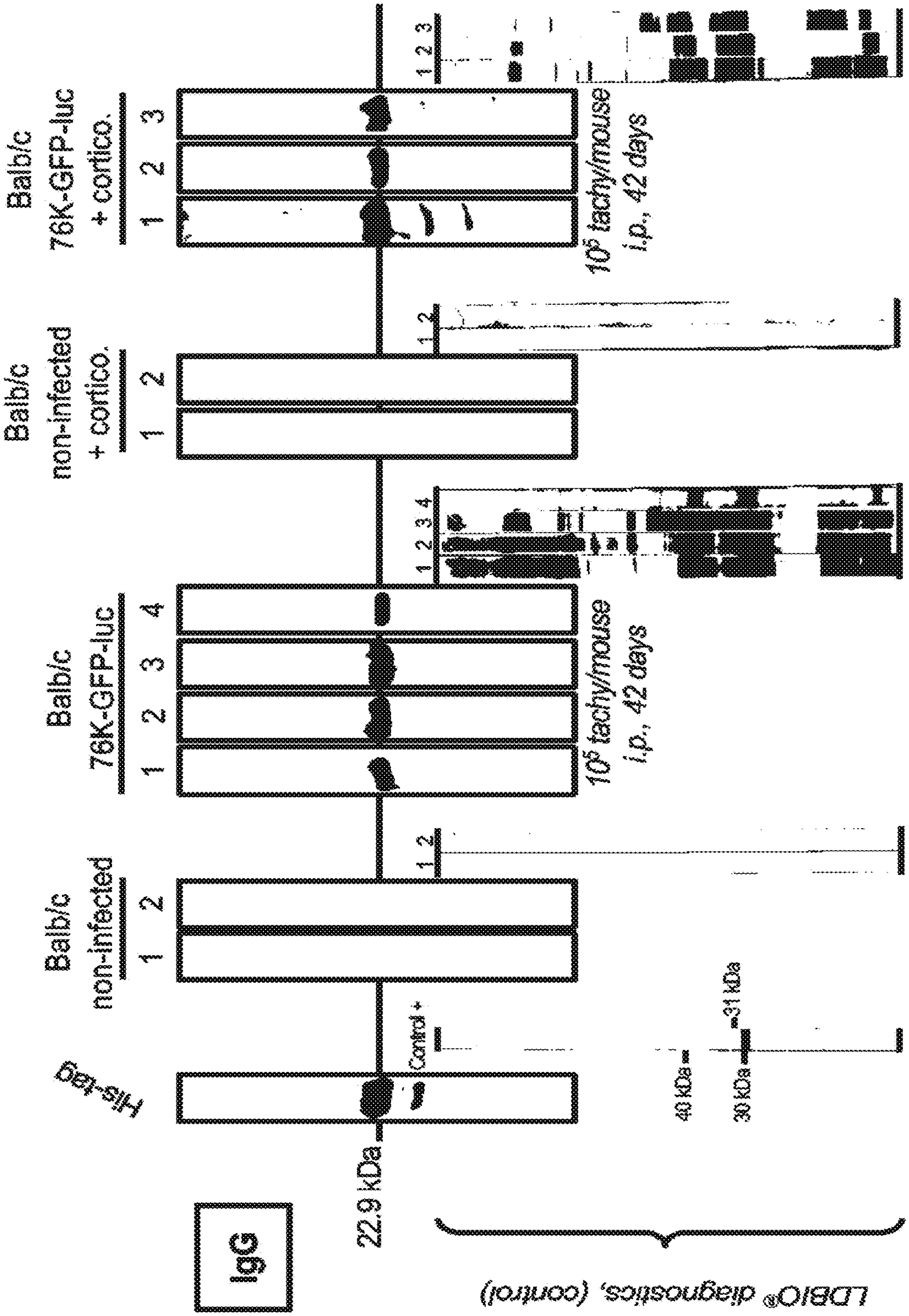

In order to obtain highly pure and abundant quantities of BCLA required for sera WB testing, we opted to recombinantly express the C-terminal domain end of BCLA (res 1100 to 1275, hereafter referred as rBCLA) which is predicted as structured, as opposed to the rest of the protein containing core repeated motifs (FIG. 2*a*). rBCLA was therefore expressed in *E. coli* as a chimeric protein with an N-Terminal poly-histidine tag. Although efficiently expressed, it is natively insoluble or secluded to insoluble inclusion bodies but can be solubilized using 0.2% N-Lauryl Sarkoside during the lysis step. After lysis and centrifugation, rBCLA was first pulled down using Nickel affinity resin (data not shown). With a theoretical Mw of 20.9 kDa and a pI of 4.7, BCLA is observed migrating on an SDS-PAGE gel between the 17 and 25 kDa molecular weight markers, also, in a pH: 8 buffer, BCLA will be strongly negatively charged. *E. coli* contaminants can therefore be efficiently removed using anion exchange chromatography (data not shown). Finally, rBCLA is eluted in soluble form from size exclusion chromatography (data not shown) although poly-disperse because of a wide volume elution range and forming multi-oligomers as the elution volume is close to the void volume of the S75 column. Upon pooling the elution fractions, a final stage of ammonium sulfate precipitation and dialysis is performed to remove nucleic acid contaminants (data not shown). After this last stage of purification, both tachyzoite antigens of RH strain (LD bio) and rBCLA, respectively, were resolved by SDS-PAGE then probed by immunoblot with mice antisera elicited by different states of toxoplasmosis to allow parallel analysis of antigen recognition by immunoglobulins G, M, and A.

rBCLA does not React with Sera of Acutely Infected Mice but Constitutes an Excellent Antigen for the Detection of Anti-*T. gondii* IgG from Chronically Infected Mice We first performed immunoblots on sera collected from mice in acute phase of infection. rBCLA protein is apparently not reacting with sera of mice acutely infected by atypical (COUG, haplotype 11), virulent (RH, type I) or cystogenic (76K, type II) strains (FIG. 8*a-c*) while all *T. gondii*-exposed mice, irrespective of their genetic background (NMRI, CBA, C57BL/6) or the route of infection (intraperitoneal or per os) seroconvert (FIG. 8*a-c* and data not shown). However, rBCLA reacts strongly with anti-*T. gondii* IgG antibodies of mice that develop latent toxoplasmosis following infection by type II cystogenic strains (Pru, ME49 or 76K) (FIG. 9*a-c*). rBCLA was detected by sera of mice at a subchronic (≥21 days, FIG. 9*d*) or chronic (≥42 days FIG. 9*a-c*) stage of infection with an extremely strong signal with sera of mice persistently infected for 22 months (FIG. 9*c*). No reactivity was detected when sera from mice left uninfected or chronically-infected with BCLA-deficient strain were assayed, demonstrating that the IgG antibodies are specifically directed in vivo against BCLA (FIG. 9*d*). Because a selection process occurs during antibody affinity maturation (Eisen, 2014), we reasoned that rBCLA antigen may be detected by IgM during acute infection compared with IgG during chronic infection. Clearly, rBCLA is not reacting with anti-*T. gondii* IgM nor IgA (data not shown). The above findings therefore strongly support that rBCLA was able to differentiate the parasite stage that infected mice, with preferential IgG reactivity for latent infections.

rBCLA is Exclusively Detected in Sera of Mice Persistently Infected by Cystogenic Strains rBCLA was shown to have specific reactivity for cystogenic strains prone to make latent infections (FIG. 9*a-d*). To sustain the argument, however, it would be necessary to show that strains that do not make cysts are unable to produce a specific antibody response directed against the rBCLA. First, serologic analyses of animals infected with the non-cystogenic virulent strain RH, and successively treated with pyrimethamine or sulfadiazine to overcome acute toxoplasmosis, revealed enriched levels of anti-tachyzoite-specific antibodies (22 days post-infection; FIG. 9*e*, low panel) while rBCLA was barely detectable (FIG. 9*e*, upper panel). Since we cannot exclude that the treatments have altered the dissemination in the deep tissues of the parasites and consequently their differentiation into bradyzoites, we monitored the IgG response to rBCLA in mice persistently infected by CTG, a type III strain that causes nonlethal chronic latent infection characterized by a proper positive serology (FIG. 9*f*, right panel). 42 days post-inoculation, no reactivity against rBCLA was observed (FIG. 9*f*). The main difference with type II infections (FIG. 9*a-d*) was that mice chronically infected with CTG had a low number of (if no) cysts in their brain (Cannella et al., 2014), suggesting a likely relationship between cyst burden and rBCLA antibody levels. Likewise, sera from mice persistently infected by a type II (PruΔku80) strain that usually produces a lower number of cysts does not react with rBCLA (FIG. 9*g*), indicating that the mice antibody response against rBCLA antigen takes place promptly after sub-chronic infection (≥21 days p.i.) and seems conditioned by the presence of cysts, at least in the murine model. Immunosuppressive therapy (corticoids) producing reactivation of latent type II infection does not enhance the antibody response against rBCLA (FIG. 9*h*), excluding the hypothesis of an immune reaction in response to the release into the circulation of bradyzoites.

Limited Proteolysis to Find Antigenic Sub-Fragments within rBCLA

Figure 11B:
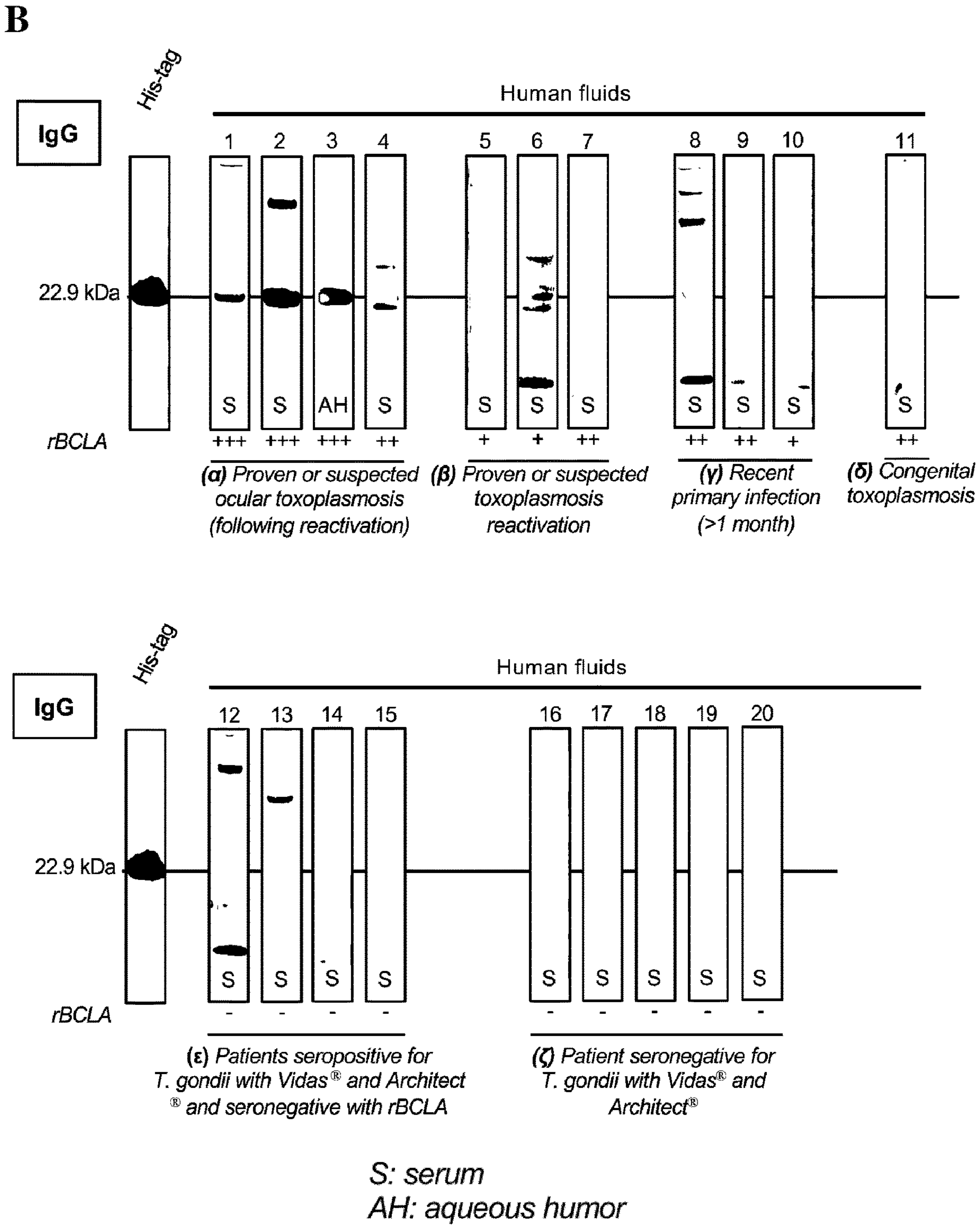

With the objective to recover a highly antigenic sub-fragment of rBCLA, a limited proteolysis on the purified sample was undertaken using trypsin, chymotrypsin, elastase and papain. Analysis of the proteolysis reaction by SDS PAGE (FIG. 10*a*) shows that rBCLA is quickly degraded by chymotrypsin and partially degraded by elastase, trypsin and papain generating stable fragments around the 17-kDa marker. When blotted against positive mouse IgG serum (FIG. 10*b*) and His Tag (FIG. 10*c*) following the same protocol as mentioned above, one can observe that most degradations occur within the C-terminus as they remain positive in the his-tag blot. These same degradations present revelation bands of lesser intensity in the anti-mouse IgG WB suggesting that further truncation of the construct does not increase specificity or sensitivity of the mouse IgGs within a western blot analysis.

rBCLA Also Reacts with Human Sera, Yet the Pattern of Positivity is Still Under Investigation We next showed that mice infected with a positive amniotic fluid from a pregnant woman primary infected during pregnancy with proof of congenital toxoplasmosis are clearly reacting with rBCLA, contrary to those infected with qPCR negative amniotic fluid or placentas (FIG. 11*a*). rBCLA makes therefore a suitable serologic maker to predict in clinical isolates their cystogenic characteristics. Following evaluation of anti-rBCLA immunoglobulins detection in murine models, we aimed at assessing the pattern of anti-rBCLA detection in humans according to the serological and clinical status of the patients (Table 3). Antibodies directed against rBCLA antigen have been detected in 3 patients with a strong suspicion or a proven ocular toxoplasmosis, either in serum only or both in serum and aqueous humor (FIG. 11*b*). These clinical cases were due to the reactivation of *T. gondii* cysts in retina and not a primary infection as no IgM was detected. In the same vein, 3 patients with reactivation of toxoplasmosis due to immunosuppression linked to haematological disease have also anti-rBCLA IgG, but the labelling in western blot was weak compared to those with ocular toxoplasmosis, although the level of antibodies was quite high using Vidas® and Architect® (Table 3). Even if the relatively small sample size limit broad generalisations, the reactivity of rBCLA to human sera resulting from toxoplasmosis reactivation provides further evidence to our murine model where we correlated the presence of rBCLA as a serological marker and cyst burden. Unexpectedly, 3 sera with recent seroconversion in pregnant women and one serum of a child with congenital toxoplasmosis also react to rBCLA (FIG. 11*b*). Although this is difficult to prove, it is possible that a recent primary infection can generate *T. gondii* cysts in peripheric tissues which in turn trigger an humoral anti-BCLA immune response. Anyhow, all serums of patients identified as seronegative for *T. gondii* do not detect rBCLA, showing a good specificity of this antigen for patients with toxoplasmosis (FIG. 11*b*).

TABLE 2

Toxoplasma strains used in the present invention

| Strain | Genotype | Reference or source |
|---|---|---|
| RH | Type I | Lab strain |
| RHΔku80 | RH Δku80 type I strain | (Huynh and Carruthers, 2009) |
| GT1 SNF$^R$ | Type I | (Behnke MS et al. 2011) |
| PruΔku80 | Prugniaud Δku80 type II strain | (Fox et al., 2011) |
| PruΔku80Δbcla | Type II | Genetically modified from (Fox et al., 2011) |
| ME49 FUDR$^R$ | Type II | (Behnke MS et al. 2011) |
| 76K-GFP-Luc | 76K type II strain expressing ectopically GFP and Luciferase type II strain | Gift from Michael Grigg (NIH) |
| 76K-GFP-Luc-Δbcla | Type II | Genetically modified from (NIH) |
| CTG | Type III | (Rosowski EE, et al. 2010) |

TABLE 3 rBCLA antigen is reacting with some sera and aqueous humours from humans

| | ID | Sex | Age (years) | Sample | Medical context | IgG Architect ® | IgG Vidas ® | IgM Architect ® | IgM Vidas ® | Serological and clinical status | rBCLA status |
|---|---|---|---|---|---|---|---|---|---|---|---|
| α | 1 | M | 89 | Serum | Corneal transplant | 32.3 | 237.0 | 0.04 | 0.04 | Past immunity, ocular toxoplasmosis (reactivation)? | +++ |
| | 2 | M | 83 | Serum | Ocular toxoplasmosis | >2000.0 | >300.0 | 0.15 | 0.11 | Past immunity, ocular toxoplasmosis (reactivation) | +++ |
| | 3 | M | 83 | Aqueous humor | Ocular toxoplasmosis | | Aqueous humor with neosynthetized Ab & PCR+ | | | Ocular toxoplasmosis (reactivation) | +++ |
| | 4 | F | 85 | Serum | Ophthalmological disease | 24.3 | 73.0 | 0.57 | 0.22 | Past immunity, residual IgM, ocular toxoplasmosis (reactivation) ? | ++ |

TABLE 3-continued rBCLA antigen is reacting with some sera and aqueous humours from humans

| | ID | Sex | Age (years) | Sample | Medical context | IgG Architect ® | IgG Vidas ® | IgM Architect ® | IgM Vidas ® | Serological and clinical status | rBCLA status |
|---|---|---|---|---|---|---|---|---|---|---|---|
| β | 5 | F | 57 | Serum | Hematology (ID) | 46.0- | >300.0 | 0.07 | 0.06 | Toxoplasmosis reactivation? | + |
| | 6 | F | 28 | Serum | Reactivation of toxoplasmosis, hematological disease | 19.7 | 26.0 | 4.93 | 6.05 | Toxoplasmosis reactivation | + |
| | 7 | F | 68 | Serum | Toxoplasmosis reactivation, hematological disease | >2000.0 | >300.0 | 2.7 | 4.11 | Toxoplasmosis reactivation | ++ |
| γ | 8 | F | 26 | Serum | Seroconversion during pregnancy | 431.8 | >300.0 | 2.65 | 1.95 | Recent seroconversion (infection ~1 month ago) | ++ |
| | 9 | F | 20 | Serum | Seroconversion during pregnancy | 12.7 | 12.0 | 1.05 | 1.06 | Recent seroconversion (infection ~1 month ago) | ++ |
| | 10 | F | 21 | Serum | Seroconversion during pregnancy | 32.0 | 19.0 | 1.56 | 1.26 | Recent seroconversion (infection ~1.5 month ago) | + |
| δ | 11 | M | 2 months | Serum | Congenital toxoplasmosis | 168.3 | 150.0 | 12.30 | 6.45 | Congenital toxoplasmosis | ++ |
| ε | 12 | M | 55 | Serum | Pre-graft monitoring (renal transplant) | 29.9 | 174.0 | 0.30 | 0.37 | Past immunity | — |
| | 13 | F | 24 | Serum | Hematological disease | 43.6 | 100.0 | 0.15 | 0.30 | Past immunity (without reactivation) | — |
| | 14 | F | 33 | Serum | Seroconversion during pregnancy | 45.9 | 30.0 | 2.41 | 1.96 | Recent seroconversion (infection ~2.5 months ago) | — |
| | 15 | F | 71 | Serum | *Cornea guttata* | 4.9 | 16 | 0.08 | 0.06 | Past immunity (no ocular toxoplasmosis) | — |
| ζ | 16 | F | 30 | Serum | Healthy | 0.15 | / | 0.04 | / | Seronegative | — |
| | 17 | F | 61 | Serum | Hematological disease | 0.20 | / | 0.09 | / | Seronegative | — |
| | 18 | M | 6 months | Serum | Serological follow-up of an infant suspected of congenital toxoplasmosis | 1.60 | 1.00 | 0.06 | 0.03 | Seronegative | — |
| | 19 | M | 64 | Serum | HIV patient | 0.20 | / | 0.12 | / | Seronegative | — |
| | 20 | F | 34 | Serum | Pregnant woman | 0.10 | / | 0.04 | / | Seronegative (serological follow-up during pregnancy) | — |

Cutoffs recommended by manufacturers for interpretation of serologic values using Vidas® and Architect®

Vidas® IgG (IU/mL): negative <4; grayzone: 4.0≤x<8.0; positive: ≥8.0

Vidas® IgM (index): negative <0.55; grayzone: 0.55≤x<0.65; positive: ≥0.65

Architect® IgG (IU/mL): negative <1.6; grayzone: 1.6≤x<3.0; positive: ≤3.0

Architect® IgM (index): negative <0.50; grayzone: 0.50≤x<0.60; positive: >0.60

Epitope Mapping in rBCLA Positive Patients Reveals a Multitude of Antigenic Regions within rBCLA and Consistent Reactivity within the Repeated Region.

With the specific immunogenic quality of rBCLA being proven by western blot in a series of sera from different clinical categories. One of the main objectives was to develop an ELISA based assay to screen larger serum cohorts in a cost-effective, robust and fast manner. However, to correctly setup such an assay, which could be almost entirely based on chemically synthetized peptides, a more precise understanding of the local epitope immunogenicity of BCLA was required. To do so, we designed and synthetized cellulose printed peptide arrays covering both the repeated region and rBCLA domain (FIG. 12*a*). These arrays are conceived using 15 aa peptides with a 3 aa gap step between peptides. We then tested several sera which were unequivocally positive by western blot against rBCLA and taking the same number of negative sera to proportionally subtract non-specific reactivity. When analysed, the total reactivity score for each peptide obtained on both the repeat region and rBCLA (FIG. 12*b*) provides us two key observations: First, rBCLA despite having several stronger zones of reactivity, notably close to peptides 13, 22, 30 and 43, has a multitude of epitopes throughout the domain and different sera will react quite differently to different zones (FIG. 12*c*). This underlines the requirement for keeping the rBCLA as a recombinant protein with in the ELISA test. Moreover, as the rBCLA domain is predicted as structured, structured epitopes would only be provided by a recombinant protein strategy, further underlining it's use. Second, the repeat motif is found to consistently react in two separate zones (peptides 3 to 7 as motif A and 13 to 16 as motif B) in almost all the tested human sera. This feature underscores the importance to include one or several peptides covering these motifs in order to obtain a more sensitive ELISA technique. From these results, we therefore designed an ELISA which combines full length BCLA recombinant protein and chemically synthetized repeat motifs.

ELISA Titration Using rBCLA and Repetition Peptides Demonstrates that BCLA Seropositivity is Higher within Acute and Chronically Infected Individuals.

Upon establishing stringent rules to categorise and differentiate different clinical profiles. 123 sera (all taken from different individuals) were tested with the developed BCLA-ELISA test. Their ELISA score, expressed in international units (UI) is displayed (FIG. 13) in accordance to the clinical profiles of the patients which lists as follows:

1) "Seronegative", which regroups all patients (healthy or with other pre-conditions) with SAG1 IgG/IgM negative serologies.
2) "Past immunity", which regroups all patients (healthy or with other conditions), which are categorised as SAG1 positive IgG but with no SAG1 reactive IgM and which do not fall into the next three categories.
3) "Active toxoplasmosis in immunocompromised patient", which regroups all SAG1 IgG positive and immunocompromised patients with a proven symptomatic toxoplasmosis (regrouping disseminated, cerebral and primary toxoplasmosis).
4) "Asymptomatic'sEpi serological reactivation in immunocompromised patients", which regroups all patients immunocompromised undergoing a serological reactivation but without visible symptoms.
5) "Ocular toxoplasmosis", which regroups patients with SAG1 positive serologies and suffering from a proven ocular toxoplasmosis.

From this analysis several observations can be made. First, all groups when compared to the seronegative group display a significant increase in median BCLA titrations and have much higher positivity rates. This proves in humans, the direct correlation between a SAG1 seropositivity status and the ability to develop a BCLA positivity status. This also shows a current discrepancy between SAG1 negative serologies and BCLA serologies which still display a false positive discovery rate of around 10%. This can be explained in some sera by non-specific interactions with the different BCLA epitopes, strongly immunogenic exogenous bacterial contaminants co-purified with rBCLA and potentially truly BCLA positive patients with negative SAG1 serologies. The second main observation is that some clinical profiles have a tendency to generate vastly stronger immunogenic reactions, most notably the "Asymptomaticstri serological reactivation in immunocompromised patients" group where BCLA serologies are titrated well beyond the median positive BCLA serology in the "past immunity" group. The final observation is that for some groups where a BCLA positivity should always be expected, such as in the case of "Active toxoplasmosis in immunocompromised patient" and "ocular toxoplasmosis", a minority of serologies remain negative or under the positivity cut-off. This observation can highlight a lack in sensitivity from the ELISA test or potentially illustrates the fact that BCLA serologies can become negative during immunosuppression.

The ELISA Test is Also Consistent in Linking Positive BCLA Serologies in Mice to a Proportional Cyst Burden.

Figure 14A:
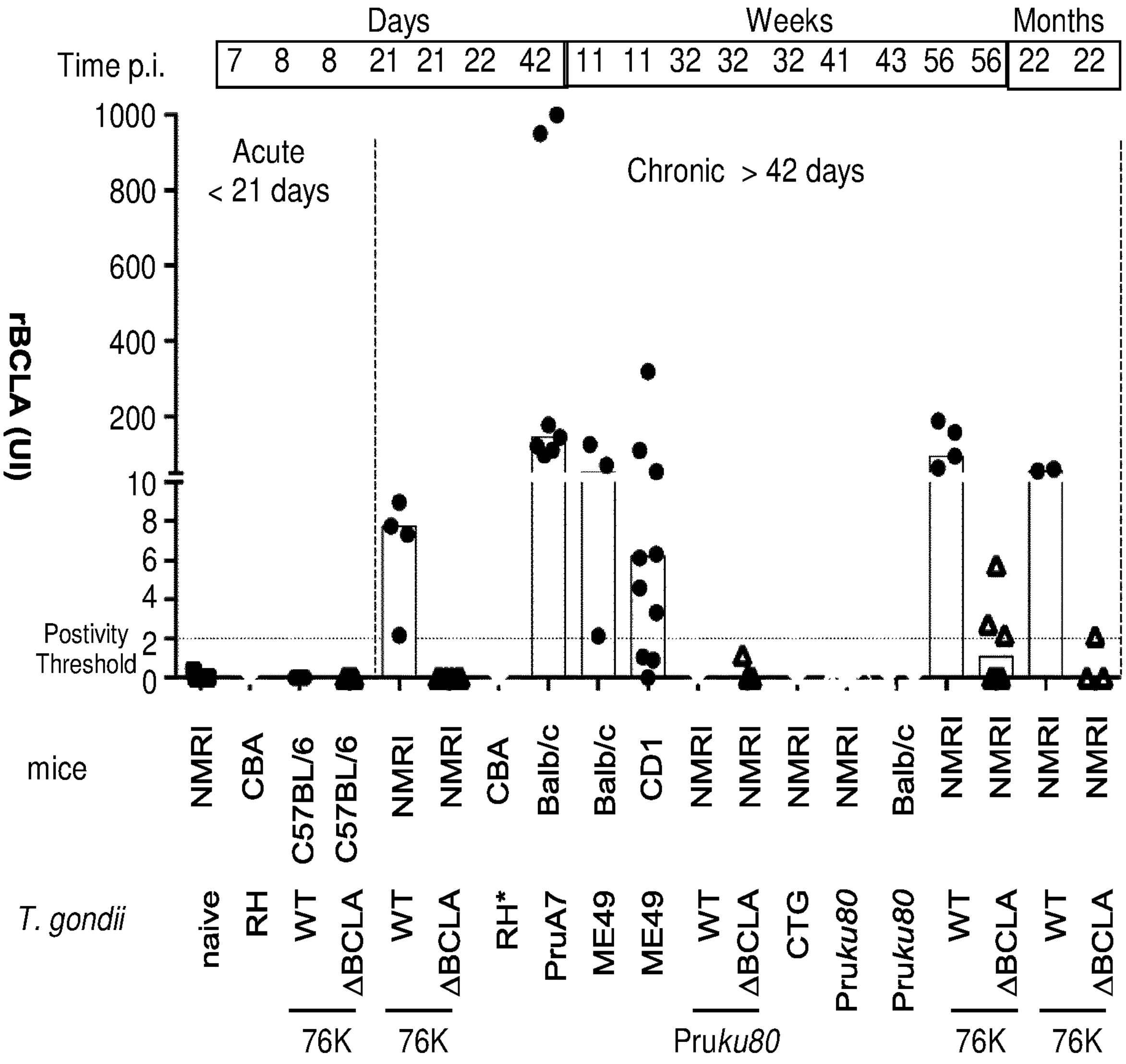
Figure 14B:
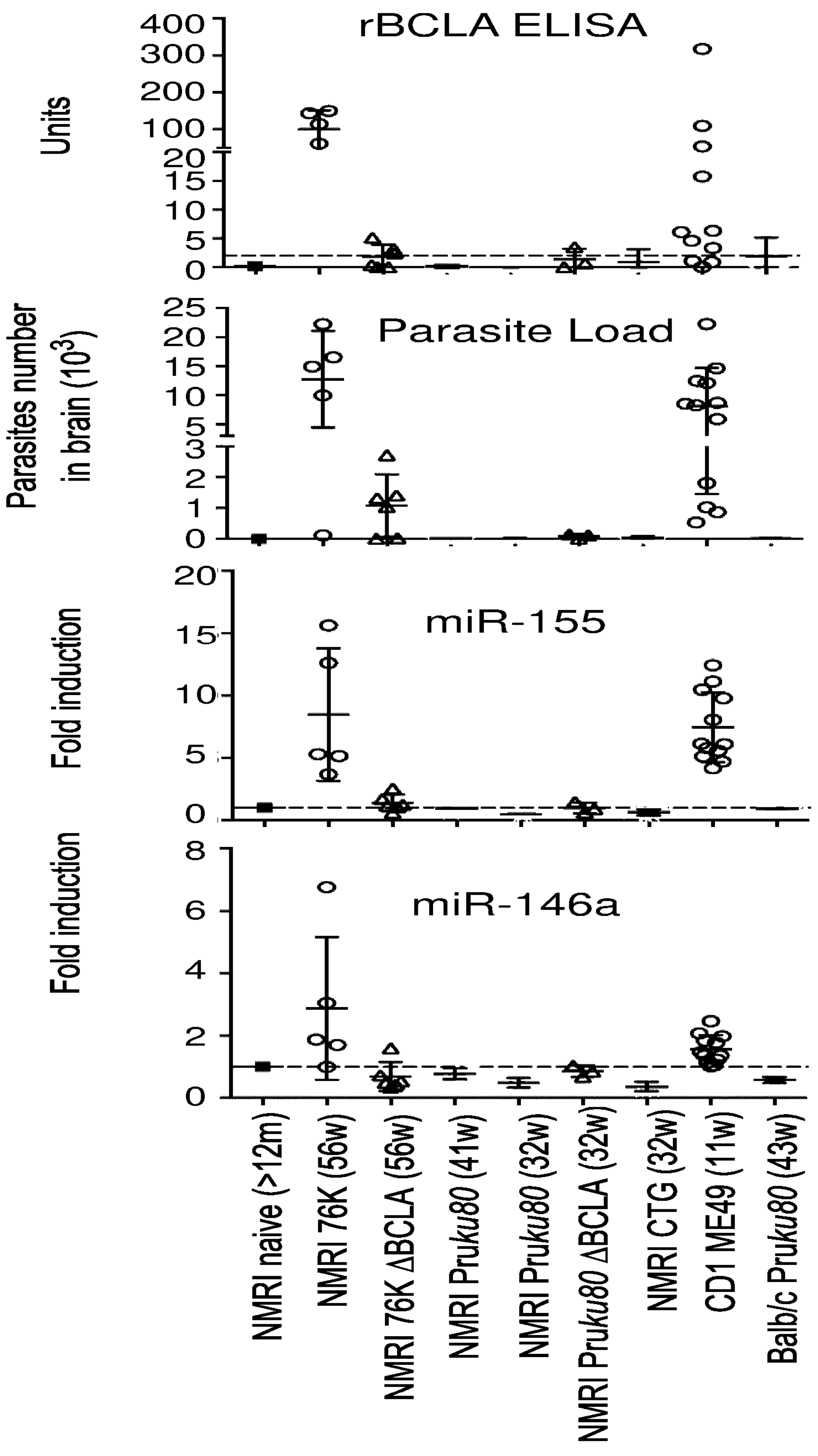

Overall, the semi-quantitative analysis of anti-rBCLA antibody titers identified BALB/c and NMRI mice likely bearing WT cysts as highly responsive to BCLA with an increased yield over time (FIG. 14A). In conjunction with quantitative PCR on brain-associated *T. gondii* DNA and quantitation of brain-associated miR-155 and miR-146 microRNAs reported to be specifically induced upon bradygenesis (Cannella et al., 2014), we brought evidence of rBCLA as a reliable antigen to serologically detect *T. gondii* bradyzoite-loaded cysts over the long-lasting protozoan persistence in rodents (FIG. 14B). These results are especially interesting as the semi-quantitative nature of the ELISA test remarkably discriminates cystogenic *T. gondii* strain responses over time.

DISCUSSION

Infections by *Toxoplasma gondii* lead to an acute systemic phase by which the zoites rapidly establish themselves and further complete their developmental program as bradyzoites enclosed in cysts surrounded by a thick cyst wall that persist in brain, heart and skeletal muscle (Jeffers et al., 2018). The host immune response is promptly able to control the tachyzoite population expansion, leading to a life-long immunity typified by seroconversion. Yet, since the developmental transitions from tachyzoite to bradyzoite are fully bidirectional any impairment of immune functions (e.g. AIDS patients, haematological diseases and immunosuppressive treatments) can result in reactivation of latent infection that may cause encephalitis and focal brain lesions, pulmonary or disseminated disease.

The diagnosis of acute and chronic toxoplasmosis in immunocompetent subjects relies mainly on serology, and because infections are often asymptomatic, serologic diagnosis is in many cases retrospective, as it is based on the demonstration of seroconversion, e.g. during pregnancy or in a graft setting (Robert-Gangneux and Darde, 2012). Increased levels of IgM and IgA antibodies are serologic indicators of primary/acute infections and, while a high IgG-avidity rules out a primary infection, persistent and steady-state IgG levels in absence of IgM typifies latent infections (Dard et al., 2016). However, the interpretation of the serological results remains difficult, even for well-trained specialists. The current challenges to overcome are: (i) to discriminate between recent and more distant infections; (ii) to diagnose congenital toxoplasmosis in infants and reactivation in immunocompromised patients; and iii) to establish the origin of infection, i.e. oocysts versus cysts. While many methods have been developed in the last decades to improve the accuracy and sensitivity of serological assays, they poorly address the aforementioned concerns. An obvious reason is that many, if not all, commercial serologic test kits are detecting lysate or recombinant antigens that are prevalently expressed at the tachyzoite stage (e.g. SAG1) or common to both the infectious stages of the parasite (e.g. GRA8).

Currently, while there is no reliable bradyzoite-specific serological assay for toxoplasmosis to estimate the sources of infection worldwide nor to discriminate accurately between acute and latent infections, progress has been made. Indeed, recent proteomic studies have shed light on the repertoire of sporozoite-specific proteins (Fritz et al., 2012;

Possenti et al., 2013), which has revealed CCp5A as a serological marker able to differentiate the parasite stage that infected chickens, pigs and mice, with specific reactivity for oocyst-infected animals (Santana et al., 2015).

However and despite early studies reporting that specific bradyzoite antigens including BAG1 contribute to the stimulation of both humoral (Mun et al., 1999) and cell-mediated immunity against *T. gondii* infection (Di Cristina et al., 2004), no bradyzoite/cyst antigens are currently considered as potential markers of latent infection in diagnostic tests. The search for bradyzoite/cyst-specific markers has been somewhat limited by the ability to harvest sufficient mouse brain cysts to analyze the specific proteome of the latent stage. In this study, we found a way to circumvent this problem by de-repressing bradyzoite genes in cell culture while manipulating the chromatin state of tachyzoite with epi-drugs. Hundred of bradyzoite-restricted proteins were therefore identified, including BCLA.

The protein BCLA was shown to be not essential to initiate or sustain latent infections, yet BCLA-deficiency resulted in a quite singular phenotype typified by the deformation and loss of circularity of cerebral cysts in murine model. So far, two cyst wall-associated proteins, i.e. BPK1 and CST1, were involved in the structural integrity of *T. gondii* cysts (Jeffers et al., 2018). In Abpk1 strain cysts are smaller and more sensitive to pepsin-acid treatment and unlike BCLA, Abpk1 strain has reduced ability to cause oral infection (Buchholz et al., 2013). CST1 is responsible for the *Dolichos biflorus* Agglutinin (DBA) lectin binding characteristic of *T. gondii* cysts. Deletion of CST1 results in reduced cyst number and a fragile brain cyst phenotype characterized by a thinning and disruption of the underlying region of the cyst wall (Tomita et al., 2013). A defect of glycosylation may also explain the deformation of Δbcla cysts. Indeed, we have preliminary interactome data showing BCLA co-purified with a Jacaline-binding protein (data not shown), which is a lectin binding to GalNAcα1-Ser/Thr oligosaccharide, that covers bradyzoites-surrounding PVM (Tomita et al., 2017). Further investigation is needed to establish whether this interaction is responsible for the BCLA deficiency-mediated peculiar phenotypes.

Having no clear BCLA-associated phenotype in mice regardless of the route and the time of infection, we oriented our investigations on the propensity of BCLA to play an immunogenic role. We therefore reach another milestone by producing rBCLA as a recombinant protein with a high degree of purity which offers the opportunity to standardize the serological tests and to some extent to reduce the manufacturing costs, in case this antigen turns out to be interesting for serology. In fact, we brought strong data supporting that rBCLA is antigenic and constitutes an excellent antigen candidate for the detection of anti-*T. gondii* IgG in chronically infected mice. Strikingly, we clearly correlated the strong detection in sera of the antigen rBCLA and the cyst burden in the brain of all mice latently infected by type II cystogenic strains. A similar study claims that MAG1 antibody level correlates with brain cyst burden but their experimental settings are somewhat biased by the use of an irrelevant model of chronic type I (GT1) infection that requires anti-*T. gondii* chemotherapy to control the proliferation of tachyzoites during the acute stage and to avoid animal death (Xiao et al., 2016).

Remarkably, rBCLA did not react with IgM nor IgA (data not shown), markers frequently associated with acute infection, but only with IgG and exclusively in subchronic infections. This result clearly contrasts with the observation that tissue cyst fed mice showed significant IgM response at day 10 (Döşkaya et al., 2018) and reinforces the idea of a humoral response against BCLA during the latent stage of infection. Likewise, mice inoculated by oral gavage with tissue cysts did not produce antibodies directed against BCLA at the time of acute infection (FIG. 8*c*), indicating that the host immune response against BCLA did not originate from the first exposure to bradyzoite and cyst proteins release from ingested parasites within the gastrointestinal tract during primary infection. This sharply contrasts with the humoral responses against BAG1 and MAG1 that occur very early after infection (Di Cristina et al., 2004; Mun et al., 1999). Our findings, suggestive of a humoral immune response to BCLA-containing tissue cysts, are in contrast to the idea that *T. gondii* cysts are predominantly found in immune-privileged sites such as the brain and skeletal muscle. Elucidating the contribution of the humoral immune response during chronic toxoplasmosis will require further work in mice and likely BCLA makes a great tool for studying these processes.

Finally, anti-rBCLA antibodies have been detected in some human sera from patients with ocular toxoplasmosis following toxoplasmic reactivation, during toxoplasmosis reactivation linked to immunosuppression or congenital toxoplasmosis. These findings are in agreement with the conclusions drawn from the murine model that rBCLA makes a fantastic serological marker of the presence of tissue cysts in the chronically infected hosts.

Example 2 (VHH Production)

Immunization

Llamas SEL005 and SEL006 were immunized via Eurogentec via 4 injections at day 0, 14, 28 and 35. Sera was obtained at day 0, day 28 and day 43. Peripheral blood mononuclear cells (PBMC) were obtained from a large bleed at day 43.

Immune Response

The immune response of SEL005 and SEL006 was tested by assessing the presence of rBCLA-specific antibodies in sera of day 43. A MaxiSorp plate was coated with 200 ng antigen per well overnight at 4° C. After three times washing with PBS containing 0.05% Tween-20 the plate was blocked with 4% milk powder in PBS (MPBS). Next, a serial dilution of the sera in 1% MPBS was added to the wells and incubated for 1 hour. Unbound antibodies were removed during washing with PBS-Tween. Subsequently, bound antibodies were detected with rabbit-anti-VHH (clone K1216) and donkey-anti-rabbit coupled to HRP. Antibody binding was quantified by the colorimetric reaction of O-phenylenediamine (OPD) in the presence of H2O2 at 490 nm. Llamas SEL005 and SEL006 show a very good response against His rBCLA.

Library Construction of SEL005 Day 43 and SEL006 Day 43

RNA Isolation and cDNA Synthesis

Peripheral blood lymphocytes were isolated from a large bleed at day 43 from which RNA was isolated at Eurogentec. Precipitated RNA was dissolved in RNase-free MQ and the RNA concentrations were measured. To assess the quality of the RNA, 5 μl of the dissolved RNA was analyzed on gel. The intact 28S and 18S rRNA was clearly visible, indicating proper integrity of the RNA.

About 40 μg RNA (4 reactions of 10 μg each) was transcribed into cDNA using a reverse transcriptase Kit (Thermo Fisher Scientific). The cDNA was purified on Macherey Nagel PCR clean-up columns. Variable domains of the heavy chains (both conventional and heavy chain-only) fragments were amplified using primers annealing at the leader sequence region and at the CH2 region. 5 μl was loaded onto a 1% TBE agarose gel for a control of the amplification.

After this control, the remaining of the sample was loaded on a 1% TAE agarose gel and the 700 bp fragment was excised and purified from the gel. A total of 80 ng of isolated PCR product was used as a template for the nested PCR (end volume 800 μl) to introduce SfiI and Eco91I restriction sites to either end of the VHH gene. The amplified VHH fragment was cleaned on Macherey Nagel PCR cleaning columns and eluted in 120 μl. The eluted DNA was first digested with SfiI, followed by Eco91I. As a control of the restriction digestion, 4 μl of this mixture was loaded onto a 1.5% TBE agarose gel.

After the restriction digestion, the samples were loaded on a 1.5% TAE agarose gel. The 400 bp fragment was excised from the gel and purified on Machery Nagel gel extraction columns. The purified 400 bp VHH fragments (~330 ng) were ligated into the pUR8100 phagemid vector (~1 μg) and transformed into TG1 *E. coli.*

Library Size

The transformed TG1 were titrated using 10-fold dilutions. 5 μl of the dilutions were spotted on LB-agar plates supplemented with 100 μg/ml ampicillin and 2% glucose. The number of transformants was calculated from the spotted dilutions of the transformed TG1 culture (keeping in mind that the final volume of the transformation is 8 ml). The total number of transformants and thereby the size of the library was calculated by counting colonies in the highest dilution and using the formula below:

Library size=(amount of colonies)*(dilution)*8(*ml*)/0.005(*ml*;spotted volume)

The VHH insert frequency in the phagemid vector was determined by picking 24 different clones and performing a colony PCR. Bands of ~700 bp indicate a successfully cloned VHH fragment. Bands of ~300 bp indicate an empty plasmid. The insert frequency for library SEL005 day 43 is 100%. For library SEL006 day 43 the insert frequency is almost 95% which is sufficient to continue with phage panning selections.

Phage Production and Selection

Phages were produced from the library as outlined below: *E. coli* TG1 containing libraries SEL005 day 43 and SEL006 day 43 were diluted from the glycerol stock up to an OD600 of 0.05 in 2×YT medium containing 2% glucose and 100 μg/ml ampicillin. The number of bacteria in this inoculum was at least 10× the library size (≥109 bacteria in the inoculum). This culture was grown at 37° C. for 2 hours to reach an OD600 of ~0.5. Subsequently, about 7 ml of the culture was infected with helper phage VCS M13 using a MOI (multiplicity of infection) of 100 for 30 minutes standing at 37° C. Infected bacteria were spun down and resuspended into 50 ml fresh 2×YT medium supplemented with both ampicillin (100 μg/ml, for the phagemid) and kanamycin (25 μg/ml, for the M13 phage) and grown overnight at 37° C., shaking. Produced phages were precipitated from the supernatant of the cultures using PEG-NaCl precipitation. Titer of the produced phages was calculated by serial dilution of the phage and infection of *E. coli* TG1. Titer of the produced phages were 3×1011/ml for SEL005 day 43 and 6×1011/ml for SEL006 day 43, respectively, which was sufficient for continuing with the selections.

For the 1st round of panning/selections, 20 μl of the precipitated phages (~1010 phages, which is >100-fold the diversity of the libraries) were applied to wells coated with His rBCLA. In short, 100 μl antigen was coated on the MaxiSorp overnight at 2 concentrations 5 μg/ml and 0.5 μg/ml. As a negative control, one well was incubated with PBS only. Next day after removal of non-bound antigen, the plate was washed three times with PBS and blocked with 4% milk powder in PBS (MPBS). At the same time freshly precipitated phages were pre-blocked with 2% MPBS for 30 minutes. Pre-blocked phages were incubated with directly coated His rBCLA for 2 hours. Upon extensive washing with PBS-Tween and PBS, bound phages were eluted with 0.1M TEA-solution, which was subsequently neutralized with 1M Tris/HCl pH7.5. Eluted phages were serially diluted and then used to infect TG1 bacteria and spotting on LB-agar plates supplemented with 2% glucose and 100 μg/ml ampicillin and incubated at 37° C.

For the 2nd round of selection, new phages were produced of rescued output from the selection on 5 μg/ml His rBCLA (highest concentration). The overnight grown rescued outputs were diluted 100-fold in 5 ml fresh 2x YT medium supplemented with 2% glucose and 100 μg/ml ampicillin and grown for 2 hours until log-phase. Subsequently 1 μl of helper phage VCS M13 was added and incubated at 37° C. for 30 minutes. Cultures were allowed to produce phages overnight at 37° C. Produced phages were precipitated from the supernatant of the cultures using PEG-NaCl precipitation.

Subsequently, for the 2nd round of panning/selection, 1 μl of the precipitated phages was applied to wells coated with His rBCLA as indicated below: antigen was coated on the MaxiSorp plate overnight at 3 concentrations (5 μg/ml, 0.5 μg/ml and 0.05 μg/ml). As a negative control, one well was incubated with PBS only. Next day, after removal of non-bound antigen, the plate was washed three times with PBS and blocked with 4% MPBS. At the same time freshly precipitated phages were pre-blocked in 2% MPBS for 30 minutes as described above. Pre-blocked phages were incubated with directly coated His rBCLA for 2 hours. Upon extensive washing with PBS-Tween and PBS, bound phages were eluted with 0.1M TEA-solution and subsequently neutralized with 1M Tris/HCl pH7.5. Eluted phages were serially diluted and then used to infect TG1 cells and spotting on LB-agar plates supplemented with 2% glucose and 100 μg/ml ampicillin and incubated overnight at 37° C.

Screening after 2 Rounds of Phage Display Selections

Rescued outputs of the 2nd round of selection on His rBCLA were plated out in order to pick single clones. For master plate ERB-1, a total of 92 single clones were picked in a 96-wells plate.

In order to screen master plate ERB-1 for His rBCLA-binders, periplasmic extracts containing monoclonal VHH were produced. The master plate was cultivated at 37° C. in 2×YT medium supplemented with 2% glucose and 100 μg/ml ampicillin and stored at −80° C. after addition of glycerol to a final concentration of 20%. For the production of periplasmic extracts, master plate ERB-1 was duplicated into a deep well plate containing 1 ml 2×YT medium supplemented with 0.1% glucose and 100 μg/ml ampicillin and grown for 3 hours at 37° C. before adding 1 mM IPTG for induction of VHH expression. The VHH expression was conducted overnight at room temperature. Periplasmic extracts were prepared by collecting the bacteria by centrifugation, resuspension of this pellet into 120 μl PBS and one freeze-thaw cycle. Bacteria were centrifuged to separate the soluble periplasmic fraction containing the VHH from the cell debris (pellet). To test the binding specificity of the monoclonal VHH by ELISA, His rBCLA (100 ng/well in PBS) was coated overnight onto a MaxiSorp plate at 4° C.

The coated plate was washed and subsequently blocked using 4% MPBS. The blocked wells were incubated with 10 μl of the periplasmic extracts and 40 μl 1% MPBS for 1 hour at room temperature. Unbound VHH were removed by washing with PBS containing 0.05% Tween-20. Subsequently, bound VHH were detected with rabbit-anti-VHH (clone K976) and donkey-anti-rabbit coupled to HRP. Binding of the VHH was quantified by the colorimetric reaction of OPD in the presence of H2O2 at 490 nm. All clones of master plate ERB-1 were able to bind specifically to His rBCLA. There is no difference shown between the two libraries used.

Sequence Analysis of his rBCLA Binding VHH

Based on the ELISA results, 17 clones (ERB-1A1, ERB-1F1, ERB-1A2, ERB-1E2, ERB-1F2, ERB-1G2, ERB-1B3, ERB-1H4, ERB-1A5, ERB-1G6, ERB-1D7, ERB-1F7, ERB-1G8, ERB-1E9, ERB-1E10, ERB-1B11 and ERB-1A12) were selected for sequence determination. These clones were picked based on binding in ELISA and should represent the majority of the clones selected from the different output Cloning and Production of VHH Selected on his rBCLA From all the sequenced clones, 7 clones (ERB-1F1, ERB-1F2, ERB-1H4, ERB-1G6, ERB-1D7, ERB-1B11 and ERB-1A12) were chosen as a good representative of the found VHH sequences. These VHH were then subcloned from the phagemid vector into the expression vector pMEK222 using SfiI and Eco91I restriction enzymes. Recloning into pMEK222 also adds a FLAG and His-tag to the C-terminus of the VHH, allowing detection and affinity purification. For the production, pre-cultures were prepared by growing the bacteria containing the plasmids with the selected VHH in 8 ml 2×YT medium supplemented with 2% glucose and 100 μg/ml ampicillin overnight at 37° C. The pre-cultures were diluted into 800 ml fresh 2×YT that was pre-warmed at 37° C. and supplemented with 100 μg/ml ampicillin and 0.1% glucose. The bacteria were grown for 2 hours at 37° C. before induction of the VHH expression with 1 mM IPTG. The VHH were expressed for 4 hours at 37° C. and bacteria were harvested by centrifugation. Bacteria pellets were resuspended into 30 ml PBS and frozen at −20° C.

Purification and Analysis of the VHH

Frozen bacteria pellets were thawed at room temperature and cell debris was spun down by centrifugation. VHH were purified from the supernatant (soluble fraction) using affinity of the His-tag to Cobalt charged sepharose beads (Immobilized Metal Affinity Chromatography (IMAC) using TALON beads). Bound VHH were eluted with 150 mM imidazole and dialyzed against PBS.

The protein concentration was measured using absorption at 280 nm and corrected according the molar extinction coefficient and the molecular weight of the different VHH.

As a quality check, 1 μg of purified VHH was loaded on a SDS-PAGE.

The binding of purified VHH to immobilized His rBCLA was analyzed by ELISA. A MaxiSorp plate was coated with 200 ng/well antigen overnight at 4° C. in PBS. After blocking the wells with 4% MPBS, a serial dilution of the VHH was added to the coated wells and incubated for 1 hour at room temperature. After washing unbound VHH, bound VHH were detected using a mouse-anti-flag (clone M2) and donkey-anti-mouse coupled to HRP. Binding was quantified by measuring colorimetric reaction of OPD+H2O2 at 490 nm. ERB-1G6, ERB-1B11 and ERB-1A12 show a subnanomolar apparent affinity to immobilized His rBCLA. ERB-1F1 and ERB-1F2 show a low nanomolar affinity. ERB-1H4 and ERB-1D7 show a molar apparent affinity to His rBCLA.

CONCLUSIONS

Immunization of the llamas SEL005 and SEL006 resulted in a good immune response. The generated libraries were of a good size and insert frequency. Phage display selections on His rBCLA has resulted in a number of good clones of which 3 (ERB-1G6, ERB-1B11 and ERB-1A12) show a very good apparent affinity of which ERB-1G6 also shows a high production level in *E. coli*.

TABLE 4

Useful amino acid sequences for practicing the invention

| SEQ ID NO | Nucleotide or amino acid sequence |
|---|---|
| 1: full lenght polypeptide BCLA | MKLFFKLVLAGVSSIFAAQCLAGAVAARAGMPEITI<br>REEEEELFPSLDDVLDTSPFPARLWMGPGEKQATES<br>HTPATIPTAYKSTPGLSATVTGGEDGSAKMVGMDV<br>AKKPVKVSVKKEEENKDVEANEDGWDYIVSKGVP<br>GKIPATVMDEARKADVVADGEAKPAMREAQERRK<br>PWETQEEKILVLPKVQRILALPKEEKKHVSTAKGEE<br>PFSSKEEERHVLLNGEERKPVVPRAGREQPAVPRQE<br>EQKLVLQKTERKPVLPEEDQKPVLPETGAKHVLPEI<br>ATKSTLTQKEVTKPVETRQDMRGTAGSMEEKKPVL<br>PGEGKRHVLPKDETKPALTEEKRTKPVEPRKEMESP<br>ARPMEEEKPVLPGEGERHVLPKDERKPALTDEKRT<br>KPGGPRTEMERPAAGSMEKDKLVLPGEGEGHVLPK<br>HETKPALTDEKRTKPGGPRTEMERPAAGSMEKEKP<br>VLPGEGEGHVLPKHETKPALTDEKRTKPGGPRTEM<br>ERPAAGSMEKDKLVLPGEGEGHVLPKHETKPALTD<br>EKRTKPGGPRTEMERPAAGSMEKDKLVLPGEGEGH<br>VLPKHETKPALTDEKRTKPGGPRTEMERPAAGSME<br>KDKLVLPGEGEGHVLPKHETKPALTEEGRTEPIEPR<br>KAMERPAGAMEKTKPVLPGEGERHVLPKAETKTA<br>LTEEERTEPGGPRMAMERPAAGSMEKKKPVSPGEG<br>EGHVLPKHETKPALTDEKRTKPGGPRTEMERPAAG<br>SMEKDKLVLPGEGERHVLPKHERKPALTDEKRTKP<br>GGPPTEMERPAAGSMEKDKLVLPGEGERHVLPKDE<br>TKPALTEEKRTKPGGPRTEMERPAAGSMEKEKPVL<br>PGEGERHASPKDEMKPALTDEKRTKPGGPRKEMER<br>PAAGSMEKEKPVLPGEGERHVLPKDEQKAALTQKE |

TABLE 4-continued

| SEQ ID NO | Nucleotide or amino acid sequence |
|---|---|
| | VTNPVEPRKEMERPAAPIEGEKGVVSSEEEKPVSPK EATRRILPKEGKESLGTRKEEVKPIVRRAKRGRRIA QKGKEKQIAPKEGKKPAVPKEGEERPAEPTEGEERP VGPKEGEERPVGPKEGEERPVVPDVDKEKPVVPEG DKEKPVVPEGDKDHPALPEQDEEKHATWEKEMIPG VGDKTEASVLDSIENAVQKVLENLLKAAAGELQPA EAEEARLLVADLKAVVDTAEQVRVEGEAFFRASVD LYEAVKNLRDSEEKLRPLTKGELVDVVRQFLATQIF VQDRASAFLRVFERLAELLAAEQMKAVFAMVEEG VSSSERVARVAGELVPMMKKDRERRYGDLVAVTS WFMRRMEHI |
| 2: rBCLA | MIPGVGDKTEASVLDSIENAVQKVLENLLKAAAGE LQPAEAEEARLLVADLKAVVDTAEQVRVEGEAFFR ASVDLYEAVKNLRDSEEKLRPLTKGELVDVVRQFL ATQIFVQDRASAFLRVFERLAELLAAEQMKAVFAM VEEGVSSSERVARVAGELVPMMKKDRERRYGDLV AVTSWFMRRMEHI |
| 3: HisTag-rBCLA | MGHHHHHHHHENLYFQGMIPGVGDKTEASVLDSI ENAVQKVLENLLKAAAGELQPAEAEEARLLVADL KAVVDTAEQVRVEGEAFFRASVDLYEAVKNLRDS EEKLRPLTKGELVDVVRQFLATQIFVQDRASAFLRV FERLAELLAAEQMKAVFAMVEEGVSSSERVARVA GELVPMMKKDRERRYGDLVAVTSWFMRRMEHI |
| 4. TgR1 | MRGTAGSMEEKKPVLPGEGKRHVLPKDETKPALT EEKRTKPVEPRKE |
| 5. TgR2 | MESPARPMEEEKPVLPGEGERHVLPKDERKPALTD EKRTKPGGPRTE |
| 6: TgR3 | MERPAAGSMEKDKLVLPGEGEGHVLPKHETKPAL TDEKRTKPGGPRTE |
| 7. TgR4 | MERPAAGSMEKEKPVLPGEGEGHVLPKHETKPALT DEKRTKPGGPRTE |
| 8. TgR5 | MERPAAGSMEKDKLVLPGEGEGHVLPKHETKPAL TDEKRTKPGGPRTE |
| 9. TgR6 | MERPAAGSMEKDKLVLPGEGEGHVLPKHETKPAL TDEKRTKPGGPRTE |
| 10. TgR7 | MERPAAGSMEKDKLVLPGEGEGHVLPKHETKPAL TEEGRTEPIEPRKA |
| 11. TgR8 | MERPAGAMEKTKPVLPGEGERHVLPKAETKTALT EEERTEPGGPRMA |
| 12. TgR9 | MERPAAGSMEKKKPVSPGEGEGHVLPKHETKPAL TDEKRTKPGGPRTE |
| 13. TgR10 | MERPAAGSMEKDKLVLPGEGERHVLPKHERKPAL TDEKRTKPGGPPTE |
| 14. TgR11 | MERPAAGSMEKDKLVLPGEGERHVLPKDETKPAL TEEKRTKPGGPRTE |
| 15. TgR12 | MERPAAGSMEKEKPVLPGEGERHASPKDEMKPAL TDEKRTKPGGPRKE |
| 16. TgR13 | MERPAAGSMEKEKPVLPGEGERHVLPKDEQKAAL TQKEVTNPVEPRKE |
| 17. Peptide 1 of TgR1 and TgR11 | EMRGTAGSMEE |
| 18. Peptide 2 of TgR1 | VLPKDETKPALT |
| 19. Peptide 1 of TgR2 | EMESPARPMEE |
| 20. Peptide 2 of TgR2 | VLPKDERKPALT |
| 21. Peptide 1 of TgR3 to TgR7 and of TgR9 to TgR13 | EMERPAAGSMEK |

Useful amino acid sequences for practicing the invention

TABLE 4-continued

| Useful amino acid sequences for practicing the invention | |
|---|---|
| SEQ ID NO | Nucleotide or amino acid sequence |
| 22. Peptide 2 of TgR3 to TgR7 and TgR9 | VLPKHETKPALT |
| 23. Peptide 1 of TgR8 | EMERPAGAMEK |
| 24. Peptide 2 of TgR8 | VLPKAETKTALT |
| 25. Peptide 2 of TgR10 | VLPKHERKPALT |
| 26. Peptide 2 of TgR12 | ASPKDEMKPALT |
| 27. Peptide 2 of TgR13 | VLPKDEQKAALT |
| 28. primer TgBCLA-KO-CRISP-FWD | aagttgatcactattcgtgaagaagg |
| 29. primer TgBCLA-KO-CRISP-REV | aaaaccttcttcacgaatagtgatca |
| 30. primer TgBCLA-HF-CRISP-FWD | aagttggaacggcggtacggcgaccg |
| 31. primer TgBCLA-HF-CRISP-REV | aaaacggtcgccgtaccgccgttcca |
| 32. domain A of rBCLA | GELQPAEAEEARLLVADLKAV |
| 33. domain B of rBCLA | VRVEGEAFFRASVDLYEA |
| 34 domain C of rBCLA | KLRPLTKGELVDVVRQ |
| 35. peptide 36 of rBCLA | TQIFVQDRASAFLRV |
| 36. peptide 44 of rBCLA | AAEQMKAVFAMVEEG |
| 37. peptide 12 of rBCLA | GELQPAEAEEARLLV |
| 38. peptide 13 of rBCLA | QPAEAEEARLLVADL |
| 39. peptide 14 of rBCLA | EAEEARLLVADLKAV |
| 40. peptide 21 of rBCLA | VRVEGEAFFRASVDL |
| 41. peptide 22 of rBCLA | EGEAFFRASVDLYEA |
| 42. peptide 23 of rBCLA | AFFRASVDLYEAVKN |
| 43. peptide 30 of rBCLA | KLRPLTKGELVDVVR |
| 44. domain A of TgR4 | AAGSMEKEKPVLPGEGEGH |
| 45. domain B of TgR4 | VLPKHETKPALTDEKRTKPGGP |
| 46. peptide 3 of TgR4 | AAGSMEKEKPVLPGE |
| 47. peptide 4 of TgR4 | GSMEKEKPVLPGEGE |
| 48. peptide 5 of TgR4 | MEKEKPVLPGEGEGH |
| 49. peptide 6 of TgR4 | KEKPVLPGEGEGHVL |
| 50. peptide 7 of TgR4 | KPVLPGEGEGHVLPG |
| 51. peptide 13 of TgR4 | HVLPKHETKPALTDEK |
| 52. peptide 14 of TgR4 | PKHETKPALTDEKRT |
| 53. peptide 15 of TgR4 | HETKPALTDEKRTKP |
| 54. peptide 16 of TgR4 | TKPALTDEKRTKPGG |
| 55. Peptide AB_F | MERPAAGSMEKEKPVLPGEGEGLPKHETKPALTDE KRTKPGGP |
| 56. Peptide A3_B | AAGSMEKDKLVLPGE |

TABLE 4-continued

Useful amino acid sequences for practicing the invention

| SEQ ID NO | Nucleotide or amino acid sequence |
|---|---|
| 57. VHH ERB-1G6 | EVQLVESGGGLVQAGGSLGLSCAASGRPGRIFTRN SMAWFRQAPGKEREFVASINWSGTSTSYADSVKGR FAISRDNDKNTVYLQMNSLKPEDTAVYYCAADSAL YGSMHKTPADYEYWGQGTQVTVSS |
| 58. VHH ERB-1B11 | EVQLVESGGGLVQAGGSLRLTCAASGRTFRRSNM AWFRQPPGKERDFVAAIKWSGSSTNYADSVKGRFT ISRDNDKNTVYLQMNVLKPEDTGVYYCAQESSLYS NYLPVVSSAYDYWGQGTQVTVSS |
| 59. VHH ERB-1A12 | EVQLVESGGGLVQAGGSLRLSCAASGRTFSRYFMG WFRQAPGKEREFVAGIIWSGTRTYYVDSVKGRFTIS RDNDKRMVYLQMNSLKPEDTAVYYCAAYKEYYG TPAQLYAAASYDYWGQGTQVTVSS |
| 60. VHH ERB-1F1 | EVQLVESGGGLVQAGDSLRLSCAASGRTFSRVTMG WFRQAPGKEREFVAGISWSGTRTDYPDSVKGRFTV SRDNAKKTMWLQMSSLRPEDTAVYHCAADSTLYG SAISNNREAYAYWGQGTQVTVSS |
| 61. VHH ERB-1F2 | EVQLVESGGGLVQVGGSLRLSCAASGRTFRRNTIG WFRQAPGKEREFVAAISWSGTRTKYADPVKGRFTI SRDNDKNTAYLQMNTLKPDDTAVYYCAADGALY GSDVSGLARVYDYWGQGTQVTVSS |
| 62. VHH ERB-1H4 | EVQLVESGGGLVQAGGSLRLSCVASGRTFSRYTVG WFRQAPGKEREFVAGISWSGSRTSYADSVKGRFTIS RDNDKTTGYLQMNSLKPEDTAVYYCAAITKLYEN NIPRSVSDYALWGQGTQVTVSS |
| 63. VHH ERB-1D7 | KVQLVESGGGLVQAGGSLRLSCAASGRTFSRRGM GWFRQAPGKEREFVATIKWSGTSTDYADSVKGRFT ISRDNAKNTVYLQMNNLQPEDTAVYYCAADRQLY RDGYVPLNEYEDWGQGTQVTVSS |
| 64. TgRx | M-Xaa1-Xaa2-Xaa3-Xaa4-Xaa5-Xaa6-Xaa7-M-E-Xaa8-Xaa9-K-Xaa10-V-Xaa11-P-G-E-G-Xaa12-Xaa13-H-Xaa14-Xaa15-P-K-Xaa16-E-Xaa17-Xaa18-L-T-Xaa19-Xaa20-Xaa21-Xaa22-T-Xaa23-P-Xaa24-Xaa25-P-Xaa26-Xaa27-Xaa28 |

Example 3

In the present longitudinal study, we imply that detection of BCLA antibodies may conceivably further sensitivity of current tests when combined properly. We have undergone testing of BCLA in the context of mother to child congenital toxoplasmosis. For the moment, only 10 couples per group of mother/child were tested so the results should be considered accordingly. Two groups are compared, one where the congenital toxoplasmosis was confirmed through a persistent Sag1 IgG titer in the child's sera long after birth, the other where congenital toxoplasmosis was excluded when the sera of the child became negative to Sag1 over time (Lebech M et al., 1996).

Figure 15A:
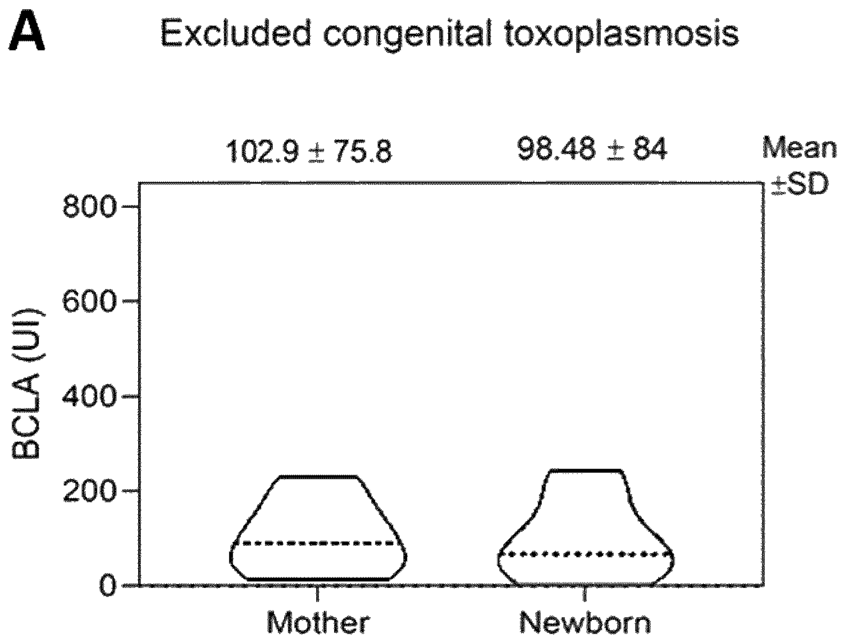
Figure 15B:
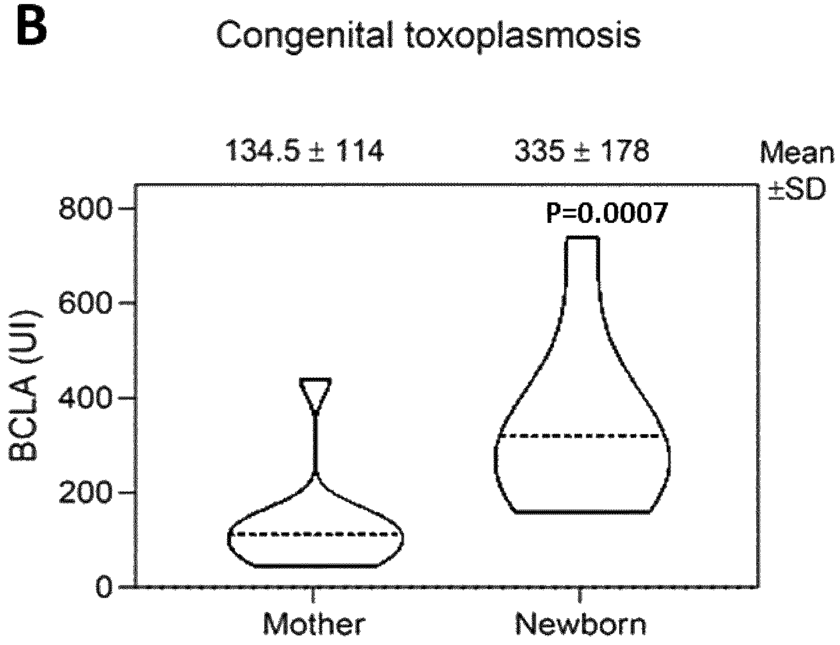
Figure 15C:
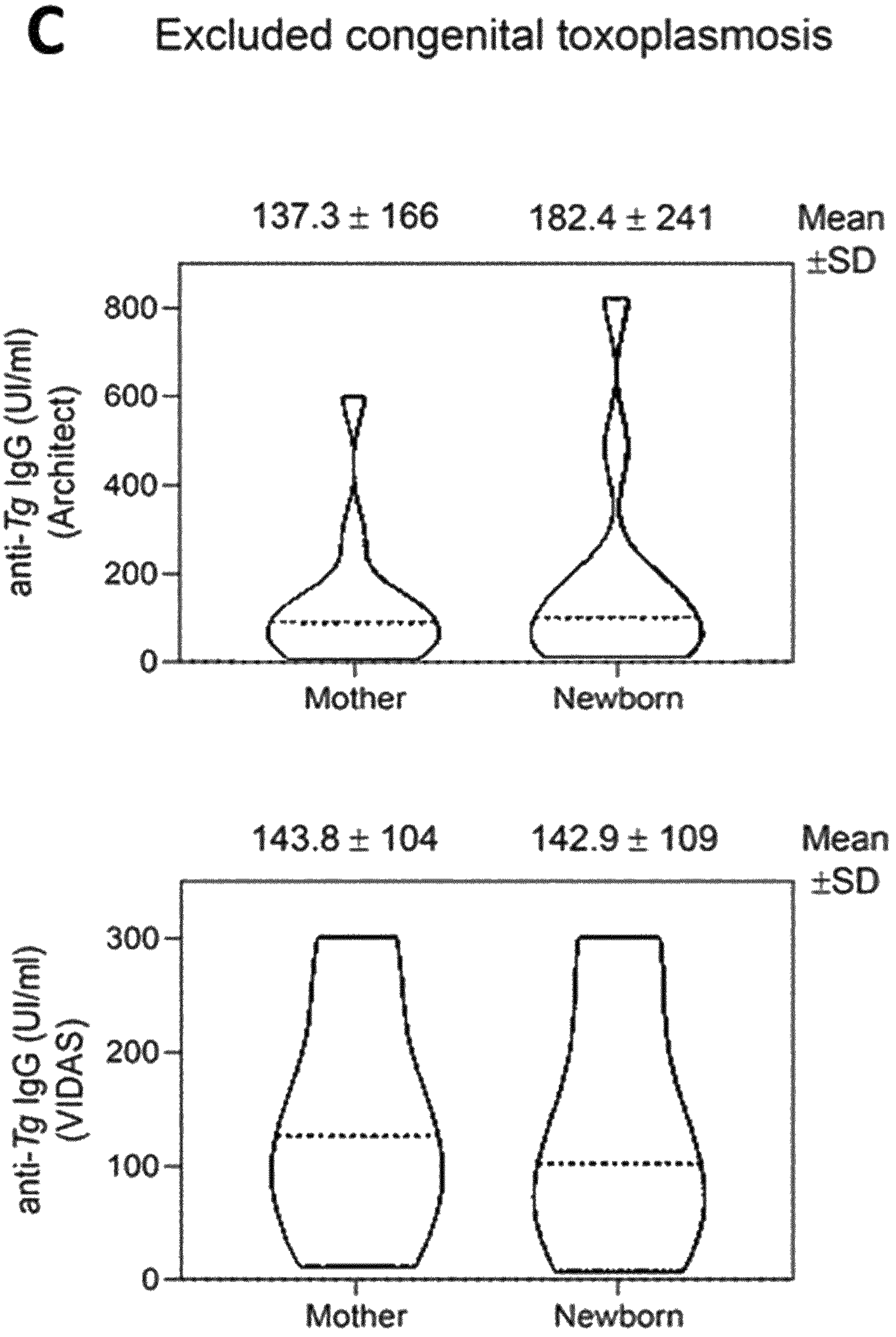
Figure 15D:
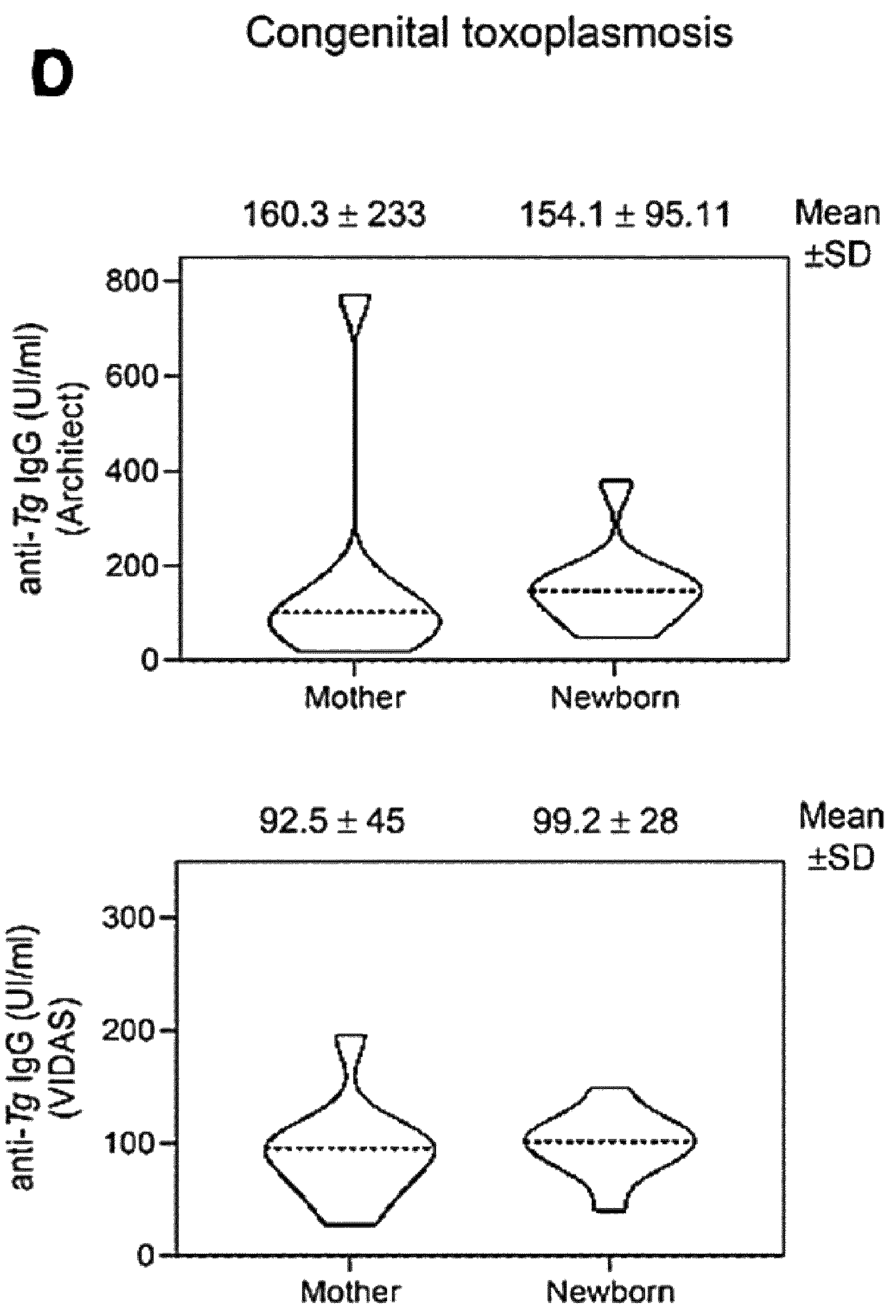

As shown by the comparative titration of Toxo IgGs by Vidas® and Architect®, at birth, infants in both groups share comparable titers with no discernable profile (FIG. 15C-D). This is explained by the fact that the mother transmits anti-Sag1 IgGs though the placental barrier therefor no definitive biological conclusion is possible at birth. When looking at BCLA ELISA titrations, the separation between congenital and excluded congenital toxoplasmosis is more clear-cut. Sera of children at birth display BCLA titrations far more reactive than that of their mothers or of excluded congenital toxoplasmosis group (FIG. 15A-B).

This observation implies that the child neo-synthetizes specifically anti-BCLA IgGs prior to birth and indicates that strong BCLA reactivity can further orient the diagnosis of congenital toxoplasmosis at the moment of birth.

REFERENCES

Throughout this application, various references describe the state of the art to which this invention pertains. The disclosures of these references are hereby incorporated by reference into the present disclosure.

Bougdour, A., Maubon, D., Baldacci, P., Ortet, P., Bastien, O., Bouillon, A., Barale, J.-C., Pelloux, H., Ménard, R., and Hakimi, M.-A. (2009). Drug inhibition of HDAC3 and epigenetic control of differentiation in Apicomplexa parasites. J. Exp. Med. 206, 953-966.

Braun, L., Brenier-Pinchart, M.-P., Yogavel, M., Curt-Varesano, A., Curt-Bertini, R.-L., Hussain, T., Kieffer-Jaquinod, S., Coute, Y., Pelloux, H., Tardieux, I., et al. (2013). A *Toxoplasma* dense granule protein, GRA24, modulates the early immune response to infection by promoting a direct and sustained host p38 MAPK activation. J. Exp. Med. 210, 2071-2086.

Buchholz, K. R., Bowyer, P. W., and Boothroyd, J. C. (2013). Bradyzoite pseudokinase 1 is crucial for efficient oral infectivity of the *Toxoplasma gondii* tissue cyst. Eukaryotic Cell 12, 399-410.

Cannella, D., Brenier-Pinchart, M.-P., Braun, L., van Rooyen, J. M., Bougdour, A., Bastien, O., Behnke, M. S., Curt, R.-L., Curt, A., Saeij, J. P. J., et al. (2014). miR-146a and miR-155 delineate a MicroRNA fingerprint associated with *Toxoplasma* persistence in the host brain. Cell Rep 6, 928-937.

Cornelissen, A. W., Overdulve, J. P., and Hoenderboom, J. M. (1981). Separation of *Isospora* (*Toxoplasma*) *gondii* cysts and cystozoites from mouse brain tissue by continuous density-gradient centrifugation. Parasitology 83, 103-108.

Dard, C., Marty, P., Brenier-Pinchart, M.-P., Garnaud, C., Fricker-Hidalgo, H., Pelloux, H., and Pomares, C. (2018). Management of toxoplasmosis in transplant recipients: an update. Expert Rev Anti Infect Ther 16, 447-460.

Di Cristina, M., Del Porto, P., Buffolano, W., Beghetto, E., Spadoni, A., Guglietta, S., Piccolella, E., Felici, F., and Gargano, N. (2004). The *Toxoplasma gondii* bradyzoite antigens BAG1 and MAG1 induce early humoral and cell-mediated immune responses upon human infection. Microbes and Infection 6, 164-171.

Döşkaya, M., Liang, L., Jain, A., Can, H., Gülçe iz, S., Felgner, P. L., Değirmenci Döşkaya, A., Davies, D. H., and Gürüz, A. Y. (2018). Discovery of new *Toxoplasma gondii* antigenic proteins using a high throughput protein microarray approach screening sera of murine model infected orally with oocysts and tissue cysts. Parasites & Vectors 11.

Dubey, J. P. (1997). Tissue cyst tropism in *Toxoplasma gondii*: a comparison of tissue cyst formation in organs of cats, and rodents fed oocysts. Parasitology 115 (Pt 1), 15-20.

Dubey, J. P. (2001). Oocyst shedding by cats fed isolated bradyzoites and comparison of infectivity of bradyzoites of the VEG strain *Toxoplasma gondii* to cats and mice. J. Parasitol. 87, 215-219.

Dzierszinski, F., Nishi, M., Ouko, L., and Roos, D.S. (2004). Dynamics of *Toxoplasma gondii* Differentiation. Eukaryotic Cell 3, 992-1003.

Eisen, H. N. (2014). Affinity enhancement of antibodies: how low-affinity antibodies produced early in immune responses are followed by high-affinity antibodies later and in memory B-cell responses. Cancer Immunol Res 2, 381-392.

Fox, B. A., Falla, A., Rommereim, L. M., Tomita, T., Gigley, J. P., Mercier, C., Cesbron-Delauw, M.-F., Weiss, L. M., and Bzik, D. J. (2011). Type II *Toxoplasma gondii* KU80 knockout strains enable functional analysis of genes required for cyst development and latent infection. Eukaryotic Cell 10, 1193-1206.

Franco, M., Panas, M. W., Marino, N. D., Lee, M.-C.W., Buchholz, K. R., Kelly, F. D., Bednarski, J. J., Sleckman, B. P., Pourmand, N., and Boothroyd, J. C. (2016). A Novel Secreted Protein, MYR1, Is Central to *Toxoplasma*'s Manipulation of Host Cells. MBio 7.

Frenkel, J. K., and Escajadillo, A. (1987). Cyst rupture as a pathogenic mechanism of toxoplasmic encephalitis. Am. J. Trop. Med. Hyg. 36, 517-522.

Fritz, H. M., Bowyer, P. W., Bogyo, M., Conrad, P. A., and Boothroyd, J. C. (2012). Proteomic analysis of fractionated *Toxoplasma* oocysts reveals clues to their environmental resistance. PLOS ONE 7, e29955.

Hakimi, M.-A., Olias, P., and Sibley, L. D. (2017). *Toxoplasma* Effectors Targeting Host Signaling and Transcription. Clinical Microbiology Reviews 30, 615-645.

Huynh, M.-H., and Carruthers, V. B. (2009). Tagging of endogenous genes in a *Toxoplasma gondii* strain lacking Ku80. Eukaryotic Cell 8, 530-539.

Jeffers, V., Tampaki, Z., Kim, K., and Sullivan, W. J. (2018). A latent ability to persist: differentiation in *Toxoplasma gondii*. Cellular and Molecular Life Sciences.

Kurdistani, S. K., and Grunstein, M. (2003). Histone acetylation and deacetylation in yeast. Nat. Rev. Mol. Cell Biol. 4, 276-284.

Lemgruber, L., Lupetti, P., Martins-Duarte, E. S., De Souza, W., and Vommaro, R. C. (2011). The organization of the wall filaments and characterization of the matrix structures of *Toxoplasma gondii* cyst form: Structure of *Toxoplasma gondii* cyst. Cellular Microbiology 13, 1920-1932.

Lueder, C. G. K., and Rahman, T. (2017). Impact of the host on *Toxoplasma* stage differentiation. Microbial Cell 4, 203-211.

Maubon, D., Bougdour, A., Wong, Y.-S., Brenier-Pinchart, M.-P., Curt, A., Hakimi, M.-A., and Pelloux, H. (2010). Activity of the histone deacetylase inhibitor FR235222 on *Toxoplasma gondii*: inhibition of stage conversion of the parasite cyst form and study of new derivative compounds. Antimicrob. Agents Chemother. 54, 4843-4850.

Mun, H., Aosai, F., and Yano, A. (1999). Role of *Toxoplasma gondii* HSP70 and *Toxoplasma gondii* HSP30/bag1 in Antibody Formation and Prophylactic Immunity in Mice Experimentally Infected with *Toxoplasma gondii*. Microbiology and Immunology 43, 471-479.

Possenti, A., Fratini, F., Fantozzi, L., Pozio, E., Dubey, J.P., Ponzi, M., Pizzi, E., and Spano, F. (2013). Global proteomic analysis of the oocyst/sporozoite of *Toxoplasma gondii* reveals commitment to a host-independent lifestyle. BMC Genomics 14, 183.

Reischl, U., Bretagne, S., Krüger, D., Ernault, P., and Costa, J.-M. (2003). Comparison of two DNA targets for the diagnosis of Toxoplasmosis by real-time PCR using fluorescence resonance energy transfer hybridization probes. BMC Infect. Dis. 3, 7.

Robert-Gangneux, F., and Darde, M.-L. (2012). Epidemiology of and Diagnostic Strategies for Toxoplasmosis. Clinical Microbiology Reviews 25, 264-296.

Saeij, J. P. J., Coller, S., Boyle, J. P., Jerome, M. E., White, M. W., and Boothroyd, J. C. (2007). *Toxoplasma* co-opts host gene expression by injection of a polymorphic kinase homologue. Nature 445, 324-327.

Saksouk, N., Bhatti, M. M., Kieffer, S., Smith, A. T., Musset, K., Garin, J., Sullivan, W. J., Cesbron-Delauw, M.-F., and Hakimi, M.-A. (2005). Histone-modifying complexes regulate gene expression pertinent to the differentiation of the protozoan parasite *Toxoplasma gondii*. Mol. Cell. Biol. 25, 10301-10314.

Sangaré, L. O., Alayi, T. D., Westermann, B., Hovasse, A., Sindikubwabo, F., Callebaut, I., Werkmeister, E., Lafont, F., Slomianny, C., Hakimi, M.-A., et al. (2016). Unconventional endosome-like compartment and retromer complex in *Toxoplasma gondii* govern parasite integrity and host infection. Nature Communications 7, 11191.

Santana, S. S., Gebrim, L. C., Carvalho, F. R., Barros, H. S., Barros, P. C., Pajuaba, A. C. A. M., Messina, V., Possenti, A., Cherchi, S., Reiche, E. M. V., et al. (2015). CCp5A Protein from *Toxoplasma gondii* as a Serological Marker of Oocyst-driven Infections in Humans and Domestic Animals. Frontiers in Microbiology 6.

Sayles, P. C., Gibson, G. W., and Johnson, L. L. (2000). B Cells Are Essential for Vaccination-Induced Resistance to Virulent *Toxoplasma gondii*. Infection and Immunity 68, 1026-1033.

Scallan, E., Hoekstra, R. M., Mahon, B. E., Jones, T. F., and Griffin, P. M. (2015). An assessment of the human health impact of seven leading foodborne pathogens in the United States using disability adjusted life years. Epidemiol. Infect. 143, 2795-2804.

Sindikubwabo, F., Ding, S., Hussain, T., Ortet, P., Barakat, M., Baumgarten, S., Cannella, D., Palencia, A., Bougdour, A., Belmudes, L., et al. (2017). Modifications at K31 on the lateral surface of histone H4 contribute to genome structure and expression in apicomplexan parasites. ELife 6.

Tomita, T., Bzik, D. J., Ma, Y. F., Fox, B. A., Markillie, L. M., Taylor, R. C., Kim, K., and Weiss, L. M. (2013). The *Toxoplasma gondii* Cyst Wall Protein CST1 Is Critical for Cyst Wall Integrity and Promotes Bradyzoite Persistence. PLOS Pathogens 9, e1003823.

Tomita, T., Sugi, T., Yakubu, R., Tu, V., Ma, Y., and Weiss, L. M. (2017). Making Home Sweet and Sturdy: *Toxoplasma gondii* ppGalNAc-Ts Glycosylate in Hierarchical Order and Confer Cyst Wall Rigidity. MBio 8.

Watts, E., Zhao, Y., Dhara, A., Eller, B., Patwardhan, A., and Sinai, A. P. (2015). Novel Approaches Reveal that *Toxoplasma gondii* Bradyzoites within Tissue Cysts Are Dynamic and Replicating Entities In Vivo. MBio 6.

Xiao, J., Li, Y., Prandovszky, E., Kannan, G., Viscidi, R. P., Pletnikov, M. V., and Yolken, R. H. (2016). Behavioral Abnormalities in a Mouse Model of Chronic Toxoplasmosis Are Associated with MAG1 Antibody Levels and Cyst Burden. PLOS Neglected Tropical Diseases 10, e0004674.

Lebech M, Joynson D H, Seitz H M, Thulliez P, Gilbert R E, Dutton G N, Ovlisen B, Petersen E. 1996. Classification system and case definitions of *Toxoplasma gondii* infection in immunocompetent pregnant women and their congenitally infected offspring. European Research Network on Congenital Toxoplasmosis. Eur J Clin Microbiol Infect Dis 15:799-805.

The invention claimed is:

1. A method for diagnosing or confirming a diagnosis of and treating a latent form of Toxoplasmosis in a patient in need thereof, wherein the latent form of Toxoplasmosis is caused by infection with type I or type II *Toxoplasma gondii*, comprising:

a) obtaining a biological sample from the patient, b) detecting via an immunoassay, in the biological sample, antibodies toward a *Toxoplasma gondii* polypeptide selected from the group consisting of i) the *Toxoplasma gondii* polypeptide BCLA amino acid sequence (SEQ ID NO: 1);

ii) the BCLA C-terminal antigenic domain amino acid sequence (SEQ ID NO:2);

iii) a BCLA internal repeated domain amino acid sequence selected from the group consisting of:

```
TgR1,        (SEQ ID NO: 4)
TgR2,        (SEQ ID NO: 5)
TgR3,        (SEQ ID NO: 6)
TgR4,        (SEQ ID NO: 7)
TgR5,        (SEQ ID NO: 8)
TgR6,        (SEQ ID NO: 9)
TgR7,        (SEQ ID NO: 10)
TgR8,        (SEQ ID NO: 11)
TgR9,        (SEQ ID NO: 12)
tgR10,       (SEQ ID NO: 13)
TgR11,       (SEQ ID NO: 14)
```

-continued

```
TgR12        (SEQ ID NO: 15)
and
TgR13;       (SEQ ID NO: 16)
```

and iv) a polypeptide selected from the group consisting of SEQ ID Nos 55-56, and c) treating the patient with a folic acid antagonist and/or an antibiotic.

2. An in vitro method for diagnosing or confirming a diagnosis of and treating congenital Toxoplasmosis in a patient in need thereof, wherein the congenital Toxoplasmosis is caused by infection with type I or type II *Toxoplasma gondii*, comprising:

a) obtaining a biological sample from the patient, b) detecting via an immunoassay, in the biological sample, antibodies toward a *Toxoplasma gondii* polypeptide selected from the group consisting of i) the *Toxoplasma gondii* polypeptide BCLA amino acid sequence (SEQ ID NO: 1);

ii) the BCLA C-terminal antigenic domain amino acid sequence (SEQ ID NO:2);

iii) a BCLA internal repeated domain amino acid sequence selected from the group consisting of:

```
TgR1,        (SEQ ID NO: 4)
TgR2,        (SEQ ID NO: 5)
TgR3,        (SEQ ID NO: 6)
TgR4,        (SEQ ID NO: 7)
TgR5,        (SEQ ID NO: 8)
TgR6,        (SEQ ID NO: 9)
TgR7,        (SEQ ID NO: 10)
```

-continued (SEQ ID NO: 11)
TgR8, (SEQ ID NO: 12)
TgR9, (SEQ ID NO: 13)
TgR10, (SEQ ID NO: 14)
TgR11, (SEQ ID NO: 15)
TgR12 and (SEQ ID NO: 16)
TgR13;

and iv) a polypeptide selected from the group consisting of SEQ ID Nos 55-56, and c) treating the patient with at least one folic acid antagonist and/or at least one antibiotic.

3. The method according to claim 1 wherein said biological sample is a fluid sample.

4. A method for treating a patient infected with latent form of Toxoplasmosis caused by infection with type I or type II *Toxoplasma gondii*, comprising:

a) detecting via an immunoassay, in a biological sample obtained from the patient, antibodies toward a *Toxoplasma gondii* polypeptide selected from the group consisting of i) the *Toxoplasma gondii* polypeptide BCLA amino acid sequence (SEQ ID NO: 1);

ii) the BCLA C-terminal antigenic domain amino acid sequence (SEQ ID NO:2);

iii) a BCLA internal repeated domain amino acid sequence selected from the group consisting of:

(SEQ ID NO: 4)
TgR1, (SEQ ID NO: 5)
TgR2,

-continued (SEQ ID NO: 6)
TgR3, (SEQ ID NO: 7)
TgR4, (SEQ ID NO: 8)
TgR5, (SEQ ID NO: 9)
TgR6, (SEQ ID NO: 10)
TgR7, (SEQ ID NO: 11)
TgR8, (SEQ ID NO: 12)
TgR9, (SEQ ID NO: 13)
TgR10, (SEQ ID NO: 14)
TgR11, (SEQ ID NO: 15)
TgR12 and (SEQ ID NO: 16)
TgR13;

and iv) a polypeptide selected from the group consisting of SEQ ID Nos 55-56, and b) administering to the patient at least one folic acid antagonist and/or at least one antibiotic, or a pharmaceutical composition comprising the at least one folic acid antagonist and the at least one antibiotic compound.

5. The method of claim 1, wherein the at least one folic acid antagonist is pyrimethamine and the at least one antibiotic is sulfadiazine or spiramycin.

6. The method of claim 2, wherein the at least one folic acid antagonist is pyrimethamine and the at least one antibiotic is sulfadiazine or spiramycin.

7. The method of claim 4, wherein the patient is asymptomatic.

* * * * *